United States Patent
Bowen et al.

(10) Patent No.: US 12,404,520 B2
(45) Date of Patent: Sep. 2, 2025

(54) INSECT INHIBITORY PROTEINS

(71) Applicant: Monsanto Technology LLC, St. Louis, MO (US)

(72) Inventors: David J. Bowen, Wildwood, MO (US); Catherine A. Chay, Ballwin, MO (US); Todd A. Ciche, San Diego, CA (US); Stanislaw Flasinski, Ballwin, MO (US); Arlene R. Howe, Clarkson Valley, MO (US); Krishnakumar Sridharan, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 18/628,578

(22) Filed: Apr. 5, 2024

(65) Prior Publication Data
US 2024/0352480 A1 Oct. 24, 2024

Related U.S. Application Data

(60) Division of application No. 17/575,318, filed on Jan. 13, 2022, now Pat. No. 11,981,908, which is a division of application No. 16/658,892, filed on Oct. 21, 2019, now Pat. No. 11,225,672, which is a continuation of application No. 15/944,114, filed on Apr. 3, 2018, now Pat. No. 10,465,205.

(60) Provisional application No. 62/480,614, filed on Apr. 3, 2017.

(51) Int. Cl.
*C12N 15/82* (2006.01)
*C07K 14/195* (2006.01)
*C07K 14/32* (2006.01)

(52) U.S. Cl.
CPC ........ *C12N 15/8286* (2013.01); *C07K 14/195* (2013.01); *C07K 14/32* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,771,131 | A | 9/1988 | Hermstadt et al. |
| 6,210,953 | B1 | 4/2001 | Osman et al. |
| 8,461,416 | B2 | 6/2013 | Niblett |
| 2011/0030096 | A1 | 2/2011 | Sampson et al. |
| 2013/0167268 | A1 | 6/2013 | Narva et al. |
| 2013/0247254 | A1 | 9/2013 | Lira et al. |
| 2015/0274786 | A1 | 10/2015 | Bowen et al. |
| 2016/0058017 | A1 | 3/2016 | Lira et al. |
| 2017/0240603 | A1 | 8/2017 | Abad et al. |

FOREIGN PATENT DOCUMENTS

| | | |
|---|---|---|
| EP | 1277763 | 12/2006 |
| WO | 1999/035910 | 7/1999 |
| WO | 2005/082077 | 9/2005 |
| WO | 2010/075352 | 7/2010 |
| WO | 2011/014749 | 2/2011 |

OTHER PUBLICATIONS

Pardo-Lopez et al. (2009) Peptides 30:589-95.*
International Search Report and Written Opinion regarding International Application No. PCT/US2018/025867, dated Aug. 9, 2018.
Ribeiro et al., "Transgenic cotton expressing Cry10Aa toxin confers high resistance to the cotton boil weevil," Plant Biotechnology Journal, Jan. 12, 2017 (Jan. 12, 2017), vol. 15, Iss. 8, pp. 997-1009. entire document.
Tounsi et al. (2003) J. Appl Microbiol 95:23-28.
De Maagd et al. (1999) Appl Environ Microbiol 65:4369-74.
Angsuthanasonnbat et al. (2001) J Biochem Mol Biol 34:402-07.
Aronson & Shai (2001) FEMS Microbiol Lett 195:1-8.
De Maagd et al. (2001) Trends Genet 17:193-99.
Guo et al. (2004) Proc Natl Acad Sci USA 101:9205-10.
Olsen et al. (2005) Trends Plant Sci 10(2):79-87.
Fourgoux-Nicol et al. (1999) Plant Mol Biol 40:857-72.
Ruiu (2013) Insects 4:476-92.

* cited by examiner

*Primary Examiner* — Russell T Boggs
(74) *Attorney, Agent, or Firm* — Dentons US LLP; David Lanzotti

(57) ABSTRACT

A pesticidal protein class exhibiting toxic activity against Coleopteran and Lepidopteran pest species is disclosed, and includes, but is not limited to, TIC7040, TIC7042, TIC7381, TIC7382, TIC7383, TIC7386, TIC7388, and TIC7389. DNA constructs are provided which contain a recombinant nucleic acid sequence encoding the TIC7040, TIC7042, TIC7381, TIC7382, TIC7383, TIC7386, TIC7388, and TIC7389 pesticidal proteins. Transgenic plants, plant cells, seed, and plant parts resistant to Coleopteran and Lepidopteran infestation are provided which contain recombinant nucleic acid sequences encoding the TIC7040, TIC7042, TIC7381, TIC7382, TIC7383, TIC7386, TIC7388, and TIC7389 pesticidal proteins of the present invention. Methods for detecting the presence of the recombinant nucleic acid sequences or the proteins of the present invention in a biological sample, and methods of controlling Coleopteran and Lepidopteran species pests using the TIC7040, TIC7042, TIC7381, TIC7382, TIC7383, TIC7386, TIC7388, and TIC7389 pesticidal proteins are also provided.

31 Claims, No Drawings
Specification includes a Sequence Listing.

INSECT INHIBITORY PROTEINS

REFERENCE TO RELATED APPLICATION

This application is a divisional of U.S. patent application Ser. No. 17/575,318, filed Jan. 13, 2022, which is a divisional of U.S. patent application Ser. No. 16/658,892, filed Oct. 21, 2019, now U.S. Pat. No. 11,225,672, which is a continuation of U.S. patent application Ser. No. 15/944,114, filed Apr. 3, 2018, now U.S. Pat. No. 10,465,205, which claims the benefit of U.S. Provisional Application No. 62/480,614, filed Apr. 3, 2017, each of which is herein incorporated by reference in its entirety.

INCORPORATION OF SEQUENCE LISTING

The file named "MONS443USD2_ST26.xml" containing a computer-readable form of the Sequence Listing was created on Mar. 13, 2024. This file is 398,784 bytes (measured in MS-Windows®) is contemporaneously filed by electronic submission (using the United States Patent Office Patent Center filing system), and is incorporated into this application by reference in its entirety.

FIELD OF THE INVENTION

The invention generally relates to the field of insect inhibitory proteins. A novel class of proteins exhibiting insect inhibitory activity against agriculturally-relevant pests of crop plants and seeds is disclosed. In particular, the disclosed protein are insecticidally active against agriculturally-relevant pests of crop plants and seeds, particularly Coleopteran and Lepidopteran species of insect pests. Plants, plant parts, and seeds containing a recombinant polynucleotide construct encoding one or more of the disclosed toxin proteins are provided.

BACKGROUND OF THE INVENTION

Improving crop yield from agriculturally significant plants including, among others, corn, soybean, sugarcane, rice, wheat, vegetables, and cotton, has become increasingly important. In addition to the growing need for agricultural products to feed, clothe and provide energy for a growing human population, climate-related effects and pressure from the growing population to use land other than for agricultural practices are predicted to reduce the amount of arable land available for farming. These factors have led to grim forecasts of food security, particularly in the absence of major improvements in plant biotechnology and agronomic practices. In light of these pressures, environmentally sustainable improvements in technology, agricultural techniques, and pest management are vital tools to expand crop production on the limited amount of arable land available for farming.

Insects, particularly insects within the Lepidoptera and Coleoptera orders, are considered a major cause of damage to field crops, thereby decreasing crop yields over infested areas. Historically, the intensive application of synthetic chemical insecticides was relied upon as the pest control agent in agriculture. Concerns for the environment and human health, in addition to emerging resistance issues, stimulated the research and development of biological pesticides. This research effort led to the progressive discovery and use of various entomopathogenic microbial species, including bacteria.

The biological control paradigm shifted when the potential of entomopathogenic bacteria, especially bacteria belonging to the genus *Bacillus*, was discovered and developed as a biological pest control agent. Strains of the bacterium *Bacillus thuringiensis* (Bt) have been used as a source for pesticidal proteins since it was discovered that Bt strains show a high toxicity against specific insects. Bt strains are known to produce delta-endotoxins that are localized within parasporal crystalline inclusion bodies at the onset of sporulation and during the stationary growth phase (e.g., Cry proteins), and are also known to produce secreted insecticidal protein. Upon ingestion by a susceptible insect, delta-endotoxins as well as secreted toxins exert their effects at the surface of the midgut epithelium, disrupting the cell membrane, leading to cell disruption and death. Genes encoding insecticidal proteins have also been identified in bacterial species other than Bt, including other *Bacillus* and a diversity of additional bacterial species, such as *Brevibacillus laterosporus, Lysinibacillus sphaericus* ("Ls" formerly known as *Bacillus sphaericus*) and *Paenibacillus popilliae*.

Crystalline and secreted soluble insecticidal toxins are highly specific for their hosts and have gained worldwide acceptance as alternatives to chemical insecticides. For example, insecticidal toxin proteins have been employed in various agricultural applications to protect agriculturally important plants from insect infestations, decrease the need for chemical pesticide applications, and increase yields. Insecticidal toxin proteins are used to control agriculturally-relevant pests of crop plants by mechanical methods, such as spraying to disperse microbial formulations containing various bacteria strains onto plant surfaces, and by using genetic transformation techniques to produce transgenic plants and seeds expressing insecticidal toxin protein.

The use of transgenic plants expressing insecticidal toxin proteins has been globally adapted. For example, in 2012, 26.1 million hectares were planted with transgenic crops expressing Bt toxins (James, C., Global Status of Commercialized Biotech/GM Crops: 2012. ISAAA Brief No. 44). The global use of transgenic insect-protected crops and the limited number of insecticidal toxin proteins used in these crops has created a selection pressure for existing insect alleles that impart resistance to the currently-utilized insecticidal proteins.

The development of resistance in target pests to insecticidal toxin proteins creates the continuing need for discovery and development of new forms of insecticidal toxin proteins that are useful for managing the increase in insect resistance to transgenic crops expressing insecticidal toxin proteins. New protein toxins with improved efficacy and which exhibit control over a broader spectrum of susceptible insect species will reduce the number of surviving insects which can develop resistance alleles. In addition, the use in one plant of two or more transgenic insecticidal toxin proteins toxic to the same insect pest and displaying different modes of action reduces the probability of resistance in any single target insect species.

Thus, the inventors herein disclose a novel protein toxin family from *Bacillus laterosporous* along with similar toxin proteins, variant proteins, and exemplary recombinant proteins that exhibit insecticidal activity against target Lepidopteran and Coleopteran, particularly against Western Corn Rootworm and Northern Corn Rootworm.

SUMMARY OF THE INVENTION

Disclosed herein is a novel group of pesticidal proteins with insect inhibitory activity (toxin proteins), referred to herein as TIC7040-related protein toxins, which are shown to exhibit inhibitory activity against one or more pests of crop plants. The TIC7040 protein and proteins in the TIC7040 protein toxin class can be used alone or in combination with other insecticidal proteins and toxic agents in formulations and in planta, thus providing alternatives to insecticidal proteins and insecticide chemistries currently in use in agricultural systems.

In one embodiment, disclosed in this application is a recombinant nucleic acid molecule comprising a heterologous promoter operably linked to a polynucleotide segment encoding a pesticidal protein or fragment thereof, wherein: (a) said pesticidal protein comprises the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:43, SEQ ID NO:46, SEQ ID NO:48, SEQ ID NO:50, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, or SEQ ID NO:127; or (b) said pesticidal protein comprises an amino acid sequence having: (i) at least 75% identity to SEQ ID NO:18, SEQ ID NO:20, SEQ ID NO:22, SEQ ID NO:24, SEQ ID NO:26, SEQ ID NO:28, SEQ ID NO:63, SEQ ID NO:65, SEQ ID NO:67, SEQ ID NO:69, SEQ ID NO:75, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, or SEQ ID NO:109; or (ii) at least 80% to SEQ ID NO:111 SEQ ID NO: 113, SEQ ID NO:115, SEQ ID NO:119, SEQ ID NO:125, or SEQ ID NO:127; or (iii) at least 85% identity to SEQ ID NO:121 or SEQ ID NO:123; or (iv) at least 90% identity to SEQ ID NO:2, SEQ ID NO:4, SEQ ID NO:6, SEQ ID NO:8, SEQ ID NO:10, SEQ ID NO:14, SEQ ID NO:34, SEQ ID NO:43, SEQ ID NO:46, SEQ ID NO:48, SEQ ID NO:50, SEQ ID NO:57, SEQ ID NO:71, SEQ ID NO:73, SEQ ID NO:77, SEQ ID NO:79, SEQ NO:81, or SEQ ID NO:117; or (v) at least 93% identity to SEQ ID NO:12, SEQ ID NO:16, SEQ ID NO:30, and SEQ ID NO:59; or (vi) at least 94% identity to SEQ ID NO:53 and SEQ ID NO:55; or (vii) at least 99% identity to SEQ ID NO:32, SEQ ID NO:61, or SEQ ID NO:83; or (c) said polynucleotide segment hybridizes to a polynucleotide having the nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:44, SEQ ID NO:45, SEQ ID NO:47, SEQ ID NO:49, SEQ ID NO:51, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, OR SEQ ID NO:126; or (d) said recombinant nucleic acid molecule is in operable linkage with a vector, and said vector is selected from the group consisting of a plasmid, phagemid, bacmid, cosmid, and a bacterial or yeast artificial chromosome. The recombinant nucleic acid molecule can comprise a sequence that functions to express the pesticidal protein in a plant; or is expressed in a plant cell to produce a pesticidally effective amount of pesticidal protein.

In another embodiment of this application are host cells comprising a recombinant nucleic acid molecule of the application, wherein the host cell is selected from the group consisting of a bacterial and a plant cell. Contemplated host cells include *Agrobacterium, Rhizobium, Bacillus, Brevibacillus, Escherichia, Pseudomonas, Klebsiella, Pantoea*, and *Erwinia*. In certain embodiments said *Bacillus* species is *Bacillus cereus* or *Bacillus thuringiensis*, said *Brevibacillus* is *Brevibacillus laterosperus*, or said *Escherichia* is *Escherichia coli*. Contemplated plant host cells include a dicotyledonous cell and a monocotyledonous cell. Further contemplated plant host cells include an alfalfa, banana, barley, bean, broccoli, cabbage, Brassica, carrot, cassava, castor, cauliflower, celery, chickpea, Chinese cabbage, citrus, coconut, coffee, corn, clover, cotton (*Gossypium* sp.), a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

In yet another embodiment, the pesticidal protein exhibits activity against Coleopteran insect, including Western Corn Rootworm, Southern Corn Rootworm, Northern Corn Rootworm, Mexican Corn Rootworm, Brazilian Corn Rootworm, Colorado Potato Beetle, Brazilian Corn Rootworm complex consisting of *Diabrotica viridula* and *Diabrotica speciosa*, Crucifer Flea Beetle, Striped Flea Beetle, and Western Black Flea Beetle.

In another embodiment, the pesticidal protein exhibits activity against a Lepidopteran insect, including Black Cutworm, Corn Earworm, Diamondback Moth, European Corn Borer, Fall Armyworm, Southern Armyworm, Soybean Looper, Southwestern Corn Borer, Tobacco Budworm, Velvetbean Caterpillar, Sugarcane Borer, Lesser Cornstalk Borer, Black Armyworm, Beet Armyworm, Old World Bollworm, Oriental leaf Worm, or Pink Bollworm.

Also contemplated in this application are plants comprising a recombinant nucleic acid molecule comprising a heterologous promoter operably linked to a polynucleotide segment encoding a pesticidal protein or fragment thereof, wherein: (a) said pesticidal protein comprises the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:43, SEQ ID NO:46, SEQ ID NO:48, SEQ ID NO:50, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, or SEQ ID NO:127; or (b) said pesticidal protein comprises an amino acid sequence having: (i) at least 75% identity to SEQ ID NO:18, SEQ ID NO:20, SEQ ID NO:22, SEQ ID NO:24, SEQ ID NO:26, SEQ ID NO:28, SEQ ID NO:63, SEQ ID NO:65, SEQ ID NO:67, SEQ ID NO:69, SEQ ID NO:75, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, or SEQ ID NO:109; or (ii) at least 80% to SEQ ID NO:111 SEQ ID NO:113, SEQ ID NO:115, SEQ ID NO:119, SEQ ID NO:125, or SEQ ID NO:127; or (iii) at least 85% identity to SEQ ID NO:121 or SEQ ID NO:123; or (iv) at least 90% identity to SEQ ID NO:2, SEQ ID NO:4, SEQ ID NO:6, SEQ ID NO:8, SEQ ID NO:10, SEQ ID NO:14, SEQ ID NO:34, SEQ ID NO:43, SEQ ID NO:46, SEQ ID NO:48, SEQ ID NO:50, SEQ ID NO:57, SEQ ID NO:71, SEQ ID NO:73, SEQ ID NO:77, SEQ ID NO:79, SEQ NO:81, or SEQ ID NO:117; or (v) at least 93% identity to SEQ ID NO:12, SEQ ID NO:16, SEQ ID NO:30, and SEQ ID NO:59; or (vi) at least 94% identity to SEQ ID NO:53 and SEQ ID NO:55; or (vii) at least 99% identity to SEQ ID NO:32, SEQ ID NO:61, or SEQ ID NO:83; or (c) said polynucleotide segment hybridizes under stringent hybridization conditions to the compliment of the nucleotide sequence of to SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:44, SEQ ID NO:45, SEQ ID NO:47, SEQ ID NO:49, SEQ ID NO:51, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, OR SEQ ID NO:126; or (d) said plant exhibits a detectable amount of said pesticidal protein. In certain embodiments the pesticidal protein comprises SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:43, SEQ ID NO:46, SEQ ID NO:48, SEQ ID NO:50, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, or SEQ ID NO:127. In one embodiment, the plant is either a monocot or a dicot. In another embodiment, the plant is selected from the group consisting of an alfalfa, banana, barley, bean, broccoli, cabbage, Brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat.

In further embodiments, seeds comprising the recombinant nucleic acid molecules are disclosed.

In another embodiment, an insect inhibitory composition comprising the recombinant nucleic acid molecules disclosed in this application are contemplated. The insect inhibitory composition can further comprise a nucleotide sequence encoding at least one other pesticidal agent that is different from said pesticidal protein. The at least one other pesticidal agent is selected from the group consisting of an insect inhibitory protein, an insect inhibitory dsRNA molecule, and an ancillary protein. The at least one other pesticidal agent in the insect inhibitory composition exhibits activity against one or more pest species of the orders Lepidoptera, Coleoptera, or Hemiptera. The at least one other pesticidal agent in the insect inhibitory composition is in one embodiment selected from the group consisting of: a Cry1A, Cry1Ab, Cry1Ac, Cry1A.105, Cry1Ae, Cry1B, Cry1C, Cry1C variants, Cry1D, Cry1E, Cry1F, Cry1A/F chimeras, Cry1G, Cry1H, Cry1I, Cry1J, Cry1K, Cry1L, Cry2A, Cry2Ab, Cry2Ae, Cry3, Cry3A variants, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC2160, TIC3131, TIC836, TIC860, TIC867, TIC869, TIC1100, VIP3A, VIP3B, VIP3Ab, AXMI-AXMI-, AXMI-88, AXMI-97, AXMI-102, AXMI-112, AXMI-117, AXMI-100, AXMI-115, AXMI-113, and AXMI-005, AXMI134, AXMI-150, AXMI-171, AXMI-184, AXMI-196, AXMI-204, AXMI-207, AXMI-209, AXMI-205, AXMI-218, AXMI-220, AXMI-221z, AXMI-222z, AXMI-223z, AXMI-224z and AXMI-225z, AXMI-238, AXMI-270, AXMI-279, AXMI-345, AXMI-335,AXMI-R1 and variants thereof, IP3 and variants thereof, DIG-3, DIG-5, DIG-10, DIG-657 DIG-11, Cry71Aa1, Cry72Aa1, PHI-4 variants, PIP-72 variants, PIP-45 variants, PIP-64 variants, PIP-74 variants, PIP-75 variants, PIP-77 variants, Axmi422, Dig-305, Axmi440, PIP-47 variants, Axmi281, BT-009, BT-0012, BT-0013, BT-0023, BT0067, BT-0044, BT-0051, BT-0068, BT-0128, DIG-17, DIG-90, DIG-79, Cry1JP578V, Cry1JPS1, and Cry1 JPS1P578V.

Commodity products comprising a detectable amount of the recombinant nucleic acid molecules disclosed in this application are contemplated. Such commodity products include commodity corn bagged by a grain handler, corn flakes, corn cakes, corn flour, corn meal, corn syrup, corn oil, corn silage, corn starch, corn cereal, and the like, and corresponding cotton commodity products such as whole or processed cotton seed, cotton oil, lint, seeds and plant parts processed for feed or food, fiber, paper, biomasses, and fuel products such as fuel derived from cotton oil or pellets derived from cotton gin waste, and corresponding soybean commodity products such as whole or processed soybean seed, soybean oil, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts, and corresponding rice, wheat, sorghum, pigeon pea, peanut, fruit, melon, and vegetable commodity products including where applicable, juices, concentrates, jams, jellies, marmalades, and other edible forms of such commodity products containing a detectable amount of such polynucleotides and or polypeptides of this application.

Also contemplated in this application is a method of producing seed comprising the recombinant nucleic acid molecules disclosed in this application. The method comprises planting at least one of the seed comprising the recombinant nucleic acid molecules disclosed in this application; growing plant from the seed; and harvesting seed from the plants, wherein the harvested seed comprises the recombinant nucleic acid molecules in this application.

In another illustrative embodiment, a plant resistant to insect infestation is provided, wherein the cells of said plant comprise: (a) a recombinant nucleic acid molecule encoding an insecticidally effective amount of a pesticidal protein as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:43, SEQ ID NO:46, SEQ ID NO:48, SEQ ID NO:50, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, or SEQ ID NO:127; or (b) an insecticidally effective amount of a protein comprising an amino acid sequence having: (i) at least 75% identity to SEQ ID NO:18, SEQ ID NO:20, SEQ ID NO:22, SEQ ID NO:24, SEQ ID NO:26, SEQ ID NO:28, SEQ ID NO:63, SEQ ID NO:65, SEQ ID NO:67, SEQ ID NO:69, SEQ ID NO:75, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, or SEQ ID NO:109; or (ii) at least 80% to SEQ ID NO:111 SEQ ID NO: 113, SEQ ID NO:115, SEQ ID NO:119, SEQ ID NO:125, or SEQ ID NO:127; or (iii) at least 85% identity to SEQ ID NO:121 or SEQ ID NO:123; or (iv) at least 90% identity to SEQ ID NO:2, SEQ ID NO:4, SEQ ID NO:6, SEQ ID NO:8, SEQ ID NO:10, SEQ ID NO:14, SEQ ID NO:34, SEQ ID NO:43, SEQ ID NO:46, SEQ ID NO:48, SEQ ID NO:50, SEQ ID NO:57, SEQ ID NO:71, SEQ ID NO:73, SEQ ID NO:77, SEQ ID NO:79, SEQ NO:81, or SEQ ID NO:117; or (v) at least 93% identity to SEQ ID NO:12, SEQ ID NO:16, SEQ ID NO:30, and SEQ ID NO:59; or (vi) at least 94% identity to SEQ ID NO:53 and SEQ ID NO:55; or (vii) at least 99% identity to SEQ ID NO:32, SEQ ID NO:61, or SEQ ID NO:83.

Also disclosed in this application are methods for controlling a Coleopteran or Lepidopteran species pest, and controlling a Coleopteran or Lepidopteran species pest infestation of a plant, particularly a crop plant. The method comprises, in one embodiment, (a) contacting the pest with an insecticidally effective amount of one or more pesticidal proteins as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:43, SEQ ID NO:46, SEQ ID NO:48, SEQ ID NO:50, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, or SEQ ID NO:127; or (b) contacting the pest with an insecticidally effective amount of one or more pesticidal proteins comprising an amino acid sequence having: (i) at least 75% identity to SEQ ID NO:18, SEQ ID NO:20, SEQ ID NO:22, SEQ ID NO:24, SEQ ID NO:26, SEQ ID NO:28, SEQ ID NO:63, SEQ ID NO:65, SEQ ID NO:67, SEQ ID NO:69, SEQ ID NO:75, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, or SEQ ID NO:109; or (ii) at least 80% to SEQ ID NO:111 SEQ ID NO: 113, SEQ ID NO:115, SEQ ID NO:119, SEQ ID NO:125, or SEQ ID NO:127; or (iii) at least 85% identity to SEQ ID NO:121 or SEQ ID NO:123; or (iv) at least 90% identity to SEQ ID NO:2, SEQ ID NO:4, SEQ ID NO:6, SEQ ID NO:8, SEQ ID NO:10, SEQ ID NO:14, SEQ ID NO:34, SEQ ID NO:43, SEQ ID NO:46, SEQ ID NO:48, SEQ ID NO:50, SEQ ID NO:57, SEQ ID NO:71, SEQ ID NO:73, SEQ ID NO:77, SEQ ID NO:79, SEQ NO:81, or SEQ ID NO:117; or (v) at least 93% identity to SEQ ID NO:12, SEQ ID NO:16, SEQ ID NO:30, and SEQ ID NO:59; or (vi) at least 94% identity to SEQ ID NO:53 and SEQ ID NO:55; or (vii) at least 99% identity to SEQ ID NO:32, SEQ ID NO:61, or SEQ ID NO:83.

Further provided herein is a method of detecting the presence of a recombinant nucleic acid molecule comprising a polynucleotide segment encoding a pesticidal protein or fragment thereof, wherein: (a) said pesticidal protein comprises the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:43, SEQ ID NO:46, SEQ ID NO:48, SEQ ID NO:50, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, or SEQ ID NO:127; or (b) said pesticidal protein comprises an amino acid sequence having: (i) at least 75% identity to SEQ ID NO:18, SEQ ID NO:20, SEQ ID NO:22, SEQ ID NO:24, SEQ ID NO:26, SEQ ID NO:28, SEQ ID NO:63, SEQ ID NO:65, SEQ ID NO:67, SEQ ID NO:69, SEQ ID NO:75, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, or SEQ ID NO:109; or (ii) at least 80% to SEQ ID NO:111 SEQ ID NO: 113, SEQ ID NO: 115, SEQ ID NO:119, SEQ ID NO:125, or SEQ ID NO:127; or (iii) at least 85% identity to SEQ ID NO:121 or SEQ ID NO:123; or (iv) at least 90% identity to SEQ ID NO:2, SEQ ID NO:4, SEQ ID NO:6, SEQ ID NO:8, SEQ ID NO:10, SEQ ID NO:14, SEQ ID NO:34, SEQ ID NO:43, SEQ ID NO:46, SEQ ID NO:48, SEQ ID NO:50, SEQ ID NO:57, SEQ ID NO:71, SEQ ID NO:73, SEQ ID NO:77, SEQ ID NO:79, SEQ NO:81, or SEQ ID NO:117; or (v) at least 93% identity to SEQ ID NO:12, SEQ ID NO:16, SEQ ID NO:30, and SEQ ID NO:59; or (vi) at least 94% identity to SEQ ID NO:53 and SEQ ID NO:55; or (vii) at least 99% identity to SEQ ID NO:32, SEQ ID NO:61, or SEQ ID NO:83; or (c) said polynucleotide segment hybridizes to a polynucleotide having the nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:44, SEQ ID NO:45, SEQ ID NO:47, SEQ ID NO:49, SEQ ID NO:51, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, or SEQ ID NO:126. In one embodiment of the invention, the method comprises contacting a sample of nucleic acids with a nucleic acid probe that hybridizes under stringent hybridization conditions with genomic DNA from a plant comprising a polynucleotide segment encoding a pesticidal protein or fragment thereof provided herein, and does not hybridize under such hybridization conditions with genomic DNA from an otherwise isogenic plant that does not comprise the segment, wherein the probe is homologous or complementary to SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:44, SEQ ID NO:45, SEQ ID NO:47, SEQ ID NO:49, SEQ ID NO:51, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, OR SEQ ID NO:126, or a sequence that encodes a pesticidal protein comprising an amino acid sequence having: (i) at least 75% identity to SEQ ID NO:18, SEQ ID NO:20, SEQ ID NO:22, SEQ ID NO:24, SEQ ID NO:26, SEQ ID NO:28, SEQ ID NO:63, SEQ ID NO:65, SEQ ID NO:67, SEQ ID NO:69, SEQ ID NO:75, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, or SEQ ID NO:109; or (ii) at least 80% to SEQ ID NO:111 SEQ ID NO: 113, SEQ ID NO:115, SEQ ID NO:119, SEQ ID NO:125, or SEQ ID NO:127; or (iii) at least 85% identity to SEQ ID NO:121 or SEQ ID NO:123; or (iv) at least 90% identity to SEQ ID NO:2, SEQ ID NO:4, SEQ ID NO:6, SEQ ID NO:8, SEQ ID NO:10, SEQ ID NO:14, SEQ ID NO:34, SEQ ID NO:43, SEQ ID NO:46, SEQ ID NO:48, SEQ ID NO:50, SEQ ID NO:57, SEQ ID NO:71, SEQ ID NO:73, SEQ ID NO:77, SEQ ID NO:79, SEQ NO:81, or SEQ ID NO:117; or (v) at least 93% identity to SEQ ID NO:12, SEQ ID NO:16, SEQ ID NO:30, and SEQ ID NO:59; or (vi) at least 94% identity to SEQ ID NO:53 and SEQ ID NO:55; or (vii) at least 99% identity to SEQ ID NO:32, SEQ ID NO:61, or SEQ ID NO:83. The method may further comprise (a) subjecting the sample and probe to stringent hybridization conditions; and (b) detecting hybridization of the probe with DNA of the sample.

Also provided by the invention are methods of detecting the presence of a pesticidal protein or fragment thereof in a sample comprising protein, wherein said pesticidal protein comprises the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:43, SEQ ID NO:46, SEQ ID NO:48, SEQ ID NO:50, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, or SEQ ID NO:127; or said pesticidal protein comprises an amino acid sequence having: (i) at least 75% identity to SEQ ID NO:18, SEQ ID NO:20, SEQ ID NO:22, SEQ ID NO:24, SEQ ID NO:26, SEQ ID NO:28, SEQ ID NO:63, SEQ ID NO:65, SEQ ID NO:67, SEQ ID NO:69, SEQ ID NO:75, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, or SEQ ID NO:109; or (ii) at least 80% to SEQ ID NO:111 SEQ ID NO: 113, SEQ ID NO:115, SEQ ID NO:119, SEQ ID NO:125, or SEQ ID NO:127; or (iii) at least 85% identity to SEQ ID NO:121 or SEQ ID NO:123; or (iv) at least 90% identity to SEQ ID NO:2, SEQ ID NO:4, SEQ ID NO:6, SEQ ID NO:8, SEQ ID NO:10, SEQ ID NO:14, SEQ ID NO:34, SEQ ID NO:43, SEQ ID NO:46, SEQ ID NO:48, SEQ ID NO:50, SEQ ID NO:57, SEQ ID NO:71, SEQ ID NO:73, SEQ ID NO:77, SEQ ID NO:79, SEQ NO:81, or SEQ ID NO:117; or (v) at least 93% identity to SEQ ID NO:12, SEQ ID NO:16, SEQ ID NO:30, and SEQ ID NO:59; or (vi) at least 94% identity to SEQ ID NO:53 and SEQ ID NO:55; or (vii) at least 99% identity to SEQ ID NO:32, SEQ ID NO:61, or SEQ ID NO:83. In one embodiment, the method comprises: (a) contacting a sample with an immunoreactive antibody; and (b) detecting the presence of the protein. In some embodiments the step of detecting comprises an ELISA, or a Western blot.

BRIEF DESCRIPTION OF THE SEQUENCES

SEQ ID NO:1 is a nucleic acid sequence obtained from *Brevibacillus laterosporus* strain DSC005019 encoding a TIC7040 pesticidal protein sequence.

SEQ ID NO:2 is the amino acid sequence of the TIC7040 protein.

SEQ ID NO:3 is a nucleic acid sequence obtained from *Brevibacillus laterosporus* strain DSC005019 encoding a TIC7040HT pesticidal protein sequence.

SEQ ID NO:4 is the amino acid sequence of the TIC7040HT protein.

SEQ ID NO:5 is a nucleic acid sequence encoding a TIC7040_4 pesticidal protein sequence which comprises a C-terminal truncation relative to the TIC7040HT protein.

SEQ ID NO:6 is the amino acid sequence of the TIC7040_4 protein, consisting of amino acids 1 through 671 of TIC7040HT.

SEQ ID NO:7 is a nucleic acid sequence encoding a TIC7040_5 pesticidal protein sequence which comprises an N-terminal and C-terminal truncation relative to the TIC7040HT protein.

SEQ ID NO:8 is the amino acid sequence of the TIC7040_5 protein, comprising amino acids 13 through 611 of TIC7040HT.

SEQ ID NO:9 is a nucleic acid sequence encoding a TIC7040_6 pesticidal protein sequence which comprises an N-terminal and C-terminal truncation relative to the TIC7040HT protein.

SEQ ID NO:10 is the amino acid sequence of the TIC7040_6 protein, comprising amino acids 13 through 671 of TIC7040HT.

SEQ ID NO:11 is a nucleic acid sequence obtained from *Brevibacillus laterosporus* strain DSC005973 encoding a TIC7042 pesticidal protein sequence.

SEQ ID NO:12 is the amino acid sequence of the TIC7042 protein.

SEQ ID NO:13 is a nucleic acid sequence obtained from *Brevibacillus laterosporus* strain DSC006713 encoding a TIC7381 pesticidal protein sequence.

SEQ ID NO:14 is the amino acid sequence of the TIC7381 protein.

SEQ ID NO:15 is a nucleic acid sequence obtained from *Brevibacillus laterosporus* strain DSC007657 encoding a TIC7382 pesticidal protein sequence.

SEQ ID NO:16 is the amino acid sequence of the TIC7382 protein.

SEQ ID NO:17 is a nucleic acid sequence obtained from *Brevibacillus laterosporus* strain DSC008106 encoding a TIC7383 pesticidal protein sequence.

SEQ ID NO:18 is the amino acid sequence of the TIC7383 protein.

SEQ ID NO:19 is a nucleic acid sequence encoding a TIC7383_2 protein which comprises an N-terminal truncation relative to the TIC7383 protein.

SEQ ID NO:20 is the amino acid sequence of the TIC7383_2 protein, comprising amino acids 15 through 1256 of TIC7383.

SEQ ID NO:21 is a nucleic acid sequence encoding a TIC7383_3 protein which comprises a C-terminal truncation relative to the TIC7383 protein.

SEQ ID NO:22 is the amino acid sequence of the TIC7383_3 protein and consists of amino acids 1 through 659 of TIC7383.

SEQ ID NO:23 is a nucleic acid sequence encoding a TIC7383_4 protein which comprises a C-terminal truncation relative to the TIC7383 protein.

SEQ ID NO:24 is the amino acid sequence of the TIC7383_4 protein and consists of amino acids 1 through 679 of TIC7383.

SEQ ID NO:25 is a nucleic acid sequence encoding a TIC7383_5 protein which comprises an N-terminal and C-terminal truncation relative to the TIC7383 protein.

SEQ ID NO:26 is the amino acid sequence of the TIC7383_5 protein and comprises amino acids 15 through 659 of TIC7383.

SEQ ID NO:27 is a nucleic acid sequence encoding a TIC7383_6 protein which comprises an N-terminal and C-terminal truncation relative to the TIC7383 protein.

SEQ ID NO:28 is the amino acid sequence of the TIC7383_6 protein, comprising amino acids 15 through 679 of TIC7383.

SEQ ID NO:29 is a nucleic acid sequence obtained from *Brevibacillus laterosporus* strain DSC007651 encoding a TIC7386 pesticidal protein sequence.

SEQ ID NO:30 is the amino acid sequence of the TIC7386 protein.

SEQ ID NO:31 is a nucleic acid sequence obtained from *Brevibacillus laterosporus* strain DSC007962 encoding a TIC7388 pesticidal protein sequence.

SEQ ID NO:32 is the amino acid sequence of the TIC7388 protein.

SEQ ID NO:33 is a nucleic acid sequence obtained from *Brevibacillus laterosporus* strain DSC006878 encoding a TIC7389 pesticidal protein sequence.

SEQ ID NO:34 is the amino acid sequence of the TIC7389 protein.

SEQ ID NO:35 is a synthetic coding sequence, CR-BREla.TIC7040.nno_Mc:1, encoding a TIC7040 pesticidal protein used for expression in plant cells.

SEQ ID NO:36 is a synthetic coding sequence, CR-BREla.TIC7040_10.nno_Mc:1, encoding a TIC7040HT pesticidal protein used for expression in plant cells.

SEQ ID NO:37 is a synthetic coding sequence, CR-BREla.TIC7040_10.nno_Mc:3, encoding a TIC7040HT pesticidal protein used for expression in plant cells.

SEQ ID NO:38 is a synthetic coding sequence, CR-BREla.TIC7040_10.nno_Mc:4, encoding a TIC7040HT pesticidal protein used for expression in plant cells.

SEQ ID NO:39 is a synthetic coding sequence, CR-BREla.TIC7040_10.nno_Mc:5, encoding a TIC7040HT pesticidal protein used for expression in plant cells.

SEQ ID NO:40 is a synthetic coding sequence, CR-BREla.TIC7040_10.nno_Mc:6, encoding a TIC7040HT pesticidal protein used for expression in plant cells.

SEQ ID NO:41 is a synthetic coding sequence, CR-BREla.TIC7040_10.nno_Mc:7, encoding a TIC7040HT pesticidal protein used for expression in plant cells.

SEQ ID NO:42 is a synthetic coding sequence, CR-BREla.TIC7040_1.nno_Mc:1, encoding a protein having an N-terminal and C-terminal truncation relative to the TIC7040HT protein used for expression in plant cells.

SEQ ID NO:43 is the amino acid sequence of the CR-BREla.TIC7040_1.nno_Mc:1 protein, comprising amino acids 15 through 651 of TIC7040HT.

SEQ ID NO: 44 is a synthetic coding sequence, CR-BREla.TIC7040_2.nno_Mc:1, encoding a TIC7040_6 (SEQ ID NO:10) pesticidal protein sequence which comprises an N-terminal and C-terminal truncation relative to the TIC7040HT protein used for expression in plant cells.

SEQ ID NO:45 is a synthetic coding sequence, CR-BREla.TIC7040_11.nno_Mc:1, encoding a protein having an N-terminal and C-terminal truncation relative to the TIC7040HT protein used for expression in plant cells.

SEQ ID NO:46 is the amino acid sequence of the CR-BREla.TIC7040_11.nno_Mc:1 protein, comprising amino acids 14 through 671 of TIC7040HT.

SEQ ID NO:47 is a synthetic coding sequence, CR-BREla.TIC7040_12.nno_Mc:2, encoding a protein having a C-terminal truncation relative to the TIC7040HT protein used for expression in plant cells.

SEQ ID NO:48 is the amino acid sequence of the CR-BREla.TIC7040_12.nno_Mc:2 protein, consisting of amino acids 1 through 660 of TIC7040HT.

SEQ ID NO:49 is a synthetic coding sequence, CR-BREla.TIC7040_13.nno_Mc:1, which encodes a protein having a C-terminal truncation relative to the TIC7040HT protein used for expression in plant cells.

SEQ ID NO:50 is the amino acid sequence of the CR-BREla.TIC7040_13.nno_Mc:1 protein, consisting of amino acids 1 through 627 of TIC7040HT.

SEQ ID NO:51 is a synthetic coding sequence, CR-BREla.TIC7042.nno_Mc:1, which encodes a TIC7042 protein (SEQ ID NO:12) used for expression in plant cells.

SEQ ID NO:52 is a synthetic coding sequence, CR-BREla.TIC7042_1.nno_Mc:1, which encodes a protein having an N-terminal and C-terminal truncation relative to the TIC7042 protein used for expression in plant cells.

SEQ ID NO:53 is the amino acid sequence of the CR-BREla.TIC7042_1.nno_Mc:1 protein, comprising amino acids 11 through 646 of TIC7042.

SEQ ID NO:54 is a synthetic coding sequence, CR-BREla.TIC7042_2.nno_Mc:1, which encodes a protein having an N-terminal and C-terminal truncation relative to the TIC7042 protein used for expression in plant cells.

SEQ ID NO:55 is the amino acid sequence of the CR-BREla.TIC7042_2.nno_Mc:1 protein, comprising amino acids 11 through 665 of TIC7042.

SEQ ID NO:56 is a synthetic coding sequence, CR-BREla.TIC7381_1.nno_Mc:1, which encodes a TIC7381 protein wherein an additional alanine codon is inserted immediately following the initiating methionine codon used for expression in plant cells.

SEQ ID NO:57 is the amino acid sequence of CR-BREla.TIC7381_1.nno_Mc:1, wherein an additional alanine amino acid is inserted immediately following the initiating methionine relative to the TIC7381 protein sequence.

SEQ ID NO:58 is a synthetic coding sequence used for expression in plant cells, CR-BREla.TIC7382_1.nno_Mc:1, which encodes a TIC7382 protein wherein an additional alanine codon is inserted immediately following the initiating methionine codon.

SEQ ID NO:59 is the amino acid sequence of CR-BREla.TIC7382_1.nno_Mc:1, wherein an additional alanine amino acid is inserted immediately following the initiating methionine relative to the TIC7381 protein sequence.

SEQ ID NO:60 is a synthetic coding sequence used for expression in plant cells, CR-BREla.TIC7382_2.nno_Mc:1, which encodes a CR-BREla.TIC7382_2.nno_Mc:1 protein comprising a C-terminal truncation relative to the TIC7382 protein and wherein an additional alanine codon is inserted immediately following the initiating methionine codon.

SEQ ID NO:61 is the amino acid sequence of CR-BREla.TIC7382_2.nno_Mc:1 comprising a C-terminal deletion and wherein an additional alanine amino acid is inserted immediately following the initiating methionine relative to the TIC7382 protein sequence, and comprises amino acids 1 through 659 of TIC7382.

SEQ ID NO:62 is a synthetic coding sequence, CR-BREla.TIC7383_1.nno_Mc:1, which encodes a TIC7383 protein wherein an additional alanine codon is inserted immediately following the initiating methionine codon used for expression in plant cells.

SEQ ID NO:63 is the amino acid sequence of CR-BREla.TIC7383_1.nno_Mc:1, wherein an additional alanine amino acid is inserted immediately following the initiating methionine relative to the TIC7383 protein sequence.

SEQ ID NO:64 is a synthetic coding sequence, CR-BREla.TIC7383_7.nno_Mc:1, which encodes a CR-BREla.TIC7383_7.nno_Mc:1 protein comprising an N-terminal and C-terminal truncation relative to the TIC7383 protein and wherein an additional alanine codon is inserted immediately following the initiating methionine codon and which is used for expression in plant cells.

SEQ ID NO:65 is the amino acid sequence of CR-BREla.TIC7383_7.nno_Mc:1 comprising an N-terminal and C-terminal deletion and wherein an additional alanine amino acid is inserted immediately following the initiating methionine relative to the TIC7383 protein sequence, and comprises amino acids 54 through 668 of TIC7383.

SEQ ID NO:66 is a synthetic coding sequence, CR-BREla.TIC7383_8.nno_Mc:1, which encodes a CR-BREla.TIC7383_8.nno_Mc:1 protein comprising a C-terminal truncation relative to the TIC7383 protein, wherein an additional alanine codon is inserted immediately following the initiating methionine codon and which is used for expression in plant cells.

SEQ ID NO:67 is the amino acid sequence of CR-BREla.TIC7383_8.nno_Mc:1 comprising a C-terminal deletion, and wherein an additional alanine amino acid is inserted immediately following the initiating methionine relative to the TIC7383 protein sequence, and comprises amino acids 1 through 661 of TIC7383.

SEQ ID NO:68 is a synthetic coding sequence, CR-BREla.TIC7383_9.nno_Mc:1, which encodes a CR-BREla.TIC7383_9.nno_Mc:1 protein comprising a C-terminal truncation relative to the TIC7383 protein, wherein an additional alanine codon is inserted immediately following the initiating methionine codon, and which is used for expression in plant cells.

SEQ ID NO:69 is the amino acid sequence of CR-BREla.TIC7383_9.nno_Mc:1, comprising a C-terminal deletion wherein an additional alanine amino acid is inserted immediately following the initiating methionine relative to the TIC7383 protein sequence, and comprises amino acids 1 through 668 of TIC7383.

SEQ ID NO:70 is a coding sequence encoding the tryptic core (TIC7040HT_Tryp) of the TIC7040HT protein as determined by mass spectrometry.

SEQ ID NO:71 is the amino acid sequence of the tryptic core (TIC7040HT_Tryp) of the TIC7040HT protein as determined by mass spectrometry, and comprises amino acids 43 through 624 of TIC7040HT.

SEQ ID NO:72 is a coding sequence encoding the chymotryptic core (TIC7040HT_Chymo) of the TIC7040HT protein as determined by mass spectrometry.

SEQ ID NO:73 is the amino acid sequence of the chymotryptic core (TIC7040HT_Chymo) of the TIC7040HT protein as determined by mass spectrometry, and comprises amino acids 45 through 641 of TIC7040HT.

SEQ ID NO:74 is a coding sequence encoding the tryptic core (TIC7383_Tryp) of the TIC7383 protein as determined by mass spectrometry.

SEQ ID NO:75 is the amino acid sequence of the tryptic core (TIC7383_Tryp) of the TIC7383 protein as determined by mass spectrometry, and comprises amino acids 55 through 668 of TIC7383.

SEQ ID NO:76 is a synthetic coding sequence, CR-BREla.TIC7040_14.nno_Mc:1, encoding a CR-BREla.TIC7040_14.nno_Mc:1 protein having an N-terminal and C-terminal truncation relative to the TIC7040HT protein, wherein an additional alanine codon is inserted immediately following the initiating methionine codon, and which is used for expression in plant cells.

SEQ ID NO:77 is the amino acid sequence of the CR-BREla.TIC7040_14.nno_Mc:1 protein, wherein an additional alanine amino acid is inserted immediately following the initiating methionine, and comprises amino acids 52 through 660 of TIC7040HT.

SEQ ID NO:78 is a synthetic coding sequence, CR-BREla.TIC7381_2.nno_Mc:1, encoding a CR-BREla.TIC7381_2.nno_Mc:1 protein having a C-terminal truncation relative to the TIC7381 protein, wherein an additional alanine codon is inserted immediately following the initiating methionine codon, and which is used for expression in plant cells.

SEQ ID NO:79 is the amino acid sequence of the CR-BREla.TIC7381_2.nno_Mc:1 protein, wherein an additional alanine amino acid is inserted immediately following the initiating methionine, and comprises amino acids 1 through 658 of TIC7381.

SEQ ID NO:80 is a synthetic coding sequence, CR-BREla.TIC7381_3.nno_Mc:1, encoding a CR-BREla.TIC7381_3.nno_Mc:1 protein having an N-terminal and C-terminal truncation relative to the TIC7381 protein, wherein an additional alanine codon is inserted immediately following the initiating methionine codon, and which is used for expression in plant cells.

SEQ ID NO:81 is the amino acid sequence of the CR-BREla.TIC7381_3.nno_Mc:1 protein, wherein an additional alanine amino acid is inserted immediately following the initiating methionine, and comprises amino acids 50 through 658 of TICTIC7381.

SEQ ID NO:82 is a synthetic coding sequence, CR-BREla.TIC7382_3.nno_Mc:1, encoding a CR-BREla.TIC7382_3.nno_Mc:1 protein having an N-terminal and C-terminal truncation relative to the TIC7382 protein, wherein an additional alanine codon is inserted immediately following the initiating methionine codon, and which is used for expression in plant cells.

SEQ ID NO:83 is the amino acid sequence of the CR-BREla.TIC7382_3.nno_Mc:1 protein, wherein an additional alanine amino acid is inserted immediately following the initiating methionine, and comprises amino acids 52 through 659 of TIC7382.

SEQ ID NO:84 is a synthetic coding sequence, CR-BREla.TIC7383_19.nno_Mc:1, encoding a CR-BREla.TIC7383_19.nno_Mc:1 protein having an N-terminal and C-terminal truncation relative to the TIC7383 protein, and which is used for expression in plant cells.

SEQ ID NO:85 is the amino acid sequence of the CR-BREla.TIC7383_19.nno_Mc:1 protein, and comprises amino acids 15 through 668 of TIC7383.

SEQ ID NO:86 is a synthetic coding sequence, CR-BREla.TIC7383_20.nno_Mc:1, encoding a CR-BREla.TIC7383_20.nno_Mc:1 protein having an N-terminal and C-terminal truncation relative to the TIC7383 protein, and which is used for expression in plant cells.

SEQ ID NO:87 is the amino acid sequence of the CR-BREla.TIC7383_20.nno_Mc:1 protein, and comprises amino acids 15 through 661 of TIC7383.

SEQ ID NO:88 is a synthetic coding sequence, CR-BREla.TIC7383_21.nno_Mc:1, encoding a CR-BREla.TIC7383_21.nno_Mc:1 protein having an N-terminal and C-terminal truncation relative to the TIC7383 protein, wherein an additional alanine codon is inserted immediately following the initiating methionine codon, and which is used for expression in plant cells.

SEQ ID NO:89 is the amino acid sequence of the CR-BREla.TIC7383_21.nno_Mc:1 protein, wherein an additional alanine amino acid is inserted immediately following the initiating methionine, and comprises amino acids 54 through 661 of TIC7383.

SEQ ID NO:90 is a synthetic coding sequence, CR-BREla.TIC7383_22.nno_Mc:1, encoding a CR-BREla.TIC7383_22.nno_Mc:1 protein having an N-terminal and C-terminal truncation relative to the TIC7383 protein, and which is used for expression in plant cells.

SEQ ID NO:91 is the amino acid sequence of the CR-BREla.TIC7383_22.nno_Mc:1 protein, and comprises amino acids 54 through 668 of TIC7383.

SEQ ID NO:92 is a synthetic coding sequence, CR-BREla.TIC7383_23.nno_Mc:1, encoding a CR-BREla.TIC7383_23.nno_Mc:1 protein having an N-terminal and C-terminal truncation relative to the TIC7383 protein, and which is used for expression in plant cells.

SEQ ID NO:93 is the amino acid sequence of the CR-BREla.TIC7383_23.nno_Mc:1 protein, and comprises amino acids 54 through 661 of TIC7383.

SEQ ID NO:94 is a synthetic coding sequence, CR-BREla.TIC7383_24.nno_Mc:2, encoding a CR-BREla.TIC7383_24.nno_Mc:2 protein having an N-terminal and C-terminal truncation relative to the TIC7383 protein, and which is used for expression in plant cells.

SEQ ID NO:95 is the amino acid sequence of the CR-BREla.TIC7383_24.nno_Mc:2 protein, and comprises amino acids 73 through 661 of TIC7383.

SEQ ID NO:96 is a synthetic coding sequence, CR-BREla.TIC7383_25.nno_Mc:3, encoding a CR-BREla.TIC7383_25.nno_Mc:3 protein having an N-terminal and C-terminal truncation relative to the TIC7383 protein, and which is used for expression in plant cells.

SEQ ID NO:97 is the amino acid sequence of the CR-BREla.TIC7383_25.nno_Mc:3 protein, and comprises amino acids 94 through 661 of TIC7383.

SEQ ID NO:98 is a synthetic coding sequence, CR-BREla.TIC7383_26.nno_Mc:1, encoding a CR-BREla.TIC7383_26.nno_Mc:1 protein having an N-terminal and C-terminal truncation relative to the TIC7383 protein, and which is used for expression in plant cells.

SEQ ID NO:99 is the amino acid sequence of the CR-BREla.TIC7383_26.nno_Mc:1 protein, and comprises amino acids 114 through 661 of TIC7383.

SEQ ID NO:100 is a synthetic coding sequence, CR-BREla.TIC7383_27.nno_Mc:1, encoding a CR-BREla.TIC7383_27.nno_Mc:1 protein having an N-terminal and C-terminal truncation relative to the TIC7383 protein, wherein an additional alanine codon is inserted immediately following the initiating methionine codon, and which is used for expression in plant cells.

SEQ ID NO:101 is the amino acid sequence of the CR-BREla.TIC7383_27.nno_Mc:1 protein, wherein an additional alanine amino acid is inserted immediately following the initiating methionine, and comprises amino acids 54 through 658 of TIC7383.

SEQ ID NO:102 is a synthetic coding sequence, CR-BREla.TIC7383_28.nno_Mc:1, encoding a CR-BREla.TIC7383_28.nno_Mc:1 protein having an N-terminal and C-terminal truncation relative to the TIC7383 protein, and which is used for expression in plant cells.

SEQ ID NO:103 is the amino acid sequence of the CR-BREla.TIC7383_28.nno_Mc:1 protein, and comprises amino acids 15 through 658 of TIC7383.

SEQ ID NO:104 is a synthetic coding sequence, CR-BREla.TIC7383_29.nno_Mc:1, encoding a CR-BREla.TIC7383_29.nno_Mc:1 protein having a C-terminal truncation relative to the TIC7383 protein, wherein an additional alanine codon is inserted immediately following the initiating methionine codon, and which is used for expression in plant cells.

SEQ ID NO:105 is the amino acid sequence of the CR-BREla.TIC7383_29.nno_Mc:1 protein, wherein an additional alanine amino acid is inserted immediately following the initiating methionine, and comprises amino acids 1 through 963 of TIC7383.

SEQ ID NO:106 is a synthetic coding sequence, CR-BREla.TIC7383_30.nno_Mc:1, encoding a CR-BREla.TIC7383_30.nno_Mc:1 protein, wherein an additional alanine codon is inserted immediately following the initiating methionine codon, and comprising mutations to the codons corresponding amino acid positions 964, 966, and 968 relative to TIC7383, and which is used for expression in plant cells.

SEQ ID NO:107 is the amino acid sequence of the CR-BREla.TIC7383_30.nno_Mc:1 protein, wherein an additional alanine amino acid is inserted immediately following the initiating methionine, and comprises the mutations, K964A; R966A; K968A, relative to TIC7383.

SEQ ID NO:108 is a synthetic coding sequence, CR-BREla.TIC7383_31.nno_Mc:1, encoding a CR-BREla.TIC7383_31.nno_Mc:1 protein having a C-terminal truncation relative to the TIC7383 protein, wherein an additional alanine codon is inserted immediately following the initiating methionine codon, and comprising mutations to the codons corresponding amino acid positions 964, 966, and 968 relative to TIC7383, and which is used for expression in plant cells.

SEQ ID NO:109 is the amino acid sequence of the CR-BREla.TIC7383_31.nno_Mc:1 protein, wherein an additional alanine amino acid is inserted immediately following the initiating methionine, and comprising amino acids 1 through 1065, and also comprises the mutations, K964A; R966A; K968A, relative to TIC7383.

SEQ ID NO:110 is a synthetic coding sequence, CR-BREla.TIC7383_32.nno_Mc:1, encoding a CR-BREla.TIC7383_32.nno_Mc:1 protein, wherein an additional alanine codon is inserted immediately following the initiating methionine codon, and comprising a deletion of the codons corresponding amino acid positions 964 through 969 relative to TIC7383, and which is used for expression in plant cells.

SEQ ID NO:111 is the amino acid sequence of the CR-BREla.TIC7383_32.nno_Mc:1 protein, wherein an additional alanine amino acid is inserted immediately following the initiating methionine, and comprising a deletion of amino acids 964 through 969 relative to TIC7383.

SEQ ID NO:112 is a synthetic coding sequence, GOI-TIC10743.nno_Mc:1, encoding a GOI-TIC10743.nno_Mc:1 chimeric protein comprised of domains one and two of TIC7383 and domain three of TIC7042.

SEQ ID NO:113 is the amino acid sequence of the GOI-TIC10743.nno_Mc:1 chimeric protein.

SEQ ID NO:114 is a synthetic coding sequence, GOI-TIC10744.nno_Mc:1, encoding a GOI-TIC10744.nno_Mc:1 chimeric protein comprised of domains one and two of TIC7383 and domain three of TIC7381.

SEQ ID NO:115 is the amino acid sequence of the GOI-TIC10744.nno_Mc:1 chimeric protein.

SEQ ID NO:116 is a synthetic coding sequence, GOI-TIC10745.nno_Mc:1, encoding a GOI-TIC10745.nno_Mc:1 chimeric protein comprised of domains one and two of TIC7383 and domain three of TIC7382.

SEQ ID NO:117 is the amino acid sequence of the GOI-TIC10745.nno_Mc:1 chimeric protein.

SEQ ID NO:118 is a synthetic coding sequence, GOI-TIC10746.nno_Mc:1, encoding a GOI-TIC10746.nno_Mc:1 chimeric protein comprised of domains one and two of TIC7382 and domain three of TIC7383.

SEQ ID NO:119 is the amino acid sequence of the GOI-TIC10746.nno_Mc:1 chimeric protein.

SEQ ID NO:120 is a synthetic coding sequence, GOI-TIC10747.nno_Mc:1, encoding a GOI-TIC10747.nno_Mc:1 chimeric protein comprised of domains one and two of TIC7381 and domain three of TIC7383.

SEQ ID NO:121 is the amino acid sequence of the GOI-TIC10747.nno_Mc:1 chimeric protein.

SEQ ID NO:122 is a synthetic coding sequence, GOI-TIC10748.nno_Mc:1, encoding a GOI-TIC10748.nno_Mc:1 chimeric protein comprised of domains one and two of TIC7042 and domain three of TIC7383.

SEQ ID NO:123 is the amino acid sequence of the GOI-TIC10748.nno_Mc:1 chimeric protein.

SEQ ID NO:124 is a synthetic coding sequence, TIC10764NTermExt1, encoding a TIC10764NTermExt1 chimeric protein comprised of domains one and two of TIC7382 and domain three of TIC7383 which also includes the N-terminal extension peptide derived from TIC7382. The N-terminal extension of TIC7382 comprises amino acids 1-51 of the TIC7382 toxin protein and is encoded by the first 153 nucleotides of the TIC7382 coding sequence.

SEQ ID NO:125 is the amino acid sequence of the TIC10764NTermExt1 chimeric protein.

SEQ ID NO:126 is a synthetic coding sequence, TIC10764NTermExt2, encoding a TIC10764NTermExt2 chimeric protein comprised of domains one and two of TIC7382 and domain three of TIC7383 which also includes the N-terminal extension peptide derived from TIC7383. The N-terminal extension of TIC7383 comprises amino acids 1-53 of the TIC7383 toxin protein and is encoded by the first 159 nucleotides of the TIC7383 coding sequence.

SEQ ID NO:127 is the amino acid sequence of the TIC10764NTermExt2 chimeric protein.

DETAILED DESCRIPTION OF THE INVENTION

The problem in the art of agricultural pest control can be characterized as a need for new toxin proteins that are efficacious against target pests, exhibit broad spectrum toxicity against target pest species, are capable of being expressed in plants without causing undesirable agronomic issues, and provide an alternative mode of action compared to current toxins that are used commercially in plants.

Novel insecticidal protein classes, exemplified by TIC7040, TIC7040HT, TIC7042, TIC7381, TIC7382, TIC7383, TIC7386, TIC7388, and TIC7389 and related family members that provide resistance against Coleopteran and Lepidopteran insect pests, and more particularly against corn rootworm pest species, are disclosed. Also disclosed are synthetic coding sequences designed for expression in a plant cell that encode TIC7040, TIC7040HT, TIC7042, TIC7381, TIC7382, and TIC7383 related family members, along with N-terminal and C-terminal truncation variants and chimeras of proteins in TIC7040 toxin class. Further disclosed are recombinant nucleic acid molecules comprising a promoter in operable linkage to a coding sequence encoding a TIC7040, TIC7040HT, TIC7042, TIC7381, TIC7382, TIC7383, TIC7386, TIC7388, or TIC7389 toxin protein, or related family members, or fragments thereof.

Reference in this application to TIC7040, "TIC7040 protein", "TIC7040 protein toxin", "TIC7040 toxin protein", "TIC7040 pesticidal protein", "TIC7040-related toxins", or "TIC7040-related toxin protein", and the like, refer to any novel pesticidal protein or insect inhibitory protein, that comprises, that consists of, that is substantially homologous to, that is similar to, or that is derived from any pesticidal protein or insect inhibitory protein sequence of TIC7040 (SEQ ID NO:2) and pesticidal or insect inhibitory segments thereof, or combinations thereof, that confer activity against Coleopteran pests or Lepidopteran pests, including any protein exhibiting pesticidal or insect inhibitory activity if alignment of such protein with TIC7040 results in amino acid sequence identity of any fraction percentage from about 90 to about 100 percent.

Reference in this application to TIC7040HT, "TIC7040HT protein", "TIC7040HT protein toxin", "TIC7040HT toxin protein", "TIC7040HT pesticidal protein", "TIC7040HT-related toxins", or "TIC7040HT-related toxin protein", and the like, refer to any novel pesticidal protein or insect inhibitory protein, that comprises, that consists of, that is substantially homologous to, that is similar to, or that is derived from any pesticidal protein or insect inhibitory protein sequence of TIC7040HT (SEQ ID NO:4) and pesticidal or insect inhibitory segments thereof, or combinations thereof, that confer activity against Coleopteran pests or Lepidopteran pests, including any protein exhibiting pesticidal or insect inhibitory activity if alignment of such protein with TIC7040HT results in amino acid sequence identity of any fraction percentage from about 90 to about 100 percent.

Reference in this application to TIC7042, "TIC7042 protein", "TIC7042 protein toxin", "TIC7042 toxin protein", "TIC7042 pesticidal protein", "TIC7042-related toxins", or "TIC7042-related toxin protein", and the like, refer to any novel pesticidal protein or insect inhibitory protein, that comprises, that consists of, that is substantially homologous to, that is similar to, or that is derived from any pesticidal protein or insect inhibitory protein sequence of TIC7042 (SEQ ID NO:12) and pesticidal or insect inhibitory segments thereof, or combinations thereof, that confer activity against Coleopteran pests or Lepidopteran pests, including any protein exhibiting pesticidal or insect inhibitory activity if alignment of such protein with TIC7042 results in amino acid sequence identity of any fraction percentage from about 93 to about 100 percent.

Reference in this application to TIC7381, "TIC7381 protein", "TIC7381 protein toxin", "TIC7381 toxin protein", "TIC7381 pesticidal protein", "TIC7381-related toxins", or "TIC7381-related toxin protein", and the like, refer to any novel pesticidal protein or insect inhibitory protein, that comprises, that consists of, that is substantially homologous to, that is similar to, or that is derived from any pesticidal protein or insect inhibitory protein sequence of TIC7381 (SEQ ID NO:14) and pesticidal or insect inhibitory segments thereof, or combinations thereof, that confer activity against Coleopteran pests or Lepidopteran pests, including any protein exhibiting pesticidal or insect inhibitory activity if alignment of such protein with TIC7381 results in amino acid sequence identity of any fraction percentage from about 90 to about 100 percent.

Reference in this application to TIC7382, "TIC7382 protein", "TIC7382 protein toxin", "TIC7382 toxin protein", "TIC7382 pesticidal protein", "TIC7382-related toxins", or "TIC7382-related toxin protein", and the like, refer to any novel pesticidal protein or insect inhibitory protein, that comprises, that consists of, that is substantially homologous to, that is similar to, or that is derived from any pesticidal protein or insect inhibitory protein sequence of TIC7382 (SEQ ID NO:16) and pesticidal or insect inhibitory segments thereof, or combinations thereof, that confer activity against Coleopteran pests or Lepidopteran pests, including any protein exhibiting pesticidal or insect inhibitory activity if alignment of such protein with TIC7382 results in amino acid sequence identity of any fraction percentage from about 93 to about 100 percent.

Reference in this application to TIC7383, "TIC7383 protein", "TIC7383 protein toxin", "TIC7383 toxin protein", "TIC7383 pesticidal protein", "TIC7383-related toxins", or "TIC7383-related toxin protein", and the like, refer to any novel pesticidal protein or insect inhibitory protein, that comprises, that consists of, that is substantially homologous to, that is similar to, or that is derived from any pesticidal protein or insect inhibitory protein sequence of TIC7383 (SEQ ID NO:18) and pesticidal or insect inhibitory segments thereof, or combinations thereof, that confer activity against Coleopteran pests or Lepidopteran pests, including any protein exhibiting pesticidal or insect inhibitory activity if alignment of such protein with TIC7383 results in amino acid sequence identity of any fraction percentage from about 75 to about 100 percent.

Reference in this application to TIC7386, "TIC7386 protein", "TIC7386 protein toxin", "TIC7386 toxin protein", "TIC7386 pesticidal protein", "TIC7386-related toxins", or "TIC7386-related toxin protein", and the like, refer to any novel pesticidal protein or insect inhibitory protein, that comprises, that consists of, that is substantially homologous to, that is similar to, or that is derived from any pesticidal protein or insect inhibitory protein sequence of TIC7386 (SEQ ID NO:30) and pesticidal or insect inhibitory segments thereof, or combinations thereof, that confer activity against Coleopteran pests or Lepidopteran pests, including any protein exhibiting pesticidal or insect inhibitory activity if alignment of such protein with TIC7386 results in amino acid sequence identity of any fraction percentage from about 75 to about 100 percent.

Reference in this application to TIC7388, "TIC7388 protein", "TIC7388 protein toxin", "TIC7388 toxin protein", "TIC7388 pesticidal protein", "TIC7388-related toxins", or "TIC7388-related toxin protein", and the like, refer to any novel pesticidal protein or insect inhibitory protein, that comprises, that consists of, that is substantially homologous to, that is similar to, or that is derived from any pesticidal protein or insect inhibitory protein sequence of TIC7388 (SEQ ID NO:32) and pesticidal or insect inhibitory segments thereof, or combinations thereof, that confer activity against Coleopteran pests or Lepidopteran pests, including any protein exhibiting pesticidal or insect inhibitory activity if alignment of such protein with TIC7388 results in amino acid sequence identity of any fraction percentage from about 99 to about 100 percent.

Reference in this application to TIC7389, "TIC7389 protein", "TIC7389 protein toxin", "TIC7389 toxin protein", "TIC7389 pesticidal protein", "TIC7389-related toxins", or "TIC7389-related toxin protein", and the like, refer to any novel pesticidal protein or insect inhibitory protein, that comprises, that consists of, that is substantially homologous to, that is similar to, or that is derived from any pesticidal protein or insect inhibitory protein sequence of TIC7389 (SEQ ID NO:34) and pesticidal or insect inhibitory segments thereof, or combinations thereof, that confer activity against Coleopteran pests or Lepidopteran pests, including any protein exhibiting pesticidal or insect inhibitory activity if alignment of such protein with TIC7389 results in amino acid sequence identity of any fraction percentage from about 90 to about 100 percent.

The term "segment" or "fragment" is used in this application to describe consecutive amino acid or nucleic acid sequences that are shorter than the complete amino acid or nucleic acid sequence describing a TIC7040, TIC7040HT, TIC7042, TIC7381, TIC7382, TIC7383, TIC7386, TIC7388, or TIC7389 protein or related family member insecticidal protein. In specific embodiments, fragments of a TIC7040, TIC7040HT, TIC7042, TIC7381, TIC7382, TIC7383, TIC7386, TIC7388, or TIC7389 protein are provided comprising at least about 50, at least about 75, at least about 95, at least about 100, at least about 125, at least about 150, at least about 175, at least about 200, at least about 225, at least about 250, at least about 275, at least about 300, at least about 500, at least about 600, at least about 700, at least about 750, at least about 800, at least about 850, at least about 900, at least about 950, at least about 1000, at least about 1050, at least about 1100, at least about 1150, at least about 1200, at least about 1250, at least about 1300, or at least about 1350 contiguous amino acids, or longer, of a protein having insecticidal activity as disclosed herein. In certain embodiments, the invention provides fragments of a protein provided herein, having the activity of the full length sequence. Methods for producing such fragments from a starting molecule are well known in the art.

A segment or fragment exhibiting insect inhibitory activity is also disclosed in this application if alignment of such segment or fragment, with the corresponding section of the TIC7040, TIC7040HT, TIC7042, TIC7381, TIC7382, TIC7383, TIC7386, TIC7388, or TIC7389 protein set forth in SEQ ID NOs:2, 4, 12, 14, 16, 18, 20, 30, 32, and 34, results in amino acid sequence identity of any fraction percentage from about 75 to about 100 percent between the segment or fragment and the corresponding section of the TIC7383 and TIC7386 proteins; or respectively results in amino acid sequence identity of any fraction percentage from about 90 to about 100 percent between the segment or fragment and the corresponding section of the TIC7040, TIC7040HT, TIC7381, and TIC7389 proteins; or respectively results in amino acid sequence identity of any fraction percentage from about 93 to about 100 percent between the segment or fragment and the corresponding section of the TIC7042 and TIC7382 proteins; or respectively results in amino acid sequence identity of any fraction percentage from about 99 to about 100 percent between the segment or fragment and the corresponding section of the TIC7388 protein.

Reference in this application to the terms "active" or "activity", "pesticidal activity" or "pesticidal" or "insecticidal activity", "insect inhibitory" or "insecticidal" refer to efficacy of a toxic agent, such as a protein toxin, in inhibiting (inhibiting growth, feeding, fecundity, or viability), suppressing (suppressing growth, feeding, fecundity, or viability), controlling (controlling the pest infestation, controlling the pest feeding activities on a particular crop containing an effective amount of the TIC7040, TIC7040HT, TIC7042, TIC7381, TIC7382, TIC7383, TIC7386, TIC7388, or TIC7389 protein or related family member insecticidal protein) or killing (causing the morbidity, mortality, or reduced fecundity of) a pest. These terms are intended to include the result of providing a pesticidally effective amount of a toxic protein to a pest where the exposure of the pest to the toxic protein results in morbidity, mortality, reduced fecundity, or stunting. These terms also include repulsion of the pest from the plant, a tissue of the plant, a plant part, seed, plant cells, or from the particular geographic location where the plant may be growing, as a result of providing a pesticidally effective amount of the toxic protein in or on the plant. In general, pesticidal activity refers to the ability of a toxic protein to be effective in inhibiting the growth, development, viability, feeding behavior, mating behavior, fecundity, or any measurable decrease in the adverse effects caused by an insect feeding on this protein, protein fragment, protein segment or polynucleotide of a particular target pest, including but not limited to insects of the order Lepidoptera, Coleoptera or Hemiptera. The toxic protein can be produced by the plant or can be applied to the plant or to the environment within the location where the plant is located. The terms "bioactivity", "effective", "efficacious" or variations thereof are also terms interchangeably utilized in this application to describe the effects of proteins of the present invention on target insect pests.

A pesticidally effective amount of a toxic agent, when provided in the diet of a target pest, exhibits pesticidal activity when the toxic agent contacts the pest. A toxic agent can be a pesticidal protein or one or more chemical agents known in the art. Pesticidal or insecticidal chemical agents and pesticidal or insecticidal protein agents can be used alone or in combinations with each other.

Chemical agents include, but are not limited to, dsRNA molecules targeting specific genes for suppression in a target pest, organochlorides, organophosphates, carbamates, pyrethroids, neonicotinoids, and ryanoids. Pesticidal or insecticidal protein agents include the protein toxins set forth in this application, as well as other proteinaceous toxic agents including those that target Lepidopteran and Coleopteran pest species, as well as protein toxins that are used to control other plant pests such as Cry proteins available in the art for use in controlling Homopteran or Hemipteran species.

It is intended that reference to a pest, particularly a pest of a crop plant, means insect pests of crop plants, particularly those that are controlled by a TIC7040, TIC7040HT, TIC7042, TIC7381, TIC7382, TIC7383, TIC7386, TIC7388, or TIC7389 protein or related family member insecticidal protein. Reference to a pest can also include Homopteran and Hemipteran insect pests of plants, as well as nematodes and fungi when toxic agents targeting these pests are co-localized or present together with a TIC7040, TIC7040HT, TIC7042, TIC7381, TIC7382, TIC7383, TIC7388, TIC7389 proteins or related family member insecticidal protein, or a protein that is about 75 to about 100 percent identical to TIC7383 and TIC7386; or a protein that is about 90 to about 100 percent identical to TIC7040, TIC7040HT, TIC7381, and TIC7389; or a protein that is about 93 to about 100 percent identical to TIC7042, TIC7386, and TIC7382; or a protein that is about 99 to about 100 percent identical to TIC7388.

The TIC7040, TIC7040HT, TIC7042, TIC7381, TIC7382, TIC7383, TIC7386, TIC7388, TIC7389 and related family member insecticidal proteins exhibit insecticidal activity towards insect pests from the Coleopteran and Lepidopteran insect species, including adults, pupae, larvae, and neonates.

The insects of the order Lepidoptera include, but are not limited to, armyworms, cutworms, loopers, and heliothines in the Family Noctuidae, e.g., fall armyworm (*Spodoptera frugiperda*), Beet armyworm (*Spodoptera exigua*), Black armyworm (*Spodoptera exempta*), Bertha armyworm (*Mamestra configurata*), Southern armyworm (*Spodoptera eridania*), Black cutworm (*Agrotis ipsilon*), Cabbage looper (*Trichoplusia ni*), Soybean looper (*Pseudoplusia includens*), Velvetbean caterpillar (*Anticarsia gemmatalis*), Green cloverworm (*Hypena scabra*), Tobacco budworm (*Heliothis virescens*), Granulate cutworm (*Agrotis subterranea*), Armyworm (*Pseudaletia unipuncta*), Western cutworm (*Agrotis orthogonia*); borers, casebearers, webworms, coneworms, cabbageworms and skeletonizers from the Family Pyralidae, e.g., European corn borer (*Ostrinia nubilalis*), Navel orangeworm (*Amyelois transitella*), Corn root webworm (*Crambus caliginosellus*), Sod webworm (*Herpetogramma licarsisalis*), Sunflower moth (*Homoeosoma electellum*), Lesser cornstalk borer (*Elasmopalpus lignosellus*); leafrollers, budworms, seed worms, and fruit worms in the Family Tortricidae, e.g., Codling moth (*Cydia pomonella*), Grape berry moth (*Endopiza viteana*), Oriental fruit moth (*Grapholita molesta*), Sunflower bud moth (*Suleima helianthana*); and many other economically important Lepidoptera, e.g., Diamondback moth (*Plutella xylostella*), Pink bollworm (*Pectinophora gossypiella*) and Gypsy moth (*Lymantria dispar*). Other insect pests of order Lepidoptera include, e.g., Cotton leaf worm (*Alabama argillacea*), Fruit tree leaf roller (*Archips argyrospila*), European leafroller (*Archips rosana*) and other *Archips* species, (*Chilo suppressalis*, Asiatic rice borer, or rice stem borer), Rice leaf roller (*Cnaphalocrocis medinalis*), Corn root webworm (*Crambus caliginosellus*), Bluegrass webworm (*Crambus teterrellus*), Southwestern corn borer (*Diatraea grandiosella*), Surgarcane borer (*Diatraea saccharalis*), Spiny bollworm (*Earias insulana*), Spotted bollworm (*Earias vittella*), Old World bollworm (*Helicoverpa armigera*), Corn earworm (*Helicoverpa zea*, also known as soybean podworm and cotton bollworm), Western bean cutworm (*Striacosta albicosta*), European grape vine moth (*Lobesia botrana*), Citrus leafminer (*Phyllocnistis citrella*), large white butterfly (*Pieris brassicae*), small white butterfly (*Pieris rapae*, also known as imported cabbageworm), Tobacco cutworm (*Spodoptera litura*, also known as cluster caterpillar), and Tomato leafminer (*Tuta absoluta*).

The insects of the order Coleoptera include, but are not limited to, *Agriotes* spp., *Anthonomus* spp., *Atomaria linearis*, *Chaetocnema tibialis*, *Cosmopolites* spp., *Curculio* spp., *Dermestes* spp., *Diabrotica* spp., *Epilachna* spp., *Eremnus* spp., *Leptinotarsa decemlineata*, *Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae*, *Sitophilus* spp., *Sitotroga* spp., *Tenebrio* spp., *Tribolium* spp. and *Trogoderma* spp, particularly when the pest is Western Corn Rootworm (*Diabrotica virgifera*, WCR), Northern Corn Rootworm (*Diabrotica barberi*, NCR), Mexican Corn Rootworm (*Diabrotica virgifera zeae*, MCR), Brazilian Corn Rootworm (*Diabrotica balteata*, BZR), Southern Corn Rootworm (*Diabrotica undecimpunctata howardii*, SCR), Colorado potato beetle (*Leptinotarsa decemlineata*, CPB), a Brazilian Corn Rootworm complex (BCR, consisting of *Diabrotica viridula* and *Diabrotica speciosa*), Crucifer Flea Beetle (*Phyllotreta cruciferae*), Striped Flea Beetle (*Phyllotreta striolata*), and Western Black Flea Beetle (*Phyllotreta pusilla*).

The insects of the order Hemiptera include, but are not limited to, Stink Bugs of the family Pentatomidae: Green Stink Bugs from the genus *Chinavia* (*Chinavia hilaris*, *Chinavia marginata*, and *Chinavia pensylvanica*), Stink bugs of the genus *Chlorochroa* (*Chlorochroa granulose*, *Chlorochroa kanei*, *Chlorochroa ligata*, *Chlorochroa lineate*, *Chlorochroa opuntiae*, *Chlorochroa persimilis*, *Chlorochroa rossiana*, *Chlorochroa sayi*, *Chlorochroa uhleri*, *Chlorochroa belfragii*, *Chlorochroa faceta*, *Chlorochroa osborni*, *Chlorochroa saucia*, and *Chlorochroa senilis*), Southern Green Stink Bug (*Nezara viridula*), Stink Bugs from the genus *Edessa* (*Edessa meditabunda*, *Edessa bifida*, and *Edessa florida*), the Neotropical Brown Stink Bug (*Euschistus heros*), stink bugs from the genus *Euschistus* (*Euschistus acuminatus*, *Euschistus biformis*, *Euschistus conspersus*, *Euschistus crenator*, *Euschistus egglestoni*, *Euschistus ictericus*, *Euschistus inflatus*, *Euschistus latimarginatus*, *Euschistus obscures*, *Euschistus politus*, *Euschistus quadrator*, *Euschistus sevus*, *Euschistus strenuous*, *Euschistus tristigmus*, and *Euschistus variolarius*), Brown Marmorated Stink Bug (*Halyomorpha halys*), Red-Shouldered Stink Bug (*Thyanta accerra*), stink bugs of the genus *Thyanta* (*Thyanta calceata*, *Thyanta custator*, *Thyanta pallidovirens*, *Thyanta perditor*, *Thyanta maculate*, and *Thyanta pseudocasta*), the Green Belly Stink Bug (*Dichelops melacanthus*) and other stink bugs of the genus *Dichelops* (*Dichelops avilapiresi*, *Dichelops bicolor*, *Dichelops dimidatus*, *Dichelops furcatus*, *Dichelops furcifrons*, *Dichelops lobatus*, *Dichelops miriamae*, *Dichelops nigrum*, *Dichelops peruanus*, *Dichelops phoenix*, and *Dichelops saltensis*), the Red Banded Stink Bug (*Piezodorus guildinni*) as well as *Piezodorus lituratus*; and insects of the family of Plataspidae such as Kudzu Bug (*Megacopta cribraria*), Western tarnished plant bug (*Lygus hesperus*), and Tarnished plant bug (*Lygus lineolaris*).

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

As described further herein, an open reading frame (ORF) encoding TIC7040 (SEQ ID NO:1), was discovered in DNA obtained from *Brevibacillus laterosporus* strain DSC005019, which encodes the protein toxin presented as SEQ ID NO:2. Upon amplification using primers designed from the TIC7040 ORF, a slightly longer coding sequence was amplified using DNA obtained from *Brevibacillus laterosporus* strain DSC005019, herein referred to as TIC7040HT (SEQ ID NO:3), which encodes the protein presented as SEQ ID NO:4. Bioassay using microbial host cell-derived TIC7040HT protein demonstrated activity against the Coleopteran pests Western Corn Rootworm (*Diabrotica virgifera virgifera*, WCR), Cry3Bb-resistant Western Corn Rootworm (*Diabrotica virgifera virgifera*, WCRHP), Northern Corn Rootworm (*Diabrotica barberi*, NCR), Southern Corn Rootworm (*Diabrotica undecimpunctata howardii*, SCR), and Colorado potato beetle (*Leptinotarsa decemlineata*, CPB), and the Lepidopteran insect pests Corn Earworm (*Helicoverpa zea*, (CEW) also known as Soybean Podworm and Cotton Bollworm), Diamondback Moth (*Plutella xylostella*, DBM), European Corn Borer (*Ostrinia nubilalis*, ECB), Fall Armyworm (*Spodoptera frugiperda*, FAW), Soybean Looper (*Pseudoplusia includes*, SBL), Southwestern Corn Borer (*Diatraea grandiosella*, SWCB), and Velvetbean Caterpillar (*Anticarsia gemmatalis*, VBC).

As described further herein, an ORF encoding TIC7042 (SEQ ID NO:11), was discovered in DNA obtained from *Brevibacillus laterosporus* strain DSC005973 which encodes the protein toxin presented as SEQ ID NO:12. Bioassay using microbial host cell-derived TIC7042 protein demonstrated activity against the Coleopteran pests WCR, WCRHP, NCR, SCR, and CPB, and the Lepidopteran insect pests BCW, CEW, DBM, FAW, SBL, and VBC.

As described further herein, an ORF encoding TIC7381 (SEQ ID NO:13), was discovered in DNA obtained from *Brevibacillus laterosporus* strain DSC006713 which encodes the protein toxin presented as SEQ ID NO:14. Bioassay using microbial host cell-derived TIC7381 protein demonstrated activity against the Coleopteran pests WCR, WCRHP, NCR, SCR, and CPB, and the Lepidopteran insect pests CEW, DBM, ECB, FAW, SBL, SWCB, and VBC.

As described further herein, an ORF encoding TIC7382 (SEQ ID NO:15), was discovered in DNA obtained from *Brevibacillus laterosporus* strain DSC007657 which encodes the protein toxin presented as SEQ ID NO:16. Bioassay using microbial host cell-derived TIC7382 protein demonstrated activity against the Coleopteran pests WCR, WCRHP, NCR, SCR, and CPB, and the Lepidopteran insect pests DBM, ECB, SBL, SWCB, and VBC.

As described further herein, an ORF encoding TIC7383 (SEQ ID NO:17), was discovered in DNA obtained from *Brevibacillus laterosporus* strain DSC008106 which encodes the protein toxin presented as SEQ ID NO:18. Bioassay using microbial host cell-derived TIC7383 protein demonstrated activity against the Coleopteran pests WCR, WCRHP, NCR, SCR, and CPB, and the Lepidopteran insect pests CEW, DBM, ECB, and VBC.

As described further herein, ORF's encoding TIC7386 (SEQ ID NO:29), TIC7388 (SEQ ID NO:31), and TIC7389 (SEQ ID NO:33) were discovered in DNA obtained from *Brevibacillus laterosporus* strains DSC007651, DSC007962, and DSC006878, respectively, and encode the proteins presented herein as SEQ ID NO:30, SEQ ID NO:32, and SEQ ID NO:34. Bioassay using microbial host cell-derived TIC7389 protein demonstrated activity against the Lepidopteran insect pest SBL and Coleopteran pests WCR and CPB.

Further described herein, chymotryptic and tryptic digests of TIC7040HT, and tryptic digests of TIC7383 maintained activity against WCR, relative to the full length TIC7040HT and TIC7383. In addition, truncations of TIC7040HT and TIC7383 maintained activity, and in some cases increased activity, against WCR and CPB, relative to the full length TIC7040HT and TIC7383.

Further described herein are chimeric toxins comprised of domains derived from TIC7381, TIC7382, TIC7383, and TIC7042. The chimeric toxin, TIC10743 (SEQ ID NO:113, encoded by SEQ ID NO:112) is comprised of domains one and two of TIC7383 and domain three of TIC7042. The chimeric toxin, TIC10744 (SEQ ID NO:115, encoded by SEQ ID NO:114) is comprised of domains one and two of TIC7383 and domain three of TIC7381. The chimeric toxin, TIC10745 (SEQ ID NO:117, encoded by SEQ ID NO:116) is comprised of domains one and two of TIC7383 and domain three of TIC7382. The chimeric toxin, TIC10746 (SEQ ID NO:119, encoded by SEQ ID NO:118) is comprised of domains one and two of TIC7382 and domain three of TIC7383. The chimeric toxin, TIC10747 (SEQ ID NO:121, encoded by SEQ ID NO:120) is comprised of domains one and two of TIC7381 and domain three of TIC7383. The chimeric toxin, TIC10748 (SEQ ID NO:123, encoded by SEQ ID NO:122) is comprised of domains one and two of TIC7042 and domain three of TIC7383. The chimeric toxin, TIC10746NTermExt1 (SEQ ID NO:125, encoded by SEQ ID NO:124) is comprised of domains one and two of TIC7382, domain three of TIC7383, and the N-terminal extension of TIC7382. The N-terminal extension of TIC7382 comprises amino acids 1-51 of the TIC7382 toxin protein and is encoded by the first 153 nucleotides of the TIC7382 coding sequence. The chimeric toxin, TIC10746NTermExt2 (SEQ ID NO:127, encoded by SEQ ID NO:126) is comprised of domains one and two of TIC7382, domain three of TIC7383, and the N-terminal extension of TIC7383. The N-terminal extension of TIC7383 comprises amino acids 1-53 of the TIC7383 toxin protein and is encoded by the first 159 nucleotides of the TIC7383 coding sequence.

For expression in plant cells, TIC7040, TIC7040HT, TIC7042, TIC7381, TIC7382, or TIC7383, or variants, truncation variants, or chimeras thereof can be expressed to reside in the cytosol or targeted to various organelles of the plant cell. For example, targeting a protein to the chloroplast may result in increased levels of expressed protein in a transgenic plant while preventing off-phenotypes from occurring. Targeting may also result in an increase in pest resistance efficacy in the transgenic event. A target peptide or transit peptide is a short (3-70 amino acids long) peptide chain that directs the transport of a protein to a specific region in the cell, including the nucleus, mitochondria, endoplasmic reticulum (ER), chloroplast, apoplast, peroxisome and plasma membrane. Some target peptides are cleaved from the protein by signal peptidases after the proteins are transported. For targeting to the chloroplast, proteins contain transit peptides which are around 40-50 amino acids. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (See, Klee et al., *Mol. Gen. Genet.* 210:437-442, 1987) or the *Petunia hybrida* EPSPS CTP (CTP4) (See, della-Cioppa et al., *Proc. Natl. Acad. Sci. USA* 83:6873-6877, 1986) has been shown to target heterologous EPSPS protein sequences to chloroplasts in transgenic plants (See, U.S. Pat. Nos. 5,627,061; 5,633,435; and 5,312,910; and EP 0218571; EP 189707; EP 508909; and EP 924299). For targeting TIC7040, TIC7040HT, TIC7042, TIC7381, TIC7382, and TIC7383 and variants, truncation variants and chimeras thereof to the chloroplast, a sequence encoding a chloroplast transit peptide is placed 5' in operable linkage and in frame to a synthetic coding sequence encoding the TIC7040, TIC7040HT, TIC7042, TIC7381, TIC7382, and TIC7383 protein, or variants, truncation variants, or chimeras thereof, that has been designed for optimal expression in plant cells.

It is contemplated that additional toxin protein sequences related to TIC7040, TIC7040HT, TIC7042, TIC7381, TIC7382, TIC7383, TIC7386, TIC7388, and TIC7389 can be created by using the naturally occurring amino acid sequence of TIC7040, TIC7040HT, TIC7042, TIC7381, TIC7382, TIC7383, TIC7386, TIC7388, and TIC7389 to create novel proteins and with novel properties. The TIC7040, TIC7040HT, TIC7042, TIC7381, TIC7382, TIC7383, TIC7386, TIC7388, and TIC7389 toxin proteins can be aligned with other proteins similar to TIC7040, TIC7040HT, TIC7042, TIC7381, TIC7382, TIC7383, TIC7386, TIC7388, and TIC7389 to combine differences at the amino acid sequence level into novel amino acid sequence variants and making appropriate changes to the recombinant nucleic acid sequence encoding the variants.

This disclosure further contemplates that improved variants of the TIC7040, TIC7040HT, TIC7042, TIC7381, TIC7382, TIC7383, TIC7386, TIC7388, and TIC7389 protein toxin classes can be engineered in planta by using various gene editing methods known in the art. Such technologies used for genome editing include, but are not limited to, ZFN (zinc-finger nuclease), meganucleases, TALEN (Transcription activator-like effector nucleases), and CRISPR (Clustered Regularly Interspaced Short Palindromic Repeats)/Cas (CRISPR-associated) systems. These genome editing methods can be used to alter the toxin protein coding sequence transformed within a plant cell to a different toxin coding sequence. Specifically, through these methods, one or more codons within the toxin coding sequence is altered to engineer a new protein amino acid sequence. Alternatively, a fragment within the coding sequence is replaced or deleted, or additional DNA fragments are inserted into the coding sequence, to engineer a new toxin coding sequence. The new coding sequence can encode a toxin protein with new properties such as increased activity or spectrum against insect pests, as well as provide activity against an insect pest species wherein resistance has developed against the original insect toxin protein. The plant cell comprising the gene edited toxin coding sequence can be used by methods known in the art to generate whole plants expressing the new toxin protein.

It is also contemplated that fragments of the TIC7040, TIC7040HT, TIC7042, TIC7381, TIC7382, TIC7383, TIC7386, TIC7388, and TIC7389 proteins or protein variants thereof can be truncated forms wherein one or more amino acids are deleted from the N-terminal end, C-terminal end, the middle of the protein, or combinations thereof with insect inhibitory activity. These fragments can be naturally occurring or synthetic variants of TIC7040, TIC7040HT, TIC7042, TIC7381, TIC7382, TIC7383, TIC7386, TIC7388, and TIC7389 or protein variants thereof, but should retain the insect inhibitory activity of TIC7040, TIC7040HT, TIC7042, TIC7381, TIC7382, TIC7383, TIC7386, TIC7388, and TIC7389.

Proteins that resemble the TIC7040, TIC7040HT, TIC7042, TIC7381, TIC7382, TIC7383, TIC7386, TIC7388, and TIC7389 proteins can be identified by comparison to each other using various computer-based algorithms known in the art. For example, amino acid sequence identities of proteins related to TIC7040, TIC7040HT, TIC7042, TIC7381, TIC7382, TIC7383, TIC7386, TIC7388, and TIC7389 can be analyzed using a Clustal W alignment using these default parameters: Weight matrix: blosum, Gap opening penalty: 10.0, Gap extension penalty: 0.05, Hydrophilic gaps: On, Hydrophilic residues: GPSNDQERK, Residue-specific gap penalties: On (Thompson, et al (1994) Nucleic Acids Research, 22:4673-4680). Percent amino acid identity is further calculated by the product of 100% multiplied by (amino acid identities/length of subject protein). Other alignment algorithms are also available in the art and provide results similar to those obtained using a Clustal W alignment.

It is intended that a protein exhibiting insect inhibitory activity against a Lepidopteran or Coleopteran insect species is related to TIC7040, TIC7040HT, TIC7042, TIC7381, TIC7382, TIC7383, TIC7386, TIC7388, and TIC7389 if alignment of such query protein with TIC7383 or TIC7386 exhibits at least 75% to about 100% amino acid identity along the length of the query protein that is about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity (or any fraction of a percentage in this range) between query and subject protein; or if alignment of such query protein with TIC7040HT, TIC7381, or TIC7389 exhibits at least 90% to about 100% amino acid identity along the length of the query protein that is about 90%, 91%, 92%, 93%, 94%, 95%, 96%, 97%, 98%, 99%, 100% amino acid sequence identity (or any fraction of a percentage in this range) between query and subject protein; or if alignment of such query protein with TIC7042, or TIC7382 exhibits at least 93% to about 100% amino acid identity along the length of the query protein that is about 93%, 94%, 95%, 96%, 97%, 98%, 99%, 100% amino acid sequence identity (or any fraction of a percentage in this range) between query and subject protein; or if alignment of such query protein with TIC7040HT, TIC7381, or TIC7388 exhibits at least 99% to about 100% amino acid identity along the length of the query protein (or any fraction of a percentage in this range) between query and subject protein.

Exemplary proteins TIC7040, TIC7040HT, TIC7042, TIC7381, TIC7382, TIC7383, TIC7386, TIC7388, and TIC7389 were aligned with each other using a Clustal W algorithm. A pair-wise matrix of percent amino acid sequence identities for each of the full-length proteins was created, as reported in Table 1. The number of identical amino acids between two sequences is indicated in parenthesis.

TABLE 1

Pair-wise matrix display of exemplary proteins TIC7040, TIC7040HT, TIC7042, TIC7381, TIC7382, TIC7383, TIC7386, TIC7388, and TIC7389.

| Toxin | TIC7042 SEQ ID NO: 12 | TIC7386 SEQ ID NO: 30 | TIC7388 SEQ ID NO: 32 | TIC7382 SEQ ID NO: 16 | TIC7040 SEQ ID NO: 2 | TIC7040HT SEQ ID NO: 4 | TIC7381 SEQ ID NO: 14 | TIC7389 SEQ ID NO: 34 | TIC7383 SEQ ID NO: 18 |
|---|---|---|---|---|---|---|---|---|---|
| TIC7042 SEQ ID NO: 12 | — | 99.1 (1254) | 92.3 (1169) | 87.8 (1111) | 85.7 (1085) | 86.3 (1093) | 86.7 (1097) | 86.7 (1098) | 73.3 (928) |
| TIC7386 SEQ ID NO: 30 | 98 (1254) | — | 91.5 (1170) | 86.7 (1109) | 85.1 (1089) | 85.7 (1096) | 86 (1100) | 86.1 (1101) | 72.6 (928) |
| TIC7388 SEQ ID NO: 32 | 92.1 (1169) | 92.2 (1170) | — | 93.7 (1189) | 88.8 (1127) | 89.4 (1135) | 89.8 (1140) | 89.9 (1141) | 76.1 (966) |
| TIC7382 SEQ ID NO: 16 | 89.2 (1111) | 89 (1109) | 95.4 (1189) | — | 90.6 (1129) | 91.4 (1139) | 91.2 (1136) | 91.5 (1140) | 76.2 (949) |
| TIC7040 SEQ ID NO: 2 | 86.2 (1085) | 86.5 (1089) | 89.5 (1127) | 89.7 (1129) | — | 99.9 (1258) | 98.5 (1240) | 99 (1247) | 76.6 (965) |
| TIC7040HT SEQ ID NO: 4 | 84.4 (1093) | 84.6 (1096) | 87.6 (1135) | 88 (1139) | 97.1 (1258) | — | 96.6 (1251) | 97.2 (1259) | 74.8 (969) |
| TIC7381 SEQ ID NO: 14 | 86.4 (1097) | 86.7 (1100) | 89.8 (1140) | 89.5 (1136) | 97.7 (1240) | 98.6 (1251) | — | 99.5 (1263) | 76.5 (971) |
| TIC7389 SEQ ID NO: 34 | 83.2 (1098) | 83.5 (1101) | 86.5 (1141) | 86.4 (1140) | 94.5 (1247) | 95.5 (1259) | 95.8 (1263) | — | 73.9 (975) |
| TIC7383 SEQ ID NO: 18 | 73.9 (928) | 73.9 (928) | 76.9 (966) | 75.6 (949) | 76.8 (965) | 77.1 (969) | 77.3 (971) | 77.6 (975) | — |

In addition to percent identity, the TIC7040, TIC7040HT, TIC7042, TIC7381, TIC7382, TIC7383, TIC7386, TIC7388, and TIC7389 proteins can also be related by primary structure (conserved amino acid motifs), by length (about 1243 to about 1259 amino acids) and by other characteristics. Bioinformatic analysis suggests that TIC7040, TIC7040HT, TIC7042, TIC7381, TIC7382, TIC7383, TIC7386, TIC7388, and TIC7389 belong to the Cry43 family of proteins. Characteristics of the T5C7040, TIC7040HT, T8C7042, T1C7381, T1C7382, TIC7383, TIC7386, TIC7388, and TIC7389 proteins are reported in Table 2.

TABLE 2

Selected characteristics of the TIC7040, TIC7040HT, TIC7042, TIC7381, TIC7382, TIC7383, TIC7386, TIC7388, and TIC7389 proteins and related family member proteins.

| Protein | Molecular Weight (in Daltons) | Amino Acid Length | Isoelectric Point | Charge at PH 7.0 | No. of Strongly Basic (−) Amino Acids | No. of Strongly Acidic Amino Acids | No. of Hydrophobic Amino Acids | No. of Polar Amino Acids |
|---|---|---|---|---|---|---|---|---|
| TIC7040 | 142822.03 | 1259 | 5.8063 | −13.0 | 154 | 151 | 618 | 641 |
| TIC7040HT | 146821.27 | 1295 | 5.8643 | −14.0 | 161 | 156 | 636 | 659 |
| TIC7040_4 | 75400.92 | 671 | 7.0053 | 2.5 | 68 | 61 | 333 | 338 |
| TIC7040_5 | 67268.98 | 600 | 7.5498 | 4.0 | 61 | 53 | 303 | 297 |
| TIC7040_6 | 74075.56 | 660 | 7.0051 | 2.5 | 67 | 60 | 332 | 338 |
| TIC7040HT_Tryp | 65150.72 | 582 | 8.1625 | 5.5 | 59 | 50 | 294 | 288 |
| TIC7040HT_Chymo | 66845.58 | 597 | 7.8790 | 4.5 | 59 | 51 | 302 | 295 |
| CR-BREla.TIC7040_1.nno_Mc:1 | 71805.04 | 640 | 6.7230 | 1.0 | 62 | 57 | 325 | 315 |

TABLE 2-continued

Selected characteristics of the TIC7040, TIC7040HT, TIC7042, TIC7381, TIC7382, TIC7383,
TIC7386, TIC7388, and TIC7389 proteins and related family member proteins.

| Protein | Molecular Weight (in Daltons) | Amino Acid Length | Isoelectric Point | Charge at PH 7.0 | No. of Strongly Basic (−) Amino Acids | No. of Strongly Acidic Amino Acids | No. of Hydrophobic Amino Acids | No. of Polar Amino Acids |
|---|---|---|---|---|---|---|---|---|
| CR-BREla.TIC7040_11.nno_Mc:1 | 65281.91 | 583 | 8.1625 | 5.5 | 59 | 50 | 295 | 288 |
| CR-BREla.TIC7040_12.nno_Mc:2 | 74125.45 | 660 | 6.5260 | 0.0 | 64 | 60 | 329 | 331 |
| CR-BREla.TIC7040_13.nno_Mc:1 | 69983.90 | 624 | 7.2157 | 3.0 | 62 | 55 | 310 | 314 |
| CR-BREla.TIC7040_14.nno_Mc:1 | 68315.18 | 611 | 6.8814 | 1.5 | 59 | 54 | 311 | 300 |
| TIC7042 | 143469.54 | 1266 | 6.1143 | −9.0 | 158 | 148 | 617 | 649 |
| CR-BREla.TIC7042_1.nno_Mc:1 | 71715.51 | 637 | 6.6825 | 1.0 | 62 | 56 | 312 | 325 |
| CR-BREla.TIC7042_2.nno_Mc:1 | 73986.03 | 657 | 6.9127 | 2.5 | 67 | 59 | 319 | 338 |
| TIC7381 | 143793.24 | 1269 | 6.2077 | −7.0 | 162 | 150 | 626 | 643 |
| CR-BREla.TIC7381_1.nno_Mc:1 | 143850.30 | 1270 | 6.2077 | −7.0 | 162 | 150 | 627 | 643 |
| CR-BREla.TIC7381_2.nno_Mc:1 | 73892.21 | 659 | 6.5260 | 0.0 | 64 | 60 | 331 | 328 |
| CR-BREla.TIC7381_3.nno_Mc:1 | 68253.10 | 611 | 6.8814 | 1.5 | 59 | 54 | 312 | 299 |
| TIC7382 | 140890.86 | 1246 | 5.7572 | −13.0 | 149 | 147 | 614 | 632 |
| CR-BREla.TIC7382_1.nno_Mc:1 | 140961.94 | 1247 | 5.7572 | −13.0 | 149 | 147 | 615 | 632 |
| CR-BREla.TIC7382_2.nno_Mc:1 | 73858.00 | 660 | 6.6112 | 0.5 | 63 | 58 | 329 | 331 |
| CR-BREla.TIC7382_3.nno_Mc:1 | 67924.61 | 610 | 6.9577 | 2.0 | 58 | 52 | 310 | 300 |
| TIC7383 | 142470.64 | 1256 | 5.5492 | −17.5 | 151 | 152 | 627 | 629 |
| TIC7383_2 | 140903.05 | 1243 | 5.5471 | −17.5 | 150 | 151 | 626 | 617 |
| TIC7383_3 | 74526.97 | 659 | 5.7950 | −3.0 | 61 | 61 | 343 | 316 |
| TIC7383_4 | 76846.56 | 679 | 5.9941 | −2.5 | 66 | 65 | 350 | 329 |
| TIC7383_5 | 72959.38 | 646 | 5.7903 | −3.0 | 60 | 60 | 342 | 304 |
| TIC7383_6 | 75278.97 | 666 | 5.9913 | −2.5 | 65 | 64 | 349 | 317 |
| TIC7383_Tryp | 69242.24 | 614 | 5.8225 | −2.5 | 57 | 57 | 326 | 288 |
| CR-BREla.TIC7383_1.nno_Mc:1 | 142541.72 | 1257 | 5.5492 | −17.5 | 151 | 152 | 628 | 629 |
| CR-BREla.TIC7383_7.nno_Mc:1 | 69545.62 | 617 | 5.8225 | −2.5 | 57 | 57 | 328 | 289 |
| CR-BREla.TIC7383_8.nno_Mc:1 | 74772.20 | 662 | 5.7950 | −3.0 | 61 | 61 | 344 | 318 |
| CR-BREla.TIC7383_9.nno_Mc:1 | 75669.20 | 669 | 5.5878 | −4.0 | 62 | 63 | 347 | 322 |
| CR-BREla.TIC7383_19.nno_Mc:1 | 74030.53 | 655 | 5.5815 | −4.0 | 61 | 62 | 345 | 310 |
| CR-BREla.TIC7383_20.nno_Mc:1 | 73133.53 | 648 | 5.7903 | −3.0 | 60 | 60 | 342 | 306 |
| CR-BREla.TIC7383_21.nno_Mc:1 | 68648.63 | 610 | 6.0997 | −1.5 | 56 | 55 | 325 | 285 |
| CR-BREla.TIC7383_22.nno_Mc:1 | 69474.54 | 616 | 5.8225 | −2.5 | 57 | 57 | 327 | 289 |
| CR-BREla.TIC7383_23.nno_Mc:1 | 68577.55 | 609 | 6.0997 | −1.5 | 56 | 55 | 324 | 285 |
| CR-BREla.TIC7383_24.nno_Mc:2 | 66643.51 | 590 | 6.6807 | 0.5 | 55 | 52 | 315 | 275 |
| CR-BREla.TIC7383_25.nno_Mc:3 | 64647.09 | 569 | 6.3851 | −0.5 | 54 | 52 | 299 | 270 |
| CR-BREla.TIC7383_26.nno_Mc:1 | 62376.52 | 549 | 6.6802 | 0.5 | 54 | 51 | 287 | 262 |
| CR-BREla.TIC7383_27.nno_Mc:1 | 68417.42 | 607 | 6.0997 | −1.5 | 56 | 55 | 324 | 283 |
| CR-BREla.TIC7383_28.nno_Mc:1 | 72902.33 | 645 | 5.7903 | −3.0 | 60 | 60 | 341 | 304 |
| CR-BREla.TIC7383_29.nno_Mc:1 | 108909.43 | 964 | 5.0905 | −17.0 | 104 | 112 | 489 | 475 |
| CR-BREla.TIC7383_30.nno_Mc:1 | 142342.42 | 1257 | 5.3793 | −20.5 | 148 | 152 | 631 | 626 |
| CR-BREla.TIC7383_31.nno_Mc:1 | 120993.09 | 1066 | 5.4956 | −13.0 | 122 | 124 | 538 | 528 |
| CR-BREla.TIC7383_32.nno_Mc:1 | 141715.71 | 1251 | 5.3252 | −21.5 | 146 | 151 | 628 | 623 |
| TIC7386 | 144952.03 | 1279 | 6.1338 | −9.0 | 161 | 150 | 621 | 658 |
| TIC7388 | 143562.87 | 1269 | 6.0794 | −9.5 | 157 | 148 | 629 | 640 |
| TIC7389 | 149398.97 | 1319 | 5.6940 | −17.5 | 162 | 160 | 652 | 667 |
| GOI-TIC10743.nno_Mc:1 | 69704.53 | 617 | 6.0297 | −2.0 | 57 | 56 | 314 | 303 |
| GOI-TIC10744.nno_Mc:1 | 69405.21 | 616 | 6.0308 | −2.0 | 57 | 56 | 317 | 299 |
| GOI-TIC10745.nno_Mc:1 | 69732.59 | 617 | 6.2812 | −1.0 | 58 | 56 | 314 | 303 |
| GOI-TIC10746.nno_Mc:1 | 67737.64 | 610 | 6.6433 | 0.5 | 57 | 53 | 324 | 286 |
| GOI-TIC10747.nno_Mc:1 | 68393.51 | 612 | 6.8012 | 1.0 | 59 | 58 | 323 | 289 |
| GOI-TIC10748.nno_Mc:1 | 68118.77 | 609 | 6.7284 | 1.0 | 59 | 54 | 312 | 297 |
| TIC10746NTermExt1 | 73599.95 | 659 | 6.3342 | −1.0 | 62 | 59 | 342 | 317 |
| TIC10746NTermExt2 | 73790.14 | 661 | 6.3342 | −1.0 | 62 | 59 | 342 | 319 |

As described further in the Examples of this application, recombinant nucleic acid molecule sequences encoding TIC7040, TIC7040HT, TIC7042, TIC7381, TIC7382, and TIC7383, and variants, truncation variants, and chimeras thereof were designed for use in plants. Exemplary plant-optimized recombinant nucleic acid molecule sequences that were designed for use in plants are presented in Table 8 of Example 5, along with the corresponding nucleotide and protein sequences, description and modifications.

Expression cassettes and vectors containing these recombinant nucleic acid molecule sequences can be constructed and introduced into corn, soybean, cotton or other plant cells in accordance with transformation methods and techniques known in the art. For example, *Agrobacterium*-mediated transformation is described in U.S. Patent Application Publications 2009/0138985A1 (soybean), 2008/0280361A1 (soybean), 2009/0142837A1 (corn), 2008/0282432 (cotton), 2008/0256667 (cotton), 2003/0110531 (wheat), 2001/0042257 A1 (sugar beet), U.S. Pat. No. 5,750,871 (canola), 7,026,528 (wheat), and 6,365,807 (rice), and in Arencibia et al. (1998) Transgenic Res. 7:213-222 (sugarcane), all of which are incorporated herein by reference in their entirety. Transformed cells can be regenerated into transformed plants that express TIC7040, TIC7040HT, TIC7042, TIC7381, TIC7382, or TIC7383. To test pesticidal activity, bioassays are performed in the presence of Lepidoptera pest larvae using plant leaf disks obtained from transformed plants, as described in the Examples. To test pesticidal activity against Coleopteran pests, transformed plants of $R_o$ and $F_1$ generation are used in root worm assay, as described in the Examples. To test pesticidal activity against Hemipteran pests, pods, corn ears or leaves of transformed plants are used in assay, either from tissue removed from the plant or remaining on the plant as described in the Examples.

As an alternative to traditional transformation methods, a DNA sequence, such as a transgene, expression cassette(s), etc., may be inserted or integrated into a specific site or locus within the genome of a plant or plant cell via site-directed integration. Recombinant DNA construct(s) and molecule(s) of this disclosure may thus include a donor template sequence comprising at least one transgene, expression cassette, or other DNA sequence for insertion into the genome of the plant or plant cell. Such donor template for site-directed integration may further include one or two homology arms flanking an insertion sequence (i.e., the sequence, transgene, cassette, etc., to be inserted into the plant genome). The recombinant DNA construct(s) of this disclosure may further comprise an expression cassette(s) encoding a site-specific nuclease and/or any associated protein(s) to carry out site-directed integration. These nuclease expressing cassette(s) may be present in the same molecule or vector as the donor template (in cis) or on a separate molecule or vector (in trans). Several methods for site-directed integration are known in the art involving different proteins (or complexes of proteins and/or guide RNA) that cut the genomic DNA to produce a double strand break (DSB) or nick at a desired genomic site or locus. As understood in the art, during the process of repairing the DSB or nick introduced by the nuclease enzyme, the donor template DNA may become integrated into the genome at the site of the DSB or nick. The presence of the homology arm(s) in the donor template may promote the adoption and targeting of the insertion sequence into the plant genome during the repair process through homologous recombination, although an insertion event may occur through non-homologous end joining (NHEJ). Examples of site-specific nucleases that may be used include zinc-finger nucleases, engineered or native meganucleases, TALE-endonucleases, and RNA-guided endonucleases (e.g., Cas9 or Cpf1). For methods using RNA-guided site-specific nucleases (e.g., Cas9 or Cpf1), the recombinant DNA construct(s) will also comprise a sequence encoding one or more guide RNAs to direct the nuclease to the desired site within the plant genome.

Recombinant nucleic acid molecule compositions that encode TIC7040, TIC7040HT, TIC7042, TIC7381, TIC7382, TIC7383, TIC7386, TIC7388, and TIC7389 or related family member insecticidal proteins are contemplated. For example, TIC7040, TIC7040HT, TIC7042, TIC7381, TIC7382, TIC7383, TIC7386, TIC7388, and TIC7389 or related family member insecticidal proteins can be expressed with recombinant DNA constructs in which a polynucleotide molecule with an ORF encoding the protein is operably linked to genetic expression elements such as a promoter and any other regulatory element necessary for expression in the system for which the construct is intended. Non-limiting examples include a plant-functional promoter operably linked to the TIC7040, TIC7040HT, TIC7042, TIC7381, TIC7382, TIC7383, TIC7386, TIC7388, and TIC7389 or related family member insecticidal protein encoding sequences for expression of the protein in plants or a Bt-functional promoter operably linked to a TIC7040, TIC7040HT, TIC7042, TIC7381, TIC7382, TIC7383, TIC7386, TIC7388, and TIC7389 or related family member insecticidal protein encoding sequences for expression of the protein in a Bt bacterium or other *Bacillus* species. Other elements can be operably linked to the TIC7040, TIC7040HT, TIC7042, TIC7381, TIC7382, TIC7383, TIC7386, TIC7388, and TIC7389 or related family member insecticidal protein encoding sequences including, but not limited to, enhancers, introns, untranslated leaders, encoded protein immobilization tags (HIS-tag), translocation peptides (i.e., plastid transit peptides, signal peptides), polypeptide sequences for post-translational modifying enzymes, ribosomal binding sites, and RNAi target sites. Exemplary recombinant polynucleotide molecules provided herewith include, but are not limited to, a heterologous promoter operably linked to a polynucleotide such as SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:44, SEQ ID NO:45, SEQ ID NO:47, SEQ ID NO:49, SEQ ID NO:51, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, and SEQ ID NO:126 that encodes a polypeptide or protein having the amino acid sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:43, SEQ ID NO:46, SEQ ID NO:48, SEQ ID NO:50, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, and SEQ ID NO:127. A heterologous promoter can also be operably linked to synthetic DNA coding sequences encoding a plastid targeted or untargeted TIC7040, TIC7040HT, TIC7042, TIC7381, TIC7382, TIC7383, variants, truncation variants, and chimeras thereof and untargeted TIC7040, TIC7040HT, TIC7042, TIC7381, TIC7382, TIC7383, variants, truncation variants, and chimeras thereof or related family member insecticidal proteins. The codons of a recombinant nucleic acid molecule encoding for proteins disclosed herein can be substituted by synonymous codons (known in the art as a silent substitution).

A recombinant DNA construct comprising an encoding sequence for TIC7040, TIC7040HT, TIC7042, TIC7381, TIC7382, TIC7383, TIC7386, TIC7388, TIC7389 or related family member insecticidal protein can further comprise a region of DNA that encodes for one or more insect inhibitory agents which can be configured to concomitantly express or co-express with a DNA sequence encoding a TIC7040, TIC7040HT, TIC7042, TIC7381, TIC7382, TIC7383, TIC7386, TIC7388, TIC7389 or related family member insecticidal protein, a protein different from a TIC7040, TIC7040HT, TIC7042, TIC7381, TIC7382, TIC7383, TIC7386, TIC7388, TIC7389 or a related family member insecticidal protein, an insect inhibitory dsRNA molecule, or an ancillary protein. Ancillary proteins include, but are not limited to, co-factors, enzymes, binding-partners, or other agents that function to aid in the effectiveness of an insect inhibitory agent, for example, by aiding its expression, influencing its stability in plants, optimizing free energy for oligomerization, augmenting its toxicity, and increasing its spectrum of activity. An ancillary protein may facilitate the uptake of one or more insect inhibitory agents, for example, or potentiate the toxic effects of the toxic agent.

A recombinant DNA construct can be assembled so that all proteins or dsRNA molecules are expressed from one promoter or each protein or dsRNA molecules is under separate promoter control or some combination thereof. The TIC7040, TIC7040HT, TIC7042, TIC7381, TIC7382, TIC7383, TIC7386, TIC7388, TIC7389 and related family member proteins of this invention can be expressed from a multi-gene expression system in which one or more TIC7040, TIC7040HT, TIC7042, TIC7381, TIC7382, TIC7383, TIC7386, TIC7388, TIC7389 or related family member proteins is expressed from a common nucleotide segment which also contains other open reading frames and promoters, depending on the type of expression system selected. For example, a bacterial multi-gene expression system can utilize a single promoter to drive expression of multiply-linked/tandem open reading frames from within a single operon (i.e., polycistronic expression). In another example, a plant multi-gene expression system can utilize multiply-unlinked expression cassettes each expressing a different protein or other agent such as one or more dsRNA molecules.

Recombinant nucleic acid molecules or recombinant DNA constructs comprising a TIC7040, TIC7040HT, TIC7042, TIC7381, TIC7382, TIC7383, TIC7386, TIC7388, TIC7389 or related family member protein encoding sequence can be delivered to host cells by vectors, e.g., a plasmid, baculovirus, synthetic chromosome, virion, cosmid, phagemid, phage, or viral vector. Such vectors can be used to achieve stable or transient expression of a TIC7040, TIC7040HT, TIC7042, TIC7381, TIC7382, TIC7383, TIC7386, TIC7388, TIC7389 or related family member protein encoding sequence in a host cell, or subsequent expression of the encoded polypeptide. An exogenous recombinant polynucleotide or recombinant DNA construct that comprises a protein encoding sequence and that is introduced into a host cell is referred herein as a "transgene."

Transgenic bacteria, transgenic plant cells, transgenic plants, and transgenic plant parts that contain a recombinant polynucleotide that expresses any one or more of the TIC7040, TIC7040HT, TIC7042, TIC7381, TIC7382, TIC7383, TIC7386, TIC7388, TIC7389 or related family member protein encoding sequences are provided herein. The term "bacterial cell" or "bacterium" can include, but is not limited to, an *Agrobacterium*, a *Bacillus*, an *Escherichia*, a *Salmonella*, a *Pseudomonas*, or a *Rhizobium* cell. The term "plant cell" or "plant" can include but is not limited to a dicotyledonous cell or a monocotyledonous cell. Contemplated plants and plant cells include, but are not limited to, alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. In certain embodiments, transgenic plants and transgenic plant parts regenerated from a transgenic plant cell are provided. In certain embodiments, the transgenic plants can be obtained from a transgenic seed, by cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a "non-regenerable" portion of a transgenic plant part is a portion that cannot be induced to form a whole plant or that cannot be induced to form a whole plant that is capable of sexual and/or asexual reproduction. In certain embodiments, a non-regenerable portion of a plant part is a portion of a transgenic seed, boll, leaf, flower, stem, or root.

Methods of making transgenic plants that comprise insect, Coleoptera- or Lepidoptera-inhibitory amounts of a TIC7040, TIC7040HT, TIC7042, TIC7381, TIC7382, TIC7383, TIC7386, TIC7388, TIC7389, variant, truncation variant, chimera or related family member protein are provided. Such plants can be made by introducing a recombinant polynucleotide that encodes any TIC7040, TIC7040HT, TIC7042, TIC7381, TIC7382, TIC7383, TIC7386, TIC7388, TIC7389, variant, truncation variant, chimera or related family member protein provided in this application into a plant cell, and selecting a plant derived from said plant cell that expresses an insect, Coleoptera- or Lepidoptera-inhibitory amount of the proteins. Plants can be derived from the plant cells by regeneration, seed, pollen, or meristem transformation techniques. Methods for transforming plants are known in the art.

Processed plant products, wherein the processed product comprises a detectable amount of a TIC7040, TIC7040HT, TIC7042, TIC7381, TIC7382, TIC7383, TIC7386, TIC7388, TIC7389, variant, truncation variant, chimera or related family member protein, an insect inhibitory segment or fragment thereof, or any distinguishing portion thereof, are also disclosed in this application. In certain embodiments, the processed product is selected from the group consisting of plant parts, plant biomass, oil, meal, sugar, animal feed, flour, flakes, bran, lint, hulls, processed seed, and seed. In certain embodiments, the processed product is non-regenerable. The plant product can comprise commodity or other products of commerce derived from a transgenic plant or transgenic plant part, where the commodity or other products can be tracked through commerce by detecting nucleotide segments or expressed RNA or proteins that encode or comprise distinguishing portions of a TIC7040, TIC7040HT, TIC7042, TIC7381, TIC7382, TIC7383, TIC7386, TIC7388, TIC7389, variant, truncation variant, chimera or related family member protein.

Plants expressing a TIC7040, TIC7040HT, TIC7042, TIC7381, TIC7382, TIC7383, TIC7386, TIC7388, TIC7389, variant, truncation variant, chimera or related family member protein can be crossed by breeding with transgenic events expressing other toxin proteins and/or expressing other transgenic traits such as herbicide tolerance genes, genes conferring yield or stress tolerance traits, and the like, or such traits can be combined in a single vector so that the traits are all linked.

As described further in the Examples, sequences encoding TIC7040, TIC7040HT, TIC7042, TIC7381, TIC7382, and TIC7383, variants of TIC7040HT, TIC7042, TIC7381, TIC7382, and TIC7383, truncation variants of TIC7040HT, TIC7042, TIC7381, TIC7382, and TIC7383, and chimeras of TIC7383, TIC7042, TIC7381 and TIC7382 were designed for use in plants and are presented in Table 8 in Example 5.

Expression cassettes and vectors containing these synthetic or artificial nucleotide sequences can be constructed and introduced into corn, cotton, and soybean plant cells in accordance with transformation methods and techniques which are known in the art. Transformed cells are regenerated into transformed plants that are observed to be expressing TIC7040, TIC7040HT, TIC7042, TIC7381, TIC7382, or TIC7383; or variants, truncation variants or chimeras thereof. To test pesticidal activity, bioassays are performed in the presence of Lepidopteran, Coleopteran and Hemipteran pests.

As further described in the Examples, sequences encoding TIC7040, TIC7040HT, TIC7042, TIC7381, TIC7382, TIC7383, variants, truncation variants, chimeras or related family member proteins and sequences having a substantial percentage identity to these proteins can be identified using methods known to those of ordinary skill in the art such as polymerase chain reaction (PCR), thermal amplification and hybridization. For example, a TIC7040, TIC7040HT, TIC7042, TIC7381, TIC7382, or TIC7383 protein and variants, truncation variants, chimeras or related family member proteins can be used to produce antibodies that bind specifically to related proteins, and can be used to screen for and to find other protein members that are closely related.

Furthermore, nucleotide sequences encoding TIC7040, TIC7040HT, TIC7042, TIC7381, TIC7382, or TIC7383 and variants, truncation variants, chimeras or related family member proteins can be used as probes and primers for screening to identify other members of the class using thermal-cycle or isothermal amplification and hybridization methods. For example, oligonucleotides derived from sequences as set forth as SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:44, SEQ ID NO:45, SEQ ID NO:47, SEQ ID NO:49, SEQ ID NO:51, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, and SEQ ID NO:126 can be used to determine the presence or absence of a TIC7040, TIC7040HT, TIC7042, TIC7381, TIC7382, or TIC7383 protein, or variants, truncation variants, chimeras, or related family member protein transgene in a deoxyribonucleic acid sample derived from a commodity product. Given the sensitivity of certain nucleic acid detection methods that employ oligonucleotides, it is anticipated that oligonucleotides derived from the sequences as set forth as SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:44, SEQ ID NO:45, SEQ ID NO:47, SEQ ID NO:49, SEQ ID NO:51, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, and SEQ ID NO:126 can be used to detect a TIC7040, TIC7040HT, TIC7042, TIC7381, TIC7382, or TIC7383, variants, truncation variants, or chimeric transgenes thereof in commodity products derived from pooled sources where only a fraction of the commodity product is derived from a transgenic plant containing any of SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:44, SEQ ID NO:45, SEQ ID NO:47, SEQ ID NO:49, SEQ ID NO:51, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, or SEQ ID NO:126. It is further recognized that such oligonucleotides can be used to introduce nucleotide sequence variation in SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:44, SEQ ID NO:45, SEQ ID NO:47, SEQ ID NO:49, SEQ ID NO:51, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, or SEQ ID NO: 126. Such "mutagenesis" oligonucleotides are useful for identification of TIC7040, TIC7040HT, TIC7042, TIC7381, TIC7382, TIC7383, TIC7386, TIC7388, TIC7389 or related family member amino acid sequence variants exhibiting a range of insect inhibitory activity or varied expression in transgenic plant host cells.

Nucleotide sequence homologs, e.g., insecticidal proteins encoded by nucleotide sequences that hybridize to each or any of the sequences disclosed in this application under hybridization conditions, are also an embodiment of the present invention. The invention also provides a method for detecting a first nucleotide sequence that hybridizes to a second nucleotide sequence, wherein the first nucleotide sequence (or its reverse complement sequence) encodes a pesticidal protein or pesticidal fragment thereof and hybridizes under stringent hybridization conditions to the second nucleotide sequence. In such case, the second nucleotide sequence can be the nucleotide sequence selected from the group consisting of: SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:44, SEQ ID NO:45, SEQ ID NO:47, SEQ ID NO:49, SEQ ID NO:51, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, and SEQ ID NO:126 under stringent hybridization conditions. Nucleotide coding sequences hybridize to one another under appropriate hybridization conditions and the proteins encoded by these nucleotide sequences cross react with antiserum raised against any one of the other proteins. Stringent hybridization conditions, as defined herein, comprise at least hybridization at 42° C. followed by two washes for five minutes each at room temperature with 2×SSC, 0.1% SDS, followed by two washes for thirty minutes each at 65° C. in 0.5×SSC, 0.1% SDS. Washes at even higher temperatures constitute even more stringent conditions, e.g., hybridization conditions of 68° C., followed by washing at 68° C., in 2×SSC containing 0.1% SDS.

One skilled in the art will recognize that, due to the redundancy of the genetic code, many other sequences are capable of encoding proteins related to TIC7040, TIC7040HT, TIC7042, TIC7381, TIC7382, TIC7383, TIC7386, TIC7388, or TIC7389, and those sequences, to the extent that they function to express pesticidal proteins either in Bacillus strains or in plant cells, are embodiments of the present invention, recognizing of course that many such redundant coding sequences will not hybridize under these conditions to the native Brevibacillus sequences encoding TIC7040, TIC7040HT, TIC7042, TIC7381, TIC7382, TIC7383, TIC7386, TIC7388, or TIC7389. This application contemplates the use of these and other identification methods known to those of ordinary skill in the art, to identify TIC7040, TIC7040HT, TIC7042, TIC7381, TIC7382, TIC7383, TIC7386, TIC7388, TIC7389 or related family member protein-encoding sequences and sequences having a substantial percentage identity thereto.

Methods of controlling insects, in particular Lepidoptera or Coleoptera infestations of crop plants, with the TIC7040, TIC7040HT, TIC7042, TIC7381, TIC7382, TIC7383, TIC7386, TIC7388, or TIC7389 or related family member proteins are also disclosed in this application. Such methods can comprise growing a plant comprising an insect-, Coleoptera-, or Lepidoptera-inhibitory amount of a TIC7040, TIC7040HT, TIC7042, TIC7381, TIC7382, TIC7383, TIC7386, TIC7388, TIC7389, variant, truncation variant, chimera or related family member toxin protein. In certain embodiments, such methods can further comprise any one or more of: (i) applying any composition comprising or encoding a TIC7040, TIC7040HT, TIC7042, TIC7381, TIC7382, TIC7383, TIC7386, TIC7388, TIC7389, variant, truncation variant, chimera or related family member toxin protein to a plant or a seed that gives rise to a plant; and (ii) transforming a plant or a plant cell that gives rise to a plant with a polynucleotide encoding a TIC7040, TIC7040HT, TIC7042, TIC7381, TIC7382, TIC7383, TIC7386, TIC7388, TIC7389, variant, truncation variant, chimera or related family member toxin protein. In general, it is contemplated that a TIC7040, TIC7040HT, TIC7042, TIC7381, TIC7382, TIC7383, TIC7386, TIC7388, TIC7389, variant, truncation variant or related family member toxin protein can be provided in a composition, provided in a microorganism, or provided in a transgenic plant to confer insect inhibitory activity against Lepidopteran or Coleopteran insects.

In certain embodiments, a recombinant nucleic acid molecule of a TIC7040, TIC7040HT, TIC7042, TIC7381, TIC7382, TIC7383, TIC7386, TIC7388, TIC7389, variant, truncation variant, chimera or related family member toxin protein is the insecticidally active ingredient of an insect inhibitory composition prepared by culturing recombinant Bacillus or any other recombinant bacterial cell transformed to express the protein. Such a composition can be prepared by desiccation, lyophilization, homogenization, extraction, filtration, centrifugation, sedimentation, or concentration of a culture of such recombinant cells expressing/producing said recombinant polypeptide. Such a process can result in a Bacillus or other entomopathogenic bacterial cell extract, cell suspension, cell homogenate, cell lysate, cell supernatant, cell filtrate, or cell pellet. By obtaining the recombinant polypeptides so produced, a composition that includes the recombinant polypeptides can include bacterial cells, bacterial spores, and parasporal inclusion bodies and can be formulated for various uses, including as agricultural insect inhibitory spray products or as insect inhibitory formulations in diet bioassays.

In one embodiment, to reduce the likelihood of resistance development, an insect inhibitory composition comprising TIC7040, TIC7040HT, TIC7042, TIC7381, TIC7382, TIC7383, TIC7386, TIC7388, TIC7389, variant, truncation variant, chimera or related family member can further comprise at least one additional polypeptide known to those of ordinary skill in the art that exhibits insect inhibitory activity against the same Lepidopteran or Coleopteran insect species, but which is different from the TIC7040, TIC7040HT, TIC7042, TIC7381, TIC7382, TIC7383, TIC7386, TIC7388, TIC7389, variant, truncation variant, chimera or related family member toxin protein. Possible additional polypeptides for such a composition include an insect inhibitory protein and an insect inhibitory dsRNA molecule. One example for the use of such ribonucleotide sequences to control insect pests is described in Baum, et al. (U.S. Patent Publication 2006/0021087 A1).

Such additional polypeptide for the control of Lepidopteran pests may be selected from the group consisting of an insect inhibitory protein, such as, but not limited to, Cry1A (U.S. Pat. No. 5,880,275), Cry1Ab, Cry1Ac, Cry1A.105, Cry1Ae, Cry1B (U.S. patent Ser. No. 10/525,318), Cry1C (U.S. Pat. No. 6,033,874), Cry1D, Cry1 Da and variants thereof, Cry1E, Cry1F, and Cry1A/F chimeras (U.S. Pat. Nos. 7,070,982; 6,962,705; and 6,713,063), Cry1G, Cry1H, Cry1I, Cry1J, Cry1K, Cry1L, Cry1-type chimeras such as, but not limited to, TIC836, TIC860, TIC867, TIC869, and TIC1100 (International Application Publication WO2016/061391 (A2)), TIC2160 (International Application Publication WO2016/061392(A2)), Cry2A, Cry2Ab (U.S. Pat. No. 7,064,249), Cry2Ae, Cry4B, Cry6, Cry7, Cry8, Cry9, Cry15, Cry43A, Cry43B, Cry51Aa1, ET66, TIC400, TIC800, TIC834, TIC1415, Vip3A, VIP3Ab, VIP3B, AXMI-001, AXMI-002, AXMI-030, AXMI-035, AND AXMI-045 (U.S. Patent Publication 2013-0117884

A1), AXMI-52, AXMI-58, AXMI-88, AXMI-97, AXMI-102, AXMI-112, AXMI-117, AXMI-100 (U.S. Patent Publication 2013-0310543 A1), AXMI-115, AXMI-113, AXMI-005 (U.S. Patent Publication 2013-0104259 A1), AXMI-134 (U.S. Patent Publication 2013-0167264 A1), AXMI-150 (U.S. Patent Publication 2010-0160231 A1), AXMI-184 (U.S. Patent Publication 2010-0004176 A1), AXMI-196, AXMI-204, AXMI-207, AXMI-209 (U.S. Patent Publication 2011-0030096 A1), AXMI-218, AXMI-220 (U.S. Patent Publication 2014-0245491 A1), AXMI-221z, AXMI-222z, AXMI-223z, AXMI-224z, AXMI-225z (U.S. Patent Publication 2014-0196175 A1), AXMI-238 (U.S. Patent Publication 2014-0033363 A1), AXMI-270 (U.S. Patent Publication 2014-0223598 A1), AXMI-345 (U.S. Patent Publication 2014-0373195 A1), AXMI-335 (International Application Publication WO2013/134523(A2)), DIG-3 (U.S. Patent Publication 2013-0219570 A1), DIG-5 (U.S. Patent Publication 2010-0317569 A1), DIG-11 (U.S. Patent Publication 2010-0319093 A1), AfIP-1A and derivatives thereof (U.S. Patent Publication 2014-0033361 A1), AfIP-1B and derivatives thereof (U.S. Patent Publication 2014-0033361 A1), PIP-1APIP-1B (U.S. Patent Publication 2014-0007292 A1), PSEEN3174 (U.S. Patent Publication 2014-0007292 A1), AECFG-592740 (U.S. Patent Publication 2014-0007292 A1), Pput_1063 (U.S. Patent Publication 2014-0007292 A1), DIG-657 (International Application Publication WO2015/195594(A2)), Pput_1064 (U.S. Patent Publication 2014-0007292 A1), GS-135 and derivatives thereof (U.S. Patent Publication 2012-0233726 A1), GS153 and derivatives thereof (U.S. Patent Publication 2012-0192310 A1), GS154 and derivatives thereof (U.S. Patent Publication 2012-0192310 A1), GS155 and derivatives thereof (U.S. Patent Publication 2012-0192310 A1), SEQ ID NO:2 and derivatives thereof as described in U.S. Patent Publication 2012-0167259 A1, SEQ ID NO:2 and derivatives thereof as described in U.S. Patent Publication 2012-0047606 A1, SEQ ID NO:2 and derivatives thereof as described in U.S. Patent Publication 2011-0154536 A1, SEQ ID NO:2 and derivatives thereof as described in U.S. Patent Publication 2011-0112013 A1, SEQ ID NO:2 and 4 and derivatives thereof as described in U.S. Patent Publication 2010-0192256 A1, SEQ ID NO:2 and derivatives thereof as described in U.S. Patent Publication 2010-0077507 A1, SEQ ID NO:2 and derivatives thereof as described in U.S. Patent Publication 2010-0077508 A1, SEQ ID NO:2 and derivatives thereof as described in U.S. Patent Publication 2009-0313721 A1, SEQ ID NO:2 or 4 and derivatives thereof as described in U.S. Patent Publication 2010-0269221 A1, SEQ ID NO:2 and derivatives thereof as described in U.S. Pat. No. 7,772,465 (B2), CF161_0085 and derivatives thereof as described in WO2014/008054 A2, Lepidopteran toxic proteins and their derivatives as described in US Patent Publications US2008-0172762 A1, US2011-0055968 A1, and US2012-0117690 A1; SEQ ID NO:2 and derivatives thereof as described in U.S. Pat. No. 7,510,878(B2), SEQ ID NO:2 and derivatives thereof as described in U.S. Pat. No. 7,812,129(B1), Cry71Aa1 and Cry72Aa1 (US Patent Publication US2016-0230187 A1), Axmi422 (US Patent Publication US2016-0201082 A1), Axmi440 (US Patent Publication US2016-0185830 A1), Axmi281 (US Patent Publication 2016-0177332 A1), BT-0044, BT-0051, BT-0068, BT-0128 and variants thereof (WO 2016-094159 A1), BT-009, BT-0012, BT-0013, BT-0023, BT0067 and variants thereof (WO 2016-094165 A1), Cry1JP578V, Cry1JPS1, Cry1 JPS1P578V (WO 2016-061208 A1); and the like.

Such additional polypeptide for the control of Coleopteran pests may be selected from the group consisting of an insect inhibitory protein, such as, but not limited to, Cry3Bb (U.S. Pat. No. 6,501,009), Cry1C variants, Cry3A variants, Cry3, Cry3B, Cry34/35, 5307, AXMI134 (U.S. Patent Publication 2013-0167264 A1) AXMI-184 (U.S. Patent Publication 2010-0004176 A1), AXMI-205 (U.S. Patent Publication 2014-0298538 A1), AXMI-207 (U.S. Patent Publication 2013-0303440 A1), AXMI-218, AXMI-220 (U.S. Patent Publication 20140245491A1), AXMI-221z, AXMI-223z (U.S. Patent Publication 2014-0196175 A1), AXMI-279 (U.S. Patent Publication 2014-0223599 A1), AXMI-R1 and variants thereof (U.S. Patent Publication 2010-0197592 A1, TIC407, TIC417, TIC431, TIC807, TIC853, TIC901, TIC1201, TIC3131, DIG-10 (U.S. Patent Publication 2010-0319092 A1), eHIPs (U.S. Patent Application Publication No. 2010/0017914), IP3 and variants thereof (U.S. Patent Publication 2012-0210462 A1) 7-Hexatoxin-Hv1a (U.S. Patent Application Publication 2014-0366227 A1), PHI-4 variants (U.S. Patent Application Publication 2016-0281105 A1), PIP-72 variants (WO 2016-144688 A1), PIP-45 variants, PIP-64 variants, PIP-74 variants, PIP-75 variants, and PIP-77 variants (WO 2016-144686 A1), DIG-305 (WO 2016109214 A1), PIP-47 variants (U.S. Patent Publication 2016-0186204 A1), DIG-17, DIG-90, DIG-79 (WO 2016-057123 A1), DIG-303 (WO 2016-070079 A1); and the like.

In other embodiments, such composition/formulation can further comprise at least one additional polypeptide that exhibits insect inhibitory activity to an insect that is not inhibited by an otherwise insect inhibitory protein of the present invention to expand the spectrum of insect inhibition obtained, e.g., an additional polypeptide that exhibits insect inhibitory activity to Hemipterans or Thysanopterans.

The possibility for insects to develop resistance to certain insecticides has been documented in the art. One insect resistance management strategy is to employ transgenic crops that express two distinct insect inhibitory agents that operate through different modes of action. Therefore, any insects with resistance to either one of the insect inhibitory agents can be controlled by the other insect inhibitory agent. Another insect resistance management strategy employs the use of plants that are not protected to the targeted Coleopteran or Lepidopteran pest species to provide a refuge for such unprotected plants. One particular example is described in U.S. Pat. No. 6,551,962, which is incorporated by reference in its entirety.

Other embodiments such as topically applied pesticidal chemistries that are designed for controlling pests that are also controlled by the proteins disclosed herein to be used with proteins in seed treatments, spray on, drip on, or wipe on formulations can be applied directly to the soil (a soil drench), applied to growing plants expressing the proteins disclosed herein, or formulated to be applied to seed containing one or more transgenes encoding one or more of the proteins disclosed. Such formulations for use in seed treatments can be applied with various stickers and tackifiers known in the art. Such formulations can contain pesticides that are synergistic in mode of action with the proteins disclosed, so that the formulation pesticides act through a different mode of action to control the same or similar pests that can be controlled by the proteins disclosed, or that such pesticides act to control pests within a broader host range or plant pest species that are not effectively controlled by the TIC7040, TIC7040HT, TIC7042, TIC7381, TIC7382, TIC7383, TIC7386, TIC7388, TIC7389, variant, truncation variant, chimera, or related family member pesticidal proteins.

The aforementioned composition/formulation can further comprise an agriculturally-acceptable carrier, such as a bait, a powder, dust, pellet, granule, spray, emulsion, a colloidal suspension, an aqueous solution, a *Bacillus* spore/crystal preparation, a seed treatment, a recombinant plant cell/plant tissue/seed/plant transformed to express one or more of the proteins, or bacterium transformed to express one or more of the proteins. Depending on the level of insect inhibitory or insecticidal inhibition inherent in the recombinant polypeptide and the level of formulation to be applied to a plant or diet assay, the composition/formulation can include various by weight amounts of the recombinant polypeptide, e.g. from 0.0001% to 0.001% to 0.01% to 1% to 99% by weight of the recombinant polypeptide.

EXAMPLES

In view of the foregoing, those of skill in the art should appreciate that changes can be made in the specific aspects which are disclosed and still obtain a like or similar result without departing from the spirit and scope of the invention. Thus, disclosed specific structural and functional details are not to be interpreted as limiting. It should be understood that the entire disclosure of each cited reference is incorporated within this disclosure.

Example 1

Discovery of TIC7040, TIC7040HT, TIC7042, TIC7381, TIC7382, TIC7383, TIC7386, TIC7388, TIC7389

This Example describes the discovery of the pesticidal proteins TIC7040, TIC7040HT, TIC7042, TIC7381, TIC7382, TIC7383, TIC7386, TIC7388, and TIC7389.

Sequences encoding novel *Brevibacillus laterosporus* (Bl) pesticidal proteins were identified, cloned, sequence confirmed and tested in insect bioassay. The pesticidal proteins TIC7040, TIC7040HT, TIC7042, TIC7381, TIC7382, TIC7383, TIC7386, TIC7388, and TIC7389 were isolated from the *Brevibacillus laterosporus* strains listed in Table 3, and represent novel pesticidal proteins belonging to the Cry43 family of toxins.

TABLE 3

Novel Cry43 pesticidal toxin proteins and corresponding *Brevibacillus laterosporus* strains.

| Toxin | DNA SEQ ID NO: | Protein SEQ ID NO: | *Brevibacillus laterosporus* strains | Length (a.a.) |
|---|---|---|---|---|
| TIC7040 | 1 | 2 | DSC005019 | 1259 |
| TIC7040HT | 3 | 4 | DSC005019 | 1295 |
| TIC7042 | 11 | 12 | DSC005973 | 1266 |
| TIC7381 | 13 | 14 | DSC006713 | 1269 |
| TIC7382 | 15 | 16 | DSC007657 | 1246 |
| TIC7383 | 17 | 18 | DSC008106 | 1256 |
| TIC7386 | 29 | 30 | DSC007651 | 1279 |
| TIC7388 | 31 | 32 | DSC007962 | 1269 |
| TIC7389 | 33 | 34 | DSC006878 | 1319 |

Polymerase chain reaction (PCR) primers were designed based upon contigs derived from sequencing of each *Brevibacillus laterosporus* strains listed in Table 3. Amplicons of the full length coding sequence for each protein toxin was produced using total DNA isolated from each strain listed in Table 3. With respect to TIC7040, a coding sequence of 3,888 bp was produced through amplification and differed from the predicted coding sequence of 3,780 bp. The amplified coding sequence and corresponding amino acid sequence were designated "TIC7040HT" to distinguish it from the original predicted contig, TIC7040. Each of the amplicons, with the exception of TIC7040, were cloned using methods known in the art into *Bacillus thuringiensis* (Bt) expression vectors in operable linkage with a Bt expressible promoter.

Example 2

TIC7040HT, TIC7042, TIC7381, TIC7382, and TIC7383 Demonstrate Coleopteran and Lepidopteran Activity in Insect Bioassay This Example illustrates inhibitory activity exhibited by TIC7040HT, TIC7042, TIC7381, TIC7382, and TIC7383 proteins against various species of Coleoptera and Lepidoptera.

The pesticidal proteins TIC7040HT, TIC7042, TIC7381, TIC7382, and TIC7383 were expressed in Bt and assayed for toxicity against various species of Lepidoptera and Coleoptera. Preparations of each toxin were assayed against the Coleopteran species Western Corn Rootworm (*Diabrotica virgifera virgifera*, WCR), Cry3Bb-resistant Western Corn Rootworm (*Diabrotica virgifera virgifera*, WCRHP), Northern Corn Rootworm (*Diabrotica barberi*, NCR), Southern Corn Rootworm (*Diabrotica undecimpunctata howardii*, SCR), and Colorado potato beetle (*Leptinotarsa decemlineata*, CPB). Preparations of each toxin were also assayed against the Lepidopteran species Black Cutworm (*Agrotis ipsilon*, BCW), Corn Earworm (*Helicoverpa zea*, (CEW), also known as Soybean Podworm and Cotton Bollworm), Diamondback Moth (*Plutella xylostella*, DBM), European Corn Borer (*Ostrinia nubilalis*, ECB), Fall Armyworm (*Spodoptera frugiperda*, FAW), Southern Armyworm (*Spodoptera eridania*, SAW), Soybean Looper (*Pseudoplusia includes*, SBL), Southwestern Corn Borer (*Diatraea grandiosella*, SWCB), tobacco budworm (*Heliothis virescens*, TBW), and Velvetbean Caterpillar (*Anticarsia gemmatalis*, VBC). The toxin preparations were also assayed against the Hemipteran species Tarnished plant bug (*Lygus lineolaris*), Western tarnished plant bug (*Lygus hesperus*), and Neotropical Brown Stink Bug (*Euschistus heros*).

Transformed Bt expressing TIC7040HT, TIC7042, TIC7381, TIC7382, or TIC7383 were grown for twenty four (24) hours, and spores as well as solubilized proteins were added to the insect diet for assay. Mortality and stunting were evaluated by comparing the growth and development of insects on a diet with a culture from a Bt strain expressing TIC7040HT, TIC7042, TIC7381, TIC7382, or TIC7383 to insects on a diet with an untreated control culture. Activity was not observed for Hemipteran insect pests for TIC7040HT, TIC7042, TIC7381, TIC7382, or TIC7383. Activity was observed for Coleopteran and Lepidopteran insect pests. The bioassay activity with respect to stunting (S) and mortality (M) observed for each protein is presented in Tables 4 (Coleoptera) and 5 (Lepidoptera), wherein "+" indicates activity, an empty cell indicates no activity observed, and "NT" indicates the toxin was not assayed against that specific insect pest.

TABLE 4

Bioassay activity of TIC7040HT, TIC7042, TIC7381, TIC7382, and TIC7383 against Coleopteran insect pests.

| Toxin | WCR S | WCR M | WCRHP S | WCRHP M | NCR S | NCR M | SCR S | SCR M | CPB S | CPB M |
|---|---|---|---|---|---|---|---|---|---|---|
| TIC7040HT | + | + | + | + | + | + | + |   | + | + |
| TIC7042 | + | + | + | + | + | + | + |   | + | + |
| TIC7381 | + | + | + | + | + | + | + | + | + | + |
| TIC7382 | + | + | + | + | + | + | + |   | + | + |
| TIC7383 | + | + | + | + | + | + | + |   | + | + |
| TIC7389 | + | + | NT | NT | NT | NT | NT | NT | + | + |

TABLE 5

Bioassay activity of TIC7040HT, TIC7042, TIC7381, TIC7382, and TIC7383 against Lepidopteran insect pests.

| Toxin | BCW S | BCW M | CEW S | CEW M | DBM S | DBM M | ECB S | ECB M | FAW S | FAW M | SAW S | SAW M | SBL S | SBL M | SWCB S | SWCB M | TBW S | TBW M | VBC S | VBC M |
|---|---|---|---|---|---|---|---|---|---|---|---|---|---|---|---|---|---|---|---|---|
| TIC7040HT |   |   | + |   | + | + | + |   | + |   |   |   | + |   | + |   |   |   | + | + |
| TIC7042 | + |   | + |   | + | + | + |   | + |   |   |   | + |   |   |   |   |   | + | + |
| TIC7381 |   |   | + |   | + | + | + |   | + | + |   |   | + | + | + |   |   |   | + |   |
| TIC7382 |   |   |   |   | + | + | + | + |   |   |   |   | + |   | + | + |   |   | + |   |
| TIC7383 |   |   | + |   | + |   | + |   |   |   |   |   |   |   |   |   |   |   | + |   |

As can be seen in Tables 4 and 5, the pesticidal proteins TIC7040HT, TIC7042, TIC7381, TIC7382, and TIC7383 demonstrated activity against many of the Coleopteran and Lepidopteran insect pest species. TIC7040HT demonstrated activity against the Coleopteran pests WCR, WCRHP, NCR, SCR, and CPB; and the Lepidopteran insect pests CEW, DBM, ECB, FAW, SBL, SWCB, and VBC. TIC7042 demonstrated activity against the Coleopteran pests WCR, WCRHP, NCR, SCR, and CPB; and the Lepidopteran insect pests BCW, CEW, DBM, ECB, FAW, SBL, and VBC. Mortality caused by TIC7042 against WCR was very high. TIC7381 demonstrated activity against the Coleopteran pests WCR, WCRHP, NCR, SCR, and CPB; and the Lepidopteran insect pests CEW, DBM, ECB, FAW, SBL, SWCB, and VBC. TIC7382 demonstrated activity against the Coleopteran pests WCR, WCRHP, NCR, SCR, and CPB; and the Lepidopteran insect pests DBM, ECB, SBL, SWCB, and VBC. TIC7383 demonstrated activity against the Coleopteran pests WCR, WCRHP, NCR, SCR, and CPB and; the Lepidopteran insect pests CEW, DBM, ECB, and VBC.

The pesticidal protein TIC7389 demonstrated activity against the Coleopteran pests, WCR and CPB. TIC7389 was also assayed against the Lepidopteran insect pest species Corn Earworm, Fall Armyworm, and Soybean Looper, as well as the Hemipteran species Tarnished plant bug and Western tarnished plant bug. Stunting was observed for SBL, but not the other two Lepidopteran species and the two Hemipteran insect pests.

The insect toxins TIC7040HT, TIC7042, TIC7381, TIC7382, TIC7383, and TIC7389 demonstrate activity against a variety of Coleopteran and Lepidopteran insect pest species. The insect toxin TIC7389 demonstrates toxicity to the Lepidopteran insect pest Soybean Looper.

Example 3

Tryptic Digested TIC7040HT and TIC7383, and Chymotryptic Digested TIC7040HT Demonstrate Activity Against Western Corn Rootworm This Example illustrates inhibitory activity exhibited by tryptic and chymotryptic digested TIC7040HT, and tryptic digested TIC7383 proteins against Western Corn Rootworm.

Protein samples of TIC7040HT were subjected to tryptic and chymotryptic digest in separate reactions. Likewise, TIC7383 was subjected to a tryptic digest. The tryptic and chymotryptic digests were performed using methods known in the art. The digested proteins were analyzed by mass spectrometry to determine the resulting protein fragments.

The resulting tryptic and chymotryptic fragments of TIC7040HT, and the resulting tryptic fragment of TIC7383 are presented in Table 6.

The digested proteins were used in bioassay against Western Corn Rootworm. Table 6 shows the assay of activity for each digested protein preparation, and the full length TIC7040HT and TIC7383 proteins.

TABLE 6

Bioassay activity of TIC7040HT, tryptic and chymotryptic digested TIC7040HT, TIC7383, and tryptic digested TIC7383 against Western Corn Rootworm.

| Toxin | DNA SEQ ID NO: | Protein SEQ ID NO: | Amino Acid Position Relative to Full Length Protein | Stunting | Mortality |
|---|---|---|---|---|---|
| TIC7040HT | 3 | 4 |  | + | + |
| TIC7040HT_Tryp | 70 | 71 | 43-624 | + | + |
| TIC7040HT_Chymo | 72 | 73 | 45-641 | + | + |
| TIC7383 | 17 | 18 |  | + | + |
| TIC7383_Tryp | 74 | 75 | 55-668 | + | + |

As can be seen in Table 6, the tryptic and chymotryptic digested TIC7040HT and the tryptic digested TIC7383 proteins retained activity against Western Corn Rootworm.

Example 4

Truncations of TIC7040HT and TIC7383 Demonstrate Coleopteran Activity in Insect Bioassay This Example illustrates inhibitory activity exhibited by truncations of the TIC7040HT and TIC7383 proteins against various species of Coleoptera.

Coding sequences encoding truncations of TIC7040HT and TIC7383 were produced using methods known in the art and cloned into bacterial expression vectors to be expressed in Bt. The truncated proteins were provided in insect diets and assayed for activity against Coleopteran insect pests. The amino acid positions of the truncated TIC7040HT and TIC7383 toxins relative to the full length TIC7040HT and TIC7383 are shown in Table 7.

Transformed Bt expressing truncations of TIC7040HT and TIC7383 were grown for twenty four (24) hours and spores, as well as solubilized proteins, were added to insect diet for assay. Mortality and stunting were evaluated by comparing the growth and development of insects on a diet with a culture from the Bt strain expressing truncations of TIC7040HT or TIC7383 to insects on a diet with an untreated control culture.

The truncations of TIC7040HT and TIC7383 were assayed for toxicity against various species of Coleoptera. Preparations of each toxin were assayed against the Coleopteran species Western Corn Rootworm, Cry3Bb-resistant Western Corn Rootworm, and Colorado potato beetle.

Activity was observed for Coleopteran insect pests. The bioassay activity with respect to stunting (S) and mortality (M) observed for each protein is presented in Table 7, wherein "+" indicates activity, an empty cell indicates no activity observed, and "NT" indicates the toxin was not assayed against that specific insect pest. The activity of the full length TIC7040HT and TIC7383 is also provided for comparison to the truncated protein activity.

TABLE 7

Bioassay activity of truncations of TIC7040HT and TIC7383 against Coleopteran insect pests.

| Toxin | DNA SEQ ID NO: | Protein SEQ ID NO: | Amino Acid Positions Relative to Full Length Protein | WCR | | WCRHP | | NCR | | SCR | | CPB | |
|---|---|---|---|---|---|---|---|---|---|---|---|---|---|
| | | | | S | M | S | M | S | M | S | M | S | M |
| TIC7040HT | 3 | 4 | | + | + | + | + | + | + | + | | + | + |
| TIC7040HT_5 | 7 | 8 | 13-611 | + | + | | | NT | NT | NT | NT | + | + |
| TIC7040HT_6 | 9 | 10 | 13-671 | + | + | | | NT | NT | NT | NT | + | + |
| TIC7383 | 17 | 18 | | + | + | + | + | + | + | + | | + | + |
| TIC7383_2 | 19 | 20 | 12-1256 | + | + | | | NT | NT | NT | NT | + | + |
| TIC7383_3 | 21 | 22 | 1-659 | + | + | + | | NT | NT | NT | NT | + | + |
| TIC7383_4 | 23 | 24 | 1-679 | + | + | | | NT | NT | NT | NT | + | + |
| TIC7383_5 | 25 | 26 | 15-659 | + | + | | | NT | NT | NT | NT | + | + |
| TIC7383_6 | 27 | 28 | 15-679 | + | + | | | NT | NT | NT | NT | + | + |

As can be seen in Table 7, truncations of TIC7040HT and TIC7383 maintained activity against WCR and CPB.

Example 5

Design of Synthetic Coding Sequences Encoding TIC7040, TIC7040HT, TIC7042, TIC7381, TIC7382, TIC7383, and Truncation Variants of TIC7040HT, TIC7042, TIC7382, and TIC7383 for Expression in Plant Cells Synthetic or artificial coding sequences were constructed for use in expression of TIC7040, TIC7040HT, TIC7042, TIC7381, TIC7382, TIC7383, and truncation variants of TIC7040HT, TIC7042, TIC7382, and TIC7383, in plants. These synthetic coding sequences were cloned into a binary plant transformation vectors, and used to transform plant cells. The synthetic nucleic acid sequences were synthesized according to methods generally described in U.S. Pat. No. 5,500,365, avoiding certain inimical problem sequences such as ATTTA and A/T rich plant polyadenylation sequences while preserving the amino acid sequence of the native Bl protein. The synthetic coding sequences for the TIC7040, TIC7040HT, TIC7042, TIC7381, TIC7382, TIC7383, and truncation variants of TIC7040HT, TIC7042, TIC7382, and TIC7383 pesticidal proteins are presented Table 8.

TABLE 8

Synthetic coding sequences used for expression in plant cells encoding TIC7040, TIC7040HT, TIC7042, TIC7381, TIC7382, TIC7383, and truncation variants of TIC7040HT, TIC7042, TIC7382, and TIC7383.

| Description | DNA SEQ ID NO: | Protein SEQ ID NO: | Additional Alanine Residue after Initiating Methionine | N-terminal Truncation | C-Terminal Truncation | Amino Acid Position Relative to Full Length Protein and Mutations |
|---|---|---|---|---|---|---|
| CR-BREla.TIC7040.nno_Mc:1 | 35 | 2 | No | No | No | |
| CR-BREla.TIC7040_10.nno_Mc:1 | 36 | 4 | No | No | No | |
| CR-BREla.TIC7040_10.nno_Mc:3 | 37 | 4 | No | No | No | |
| CR-BREla.TIC7040_10.nno_Mc:4 | 38 | 4 | No | No | No | |
| CR-BREla.TIC7040_10.nno_Mc:5 | 39 | 4 | No | No | No | |
| CR-BREla.TIC7040_10.nno_Mc:6 | 40 | 4 | No | No | No | |
| CR-BREla.TIC7040_10.nno_Mc:7 | 41 | 4 | No | No | No | |
| CR-BREla.TIC7040_1.nno_Mc:1 | 42 | 43 | No | Yes | Yes | 15-651 |
| CR-BREla.TIC7040_2.nno_Mc:1 | 44 | 10 | No | Yes | Yes | 13-671 |
| CR-BREla.TIC7040_11.nno_Mc:1 | 45 | 46 | No | Yes | Yes | 14-671 |
| CR-BREla.TIC7040_12.nno_Mc:2 | 47 | 48 | No | No | Yes | 1-660 |
| CR-BREla.TIC7040_13.nno_Mc:1 | 49 | 50 | No | No | Yes | 1-627 |
| CR-BREla.TIC7040_14.nno_Mc:1 | 76 | 77 | Yes | Yes | Yes | 52-660 |
| CR-BREla.TIC7042.nno_Mc:1 | 51 | 12 | No | No | No | |
| CR-BREla.TIC7042_1.nno_Mc:1 | 52 | 53 | No | Yes | Yes | 11-646 |
| CR-BREla.TIC7042_2.nno_Mc:1 | 54 | 55 | No | Yes | Yes | 11-665 |
| CR-BREla.TIC7381_1.nno_Mc:1 | 56 | 57 | Yes | No | No | |
| CR-BREla.TIC7381_2.nno_Mc:1 | 78 | 79 | Yes | No | Yes | 1-658 |
| CR-BREla.TIC7381_3.nno_Mc:1 | 80 | 81 | Yes | Yes | Yes | 50-658 |
| CR-BREla.TIC7382_1.nno_Mc:1 | 58 | 59 | Yes | No | No | |
| CR-BREla.TIC7382_2.nno_Mc:1 | 60 | 61 | Yes | No | Yes | 1-659 |
| CR-BREla.TIC7382_3.nno_Mc:1 | 82 | 83 | Yes | Yes | Yes | 52-659 |
| CR-BREla.TIC7383_1.nno_Mc:1 | 62 | 63 | Yes | No | No | |
| CR-BREla.TIC7383_7.nno_Mc:1 | 64 | 65 | Yes | Yes | Yes | 54-668 |
| CR-BREla.TIC7383_8.nno_Mc:1 | 66 | 67 | Yes | No | Yes | 1-661 |
| CR-BREla.TIC7383_9.nno_Mc:1 | 68 | 69 | Yes | No | Yes | 1-668 |
| CR-BREla.TIC7383_19.nno_Mc:1 | 84 | 85 | No | Yes | Yes | 15-668 |
| CR-BREla.TIC7383_20.nno_Mc:1 | 86 | 87 | No | Yes | Yes | 15-661 |
| CR-BREla.TIC7383_21.nno_Mc:1 | 88 | 89 | Yes | Yes | Yes | 54-661 |
| CR-BREla.TIC7383_22.nno_Mc:1 | 90 | 91 | No | Yes | Yes | 54-668 |
| CR-BREla.TIC7383_23.nno_Mc:1 | 92 | 93 | No | Yes | Yes | 54-661 |
| CR-BREla.TIC7383_24.nno_Mc:2 | 94 | 95 | No | Yes | Yes | 73-661 |
| CR-BREla.TIC7383_25.nno_Mc:3 | 96 | 97 | No | Yes | Yes | 94-661 |
| CR-BREla.TIC7383_26.nno_Mc:1 | 98 | 99 | No | Yes | Yes | 114-661 |
| CR-BREla.TIC7383_27.nno_Mc:1 | 100 | 101 | Yes | Yes | Yes | 54-658 |
| CR-BREla.TIC7383_28.nno_Mc:1 | 102 | 103 | No | Yes | Yes | 15-658 |
| CR-BREla.TIC7383_29.nno_Mc:1 | 104 | 105 | Yes | No | Yes | 1-963 |
| CR-BREla.TIC7383_30.nno_Mc:1 | 106 | 107 | Yes | No | No | K964A; R966A; K968A |
| CR-BREla.TIC7383_31.nno_Mc:1 | 108 | 109 | Yes | No | Yes | 1-1065; K964A; R966A; K968A |
| CR-BREla.TIC7383_32.nno_Mc:1 | 110 | 111 | Yes | No | No | Deletion 964-969 |

Example 6

Expression Cassettes for Expression of TIC7040, TIC7040HT, TIC7042, TIC7381, TIC7382, TIC7383, and Truncation Variants of TIC7040HT, TIC7042, TIC7382, and TIC7383 in Plant Cells A variety of plant expression cassettes were designed with the sequences as set forth in Table 8. Such expression cassettes are useful for transient expression in plant protoplasts or transformation of plant cells. Typical expression cassettes are designed with respect to the eventual placement of the protein within the plant cell. For a plastid targeted protein, the synthetic TIC7040, TIC7040HT, TIC7042, TIC7381, TIC7382, TIC7383 or truncation variant of TIC7040HT, TIC7042, TIC7382, or TIC7383 pesticidal protein coding sequences are operably linked in frame with a chloroplast targeting signal peptide coding sequence. The resulting plant transformation vectors comprise a first transgene cassette for expression of the pesticidal protein which comprises a constitutive promoter, operably linked 5' to a leader, operably linked 5' to an intron (or optionally no intron), operably linked 5' to a synthetic coding sequence encoding a plastid targeted or untargeted TIC7040, TIC7040HT, TIC7042, TIC7381, TIC7382, TIC7383, or truncation variant of TIC7040HT, TIC7042, TIC7382, or TIC7383 protein, which is in turn operably linked 5' to a 3' UTR and, a second transgene cassette for the selection of transformed plant cells using glyphosate or antibiotic selection. All of the elements described above are arranged contiguously often with additional sequence provided for the construction of the expression cassette such as restriction endonuclease sites or ligation independent cloning sites.

Example 7

TIC7382 Provides Efficacious Resistance to Western Corn Rootworm when Expressed in Stably Transformed Corn Plants This Example illustrates the inhibitory activity exhibited by truncations of TIC7382 against Coleoptera, such as Western Corn Rootworm, when expressed in plants and provided as a diet to the respective insect pest.

Binary plant transformation vectors comprising transgene cassettes designed to express untargeted TIC7382 (CR-BREla.TIC7382_1.nno_Mc:1) and the truncation variants CR-BREla.TIC7382_2.nno_Mc:1 and CR-BREla.TIC7382_3.nno_Mc:1 were cloned using methods known in the art. The plant transformation vectors comprised a first transgene cassette for expression of the TIC7382 pesticidal protein or one of the truncation variants which comprised a root preferred promoter, operably linked 5' to a leader, operably linked 5' to an intron, operably linked 5' to a synthetic coding sequence encoding TIC7382 or the truncation variants, each of which comprised an additional alanine residue immediately following the initiating methionine, which was in turn was operably linked 5' to a 3' UTR and, a second transgene cassette for the selection of transformed plant cells using glyphosate. The resulting vectors were used to stably transform corn plants using methods known in the art. Single T-DNA insertion events were selected and grown. Pesticidal activity was assayed against Western Corn Rootworm feeding on the roots of the stably transformed corn plants.

$R_0$ stably transformed plants were used to assay for Coleopteran resistance as well as generating $F_1$ progeny. Multiple single copy events were selected from each binary vector transformation. A portion of those events arising from each binary vector transformation were used in the Coleopteran assay, while another portion of events were used to generate $F_1$ progeny for further testing.

The $R_0$ assay plants were transplanted to eight inch pots. The plants were inoculated with eggs from Western Corn Rootworm. The eggs were incubated for approximately ten (10) days prior to inoculation to allow hatching to occur four (4) days after inoculation to ensure a sufficient number of larvae survive and are able to attack the corn roots. The transformed plants were inoculated at approximately V2 to V3 stage. The plants were grown after infestation for approximately twenty eight (28) days. The plants were removed from the pots with the roots being carefully washed to remove all soil. The damage to the roots was assessed using a damage rating scale of 1-5, as presented in Table 9. Comparison was also made to the negative control to assure the assay has been performed properly. Low root damage scores indicate resistance conferred by the TIC7382 protein or the truncation variants to WCR. An RDR score of 1.0 to 2.5 represents good efficacy, an RDR score of 2.6 to 3.5 represents medium efficacy, and an RDR score of 3.6 to 5.0 represents low efficacy.

TABLE 9

$R_0$ root damage rating scores.

| Root Damage Score | Description |
| --- | --- |
| 1 | No visible feeding |
| 2 | Some feeding; no pruning |
| 3 | Pruning of at least one root |
| 4 | Entire node pruned |
| 5 | More than one node pruned |

For $F_1$ assay, eggs from Western Corn Rootworm were incubated for approximately ten (10) days to allow hatching within four (4) days after inoculation. The plants were inoculated at approximately V2 to V3 stage. Each pot was inoculated with about two thousand eggs. The plants were grown after infestation for approximately twenty eight (28) days. The plants were removed from the pots with the roots being carefully washed to remove all soil. The damage to the roots were assessed using a damage rating scale of 0-3, as presented in Table 10. Comparison was made to the negative control to assure the assay was performed properly. Low root damage scores indicate resistance conferred TIC7382, or the truncation to WCR. An RDR at F1 of 0.0 to 0.75 represents good efficacy, an RDR of 0.76 to 1.5 represents medium efficacy, and an RDR of 1.6 to 3.0 represents low efficacy.

TABLE 10

$F_1$ root damage rating scores.

| Root Damage Score | Description |
| --- | --- |
| 0 | No visible feeding |
| 0.01-0.09 | Feeding scars and tracks |
| 0.1-0.9 | Root pruning, but less than a full node |
| 1.0-1.9 | At least a full node (or equivalent) destroyed to within 1.5 inches of plant |
| 2.0-2.9 | Two or more nodes gone |
| 3 | Three or more nodes gone |

Table 11 shows the average Root Damage Rating (RDR) assayed for the TIC7382 protein and truncation variants.

TABLE 11

Average Root Damage Rating (RDR) of transgenic corn plants expressing TIC7382 or truncation variants.

| Description | Coding Sequence SEQ ID NO: | Protein SEQ ID NO: | Amino Acid Position Relative to Full Length Protein | Average $R_0$ RDR | Average $F_1$ RDR |
|---|---|---|---|---|---|
| CR-BREla.TIC7382_1.nno_Mc:1 | 58 | 59 |  | 3.7 | 2.4 |
| CR-BREla.TIC7382_2.nno_Mc:1 | 60 | 61 | 1-658 | 3.3 | 1.1 |
| CR-BREla.TIC7382_3.nno_Mc:1 | 82 | 83 | 50-658 | 1.6 | 1.0 |

As can be seen in Table 11, a C-terminal truncation of the TIC7382 protein giving rise to the truncation variant, CR-BREla.TIC7382_2.nno_Mc:1, improved efficacy relative to the Root Damage Ratings of CR-BREla.TIC7382_1.nno_Mc:1. Truncation of the TIC7382 protein at both the N-terminus and C-terminus giving rise to the truncation variant, CR-BREla.TIC7382_3.nno_Mc:1, resulted in less damage to the corn roots and further improved efficacy as demonstrated by a lower $R_0$ Root Damage Rating when compared to the Root Damage Ratings of CR-BREla.TIC7382_1.nno_Mc:1 and CR-BREla.TIC7382_2.nno_Mc:1.

Example 8

Assay of Activity of TIC7040, TIC7040HT, TIC7042, TIC7381, TIC7382, TIC7383, and Truncation Variants of TIC7040HT, TIC7042, TIC7382, or TIC7383 Against Coleopteran Corn Rootworm Pests when Expressed in Stably Transformed Corn Plants This Example illustrates the inhibitory activity of TIC7040, TIC7040HT, TIC7042, TIC7381, TIC7382, TIC7383, or truncation variants of TIC7040HT, TIC7042, TIC7382, or TIC7383 against different Coleopteran species that feed on corn roots.

Binary plant transformation vectors comprising transgene cassettes designed to express both plastid targeted and untargeted TIC7040, TIC7040HT, TIC7042, TIC7381, TIC7382, TIC7383, or truncation variants of TIC7040HT, TIC7042, TIC7382, or TIC7383 are cloned using methods known in the art and comprise the sequences as shown in Table 8. The resulting vectors are used to stably transform corn plants using methods known in the art. Single T-DNA insertion events are selected and grown. Pesticidal activity is assayed against the Coleopteran pests Western Corn Rootworm (*Diabrotica virgifera virgifera*, WCR), Northern Corn Rootworm (*Diabrotica barberi*, NCR), Mexican Corn Rootworm (*Diabrotica virgifera zeae*, MCR), Brazilian Corn Rootworm (*Diabrotica balteata*, BZR), Southern Corn Rootworm (*Diabrotica undecimpunctata howardii*, SCR), Colorado potato beetle (*Leptinotarsa decemlineata*, CPB), or a Brazilian Corn Rootworm complex (BCR, consisting of *Diabrotica viridula* and *Diabrotica speciosa*) feeding on the roots of the stably transformed corn plants.

$R_0$ stably transformed plants are used to assay for Coleopteran resistance as well as generating $F_1$ progeny. Multiple single copy events are selected from each binary vector transformation. A portion of the events arising from each binary vector transformation are used in the $R_0$ Coleopteran assay, while another portion of events are used to generate $F_1$ progeny for further testing.

The $R_0$ assay plants are transplanted to eight inch pots. The plants are inoculated with eggs from Western Corn Rootworm, Northern Corn Rootworm, or Southern Corn Rootworm. The eggs are incubated for approximately ten (10) days prior to inoculation to allow hatching to occur four (4) days after inoculation to ensure a sufficient number of larvae survive and are able to attack the corn roots. The transformed plants are inoculated at approximately V2 to V3 stage. The plants are grown after infestation for approximately twenty eight (28) days. The plants are removed from the pots with the roots being carefully washed to remove all soil. The damage to the roots is assessed using a damage rating scale of 1-5, as presented in Table 9 in Example 5. Comparison is also made to the negative controls to assure the assay has been performed properly. Multiple $R_0$ events for each binary vector transformation are used in the Coleopteran assay. Low root damage scores indicate resistance conferred by TIC7040, TIC7040HT, TIC7042, TIC7381, TIC7382, TIC7383, or truncation variants of TIC7040HT, TIC7042, TIC7382, or TIC7383 to the tested Coleopteran pest.

A portion of the $R_0$ stably transformed events arising from each binary vector transformation are used to produce $F_1$ progeny. The $R_0$ stably transformed plants are allowed to self-fertilize, producing $F_1$ progeny. The $F_1$ seed is planted. Heterozygous plants are identified through molecular methods known in the art and used for assay against Coleopteran pests, as well as ELISA expression measurements of toxin protein. A portion of the heterozygous $F_1$ progeny from each event are used for insect assay, while another portion is used to measure toxin protein expression.

Eggs from Western Corn Rootworm, Northern Corn Rootworm, or Southern Corn Rootworm are incubated for approximately ten (10) days to allow hatching within four (4) days after inoculation. For WCR, each pot is inoculated with about two thousand eggs. For NCR, less eggs may be used due to the lower availability of eggs from this species. The plants are inoculated at approximately V2 to V3 stage. The plants are grown after infestation for approximately twenty eight (28) days. The plants are removed from the pots with the roots being carefully washed to remove all soil. The damage to the roots are assessed using a damage rating scale of 0-3, as presented in Table 10 in Example 5. Comparison is made to the negative control to assure the assay has been performed properly. Low root damage scores indicate resistance conferred by TIC7040, TIC7040HT, TIC7042, TIC7381, TIC7382, TIC7383, or truncation variants of TIC7040HT, TIC7042, TIC7382, or TIC7383 protein to the Coleopteran pest.

Example 9

Assay of Activity of TIC7040, TIC7040HT, TIC7042, TIC7381, TIC7382, TIC7383, or Truncation Variants of TIC7040HT, TIC7042, TIC7382, or TIC7383 Against Lepidopteran Pests when Expressed in Stably Transformed Corn, Soybean, or Cotton Plants This Example illustrates the assay of activity against various Lepidopteran pest species fed tissue from stably transformed corn, soybean or cotton plants expressing TIC7040, TIC7040HT, TIC7042, TIC7381, TIC7382, TIC7383, or truncation variants of TIC7040HT, TIC7042, TIC7382, or TIC7383.

Binary plant transformation vectors comprising transgene cassettes designed to express both plastid targeted and untargeted TIC7040, TIC7040HT, TIC7042, TIC7381, TIC7382, TIC7383, or truncation variants of TIC7040HT, TIC7042, TIC7382, or TIC7383 are cloned using methods known in the art and comprise the coding sequences as presented in Table 8.

Corn, soybean, or cotton is transformed with the binary transformation vectors described above using an *Agrobacterium*-mediated transformation method. The transformed cells are induced to form plants by methods known in the art. Bioassays using plant leaf disks are performed analogous to those described in U.S. Pat. No. 8,344,207. A non-transformed corn, soybean, or cotton plant is used to obtain tissue to be used as a negative control. Multiple transformation events from each binary vector are assessed against Lepidopteran pests such as, but not limited to, Black Cutworm, Corn Earworm, Diamondback Moth, European Corn Borer, Fall Armyworm, Southern Armyworm, Soybean Looper, Southwestern Corn Borer, Tobacco budworm, and Velvetbean Caterpillar. Those insects demonstrating stunting and/or mortality in the insect bioassay are determined to be susceptible to the effects of the tested TIC7040, TIC7040HT, TIC7042, TIC7381, TIC7382, TIC7383, or truncation variant of TIC7040HT, TIC7042, TIC7382, or TIC7383 insect toxin pesticidal protein.

Example 10

Assay of Activity of TIC7040, TIC7040HT, TIC7042, TIC7381, TIC7382, TIC7383, or Truncation Variants of TIC7040HT, TIC7042, TIC7382, or TIC7383 Against Flea Beetle Pests when Expressed in Stably Transformed Canola Plants This Example illustrates the assay of activity against various species of Flea Beetle when allowed to feed on whole transgenic canola plants or tissues derived from transgenic canola plants expressing TIC7040, TIC7040HT, TIC7042, TIC7381, TIC7382, TIC7383, or truncation variants of TIC7040HT, TIC7042, TIC7382, or TIC7383.

Binary plant transformation vectors comprising transgene cassettes designed to express both plastid targeted and untargeted TIC7040, TIC7040HT, TIC7042, TIC7381, TIC7382, TIC7383, or truncation variants of TIC7040HT, TIC7042, TIC7382, or TIC7383 are cloned using methods known in the art and comprise the coding sequences as presented in Table 8.

The resulting binary transformation vectors are used to stably transform canola plant cells using methods known in the art. The transformed cells are induced to form plants. Bioassays using plant leaf disks are performed analogous to those described in U.S. Pat. No. 8,344,207 using field collected Flea Beetles. A non-transformed canola plant is used to obtain tissue to be used as a negative control. Multiple transformation events from each binary vector are assessed against Coleopteran Flea Beetle pests such as, but not limited to, Crucifer Flea Beetle (*Phyllotreta cruciferae*), Striped Flea Beetle (*Phyllotreta striolata*), and Western Black Flea Beetle (*Phyllotreta pusilla*). Flea Beetle mortality is determined each day as the Beetles continue to feed. Leaf discs are changed every two (2) to three (3) days over a twelve (12) day period to assure fresh material is available to the Flea Beetles for feeding, and to reduce any impact of protein degradation in the sample.

Alternatively, transformed canola plants can be planted in a field where Flea Beetle infestations are present. The plants can be housed in a tent to prevent those Flea Beetles that emerge from the soil from escaping the experimental plots. Damage ratings of the canola leaves can be taken to determine which plants experienced lesser damage and demonstrated resistance to the Flea Beetles.

Example 11

Truncation of TIC7383 Improves Efficacy Against Corn Rootworm in Stably Transformed Corn Plants This Example illustrates the improvement of efficacy of the TIC7383 through truncations at the N-terminus, the C-terminus, or both termini.

Binary plant transformation vectors comprising transgene cassettes designed to express untargeted TIC7383 and truncation variants were cloned using method known in the art. The plant transformation vectors comprised a first transgene cassette for expression of the TIC7383 pesticidal protein or the truncation variants which comprised a root preferred promoter, operably linked 5' to a leader, operably linked 5' to an intron, operably linked 5' to a synthetic coding sequence encoding TIC7383 or the truncation variants, some of which comprised an additional alanine residue immediately following the initiating methionine, which was in turn was operably linked 5' to a 3' UTR and, a second transgene cassette for the selection of transformed plant cells using glyphosate. The resulting vectors were used to stably transform corn plants using methods known in the art. Single T-DNA insertion events were selected and grown. Pesticidal activity was assayed against Western Corn Rootworm feeding on the roots of the stably transformed corn plants.

$R_0$ stably transformed plants were used to assay for resistance to Western Corn Rootworm as well as generating $F_1$ progeny. Multiple single copy events were selected from each binary vector transformation. A portion of those events arising from each binary vector transformation were used in the Coleopteran assay, while another portion of events were used to generate $F_1$ progeny for further testing. $R_0$ and $F_1$ Root Damage Rating scores were determined using the Root Damage Rating scores as presented in Tables 9 and 10, respectively, presented in Example 7. Table 12 shows the average Root Damage Rating scores obtained from the $R_0$ and $F_1$ stably transformed corn plants expressing TIC7383 and truncation variants. Protein expression levels of TIC7383 and the corresponding truncation variants are also shown in Table 12 and are expressed as parts per million (ppm).

As can be seen in Table 12, truncations at the N-terminus, C-terminus, or both termini improved efficacy in some of the truncation variants as demonstrated by lower average Root Damage Rating scores relative to the full length TIC7383 protein (CR-BREla.TIC7383_1.nno_Mc:1). Truncations of the TIC7383 toxin also improved expression within the plant in most instances as well.

TABLE 12

Average Root Damage Rating (RDR) scores of stably transformed corn plants expressing TIC7383 and truncation variants.

| Description | Additional Alanine Residue after Initiating Methionine | Amino Acid Position Relative to CR-BREla.TIC7383_1.nno_Mc:1 | Protein Expression (ppin) | Average $R_0$ RDR | Average $F_1$ RDR |
|---|---|---|---|---|---|
| CR-BREla.TIC7383_1.nno_Mc:1 | Yes | | 11.9 | 3.8 | 2.2 |
| CR-BREla.TIC7383_7.nno_Mc:1 | Yes | 54-668 | 421.3 | 2.9 | 1.6 |
| CR-BREla.TIC7383_8.nno_Mc:1 | Yes | 1-661 | 289.2 | 2.4 | |
| CR-BREla.TIC7383_9.nno_Mc:1 | Yes | 1-668 | 317.2 | 3.3 | |
| CR-BREla.TIC7383_19.nno_Mc:1 | No | 15-668 | 23.7 | 3.3 | |
| CR-BREla.TIC7383_20.nno_Mc:1 | No | 15-661 | 29.1 | 3.9 | |
| CR-BREla.TIC7383_21.nno_Mc:1 | Yes | 54-661 | 617.4 | 2.7 | |
| CR-BREla.TIC7383_22.nno_Mc:1 | No | 54-668 | 451.3 | 2.6 | |
| CR-BREla.TIC7383_23.nno_Mc:1 | No | 54-661 | 343.1 | 2.8 | |
| CR-BREla.TIC7383_24.nno_Mc:2 | No | 73-661 | 356.5 | 2.9 | |
| CR-BREla.TIC7383_26.nno_Mc:1 | No | 114-661 | 8.5 | 3.9 | |
| CR-BREla.TIC7383_27.nno_Mc:1 | Yes | 54-658 | 356.2 | 2.9 | |
| CR-BREla.TIC7383_28.nno_Mc:1 | No | 15-658 | 25.4 | 3.7 | |

Example 12

Assay of Activity of Chimeras of TIC7381, TIC7382, TIC7383 and TIC7042 Against Western Corn Rootworm in Stably Transformed Corn Plants This Example illustrates the design of chimeras of TIC7381, TIC7382, TIC7383, and TIC7042 and the assay of activity against Western Corn Rootworm (WCR) in stably transformed corn plants expressing the chimeras.

Chimeras of TIC7381, TIC7382, TIC7383, and TIC7042 were designed wherein domains one and two (D1D2) of one toxin were combined with the third domain (D3) of another toxin. Table 13 below shows the composition of each chimera.

TABLE 13

Composition of the TIC7381, TIC7382, TIC7383, and TIC7042 chimeras.

| Description | Nucleotide SEQ ID NO: | Protein SEQ ID NO: | D1D2 | D3 |
|---|---|---|---|---|
| GOI-TIC10743.nno_Mc:1 | 112 | 113 | TIC7383 | TIC7042 |
| GOI-TIC10744.nno_Mc:1 | 114 | 115 | TIC7383 | TIC7381 |
| GOI-TIC10745.nno_Mc:1 | 116 | 117 | TIC7383 | TIC7382 |
| GOI-TIC10746.nno_Mc:1 | 118 | 119 | TIC7382 | TIC7383 |
| GOI-TIC10747.nno_Mc:1 | 120 | 121 | TIC7381 | TIC7383 |
| GOI-TIC10748.nno_Mc:1 | 122 | 123 | TIC7042 | TIC7383 |

Binary plant transformation vectors comprising transgene cassettes designed to express untargeted chimeras of TIC7381, TIC7382, TIC7383, and TIC7042 were cloned using methods known in the art. The plant transformation vectors comprised a first transgene cassette for expression of the chimeric toxin pesticidal protein which comprised a root preferred promoter, operably linked 5' to a leader, operably linked 5' to an intron, operably linked 5' to a synthetic coding sequence encoding the chimeras of TIC7381, TIC7382, TIC7383, and TIC7042, which comprised an additional alanine residue immediately following the initiating methionine, which was in turn was operably linked 5' to a 3' UTR and, a second transgene cassette for the selection of transformed plant cells using glyphosate. The resulting vectors were used to stably transform corn plants using methods known in the art. Single T-DNA insertion events were selected and grown. Pesticidal activity was assayed against Western Corn Rootworm feeding on the roots of the stably transformed corn plants.

$R_0$ stably transformed plants were used to assay for resistance to Western Corn Rootworm as well as generating $F_1$ progeny. Multiple single copy events were selected from each binary vector transformation. A portion of those events arising from each binary vector transformation were used in the Coleopteran assay, while another portion of events were used to generate $F_1$ progeny for further testing. $R_0$ and $F_1$ Root Damage Rating scores were determined using the Root Damage Rating scores as presented in Tables 9 and 10, respectively, presented in Example 7. Table 14 shows the average Root Damage Rating scores obtained from the $R_0$ and $F_1$ stably transformed corn plants expressing the chimeras of TIC7381, TIC7382, TIC7383, and TIC7042 or truncation variants, wherein "NT" indicates not tested. Comparison is made to a TIC7382 variant truncated at the N-terminus and C-terminus protoxin domain (CR-BREla.TIC7382_3.nno_Mc:1) and a TIC7383 variant truncated at the N-terminus and C-terminus protoxin domain (CR-BREla.TIC7383_7.nno_Mc:1).

TABLE 14

Average Root Damage Rating (RDR) scores of stably transformed corn plants expressing chimeras of TIC7381, TIC7382, TIC7383, and TIC7042 against Western Corn Rootworm.

| Description | Average $R_0$ RDR | Average $F_1$ RDR |
|---|---|---|
| Negative Control | | 2.8 |
| GOI-TIC10743.nno_Mc:1 | 3.4 | 2 |
| GOI-TIC10744.nno_Mc:1 | 3.3 | 2.3 |
| GOI-TIC10745.nno_Mc:1 | 3.8 | 2.6 |
| GOI-TIC10746.nno_Mc:1 | 1.3 | 0.4 |
| GOI-TIC10747.nno_Mc:1 | NT | NT |
| GOI-TIC10748.nno_Mc:1 | 3.3 | 2.7 |

TABLE 14-continued

Average Root Damage Rating (RDR) scores
of stably transformed corn plants expressing
chimeras of TIC7381, TIC7382, TIC7383,
and TIC7042 against Western Corn Rootworm.

| Description | Average $R_0$ RDR | Average $F_1$ RDR |
|---|---|---|
| CR-BREla.TIC7382_3.nno_Mc:1 | 1.6 | 1.0 |
| CR-BREla.TIC7383_7.nno_Mc:1 | 3 | 1.5 |

As can be seen in Table 14, the chimeric toxin GOI-TIC10746.nno_Mc:1 comprised of domains one and two of TIC7382 and domain three of TIC7383 gave better efficacy at $R_0$ and $F_1$ relative to the negative control, CR-BREla.TIC7382_3.nno_Mc:1, and CR-BREla.TIC7383_7.nno_Mc:1. Four $F_1$ events expressing GOI-TIC10746.nno_Mc:1 were included in the assay. Root Damage Ratings scores ranged from 0.11 to 0.79 with (RDR: 0.11, 0.20, 0.30, and 0.79). The one GOI-TIC10746.nno_Mc:1 expressing event with an RDR of 0.11 was equal to a commercial control. In addition to the data presented above, protein isolated from bacteria expressing the chimeric toxin GOI-TIC10746.nno_Mc:1 also demonstrated activity against Northern Corn Rootworm when presented in a diet bioassay.

Example 13

Assay of Activity of Chimeras of TIC7382 and TIC7383 Corn Rootworm in Stably Transformed Corn Plants This Example illustrates the design of chimeras of TIC7382 and TIC7383 and the assay of activity against Western Corn Rootworm (WCR) in stably transformed corn plants expressing the chimeras.

Synthetic coding sequences encoding chimeric toxins comprised of domains one and two of TIC7382 and domain three of TIC7383 designed for expression in plants are cloned using methods known in the art. The chimeric toxin, TIC10746NTermExt1 (SEQ ID NO:125, encoded by SEQ ID NO:124) comprises the N-terminal extension of TIC7382. The chimeric toxin, TIC10746NTermExt2 (SEQ ID NO:127, encoded by SEQ ID NO:126) comprises the N-terminal extension of TIC7383. The synthetic coding sequences are cloned in binary plant transformation vectors similar to those described in Example 12 and used to transform corn plants. Root assays are performed as previously described in Example 8 for $R_0$ and $F_1$ plants after infestation of such corn rootworm species as Western Corn Rootworm (*Diabrotica virgifera virgifera*, WCR), Northern Corn Rootworm (*Diabrotica barberi*, NCR), Mexican Corn Rootworm (*Diabrotica virgifera zeae*, MCR), Brazilian Corn Rootworm (*Diabrotica balteata*, BZR), Southern Corn Rootworm (*Diabrotica undecimpunctata howardii*, SCR), Colorado potato beetle (*Leptinotarsa decemlineata*, CPB), or a Brazilian Corn Rootworm complex (BCR, consisting of *Diabrotica viridula* and *Diabrotica speciosa*). Average low Root Damage Rating (RDR) scores of $R_0$ and F1 plants relative to non-transformed corn plant controls are demonstrative of resistant to the corn rootworm species conferred by expression of the chimeric toxins.

All of the compositions disclosed and claimed herein can be made and executed without undue experimentation in light of the present disclosure. While the compositions of this invention have been described in terms of the foregoing illustrative embodiments, it will be apparent to those of skill in the art that variations, changes, modifications, and alterations may be applied to the compositions described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

All publications and published patent documents cited in the specification are incorporated herein by reference to the same extent as if each individual publication or patent application was specifically and individually indicated to be incorporated by reference.

SEQUENCE LISTING

```
Sequence total quantity: 127
SEQ ID NO: 1           moltype = DNA  length = 3780
FEATURE                Location/Qualifiers
misc_feature           1..3780
                       note = A nucleic acid encoding a TIC7040 pesticidal protein
                        sequence obtained from Brevibacillus laterosporus species
                        DSC005019.
source                 1..3780
                       mol_type = unassigned DNA
                       organism = Brevibacillus laterosporus
SEQUENCE: 1
atgaatcaga atcagaatca aaataaaaat gaactgcaaa tcatagaacc ttcaagtgat  60
tctttgcttt atagtcacaa caattatccg tatgcaactg atccaaatac agtattagaa  120
ggtaggaatt ataaagagtg gctaaataag tgcacagata attatacaga cgctttacag  180
ggtcccgaag ctactgctat atcaaaagga gctgtctctg ctgcgatttc tatcagcacc  240
aaagttctta gtttattagg tgttccgttt gcagctcaaa tcggacaact ttggaccttc  300
atattgaatg cgttatggcc ttcagacaat actcaatggg aagagttcat gagacatgta  360
gaagaactca taaaccaacg aatagccgat tatgcaagaa gtaaggcact tgcagaatta  420
acgggtttag gtaataactt agatttatat atagaagctc ttgaagattg gaaacgaaat  480
cctactagtc aacaagcgaa agaccgtgta aaagatagat tccgtatagc agatggttta  540
tttgaagcgt atatgccttc atttagagta tcaggttatg aagtaccatt attaacagtg  600
tatgcagccg ctgcaaatct ccatttactt ttattaagag attgctctat ttacggaatc  660
caatggggat ttagtcaaac gaatgttaac gagaattaca atcgccaaat aagacacacc  720
gcagagtatg caaatcattg tacaacttgg taccaaactg gtttagaaag attgcgaggt  780
```

```
accaatgctt ccagttgggt cccttataat cgtttccgaa gagaaatgac gttaactgta   840
ttggatattt gttccttatt ttcaaattat gattatcgta gttatccagc agaggtaagg   900
gcagagctta caagagaaat ttatacggac ccagttgtaa gcactagctt gtggatgaat   960
aatgcaccat cattcggaga aatagaaaat ctagcaatta gggcgccaag aaccgttact  1020
tggttaaatt ctacaagaat ttctacaggg accttgcagg gctggagtgg ttctaacaga  1080
tattgggcag ctcacatgca aaacttttca gaaaccaatt caggaaatat aggatttgac  1140
ggtcctctct atgggtcgac ggtaggtact attattcgtg atgataatta cgaaatggtg  1200
aaccgagata tttacaccat tacttcagag gctgttgccg ccctttggcc aactggtcaa  1260
attgtgttgg gagtcgcttc ggctagattt actttaagaa atcttaacaa taatcttaca  1320
caggcgctgg tgtatgagaa cccaataagt tcaagttta ataggtcaac tttaactcgt  1380
gaattacctg gggaaaactc agataggcca acttcaagcg actatagtca tagactaacg  1440
tctattacag cttttcgagc tggaagtaat gggacgattc cggtttttgg atggacatct  1500
ataagtgtta atcgtgacaa tatcttgag cgaaacaaaa taacacaatt cccaggcgtt  1560
aagtcacaca ctctcaacaa ttgtcaagta gttagaggta ctggattac aggaggagac  1620
tggttgagac caaataataa tggttcattt agattaacta ttacttcatt ctcgagccaa  1680
tcttaccgaa tccgcttacg ttatgcttcc gcagcaaata cttctttgcg tatatcttct  1740
tctgcagccg gtatttcttc cacaaccgtt ccgcttacct caacaataac atcactgcca  1800
caaactgctg taccatatga agcttttaga gttatagatt tacctattac ttttacaaca  1860
gctacccaaa gtaattatac ttttgattt gttctccaaa atccatcaaa cgcaaatgta  1920
ttcattgata gatttgaatt tgtccaatt gggggttctt tgtctgagta tgaaaccaaa  1980
catcagctag aaaagcaag gaaagcgtg aacgattgt ttaccaatga atcgaaaat  2040
gtgttaaaaa aatacacgac cgattatgat atagatcagg ctgcaaactt ggtagaatgt  2100
gtatctgatg aatgtgcaaa tgctaaaatg atcctattag atgaagtaaa atatgcgaaa  2160
caactcagcg aagcccgcaa tctacttctg aatggtaatt ttgaatacca agatagagat  2220
ggggagaatc catggaaaac aagtccaaat gttaccatcc aggaaaataa ccccattttt  2280
aaaggccgtt atctcagtat gtcgggtgca aactatatcg aggcaacaaa tgatactttc  2340
cccacttatg cataccaaaa aatagatgaa gcaaaattaa aacccctatac ccgttataaa  2400
gttcgagggt tgttggaaa tagtaaagat ttagagttgt tgattaaacg gtatgatgaa  2460
gaagtggatg cgattttaaa tgtaccaaat gatataccac atgctccgac acctttctgc  2520
ggtgatttg atcgatgcaa gccacattct tatattccta tgaatccaga atgtcaccat  2580
gatgtaataa ataacattga aatatcctct ccttgccaac acaataagat gttggataac  2640
gctgatatat cttctcgcca tagtgaatta ggtaaaaaac gtggaatttg tcatgaatct  2700
catcattttg aattccatat tgatacagga aaaatcgatt tgaacgaaaa tttgggaatt  2760
tgggttatat ttaaaatatg ttccacagat ggttacgcaa cattagataa tttggagtt  2820
attgaagagg gtcctttagg agccgaatca ttagaacgtg tgaaaagaag agaaaagaaa  2880
tggaaacatc acatggaaca caagtgttca gaaactaaac ttgcatatca tgctgcaaaa  2940
caagcgctgg tggggttatt cacaaacact aaatatgata gattaaagtt cgaaacaacc  3000
atatccaata ttcttttttgc tgattatctc gtgcagtcaa ttccgtatgt atataataaa  3060
tggttaccag atgttccagg tatgaattac gatatctata cagaattaaa aaatctgttt  3120
acgggagctt tcaatttata tgatcagcga aatattataa aaaatggaga ctttaatcgc  3180
gggctcatgc attggcatgc gacacctcat gcaagagtag agcaaataga taataggtct  3240
gtgctggtgc ttcaaattta tgctgccaat gttttcacaag aggtttgttt agaacacaat  3300
cgtgttatg tattacgtgt aacggcgaaa aagaaggcc ctggaattgg atatgttaca  3360
ttcagtgatt gtgcaaataa tatagaaaaa ctgacatttg cttcttgcga ttatggtaca  3420
aacgaagtga catatgagca atctaattat catacagacg gagtaccgta cgaacaatct  3480
aattatccta cagacggagt accgtacgaa caacatggtt gtcatacaga cggagtaccg  3540
tacgaacaat ctagttatcc tacagacgga gtaccgtaca aacacatgg ttgtcgtaca  3600
gacggagtac tatacaaaca acatggttgt cgtacagaca gatcaagag tgaacaactt  3660
gattatgtga caaaaacgat tgatgtattc cctgatactg ataaagtacg tatcgacatt  3720
ggagaaaccg aaggtacctt taagtagaaa agtgtggaac tgattttat ggaagagtaa  3780
```

```
SEQ ID NO: 2          moltype = AA   length = 1259
FEATURE               Location/Qualifiers
REGION                1..1259
                      note = The amino acid sequence of the TIC7040 protein.
source                1..1259
                      mol_type = protein
                      organism = Brevibacillus laterosporus
SEQUENCE: 2
MNQNQNQNKN ELQIIEPSSD SLLYSHNNYP YATDPNTVLE GRNYKEWLNK CTDNYTDALQ    60
GPEATAISKG AVSAAISIST KVLSLLGVPF AAQIGQLWTF ILNALWPSDN TQWEEFMRHV   120
EELINQRIAD YARSKALAEL TGLGNNLDLY IEALEDWKRN PTSQQAKDRV KDRFRIADGL   180
FEAYMPSFRV SGYEVPLLTV YAAAANLHLL LLRDCSIYGI QWGFSQTNVN ENYNRQIRHT   240
AEYANHCTTW YQTGLERLRG TNASSWVPYN RFRREMTLTV LDICSLFSNY DYRSYPAEVR   300
AELTREIYTD PVVSTSLWMN NAPSFGEIEN LAIRAPRTVT WLNSTRISTG TLQGWSGSNR   360
YWAAHMQNFS ETNSGNIGFD GPLYGSTVGT IIRDDNYEMV NRDIYTITSE AVAALWPTGQ   420
IVLGVASARF TLRNLNNNLT QALVYENPIS SSFNRSTLTR ELPGENSDRP TSSDYSHRLT   480
SITAFRAGSN GTIPVPGWTS ISVNRDNILE RNKITQFPSV KSHTLNNCQV VRGTGFTGGD   540
WLRPNNNGSF RLTITSFSSQ SYRIRLRYAS AANTSLRISS SAAGISSSTTV PLTSTITSLP   600
QTAVPYEAFR VIDLPITFTT ATQSNYTFDF VLQNPSNANV FIDRFEFVPI GGSLSEYETK   660
HQLEKARKAV NDLFTNESKN VLKKYTTDYD IDQAANLVEC VSDECANAKM ILLDEVKYAK   720
QLSEARNLLL NGNFEYQDRD GENPWKTSPN VTIQENNPIF KGRYLSMSGA NYIEATNDTF   780
PTYAYQKIDE AKLKPYTRYK VRGFVGNSKD LELLIKRYDE EVDAILNVPN DIPHAPTPFC   840
GGFDRCKPHS YIPMNPECHH DVINNIEISS PCQHNKMLDN ADISSRHSEL GKKRGICHES   900
HHFEFHIDTG KIDLNENLGI WVIFKICSTD GYATLDNLEV IEEGPLGAES LERVKRREKK   960
WKHHMEHKCS ETKLAYHAAK QALVGLFTNT KYDRLKFETT ISNILFADYL VQSIPYVYNK  1020
WLPDVPGMNY DIYTELKNLF TGAFNLYDQR NIIKNGDFNR GLMHWHATPH ARVEQIDNRS  1080
VLVLPNYAAN VSQEVCLEHN RGYVLRVTAK KEGPGIGYVT FSDCANNIEK LTFTSCDYGT  1140
NEVTYEQSNY HTDGVPYEQS NYPTDGVPYE QHGCHTDGVP YEQSSYPTDG VPYEQHGCRT  1200
```

-continued

```
DGVLYKQHGC RTDRSRDEQL DYVTKTIDVF PDTDKVRIDI GETEGTFKVE SVELIFMEE   1259

SEQ ID NO: 3           moltype = DNA  length = 3888
FEATURE                Location/Qualifiers
misc_feature           1..3888
                       note = A nucleic acid encoding a TIC7040HT pesticidal
                        protein sequence obtained from Brevibacillus laterosporus
                        species DSC00519.
source                 1..3888
                       mol_type = unassigned DNA
                       organism = Brevibacillus laterosporus
SEQUENCE: 3
atgaatcaga atcagaatca aaataaaaat gaactgcaaa tcatagaacc ttcaagtgat  60
tctttgcttt atagtcacaa caattatccg tatgcaactg atccaaatac agtattagaa  120
ggtaggaatt ataaagagtg gctaaataag tgcacagata attatacaga cgctttacag  180
ggtcccgaag ctactgctat atcaaaagga gctgtctctg ctgcgatttc tatcagcacc  240
aaagttctta gtttattagg tgttccgttt gcagctcaaa tcggacaact ttggaccttc  300
atattgaatg cgttatggcc ttcagacaat actcaatggg aagagttcat gagacatgta  360
gaagaactca taaaccaacg aatagccgat tatgcaagaa gtaaggcact tgcagaatta  420
acgggtttag gtaataactt agatttatat atagaagctc ttgaagattg gaaacgaaat  480
cctactagtc aacaagcgaa agaccgtgta aaagatagat tccgtatagc agatggttta  540
tttgaagcgt atatgccttc atttagagta tcaggttatg aagtaccatt attaacagtg  600
tatgcagccg ctgcaaatct ccatttactt ttattaagag attgctctat ttacggaatc  660
caatggggat ttagtcaaac gaatgttaac gagaattaca atcgccaaat aagacacacc  720
gcagagtatg caaatcattg tacaacttgg taccaaactg gtttagaaag attgcgaggt  780
accaatgctt ccagttgggt cccttataat cgtttccgaa gagaaatgac gttaactgta  840
ttggatattt gttccttatt ttcaaattat gattatcgta gttatccagc agaggtaagg  900
gcagagctta caagagaaat ttatacggac ccagttgtaa gcactagctt gtggatgaat  960
aatgcaccat cattcggaga aatagaaaat ctagcaatta gggcgccaag aaccgttact  1020
tggttaaatt ctacaagaat ttctacaggg accttgcagg gctggagtgg ttctaacaga  1080
tattgggcag ctcacatgca aaacttttca gaaaccaatt caggaaatat aggatttgac  1140
ggtcctctct atgggtcgac ggtaggtact attattcgtg atgataatta cgaaatggtg  1200
aaccgagata tttacaccat tacttcagag gctgttgccg cccttttggcc aactggtcaa  1260
attgtgttgg gagtcgcttc ggctagattt actttaagaa atcttaacaa taatcttaca  1320
caggcgctgg tgtatgagaa cccaataagt tcaagtttta ataggtcaac tttaactcgt  1380
gaattacctg gggaaaactc agataggcca acttcaagcg actatagtca tagactaacg  1440
tctattacag cttttcgagc tggaagtaat gggacgattc cggtttttgg atggacatct  1500
ataagtgtta atcgtgacaa tatacttgag cgaaacaaaa taacacaatt cccaggcgtt  1560
aagtcacaca ctctcaacaa ttgtcaagta gttagaggta ctggatttac aggaggagac  1620
tggttgagac caaataataa tggttcattt agattaacta ttacttcatt ctcgagccaa  1680
tcttaccgaa tccgcttacg ttatgcttcc gcagcaaata cttctttgcg tatatcttct  1740
tctgcagccg gtatttcttc cacaaccgtt ccgcttacct caacaataac atcactgcca  1800
caaactgctg taccatatga agcttttaga gttatagatt tacctattac ttttacaaca  1860
gctacccaaa gtaattatac ttttgatttt gttctccaaa atccatcaaa cgcaaatgta  1920
ttcattgata gatttgaatt tgttccaatt gggggttctt tgtctgagta tgaaaccaaa  1980
catcagctag aaaaagcaag gaaagcggtg aacgatttgt ttaccaatga atcgaaaaat  2040
gtgttaaaaa aatacacgac cgattatgat atagatcaag ctgcaaactt ggtagaatgt  2100
gtatctgatg aatgtgcaaa tgctaaaatg atcctattag atgaagtaaa atatgcgaaa  2160
caactcagcg aagcccgcaa tctacttctg aatggtaatt ttgaatacca agatagagat  2220
ggggagaatc catggaaaac aagtccaaat gttaccatcc aggaaaataa ccccattttt  2280
aaaggccgtt atctcagtat gtcgggtgca aactatatcg aggcaacaaa tgatactttc  2340
cccacttatg cataccaaaa aatagatgaa gcaaaattaa aaccctatac ccgttataaa  2400
gttcgagggt ttgttggaaa tagtaaagat ttagagttgt tgattaaacg gtatgatgaa  2460
gaagtggatg cgattttaaa tgtaccaaat gatataccac atgctccgac acctttctgc  2520
ggtggatttg atcgatgcaa gccacattct tatattccta tgaatccaga atgtcaccat  2580
gatgtaataa ataacattga aatatcctct ccttgccaac acaataagat gttggataac  2640
gctgatatat cttctcgcca tagtgaatta ggtaaaaaac gtggaatttg tcatgaatct  2700
catcattttg aattccatat tgatacagga aaaatcgatt tgaacgaaaa tttgggaatt  2760
tgggttatat ttaaaatatg ttccacagat ggttacgcaa cattagataa tttggaagtt  2820
attgaagagg gtcctttagg agccgaatca ttagaacgtg tgaaaagaag agaaaagaaa  2880
tggaaacatc acatggaaca caagtgttca gaaactaaac ttgcatatca tgctgcaaaa  2940
caagcgctgg tggggttatt cacaaacact aaatatgata gattaaagtt cgaaacaacc  3000
atatccaata ttctttttgc tgattatctc gtgcagtcaa ttccgtatgt atataataaa  3060
tggttaccag atgttccagg tatgaattac gatatctata cagaattaaa aaatctgttt  3120
acgggagctt tcaatttata tgatcagcga aatattataa aaaatggaga ctttaatcgc  3180
gggctcatgc attggcatgc gacacctcat gcaagagtag agcaaataga taataggtct  3240
gtgctggtgc ttccaaatta tgctgccaat gtttcacaag aggtttgttt agaacacaat  3300
cgtggttatg tattacgtgt aacggcgaaa aaagaaggcc ctggaattgg atatgttaca  3360
ttcagtgatt gtgcaaataa tatagaaaaa ctgacattta cttcttgcga ttatggtaca  3420
aacgaagtga catatgagca atctaattat catacagacg gagtaccgta cgaacaatct  3480
aattatccta cagacggagt accgtacgaa caacatggtt gtcatacaga cggagtaccg  3540
tacgaacaat ctaattatcc tacagacgga gtaccgtacg aacaacatgg ttgtcataca  3600
gacggagttc cgtacgaaca acatggttgt catacagacg gagtaccgta cgaacaacat  3660
ggttgtcata cagacggagt accatacaaa caacatggtt gtcgtacaga cggagtacta  3720
tacaaacaac atggttgtcg tacagacaga tcaagagatg aacaacttga ttatgtgaca  3780
aaaacgattg atgtattccc tgatactgat aaagtacgta tcgacattgg agaaaccgaa  3840
ggtaccttta aagtagaaag tgtggaactg atttttatgg aagagtaa             3888

SEQ ID NO: 4           moltype = AA  length = 1295
```

```
FEATURE                 Location/Qualifiers
REGION                  1..1295
                        note = The amino acid sequence of the TIC7040HT protein.
source                  1..1295
                        mol_type = protein
                        organism = Brevibacillus laterosporus
SEQUENCE: 4
MNQNQNQNKN ELQIIEPSSD SLLYSHNNYP YATDPNTVLE GRNYKEWLNK CTDNYTDALQ    60
GPEATAISKG AVSAAISIST KVLSLLGVPF AAQIGQLWTF ILNALWPSDN TQWEEFMRHV   120
EELINQRIAD YARSKALAEL TGLGNNLDLY IEALEDWKRN PTSQQAKDRV KDRFRIADGL   180
FEAYMPSFRV SGYEVPLLTV YAAAANLHLL LLRDCSIYGI QWGFSQTNVN ENYNRQIRHT   240
AEYANHCTTW YQTGLERLRG TNASSWVPYN RFRREMTLTV LDICSLFSNY DYRSYPAEVR   300
AELTREIYTD PVVSTSLWMN NAPSFGEIEN LAIRAPRTVT WLNSTRISTG TLQGWSGSNR   360
YWAAHMQNFS ETNSGNIGFD GPLYGSTVGT IIRDDNYEMV NRDIYTITSE AVAALWPTGQ   420
IVLGVASARF TLRNLNNNLT QALVYENPIS SSFNRSTLTR ELPGENSDRP TSSDYSHRLT   480
SITAFRAGSN GTIPVFGWTS ISVNRDNILE RNKITQFPGV KSHTLNNCQV VRGTGFTGGD   540
WLRPNNNGSF RLTITSFSSQ SYRIRLRYAS AANTSLRISS SAAGISSTTV PLTSTITSLP   600
QTAVPYEAFR VIDLPITFTT ATQSNYTFDF VLQNPSNANV FIDRFEFVPI GGSLSEYETK   660
HQLEKARKAV NDLFTNESKN VLKKYTTDYD IDQAANLVEC VSDECANAKM ILLDEVKYAK   720
QLSEARNLLL NGNFEYQDRD GENPWKTSPN VTIQENNPIF KGRYLSMSGA NYIEATNDTF   780
PTYAYQKIDE AKLKPYTRYK VRGFVGNSKD LELLIKRYDE EVDAILNVPN DIPHAPTPFC   840
GGFDRCKPHS YIPMNPECHH DVINNIEISS PCQHNKMLDN ADISSRHSEL GKKRGICHES   900
HHFEFHIDTG KIDLNENLGI WVIFKICSTD GYATLDNLEV IEEGPLGAES LERVKRREKK   960
WKHHMEHKCS ETKLAYHAAK QALVGLFTNT KYDRLKFETT ISNILFADYL VQSIPYVYNK  1020
WLPDVPGMNY DIYTELKNLF TGAFNLYDQR NIIKNGDFNR GLMHWHATPH ARVEQIDNRS  1080
VLVLPNYAAN VSQEVCLEHN RGYVLRVTAK KEGPGIGYVT FSDCANNIEK LTFTSCDYGT  1140
NEVTYEQSNY HTDGVPYEQS NYPTDGVPYE QHGCHTDGVP YEQSNYPTDG VPYEQHGCHT  1200
DGVPYEQHGC HTDGVPYEQH GCHTDGVPYK QHGCRTDGVL YKQHGCRTDR SRDEQLDYVT  1260
KTIDVFPDTD KVRIDIGETE GTFKVESVEL IFMEE                            1295

SEQ ID NO: 5            moltype = DNA  length = 2016
FEATURE                 Location/Qualifiers
misc_feature            1..2016
                        note = A nucleic acid encoding a TIC7040HT_4 pesticidal
                         protein sequence which comprises a C-terminal truncation
                         relative to the TIC7040HT protein.
source                  1..2016
                        mol_type = other DNA
                        organism = synthetic construct
SEQUENCE: 5
atgaatcaga atcagaatca aaataaaaat gaactgcaaa tcatagaacc ttcaagtgat    60
tctttgcttt atagtcacaa caattatccg tatgcaactg atccaaatac agtattagaa   120
ggtaggaatt ataaagagtg gctaaataag tgcacagata attatacaga tgcttttacag   180
ggtcccgaag ctactgctat atcaaaagga gctgtctctg ctgcgatttc tatcagcacc   240
aaagttctta gtttattagg tgttccgttt gcagctcaaa tcggacaact ttggaccttc   300
atattgaatg cgttatggcc ttcagacaat actcaatggg aagagttcat gagacatgta   360
gaagaactca taaccaacg aatagccgat tatgcaagga taaggcaact tgcagaatta   420
acgggtttag gtaataactt agatttatat ataagaagctc ttgaagattg gaaacgaaat   480
cctactagtc aacaagcgaa agaccgtgta aaagatagat ccgtatagc agatggttta   540
tttgaagcgt atatgccttc atttagagta tcaggttatg aagtaccatt attaacagtg   600
tatgcagccg ctgcaaatct ccatttactt ttattaagag attgctctat ttacggaatc   660
caatggggat ttagtcaaac gaatgttaac gagaattaca atcgccaaat aagcacaccc   720
gcagagtatg caaatcattg tacaacttgg taccaaactg gttagaaag attgcgaggt   780
accaatgctt ccagttgggt cccttataat cgtttccgaa gagaaatgac gttaactgta   840
ttggatatttt gttccttatt tcaaattat gattatcgta gttatccagc agaggtaagg   900
gcagagctta caagagaaat ttatacggac ccagttgtaa gcactagctt gtggatgaat   960
aatgcaccat cattcggaga aatagaaaat ctagcaatta gggcgccaag aaccgttact  1020
tggttaaatt ctacaagaat ttctacaggg accttgcagg gctggagtgg ttctaacaga  1080
tattgggcag ctcacatgca aaactttca gaaaccaatt caggaaatat aggatttgac  1140
ggtcctctct atgggtcgac ggtaggtact attattcgtg atgataatta cgaaatggtg  1200
aaccgagata tttacaccat tacttcgag gctgttgccg ccctttggcc aactggtcaa  1260
attgtgttgg gagtcgcttc ggctagattt actttaagaa atcttaacaa taatcttaca  1320
caggcgctgt tgtatgagaa cccaataagt tcaagtttta ataggtcaac tttaactcgt  1380
gaattacctg gggaaaactc agataggcca acttcaagcg actatagtca tagactaacg  1440
tctattacag cttttcgagc tggaagtaat gggacgattc cggttttggg atggacatct  1500
ataagtgtta atcgtgacaa tatacttgag cgaaacaaaa taacacaatt cccaggcgtt  1560
aagtcacaca ctctcaacaa ttgtcaagta gttagaggta ctggatttac aggaggagac  1620
tggttgagac aaataataa tggttcattt agattaacta ttacttcatt ctcgagcaga  1680
tcttaccgaa tccgcttacg ttatgcttcc gcagcaaata cttctttgcg tatatcttct  1740
tctgcagccg gtatttcttc cacaaccgtt ccgcttacct caacaataac atcactgcca  1800
caaactgctg taccatatga agcttttaga gttatagatt tacctattac ttttacaaca  1860
gctacccaaa gtaattatac ttttgatttt gttctccaaa atccatcaaa cgcaaatgta  1920
ttcattgata gatttgaatt tgttccaatt ggggggtctt tgtctgagta tgaaaccaaa  1980
catcagctag aaaaagcaag gaaagcggtg aactaa                            2016

SEQ ID NO: 6            moltype = AA  length = 671
FEATURE                 Location/Qualifiers
REGION                  1..671
                        note = The amino acid sequence of the TIC7040HT_4 protein,
```

```
                         consisting of amino acids 1 through 671 of TIC7040HT.
source                   1..671
                         mol_type = protein
                         organism = synthetic construct
SEQUENCE: 6
MNQNQNQNKN ELQIIEPSSD SLLYSHNNYP YATDPNTVLE GRNYKEWLNK CTDNYTDALQ    60
GPEATAISKG AVSAAISIST KVLSLLGVPF AAQIGQLWTF ILNALWPSDN TQWEEFMRHV   120
EELINQRIAD YARSKALAEL TGLGNNLDLY IEALEDWKRN PTSQQAKDRV KDRFRIADGL   180
FEAYMPSFRV SGYEVPLLTV YAAAANLHLL LLRDCSIYGI QWGFSQTNVN ENYNRQIRHT   240
AEYANHCTTW YQTGLERLRG TNASSWVPYN RFRREMTLTV LDICSLFSNY DYRSYPAEVR   300
AELTREIYTD PVVSTSLWMN NAPSFGEIEN LAIRAPRTVT WLNSTRISTG TLQGWSGSNR   360
YWAAHMQNFS ETNSGNIGFD GPLYGSTVGT IIRDDNYEMV NRDIYTITSE AVAALWPTGQ   420
IVLGVASARF TLRNLNNNLT QALVYENPIS SSFNRSTLTR ELPGENSDRP TSSDYSHRLT   480
SITAFRAGSN GTIPVFGWTS ISVNRDNILE RNKITQFPGV KSHTLNNCQV VRGTGFTGGD   540
WLRPNNNGSF RLTITSFSSQ SYRIRLRYAS AANTSLRISS SAAGISSTTV PLTSTITSLP   600
QTAVPYEAFR VIDLPITFTT ATQSNYTFDF VLQNPSNANV FIDRFEFVPI GGSLSEYETK   660
HQLEKARKAV N                                                       671

SEQ ID NO: 7             moltype = DNA  length = 1923
FEATURE                  Location/Qualifiers
misc_feature             1..1923
                         note = A nucleic acid encoding a TIC7040HT_5 pesticidal
                          protein sequence which comprises an N-terminal and
                          C-terminal truncation relative to the TIC7040HT protein.
source                   1..1923
                         mol_type = other DNA
                         organism = synthetic construct
SEQUENCE: 7
atgcaaatca tagaaccttc aagtgattct ttgctttata gtcacaacaa ttatccgtat    60
gcaactgatc caaatacagt attagaaggt aggaattata aagagtggct aaataagtgc   120
acagataatt atacgacgc tttacagggt cccgaagcta ctgctatatc aaaaggagct   180
gtctctgctg cgatttctat cagcaccaaa gttcttagtt tattaggtgt tccgtttgca   240
gctcaaatcg acaactttg gaccttcata ttgaatgcgt tatggccttc agacaatact   300
caatgggaag agttcatgag acatgtagaa gaactcataa accaacgaat agccgattat   360
gcaagaagta aggcacttgc tgaattaacg ggtttaggta taacttaga tttatatata   420
gaagctcttg aagattggaa acgaaatcct actagtcaac aagcgaaaga ccgtgtaaaa   480
gatagattcc gtatagcaga tggtttattt gaagcgtata tgccttcatt tagagtatca   540
ggttatgaag taccattatt aacagtgtat gcagccgctg caaatctcca tttacttta   600
ttaagagatt gctctattta cggaatccaa tggggattta gtcaaacgaa tgttaacgag   660
aattacaatc gccaaataag cacaccgca gagtatgcaa atcattgtac aacttggtac   720
caaactggtt tagaaagatt gcgaggtacc aatgcttcca gttgggtccc ttataatcgt   780
ttccgaagag aaatgacgtt aactgtattg gatatttgtt ccttatttc aaattatgat   840
tatcgtagtt atccagcaga ggtaagggca gagcttacag agaaattta racggaccca   900
gttgtaagca ctagcttgtg gatgaataat gcaccatcat tcggagaaat agaaaatcta   960
gcaattaggg cgccaagaac cgttacttgg ttaaattcta caagaatttc tacagggacc  1020
ttgcagggct ggagtggttc taacagatat tgggcagctc acatgcaaaa cttttcagaa  1080
accaattcag gaaatatagg atttgacggt cctctctata ggtcgacggt aggtactatt  1140
attcgtgatg ataattacga aatggtgaac cgagatattt acaccattac ttcagaggct  1200
gttgccgcc tttggccaac tggtcaaatt gtgttgggag tcgcttcggc tagatttact  1260
ttaagaaatc ttaacaataa tcttacacag gcgctggtgt atgagaaccc aataagttca  1320
agttttaata ggtcaacttt aactcgtgaa ttacctggga aaaactcaga taggccaact  1380
tcaagcgact atagtcatag actaacgtct attacagctt ttcgagctgg aagtaatggg  1440
acgattccgg ttttggatg gacatctata agtgttaatc gtgacaatat acttgagcga  1500
aacaaaataa cacaattccc aggcgttaag tcacacactc tcaacaattg tcaagtagtt  1560
agaggtactg gatttgcagg aggagactgg ttgagaccaa ataataagg ttcatttaga  1620
ttaactatta cttcattctc gagccaatct taccgaatcc gcttacgtta tgcttccgca  1680
gcaaatactt ctttgcgtat atcttcttct gcagccggta tttcttccac aaccgttccg  1740
cttacctcaa caataacatc actgccacaa actgctgtac catatgaagc ttttagagtt  1800
atagatttac ctattacttt tacaacagct acccaaagta attatacttt tgattttgtt  1860
ctccaaaatc catcaaacgc aaatgtattc attgatagat ttgaatttgt tccaattggg  1920
taa                                                                1923

SEQ ID NO: 8             moltype = AA  length = 600
FEATURE                  Location/Qualifiers
REGION                   1..600
                         note = The amino acid sequence of the TIC7040HT_5 protein,
                          comprising amino acids 13 through 611 of TIC7040HT.
source                   1..600
                         mol_type = protein
                         organism = synthetic construct
SEQUENCE: 8
MQIIEPSSDS LLYSHNNYPY ATDPNTVLEG RNYKEWLNKC TDNYTDALQG PEATAISKGA    60
VSAAISISTK VLSLLGVPFA AQIGQLWTFI LNALWPSDNT QWEEFMRHVE ELINQRIADY   120
ARSKALAELT GLGNNLDLYI EALEDWKRNP TSQQAKDRVK DRFRIADGLF EAYMPSFRVS   180
GYEVPLLTVY AAAANLHLLL LRDCSIYGIQ WGFSQTNVNE NYNRQIRHTA EYANHCTTWY   240
QTGLERLRGT NASSWVPYNR FRREMTLTVL DICSLFSNYD YRSYPAEVRA ELTREIYTDP   300
VVSTSLWMNN APSFGEIENL AIRAPRTVTW LNSTRISTGT LQGWSGSNRY WAAHMQNFSE   360
TNSGNIGFDG PLYGSTVGTI IRDDNYEMVN RDIYTITSEA VAALWPTGQI VLGVASARFT   420
LRNLNNNLTQ ALVYENPISS SFNRSTLTRE LPGENSDRPT SSDYSHRLTS ITAFRAGSNG   480
```

```
TIPVFGWTSI SVNRDNILER NKITQFPGVK SHTLNNCQVV RGTGFTGGDW LRPNNNGSFR    540
LTITSFSSQS YRIRLRYASA ANTSLRISSS AAGISSTTVP LTSTITSLPQ TAVPYEAFRV    600

SEQ ID NO: 9            moltype = DNA   length = 1983
FEATURE                 Location/Qualifiers
misc_feature            1..1983
                        note = A nucleic acid encoding a TIC7040HT_6 pesticidal
                        protein sequence which comprises an N-terminal and
                        C-terminal truncation relative to the TIC7040HT protein.
source                  1..1983
                        mol_type = other DNA
                        organism = synthetic construct
SEQUENCE: 9
atgcaaatca tagaaccttc aagtgattct ttgctttata gtcacaacaa ttatccgtat     60
gcaactgatc caaatacagt attagaaggt aggaattata aagagtggct aaataagtgc    120
acagataatt atacagacgc tttacagggt cccgaagcta ctgctatatc aaaaggagct    180
gtctctgctg cgatttctat cagcaccaaa gttcttagtt tattaggtgt tccgtttgca    240
gctcaaatcg gacaactttg gaccttcata ttgaatgcct tatgccttc agacaatact    300
caatgggaag agttcatgag acatgtagaa gaactcataa accaacgaat agccgattat    360
gcaagaagta aggcacttgc agaattaacg ggtttaggta ataacttaga tttatatata    420
gaagctcttg aagattggaa acgaaatcct actagtcaac aagcgaaaga ccgtgtaaaa    480
gatagattcc gtatagcaga tggtttattt gaagcgtata tgccttcatt tagagtatca    540
ggttatgaag taccattatt aacagtgtat gcagccgctg caaatctcca tttactttta    600
ttaagagatt gctctattta cggaatccaa tggggattta gtcaaacgaa tgttaacgag    660
aattacaatc gccaaataag acacaccgca gagtatgcaa atcattgtac aacttggtac    720
caaactggtt tagaaagatt gcgaggtacc aatgcttcca gttgggtccc ttataatgct    780
ttccgaagag aaatgacgtt aactgtattg gatatttgtt ccttatttc aaattatgat    840
tatcgtagtt atccagcaga ggtaagggca gagcttacaa gagaaattta acggaccca    900
gttgtaagca ctagcttgtg gatgaataat gcaccatcat cggagaaat agaaaatcta    960
gcaattaggg cgccaagaac cgttacttgg ttaaattca caagaatttc tacagggacc   1020
ttgcagggct ggagtggttc taacagatat tgggcagctc acatgcaaaa cttttcagaa   1080
accaattcag gaaatatagg atttgacggt cctctctatg ggtcgacggt aggtactatt   1140
attcgtgatg ataattacga aatggtgaac cgagatattt acaccattac ttcagaggct   1200
gttgccgccc tttggccaac tggtcaaatt gtgttgggag tcgcttcggc tagatttact   1260
ttaagaaatc ttaacaataa tctttacacag gcgctggtgt atgagaaccc aataagttca   1320
agttttaata ggtcaacttt aactcgtgaa ttacctgggg aaaactcaga taggccaact   1380
tcaagcgact atagtcatag actaacgtct attacagctt tcgagctgg aagtaatggg   1440
acgattccgg ttttggatg gacatctata agtgttaatc gtgacaatat acttgagcga   1500
aacaaaataa cacaattccc aggcgttaag tcacacactc tcaacaattg tcaagtagtt   1560
agaggtactg gatttacagg aggagactgg ttgagaccaa ataataatgg ttcatttaga   1620
ttaactatta cttcattctc gagccaatct taccgaatcc gcttacgtta tgcttccgca   1680
gcaaatactt ctttgcgtat atcttcttct gcagccggta tttcttccac aaccgttccg   1740
cttacctcaa caataacatc actgccacaa actgctgtac catatgaagc ttttagagtt   1800
atagatttac ctattacttt tacaacagct cccaaagta attatacttt tgattttgtt   1860
ctccaaaatc catcaaacgc aaatgtattc attgatagat ttgaatttgt tccaattggg   1920
ggttctttgt ctgagtatga aaccaaacat cagctagaaa aagcaaggaa agcggtgaac   1980
taa                                                                1983

SEQ ID NO: 10           moltype = AA    length = 660
FEATURE                 Location/Qualifiers
REGION                  1..660
                        note = The amino acid sequence of the TIC7040HT_6 protein,
                        comprising amino acids 13 through 671 of TIC7040HT.
source                  1..660
                        mol_type = protein
                        organism = synthetic construct
SEQUENCE: 10
MQIIEPSSDS LLYSHNNYPY ATDPNTVLEG RNYKEWLNKC TDNYTDALQG PEATAISKGA     60
VSAAISISTK VLSLLGVPFA AQIGQLWTFI LNALWPSDNT QWEEFMRHVE ELINQRIADY    120
ARSKALAELT GLGNNLDYI EALEDWKRNP TSQQAKDRVK DRFRIADGLF EAYMPSFRVS    180
GYEVPLLTVY AAAANLHLLL LRDCSIYGIQ WGFSQTNVNE NYNRQIRHTA EYANHCTTWY    240
QTGLERLRGT NASSWVPYNR FRREMTLTVL DICSLFSNYD YRSYPAEVRA ELTREIYTDP    300
VVSTSLWMNN APSFGEIENL AIRAPRTVTW LNSTRISTST LQGWSGSNRY WAAHMQNFSQ    360
TNSGNIGFDG PLYGSTVGTI IRDDNYEMVN RDIYTITSEA VAALWPTGQI VLGVASARFT    420
LRNLNNNLTQ ALVYENPISS SFNRSTLTRE LPGENSDRPT SSDYSHRLTS ITAFRAGSNG    480
TIPVFGWTSI SVNRDNILER NKITQFPGVK SHTLNNCQVV RGTGFTGGDW LRPNNNGSFR    540
LTITSFSSQS YRIRLRYASA ANTSLRISSS AAGISSTTVP LTSTITSLPQ TAVPYEAFRV    600
IDLPITFTTA TQSNYTFDFV LQNPSNANVF IDRFEFVPIG GSLSEYETKH QLEKARKAVN    660

SEQ ID NO: 11           moltype = DNA   length = 3801
FEATURE                 Location/Qualifiers
misc_feature            1..3801
                        note = A nucleic acid encoding a TIC7042 pesticidal protein
                        sequence obtained from Brevibacillus laterosporus species
                        DSC005973.
source                  1..3801
                        mol_type = unassigned DNA
                        organism = Brevibacillus laterosporus
SEQUENC

```
atgaatcaga atcaaaataa aaatgaaatg caaatcatag aaccttcaag tgattcttttt    60
ctttatagtc acaacaatta tccgtatgct actgatccag atacaatatt aaaaggtagg   120
aattataaag agtggctaaa tatgtgtaca gatacagacg attcacgaag tcccgaagct   180
gcttctactg caagatcagc tatttctgtt gcgattacta taagcaccac aattcttggc   240
ttactaggtg ttccgtttgc atctcaaatt ggagcatttt ataacttcgt attgaatacg   300
gtatggcctc agggaaataa ccaatgggaa gagttcatga gacatgtaga aaatctcata   360
aacgaacgaa tagctgatta tgcaagagat aaggcacttg cagaattaac gggtttaggt   420
aataacttaa atttatatag agaagctttt gaagattgga gacgaaatcc tactagtcaa   480
gaagctaaaa cccgtgtaat agatagattc cgtatactag atggttttat tgaaacatat   540
atgccttcat ttgcagtacg aaattttgaa gtacaattat taacagtgta tgcatccgct   600
gcaaatatcc atttattttt attaagagat agctctattt acggtttgga ttggggatta   660
agtcaaacta atgttaacga aaattacaat cgccaaataa ggcacgccgc aacgtatgca   720
aatcattgta caacttggta tcaaactggt ttacaaagat gcaaggtac caatgctacc   780
agttgggtcg cttataatag atttagaaga gaaatgacgt taacagtatt agatatttgt   840
tcattatttt caaattatga ttatcgtagt tatccaacag aggtaaaggg agagcttacg   900
agagaaattt atacggatcc agtaggtaga aactggcaga atgttgcacc atcattcgct   960
gaaatagaaa atctaacaat tagggcacca agaaccgtta cttggttaaa ttcaacaaga  1020
atttttacag ggactttgac aggctggagt ggttctaaca gatattgggc agctcacatg  1080
caaaactttt cagaaaccaa ttcaggaaat ataggatttg acggtcctca atatgggtcg  1140
acggtaggta ctattcatcg tactgatgat tacgatatgg tgaatcgaga tatttacacc  1200
attacttcac aagctgttgc cgccctttgg ccaactggtc aaactgtgtt gggagtcgct  1260
tcgactagat ttactttaag aaaccttaac aataattcta cagaggcgct ggtgtatgag  1320
aacgcaaata gttcaagttt tgttagttca actttaactc atgaattacc tggagaaaac  1380
tcagataggc caacttctag cgactatagt catagactat cgagtatcac aggttttcga  1440
gctggagcta atgaacggt cccagtgttt ggttggacat ctgcaactgt tgatcgtaac  1500
aatataattg agcaaaacaa aataacacaa ttcccaggtg ttaagtcaca cactctcaac  1560
aattgtcaag tagttagggg tactggattt acaggaggag actggttgag accaaataat  1620
aatggtacat ttagactaac tattacttca ttctccagcc aatcttaccg aattcgctta  1680
cgttatgcta cttcagtagg gaatacttct ttagttatat cttcttctga tgcaggtatt  1740
tcttccacaa caattccgct tacctaacaa taacatac tgccacaaac tgtaccatac  1800
caagctttta gggttgtaga tttacctatt acttttacaa cacctactac ccaaagaaat  1860
tatacgtttg atttccgtct ccaaaatcca tcaaacgcaa atgtattcat tgatagattt  1920
gaatttgttc caattggggg ttcttttgtct gagtatgaaa ccaaacatca gctagaaaaa  1980
gcaaggaaag cggtgaacga tttgtttacc aatgaatcga aaaatgtgtt aaaaaaagac  2040
acgaccgatt atgatataga tcaagctgca aacttggtag aatgtgtatc tgatgaatgt  2100
gcaaatgcta aaatgatcct attagatgaa gtaaaatatg cgaaacaact agcgaagcc   2160
cgcaatctac ttcaaatgg taattttgaa taccaagata gagatgggga gaatccatgg   2220
aaaacaagtc ccaatgttac catccaagag aataacccca ttttttaaagg ccgctatctc  2280
agtatgtcag gtgcgaacaa tatcgaggca accaatgaga tatttcccac ttatgtatac   2340
caaaaaattg atgaatccaa attaaaacct tatcccgtt ataaagttcg aggttttgtt    2400
ggaaatagta aagatttaga attattggtt acacggtatg atgaagaagt agatgcgatt   2460
ttaaatgtat caaatgatat accacatgct ccgccaccct tctgcggtga atttgatcga   2520
tgcaagccgc attcttatcc tcctattaat ccagaatgct aacatgatgt aataataac   2580
attgaaatat cctctccttg ccaacacaat aagatggtag atagcgctga tatatcttat   2640
cgccatagcc gaataagtaa aaaacatgg atttgtcatg aatctcatca ttttgaattc   2700
catattgata cagggaaaat cgatttggtc gaaaatttgg gaatttgggt tatatttaaa   2760
atatgttcca cagatggta cgcaacatta gataatttgg aagttattga agagggtcct   2820
ttaggagccg aatccttaga acgtgtgaaa agaagagaaaa agaaatggaa acatcacatg  2880
gaacacaaat gttcagaaac taaacatgca tatcatgccg caaacaagc ggtggtggcg    2940
ttattcacca actctaaata tgatagatta aagttcgaaa caaccatatc caatattctt   3000
tttgctgatt atctcgtgca gtcaattccg tatgtatata ataatggtt accaggtgtt   3060
ccaggtatga attacgatat ctatacagaa ttaaaaaatc tgtttacggg agctttcaat   3120
ctatatgatc agcgaaatat tataaaaaat ggagacttta tcgtgggct catgcattgg    3180
catgcgacac tcatgcaag agtagagcaa ataatagata taggtctgt gctagtgctt    3240
ccaaattatg ctgccaatgt ttcacaagag gtttgtttag aacacaatcg tggttatgta   3300
ttacgtgtaa cggcgaaaaa agaaggcccct ggaattggat atgttacatt cagtgattgt   3360
gcaaatcata tagaaaagct tacatttact tcttgcgatt atggtacaaa cgtagtgcca   3420
tatgaacaat ctaattatcc tacagacgga gtaccatatg acaacatgg ttgtaatata    3480
gacggagtac cgtatgaaca atccggttat cgtacagacg gagtaccgta cgaacttggt   3540
catcgtacag atggagtacc gtacgaacaa tctggttatc gtacagacgg agtaccatgc   3600
gaacaacatg gttgtcatac agacggacta ccacacatca aacatggttg tcgtacagac  3660
agatcaagag atgaactact tggttatgtg acaaaaacga ttgatgtatt ccctaataca   3720
gataaagtac gtatcgacat tggagaaacc gaaggtactt taaagtagaa agtgtagaa    3780
ctgatttgta tggaagagta a                                            3801

SEQ ID NO: 12          moltype = AA   length = 1266
FEATURE                Location/Qualifiers
REGION                 1..1266
                       note = The amino acid sequence of the TIC7042 protein.
source                 1..1266
                       mol_type = protein
                       organism = Brevibacillus laterosporus
SEQUENCE: 12
MNQNQNKNEM QIIEPSSDSF LYSHNNYPYA TDPDTILKGR NYKEWLNMCT DTDDSRSPEA    60
ASTARSAISV AITISTTILG LLGVPFASQI GAFYNFVLNT VWPQGNNQWE EFMRHVENLI   120
NERIADYARD KALAELTGLG NNLNLYREAF EDWRRNPTSQ EAKTRVIDRF RILDGLFETY   180
MPSFAVRNFE VQLLTVYASA ANIHLFLLRD SSIYGLDWGL SQTNVNENYN RQIRHAATYA   240
NHCTTWYQTG LQRLQGTNAT SWVAYNRFRR EMTLTVLDIC SLFSNYDYRS YPTEVKGELT   300
REIYTDPVGR NWQNVAPSFA EIENLTIRAP RTVTWLNSTR IFTGTLTGWS GSNRYWAAHM   360
```

-continued

```
QNFSETNSGN IGFDGPQYGS TVGTIHRTDD YDMVNRDIYT ITSQAVAALW PTGQTVLGVA  420
STRFTLRNLN NNSTEALVYE NAISSSFVSS TLTHELPGEN SDRPTSSDYS HRLSSITGFR  480
AGANGTVPVF GWTSATVDRN NIIEQNKITQ FPGVKSHTLN NCQVVRGTGF TGGDWLRPNN  540
NGTFRLTITS FSSQSYRIRL RYATSVGNTS LVISSSDAGI SSTTIPLTST ITSLPQTVPY  600
QAFRVVDLPI TFTTPTTQRN YTFDFRLQNP SNANVFIDRF EFVPIGGSLS EYETKHQLEK  660
ARKAVNDLFT NESKNVLKKD TTDYDIDQAA NLVECVSDEC ANAKMILLDE VKYAKQLSEA  720
RNLLLNGNFE YQDRDGENPW KTSPNVTIQE NNPIFKGRYL SMSGANNIEA TNEIFPTYVY  780
QKIDESKLKP YTRYKVRGFV GNSKDLELLV TRYDEEVDAI LNVSNDIPHA PPPFCGEFDR  840
CKPHSYPPIN PECHHDVINN IEISSPCQHN KMVDSADISY RHSRISKKHG ICHESHHFEF  900
HIDTGKIDLV ENLGIWVIFK ICSTDGYATL DNLEVIEEGP LGAESLERVK RREKKWKHHM  960
EHKCSETKHA YHAAKQAVVA LFTNSKYDRL KFETTISNIL FADYLVQSIP YVYNKWLPGV  1020
PGMNYDIYTE LKNLFTGAFN LYDQRNIIKN GDFNRGLMHW HATPHARVEQ IIDNRSVLVL  1080
PNYAANVSQE VCLEHNRGYV LRVTAKKEGP GIGYVTFSDC ANHIEKLTFT SCDYGTNVVP  1140
YEQSNYPTDG VPYGQHGCNI DGVPYEQSGY RTDGVPYELG HRTDGVPYEQ SGYRTDGVPC  1200
EQHGCHTDGL PHIQHGCRTD RSRDELLGYV TKTIDVFPNT DKVRIDIGET EGTFKVESVE  1260
LICMEE                                                            1266

SEQ ID NO: 13          moltype = DNA  length = 3810
FEATURE                Location/Qualifiers
misc_feature           1..3810
                       note = A nucleic acid encoding a TIC7381 pesticidal protein
                        sequence obtained from Brevibacillus laterosporus species
                        DSC006713.
source                 1..3810
                       mol_type = unassigned DNA
                       organism = Brevibacillus laterosporus
SEQUENCE: 13
atgaatcaga atcaaaataa aaatgaactg caaatcatag aaccttcaag tgattctttg  60
ctttatagtc acaacaatta tccgtatgca actgatccaa atacagtatt agaaggtagg  120
aattataaag agtggctaaa taagtgcaca gataattata cagacgcttt acagggtccc  180
gaagctactg ctatatcaaa aggagctgtc tctgctgcga tttctatcag caccaaagtt  240
cttagtttat taggtgttcc gtttgcagct caaatcggac aactttggac cttcatattg  300
aatgcgttat ggccttcaga caatactcaa tgggaagagt tcatgagaca tgtagaagaa  360
ctcataaacc aacgaatagc cgattatgca agaagtaagg cacttgcaga attaacgggt  420
ttaggtaata acttagattt atatatagaa gctcttgaag attggaaacg aaatcctact  480
agtcaacaag cgaaagaccg tgtaaaagat agattccgta tagcagatgg tttatttgaa  540
gcgtatatgc cttcatttag agtatcaggt tatgaagtac cattattaac agtgtatgca  600
gccgctgcaa atctccattt acttttatta agagattgct ctatttacgg aatccaatgg  660
ggatttagtc aaacgaatgt taacgagaat tacaatcgcc aaataagaca caccgcagag  720
tatgcaaatc attgtacaac ttggtaccaa actggtttag aaagattgcg aggtaccaat  780
gcttccagtt gggtccctta taatcgtttc cgaagagaaa tgacgttaac tgtattggat  840
atttgttcct tattttcaaa ttatgattat cgtagttatc cagcagaggt aagggcagag  900
cttacaagag aaatttatac ggacccagtt gtaagcacta gcttgtgggt gaataatgca  960
ccatcattcg gagaaataga aaatctagca attagggcgc caagaaccgt tacttggtta  1020
aattctacaa gaatttctac agggaccttg cagggctgga gtggttctaa cagatattgg  1080
gcagctcaca tgcaaaactt ttcagaaacc aattcaggaa atataggatt tgacggtcct  1140
ctctatgggt cgacggtagg tactattatt cgtgatgata attacgaaat ggtgaaccga  1200
gatatttaca ccattacttc agaggctgtt gccgcccttt ggccaactgg tcaaattgtg  1260
ttgggagtcg cttcggctag atttacttta agaaatctta acaataatct tacacaggcg  1320
ctggtgtatg agaacccaat aagttcaagt tttaataggt caactttaac tcgtgaatta  1380
cctggggaaa actcagatag gccaacttca agcgactata gtcatagact aacgtctatt  1440
acagcttttc gagctggaag taatgggacg attccggttt ttggatggac atctataagt  1500
gttaatcgtg acaatatact tgagcgaaac aaaataacac aattcccagg cgttaagtca  1560
cacactctca acaattgtca agtagttaga ggtactggat ttacaggagg agactggttg  1620
agaccaaata ataatggttc atttagatta actattactt cattctcgag ccaatcttac  1680
cgaatccgct tacgttatgc ttccgcagca aatacttctt tgcgtatatc ttcttctgca  1740
gccggtattt cttccacaac cgttccgctt gcctcaacaa taacatcact gccacaaact  1800
gctgtaccat atgaagcttt tagagttata gatttaccta ttacttttac aacagctacc  1860
caaagtaatt atacttttga ttttgttctc caaaatccat caaacgcaaa tgtattcatt  1920
gatagatttg aatttgttcc aattgggggt tctttgtctg agtatgaaac caaacatcag  1980
ctagaaaaag caaggaaagc ggtgaacgat ttgtttacca atgaatcgaa aaatgtgtta  2040
aaaaaataca cgaccgatta tgatatagat caagctgcaa acttggtaga atgtgtatct  2100
gatgaatgtg caaatgctaa aatgatccta ttagatgaag taaaatatgc gaaacaactc  2160
agcgaagccc gcaatctact tctgaatggt aattttgaat accaagatag agatggggag  2220
aatccatgga aaacaagtcc aaatgttact atccaggaaa ataaccccat ttttaaaggc  2280
cgttatctca gtatgtcggg tgcaaactat atcgaggcaa caaatgatac tttccccact  2340
tatgcatacc aaaaaataga tgaagcaaaa ttaaaaccct atacccgtta taaagttcga  2400
gggtttgttg gaaatagtaa agatttagag ttgttgatta aacggtatga tgaagaagtg  2460
gatgcgattt taaatgtacc aaatgatata ccacatgctc cgacaccttt ctgcggtgga  2520
tttgatcgat gcaagccaca ttcttatatt cctatgaatc cagaatgtca ccatgatgta  2580
ataaataaca ttgaaatatc ctctccttgc caacacaata agatgttgga taacgctgat  2640
atatcttctc gccatagtga attaggtaaa aaacatggaa tttgtcatga atctcatcat  2700
tttgaattcc atattgatac aggaaaaatc catttgaacg aaaatttggg aatttgggtt  2760
atatttaaaa tatgttccac agatggttac gcaacattag ataatttgga agttattgaa  2820
gagggtcctt taggagccga atcattagaa cgtgtgaaaa gaagagaaaa gaaatggaaa  2880
catcacatgg aacacaagtg ttcagaaact aaacttgcat atcatgctgc aaaacaagcg  2940
ctggtggggt tattcacaaa cactaaatat gatagattaa agttcgaaac aaccatatcc  3000
aatattcttt ttgctgatta tctcgtgcag tcaattccgt atgtatataa taaatggtta  3060
ccagatgttc caggtatgaa ttacgatatc tatacagaat taaaaaatct gtttacggga  3120
```

```
gctttcaatc tatatgatca gcgaaatatt ataaaaaatg gagactttaa tcgcgggctc  3180
atgcattggc atgcgacacc tcatgcaaga gtagagcaaa tagataatag gtctgtgctg  3240
gtgcttccaa attatgctgc caatgtttca caagaggttt gtttagaaca caatcgtggt  3300
tatgtattac gtgtaacggc gaaaaaagaa ggccctggaa ttggatatgt tacattcagt  3360
gattgtgcaa ataatataga aaactgaca tttacttctt gcgattatgg tacaaacgaa  3420
gtgacatatg agcaatctaa ttatcctaca gacggagtac cgtacgaaca acatggttgt  3480
catacagacg gagtaccgta cgaacaacat ggttgtcata cagacggagt accgtacgaa  3540
caacatggtt gtcatacaga cggaatacca tacaaacaac atggttgtcg tacagacgga  3600
gtaccataca aacaacatgg ttgtcgtaca gacggagtac catacaaaca acatggttgt  3660
cgtacagaca gatcaagaga tgaacaactt gattatgtga caaaaacgat tgatgtattc  3720
cctgatactg ataaagtacg tatcgacatt ggagaaaccg aaggtacctt taaagtagaa  3780
agtgtggaac tgatttttat ggaagagtaa                                   3810
```

```
SEQ ID NO: 14          moltype = AA  length = 1269
FEATURE                Location/Qualifiers
REGION                 1..1269
                       note = The amino acid sequence of the TIC7381 protein.
source                 1..1269
                       mol_type = protein
                       organism = Brevibacillus laterosporus
SEQUENCE: 14
MNQNQNKNEL QIIEPSSDSL LYSHNNYPYA TDPNTVLEGR NYKEWLNKCT DNYTDALQGP  60
EATAISKGAV SAAISISTKV LSLLGVPFAA QIGQLWTFIL NALWPSDNTQ WEEFMRHVEE  120
LINQRIADYA RSKALAELTG LGNNLDLYIE ALEDWKRNPT SQQAKDRVKD RFRIADGLFE  180
AYMPSFRVSG YEVPLLTVYA AAANLHLLLL RDCSIYGIQW GFSQTNVNEN YNRQIRHTAE  240
YANHCTTWYQ TGLERLRGTN ASSWVPYNRF RREMTLTVLD ICSLFSNYDY RSYPAEVRAE  300
LTREIYTDPV VSTSLWVNNA PSFGEIENLA IRAPRTVTWL NSTRISTGTL QGWSGSNRYW  360
AAHMQNFSET NSGNIGFDGP LYGSTVGTII RDDNYEMVNR DIYTITSEAV AALWPTGQIV  420
LGVASARFTL RNLNNNLTQA LVYENPISSS FNRSTLTREL PGENSDRPTS SDYSHRLTSI  480
TAFRAGSNGT IPVFGWTSIS VNRDNILERN KITQFPGVKS HTLNNCQVVR GTGFTGGDWL  540
RPNNNGSFRL TITSFSSQSY RIRLRYASAA NTSLRISSSA AGISSTTVPL ASTITSLPQT  600
AVPYEAFRVI DLPITFTTAT QSNYTFDFVL QNPSNANVFI DRFEFVPIGG SLSEYETKHQ  660
LEKARKAVND LFTNESKNVL KKYTTDYDID QAANLVECVS DECANAKMIL LDEVKYAKQL  720
SEARNLLLNG NFEYQDRDGE NPWKTSPNVT IQENNPIFKG RYLSMSGANY IEATNDTFPT  780
YAYQKIDEAK LKPYTRYKVR GFVGNSKDLE LLIKRYDEEV DAILNVPNDI PHAPTPFCGG  840
FDRCKPHSYI PMNPECHHDV INNIEISSPC QHNKMLDNAD ISSRHSELGK KHGICHESHH  900
FEFHIDTGKI HLNENLGIWV IFKICSTDGY ATLDNLEVIE EGPLGAESLE RVKRREKKWK  960
HHMEHKCSET KLAYHAAKQA LVGLFTNTKY DRLKFETTIS NILFADYLVQ SIPYVYNKWL  1020
PDVPGMNYDI YTELKNLFTG AFNLYDQRNI IKNGDFNRGL MHWHATPHAR VEQIDNRSVL  1080
VLPNYAANVS QEVCLEHNRG YVLRVTAKKE GPGIGYVTFS DCANNIEKLT FTSCDYGTNE  1140
VTYEQSNYPT DGVPYEQHGC HTDGVPYEQH GCHTDGVPYE QHGCHTDGIP YKQHGCRTDG  1200
VPYKQHGCRT DGVPYKQHGC RTDRSRDEQL DYVTKTIDVF PDTDKVRIDI GETEGTFKVE  1260
SVELIFMEE                                                          1269
```

```
SEQ ID NO: 15          moltype = DNA  length = 3741
FEATURE                Location/Qualifiers
misc_feature           1..3741
                       note = A nucleic acid encoding a TIC7382 pesticidal protein
                        sequence obtained from Brevibacillius laterosporus species
                        DSC007657.
source                 1..3741
                       mol_type = unassigned DNA
                       organism = Brevibacillus laterosporus
SEQUENCE: 15
atgaatcaga atcagaatca aaataaaaat gaaatgcaaa ttatagaacc ttcaagtgat  60
tcttttcttt atagtcacaa caattatccg tatgcaactg atccaaatac agtattagaa  120
ggtaggaatt ataaagagtg gctaaataag tgtacaaata attatacaga cgctttacag  180
agtcccgaag ctactgctat ttcaaaagga gctgtttctg ctgcgatttc tataagcacc  240
aaagttcttg gtttattagg tgttccattt gcagctcaaa tcgggcaact ttggaccttc  300
atattaaatg cgttatggcc ttcagacaat actcaatggg aagagttcat gagacatgta  360
gaagaactca taaaccaacg aatagccgat tatgcaagaa ataaggcact tgcagaatta  420
acgggtttag gtaataatct agatttatat atagaggctc ttgatgattg gaaacgaaat  480
cctactagtc aagaagctaa aacccgtgta atagatagat tccgtatagt agatggatta  540
tttgaagcat atataccttc atttgcagta tcaggttatc aagtacaatt attaacggtg  600
tatgcagccg ctgcaaatct ccacttactt ttattaagag attccactat ttacggaatt  660
gattggggat taagtcaaac taatgttaat gataattaca atcgccaaat aagactcacc  720
gcaacgtatg caaatcattg tacaacttgg tatcaaactg gtttagaaag attgaggggt  780
tccaatgctt ccagttgggt cacttataat aggtttcgaa gagaaatgac gttaaccgta  840
ttggatattt gctccttatt ttcaaattat gattatcgta gttacccagc agaggtaagg  900
ggagagatta cgagagaaat ttatacggac ccagtaggtg taggctgggt ggatagtgca  960
ccatcattcg gagaaataga aaatctagca attagggcgc caagaaccgt tacttggtta  1020
aattcaacaa gaatttctac aggaccttg agtggctgga gtggttctaa cagatattgg  1080
gcagctcaca tgcaaaactt ttcagaaacc aattcaggaa atataggatt tgacggtcct  1140
ctctatgggt cgacggtagg tactattcat cgtactgatg attacgatat ggggaatcga  1200
gatatttaca ccattacttc acaagctgtt ttaggccttt ggccaactgg tcaaagggtg  1260
ttgggagtcg cttcggctag atttacttta agaaatcttt tcaataatct tacacaggtg  1320
ctggtgtatg agaacccaat aagttcaaat tttggaagtt caactttaac tcatgaatta  1380
tctggagaaa actcagatag gccaacttct agcgactata gtcatagact aacgagtatc  1440
acaggtttc gagctggagc taatggaacg gtcccagtgt ttggttggac atctgcaact  1500
```

-continued

```
gttgatcgta acaatataat tgagcgaaac aaaataacac aattcccagg tgttaagtca  1560
cacactctca acaattgtca agtagttagg ggtactggat ttacaggagg agactggttg  1620
agaccaaata ataatggtac atttagacta actattactt cattctcgag ccaatcttac  1680
cgaatccgct tacgttatgc tacttcagta gggaatactt ctttagttat atcttcttct  1740
gatgcaggta tttcttccac aacaattccg cttacctcaa caataacatc actgccccaa  1800
actgtaccat accaggcttt tagggttgta gatttaccta ttacttttac aacacctact  1860
acccaaagaa attatacgtt tgatttccgt ctccaaaatc catcaaacgc aaatgtattc  1920
attgatagat ttgaatttgt tccaattggg ggttctttgt ctgagtatga aaccaaacat  1980
cagctagaaa aagcaaggaa agcggtgaac gatttgttta ccaatgaatc gaaaaatgtg  2040
ttaaaaaaag aaactactga ttatgacata gatcaagcag caaacttggt agaatgtata  2100
tcagatgaat gtgcaaatgc aaaaatgatc ctattagatg aagtaaaata tgcgaaacaa  2160
ctcagcgaag cccgcaatct acttctaaat ggtaattttg ataacctaga tagaaatggg  2220
gagaatccat ggaaaacaag tcccaatgtt accatccaag agaataaccc catttttaaa  2280
ggccgctatc tcagtatgtc aggtgcgaac aatatcgagg ccaccaatga gatatttccc  2340
acttatgtat accaaaaaat agatgaagca aaattaaaac cttatacccg ttataaagtt  2400
cgagggtttg ttggaagtag taaagattta gaattattgg ttacacggta tgatgaagaa  2460
gtagatgcaa ttttaaatgt actaaatgat ataccacatg ctccgccacc tttctgcggt  2520
ggatttgatc gatgcaagcc acattcttat cctcctatga atccagaatg tcaccatgat  2580
gtaataaata acattgaaat atcctctcct tgccaacaca ataagatgtt ggataacgct  2640
gatatatttt ctcgccatag tgaattaggt aaaaaacatg gaatttgtca tgaatctcat  2700
cattttgaat tccatattga tacaggaaaa atcgatttga acgaaaattt gggaatttgg  2760
gttatattta aaatatgttc cacagatggt tacgcaacat tagataattt ggaagttatt  2820
gaagagggtc ctttaggagc cgaatcatta gaacgtgtga aaagaagaga aaagaaatgg  2880
aaacatcaca tggaacacaa gtgttcagaa actaaacttg catatcatgc tgcaaaacaa  2940
gcgctggtag ggttattcac aaacactaaa tatgatagat taaagttcga aacaactata  3000
tccaatattc tttttgctga ttatctcgtg cagtcaattc cgtatgtata taataaatgg  3060
ttaccagatg ttccaggtat gaattacgat atctatacag aattaaaaaa tctgtttacg  3120
ggagctttca atctatatga tcagcgaaat attataaaaa atggagactt taatcgcggg  3180
ctcatgcatt ggcatgcgac acctcatgca agagtagagc aaatagataa taggtctgtg  3240
ctggtgcttc caaattatgc tgccaatgtt tcacaagagg tttgtttaga acacaatcgt  3300
ggttatgtat tacgtgtaac ggcgaaaaaa gaaggccctg gaattggata tgttacattt  3360
agtgattgtg caaataatat agaaaagctg acatttactt cttgcgatta tggtacaaac  3420
gaagtgccat atgaacaatc tggttatggt acaaacgaag tgccatatga acaatctggt  3480
tatggtacaa acgaagtgcc atatgaacaa tctggttatc gtacagacgg agtaccatac  3540
aaacaacatg gttgtcgtac agacggagta ccgtacgaac aatctggttg tcgtacagac  3600
agatcaagag atgaacaact tgattatgtg acaaaaacga ttgatgtatt ccctgataca  3660
gataaagtac gtatcgacat tggagaaacc gaaggtacct ttaaagtaga aagtgtggaa  3720
ctgttttgta tggaagagta a                                            3741

SEQ ID NO: 16          moltype = AA  length = 1246
FEATURE                Location/Qualifiers
REGION                 1..1246
                       note = The amino acid sequence of the TIC7382 protein.
source                 1..1246
                       mol_type = protein
                       organism = Brevibacillus laterosporus
SEQUENCE: 16
MNQNQNQNKN EMQIIEPSSD SFLYSHNNYP YATDPNTVLE GRNYKEWLNK CTNNYTDALQ  60
SPEATAISKG AVSAAISIST KVLGLLGVPF AAQIGQLWTF ILNALWPSDN TQWEEFMRHV  120
EELINQRIAD YARNKALAEL TGLGNNLDLY IEALDDWKRN PTSQEAKTRV IDRFRIVDGL  180
FEAYIPSFAV SGYQVQLLTV YAAAANLHLL LLRDSTIYGI DWGLSQTNVN DNYNRQIRLT  240
ATYANHCTTW YQTGLERLRG SNASSWVTYN RFRREMTLTV LDICSLFSNY DYRSYPAEVR  300
GEITREIYTD PVGVGWVDSA PSFGEIENLA IRAPRTVTWL NSTRISTGTL SGWSGSNRYW  360
AAHMQNFSET NSGNIGFDGP LYGSTVGTIH RTDDYDMGNR DIYTITSQAV LGLWPTGQRV  420
LGVASARFTL RNLFNNLTQV LVYENPISSN FGSSTLTHEL SGENSDRPTS SDYSHRLTSI  480
TGFRAGANGT VPVFGWTSAT VDRNNIIERN KITQFPGVKS HTLNNCQVVR GTGFTGGDWL  540
RPNNNGTFRL TITSFSSQSY RIRLRYATSV GNTSLVISSS DAGISSTTIP LTSTITSLPQ  600
TVPYQAFRVV DLPITFTTPT TQRNYTFDFR LQNPSNANVF IDRFEFVPIG GSLSEYETKH  660
QLEKARKAVN DLFTNESKNV LKKETTDYDI DQAANLVECI SDECANAKMI LLDEVKYAKQ  720
LSEARNLLLN GNFDNLDRNG ENPWKTSPNV TIQENNPIFK GRYLSMSGAN NIEATNEIFP  780
TYVYQKIDEA KLKPYTRYKV RGFVGSSKDL ELLVTRYDEE VDAILNVLND IPHAPPPFCG  840
GFDRCKPHSY PPMNPECHHD VINNIEISSP CQHNKMLDNA DIFSRHSELG KKHGICHESH  900
HFEFHIDTGK IDLNENLGIW VIFKICSTDG YATLDNLEVI EEGPLGAESL ERVKRREKKW  960
KHHMEHKCSE TKLAYHAAKQ ALVGLFTNTK YDRLKFETTI SNILFADYLV QSIPYVYNKW  1020
LPDVPGMNYD IYTELKNLFT GAFNLYDQRN IIKNGDFNRG LMHWHATPHA RVEQIDNRSV  1080
LVLPNYAANV SQEVCLEHNR GYVLRVTAKK EGPGIGYVTF SDCANNIEKL TFTSCDYGTN  1140
EVPYEQSGYG TNEVPYEQSG YGTNEVPYEQ SGYRTDGVPY KQHGCRTDGV PYEQSGCRTD  1200
RSRDEQLDYV TKTIDVFPDT DKVRIDIGET EGTFKVESVE LFCMEE                  1246

SEQ ID NO: 17          moltype = DNA  length = 3771
FEATURE                Location/Qualifiers
misc_feature           1..3771
                       note = A nucleic acid encoding a TIC7383 pesticidal protein
                        sequence obtained from Brevibacillus laterosporus species
                        DSC008106.
source                 1..3771
                       mol_type = unassigned DNA
                       organism = Brevibacillus laterosporus
SEQUENCE: 17
```

```
atgaatcaga atcagaatca gaatcaaaat aaaaatgaac tgcaaatcat agaaccttca    60
agtgattctt tgctttatag tcacaacaat tatccgtatg caactgatcc aaatacagta   120
ttagaaggta ggaattataa agagtggcta aataagtgta cagataatta tacagacgct   180
ttacagggtc ccgaagctac tgctatatca aaaggagctg tctctgctgc gatttctatc   240
agcaccaaag ttcttggttt attaggtgtt ccatttgcag ctcaaatcgg gcaactttgg   300
accttcatat tgaatgcgtt atggccttca gacaatactc aatgggaaga gttcatgaga   360
catgtagaag aactcataaa ccaacgaata gccgattatg caagaaataa ggcacttgca   420
gaattaacgg ggttaggtaa taacttagat ttatatatag aggctcttga agattggaaa   480
cgaaatccta ctagtcaaca agcgaaagac cgtgtaatag atagattccg tatagcagat   540
ggttatttg  aagggtatat gccttcattt agagtatcga gttatgaagt accattatta   600
acagtgtatg cagccgctgc aaatctccat ttacttttat taagagattg ctctatttac   660
ggaatccaat ggggatttag tcaaacgaat gttaacgaga attacaatcg ccaaataaga   720
cacaccgcag agtatgcaaa tcattgtaca acttggtacc aaactggttt agaaagattg   780
cgaggtacca atgctttcag ttggatcaat tataatcgat tccgtagaga aatgacgtta   840
accgtattgg atgtttgttc attatttcta aattatgatt atcgtacgta tccaacagag   900
gtaagagcag agcttacgag agaaatttat acggacccaa taggttttca aaatagtcct   960
cttcctggcg ttgttcctaa ttggtacgat tacgcacgat cgttcgcaga gatagaaaat  1020
atagccattc gagcgccacg aactgttact tggttaaatt ctacaactat ttatacaggt  1080
agattaaatg gctataacaa tagtaattat tattgggcag gtttcaggca aaatttttca  1140
gaaaccaatt caggcagttc atttaacggt cctgacttag gggatttaac acctaattat  1200
cgtatagaaa cattggatat ggtgaatcgg atatttact  ccatttattc aagagttgtt  1260
tcacaatctt ggccaattgg caacgttaaa ttgtttggta tctcttcatc tactctttca  1320
ttcagagatc ttaacaataa ttcttcaggg acgctggtat atgaaaaccc gacaaatttt  1380
agtagccaat atctaactac cgaattccct ggggaaaact cagaaagacc aacttttacc  1440
gattatagtc acagactaac ttgtctcaca cgtattgggg ctgaaattta tggattggtt  1500
ctatgcgccg gctggacatc tagtagtgtt gagcgtgaca acagactcca gccggacaaa  1560
ataacacaat acccggctgt aaaggattc  aacctcgatg gttttacagt agtaaaaggt  1620
actgggttta caggggggaaa ttggttgaga tctagtcgtg ttacaggtag ctttagacta  1680
aatgtttatt caccgtctgt ccaaactttat cgcatgcgta tacgttatgc ttctccactg  1740
ggaaattcta ctctaggtat atcttctact gatgctggta ttagtttcac aagttttcca  1800
cttccctcaa caataggatc aatgccatca actgtaccat acgaagcttt tagagttcta  1860
gatatatccta tcactgttac agtagctagt caaagaaatt ataatttat tttcgatatt  1920
ctaaatccat cagtcggagc agtatacatt gacagaattg aattcgttcc agttgggtct  1980
tctgtatttg aatatgaaac caagcatgag ctagaaaaag ttaagaaagc ggtgaacgat  2040
ttgtttacca atgaatcgaa aaatatgtta aaaaaagaca caaccgatta tgatatagat  2100
caagctgcgg acttggtaga atgtgtatca gatgaatgcg cacatgccaa gatgatacta  2160
ctagatgaag tgaaatatgc aaaacagctc agcgaagccc gtaatctact tcaaaatggt  2220
aattttaaag tcctagatgt agataataat aatcctgga  ctaccagccc caatgttacc  2280
atccaagaga ataacccat  ttttaaaggt cattatctta gtatgtcggg tgcaaacgct  2340
atcgaggcaa cgaatgaagt attccccact tatgtatacc aaaaaataga ggaatcaaaa  2400
ctaaaaccat atacccgtta taagttcgt  ggttttattg gcaaagtaa  agatgtagag  2460
ttgttggtta cacgatatga cgaagaagta gatgcgattc taaatgtacc caatgactta  2520
aaatatgctg ttccgacaca tttaagtggt gaatttaatc gatgcaaacc acacacttat  2580
ccagctacgg atccaagatg tcacgatgat gtaatagata agattgatat atcctctcca  2640
tgccaaaaca atattatgtt aagtgacgct gatatatctt ctctccatag tggattaggt  2700
aaaaaacatg gcatttgtca tgaatctcat catttgtaat tccatattga tactgggaaa  2760
atcgatttgg tcgaaaattt gggaatttgg gttatattta aaatatgttc cacagatggt  2820
tacgcaacat tagataatct ggaagttatt gaagagggtc ctttaggagc cgaatcatta  2880
gaacgtgtga aaagaagaga aaagaaatgg aaacacaaca tggaacataa gtgttcagaa  2940
acgaaacatg cctatcatgc cgcaaaacaa gcggtggagg cgttattcac aaattttaaa  3000
gatgaaagat tgaagttcga aacaacgtac tccaatattc tttcagctga gtatcttgca  3060
cagtccattc cgtatgtata taataaatgc ctatcagatg ttccaggtat gaattatgac  3120
atatatacag aattaaaaaa tcggatctgg caagcttta  atttatatga tcagcgaaat  3180
attattaaaa atggacactt taaccacggg ctcatgcatt ggcatgcgac acctcatgca  3240
aacgtacagc aaatagatgg tatatctgtg ttagtgcttc caaattgggg tgccaatgtt  3300
tcacaagagg tttgtttaaa acacaatcgc ggttatgtat acgtgtaac  agccaaagaa  3360
gaaggccatg gaaagggata tgttacaatc agtgattgtg caaatcaagt agaaaagctg  3420
tcatttactt ctcgcgatta tagtacagac ggagtgccat atgagcaatc taattatcct  3480
acagacggag tttcatacgg acaacatggt tgtaatatag acagagtacc gtacgaacaa  3540
tctggttatc ctacagacgg agtaccgtac gaacaatctg ttatcgtac  agacggagta  3600
ccatacaaac aacatggttg tcattcagac ggatcaagag aagaacaaca tggttacgtg  3660
acaaaaacga ttgatgtatt ccctgataca gataaagtac gtatcgacat tggagaaacc  3720
gaaggtacct taaagtaga  aagtgtggaa ctgatttgta tggaagagta a            3771
SEQ ID NO: 18         moltype = AA  length = 1256
FEATURE               Location/Qualifiers
REGION                1..1256
                      note = The amino acid sequence of the TIC7383 protein.
source                1..1256
                      mol_type = protein
                      organism = Brevibacillus laterosporus
SEQUENCE: 18
MNQNQNQNQN KNELQIIEPS SDSLLYSHNN YPYATDPNTV LEGRNYKEWL NKCTDNYTDA    60
LQGPEATAIS KGAVSAAISI STKVLGLLGV PFAAQIGQLW TFILNALWPS DNTQWEEFMR   120
HVEELINQRI ADYARNKALA ELTGLGNNLD LYIEALEDWK RNPTSQQAKD RVIDRFRIAD   180
GLFEGYMPSF RVSGYEVPLL TVYAAAANLH LLLLRDCSIY GIQWGFSQTN VNENYNRQIR   240
HTAEYANHCT TWYQTGLERL RGTNAFSWIN YNRFRREMTL TVLDVCSLFS NYDYRTYPTE   300
VRAELTREIY TDPIGFQNSP LPGVVPNWYD YARSFAEIEN IAIRAPRTVT WLNSTTIYTG   360
RLNGYNNSNY YWAGFRQNFS ETNSGSSFNG PDLGDLTPNY RIETLDMVNR DIYSIYSRVV   420
```

```
SQSWPIGNVK LFGVSSSTLS FRDLNNNSSG TLVYENPTNF SSQYLTTEFP GENSERPTFT    480
DYSHRLTCLT RIGAGNYGLV LCAGWTSSSV ERDNRLQPDK ITQYPAVKGF NLDGFTVVKG    540
TGFTGGNWLR SSRVTGSFRL NVYSPSVQTY RMRIRYASPL GNSTLGISST DAGISFTSFP    600
LPSTIGSMPS TVPYEAFRVL DIPITVTVAS QRNYNFIFDI LNPSVGAVYI DRIEFVPVGS    660
SVFEYETKHE LEKAKKAVND LFTNESKNML KKDTTDYDID QAADLVECVS DECAHAKMIL    720
LDEVKYAKQL SEARNLLQNG NFKVLDVDNN NPWTTSPNVT IQENNPIFKG HYLSMSGANA    780
IEATNEVFPT YVYQKIEESK LKPYTRYKVR GFIGQSKDVE LLVTRYDEEV DAILNVPNDL    840
KYAVPTHLSG EFNRCKPHTY PATDPRCHDD VIDKIDISSP CQNNIMLSDA DISSLHSGLG    900
KKHGICHESH HFEFHIDTGK IDLVENLGIW VIFKICSTDG YATLDNLEVI EEGPLGAESL    960
ERVKRREKKW KHNMEHKCSE TKHAYHAAKQ AVEALFTNFK DERLKFETTI SNILSAEYLV   1020
QSIPYVYNKW LSDVPGMNYD IYTELKNRIW QAFNLYDQRN IIKNGHFNHG LMHWHATPHA   1080
NVQQIDGISV LVLPNWGANV SQEVCLKHNR GYVLRVTAKE EGHGKYVTI SDCANQVEKL    1140
SFTSRDYSTD GVPYEQSNYP TDGVSYGQHG CNIDRVPYEQ SGYPTDGVPY EQSGYRTDGV   1200
PYKQHGCHSD GSREEQHGYV TKTIDVFPDT DKVRIDIGET EGTFKVESVE LICMEE       1256

SEQ ID NO: 19           moltype = DNA   length = 3732
FEATURE                 Location/Qualifiers
misc_feature            1..3732
                        note = A nucleic acid encoding a TIC7383_2 protein which
                         comprises an N-terminal truncation relative to the TIC7383
                         protein.
source                  1..3732
                        mol_type = other DNA
                        organism = synthetic construct
SEQUENCE: 19
atgcaaatca tagaaccttc aagtgattct ttgctttata gtcacaacaa ttatccgtat     60
gcaactgatc caaatacagt attagaaggt aggaattata aagagtggct aaataagtgt    120
acagataatt atacagacgc tttacagggt cccgaagcta ctgctatatc aaaaggagct    180
gtctctgctg cgatttctat cagcaccaaa gttcttggtt tattaggtgt tccatttgca    240
gctcaaatcg ggcaactttg gaccttcata ttgaatgcct tatgccttc agacaatact    300
caatgggaag agttcatgag acatgtagaa gaactcataa accaacgaat agccgtattat  360
gcaagaaata aggcacttgc agaattaacg gggttaggta ataacttaga tttatatata    420
gaggctcttg aagattggaa acgaaatcct actagtcaac aagcgaaaga ccgtgtaata    480
gatagattcc gtatagcaga tggtttattt gaagggtata tgccttcatt tagagtatca    540
ggttatgaag taccattatt aacagtgtat gcagccgctg caaatctcca tttacttta    600
ttaagagatt gctctattta cggaatccaa tggggattta gtcaaacgaa tgttaacgag    660
aattacaatc gccaaataag acacaccgca gagtatgcaa atcattgtac aacttggtac    720
caaactggtt tagaaagatt gcgaggtacc aatgctttca gttggatcaa ttataatcga    780
ttccgtagag aaatgacgtt aaccgtattg gatgtttgtt cattatttc aaattatgat    840
tatcgtacgt atccaacaga ggtaagagca gagcttacga gagaaattta tacggaccca    900
ataggttttc aaaatagtcc tcttcctggc gttgttccta attggtacga ttacgcacga    960
tcgttcgcag agatagaaaa tatagccatt cgagcgccac gaactgttac ttggttaaat   1020
tctacaacta tttatacagg tagattaaat ggctataaca atagtaatta ttattgggca   1080
ggtttcaggc aaaattttc agaaaccaat tcaggcagtt catttaacgg tcctgactta   1140
ggggattta cacctaatta tcgtatagaa acattggata tggtgaatcg ggatatttac   1200
tccatttatt caagagttgt ttcacaatct tggccaattg caacgttaa attgtttgga   1260
gtctcttcat ctactctttc attcagagat cttaacaata attcttcagg gacgctggta   1320
tatgaaaacc cgacaaattt tagtagccaa tatctaacta ccgaattccc tggggaaaac   1380
tcagaaagac caacttttac cgattatagt cacagactaa cttgtctcac acgtattggg   1440
gctggaaatt atggattggt tctatgcgcc ggctggacat tagtagtgt tgagcgtgac   1500
aacagactcc agccggacaa aataacacaa tacccgtcg ttaaaggat caacctcgat   1560
ggttttacag tagtaaaagg tactgggttt acaggggaa attggttgag atctagtcgt   1620
gttacaggta gctttagact aaatgtttat tcaccgtctg tccaaactta tcgcatgcgt   1680
atacgttatg cttctccact gggaaattct actctaggta tatcttctac tgatgctggt   1740
attagtttca caagttttcc acttccctca acaatagat caatgccatc aactgtacca   1800
tacgaagctt ttagagttct agatatacct atcactgtta cagtagctag tcaaagaaat   1860
tataatttta ttttcgatat tctaaatcca tcagtcggag cagtatacat tgacagaatt   1920
gaattcgttc cagttgggtc ttctgtattt gaatatgaaa ccaagcatga gctagaaaaa   1980
gctaagaaag cggtgaacga tttgtttacc aatgaatcga aaaatatgtt aaaaaaagac   2040
acaaccgatt atgatataga tcaagctgcg gacttggtag aatgtgtatc agatgaatgc   2100
gcacatgcca agatgatact actagatgaa gtgaaatatg caaaacagct cagcgaagcc   2160
cgtaatctac ttcaaaatgg taatttaaa gtcctagatg tagataataa taatccatgg   2220
actaccagcc ccaatgttac catccaagag aataacccca ttttaaagg tcattatctt   2280
agtatgtcgg gtgcaaacgc tatcgaggca acgaatgaag tattccccac ttatgtatca   2340
caaaaaatag aggaatcaaa actaaaacca tatcccgtt ataaagttcg tggttttatt   2400
gggcaaagta agatgtaga gttgttggtt acacgatatg acgaagaagt agatgcgatt   2460
ctaaatgtac ccaatgactt aaaatatgct gttccgacac atttaagtgg tgaatttaat   2520
cgatgcaaac cacacactta tccagctacg gatccagatg gtcacgatga tgtaatagat   2580
aagattgata tatcctctcc atgccaaaac aatattatgt taagtgacgc tgatatatct   2640
tctctccata gtggattagg taaaaaacat ggcatttgtc atgaatctca tcatttttgaa  2700
ttccatattg atactgggaa aatcgatttg gtcgaaaatt tgggaatttg gttatatttt  2760
aaaatatgtt ccacagatgg ttacgcaaca ttagataatc tggaagttat tgaagagggt  2820
cctttaggag ccgaatcatt agaacgtgtg aaaagaagag aaaagaaatg gaaacacaac  2880
atggaagttc agatcga aacgaaacat gcctatcatg ccgcaaaaca agcggtggag   2940
gcgttattca caattttaa agatgaaaga ttgaagttcg aaacaacgat ctccaatatt  3000
ctttcagctg agtatcttgt ccagtccatt ccgtatgtat ataataaatg gctatcagat  3060
gttccaggta tgaattatga catatataca gaattaaaaa atcggatctg caagctttt   3120
aatttatatg atcagcgaaa tattattaaa aatggacact ttaaccacgg gctcatgcat  3180
tggcatgcga cacctcatgc aaacgtacag caaatagatg gtatatctgt gttagtgctt  3240
```

```
ccaaattggg gtgccaatgt tcacaagag gtttgtttaa aacacaatcg cggttatgta  3300
ttacgtgtaa cagccaaaga agaaggccat ggaaagggat atgttacaat cagtgattgt  3360
gcaaatcaag tagaaaagct gtcatttact tctcgcgatt atagtacaga cggagtgcca  3420
tatgagcaat ctaattatcc tacagacgga gtttcatacg acaacatgg ttgtaatata  3480
gacagagtac cgtacgaaca atctggttat cctacagacg gagtaccgta cgaacaatct  3540
ggttatcgta cagacggagt accatacaaa caacatggtt gtcattcaga cggatcaaga  3600
gaagaacaac atggttacgt gacaaaaacg attgatgtat tccctgatac agataaagta  3660
cgtatcgaca ttggagaaac cgaaggtacc tttaaagtag aaagtgtgga actgatttgt  3720
atggaagagt aa                                                    3732
```

| SEQ ID NO: 20 | moltype = AA  length = 1243 |
| --- | --- |
| FEATURE | Location/Qualifiers |
| REGION | 1..1243 |
| | note = The amino acid sequence of the TIC7383_2 protein, comprising amino acids 15 through 1256 of TIC7383. |
| source | 1..1243 |
| | mol_type = protein |
| | organism = synthetic construct |

SEQUENCE: 20
```
MQIIEPSSDS LLYSHNNYPY ATDPNTVLEG RNYKEWLNKC TDNYTDALQG PEATAISKGA  60
VSAAISISTK VLGLLGVPFA AQIGQLWTFI LNALWPSDNT QWEEFMRHVE ELINQRIADY  120
ARNKALAELT GLGNNLDLYI EALEDWKRNP TSQQAKDRVI DRFRIADGLF EGYMPSFRVS  180
GYEVPLLTVY AAAANLHLLL LRDCSIYGIQ WGFSQTNVNE NYNRQIRHTA EYANHCTTWY  240
QTGLERLRGT NAFSWINYNR FRREMTLTVL DVCSLFSNYD YRTYPTEVRA ELTREIYTDP  300
IGFQNSPLPG VVPNWYDYAR SFAEIENIAI RAPRTVTWLN STTIYTGRLN GYNNSNYYWA  360
GFRQNFSETN SGSSFNGPDL GDLTPNYRIE TLDMVNRDIY SIYSRVVSQS WPIGNVKLFG  420
VSSSTLSFRD LNNNSSGTLV YENPTNFSSQ YLTTEFPGEN SERPTFTDYS HRLTCLTRIG  480
AGNYGLVLCA GWTSSSVERD NRLQPDKITQ YPAVKGFNLD GFTVVKGTGF TGGNWLRSSR  540
VTGSFRLNVY SPSVQTYRMR IRYASPLGNS TLGISSTDAG ISFTSFPLPS TIGSMPSTVP  600
YEAFRVLDIP ITVTVASQRN YNFIFDILNP SVGAVYIDRI EFVPVGSSVF EYETKHELEK  660
AKKAVNDLFT NESKNMLKKD TTDYDIDQAA DLVECVSDEC AHAKMILLDE VKYAKQLSEA  720
RNLLQNGNFK VLDVDNNNPW TTSPNVTIQE NNPIFKGHYL SMSGANAIEA TNEVFPTYVY  780
QKIEESKLKP YTRYKVRGFI GQSKDVELLV TRYDEEVDAI LNVPNDLKYA VPTHLSGEFN  840
RCKPHTYPAT DPRCHDDVID KIDISSPCQN NIMLSDADIS SLHSGLGKKH GICHESHHFE  900
FHIDTGKIDL VENLGIWVIF KICSTDGYAT LDNLEVIEEG PLGAESLERV KRREKKWKHN  960
MEHKCSETKH AYHAAKQAVE ALFTNFKDER LKFETTISNI LSAEYLVQSI PYVYNKWLSD  1020
VPGMNYDIYT ELKNRIWQAF NLYDQRNIIK NGHFNHGLMH WHATPHANVQ QIDGISVLVL  1080
PNWGANVSQE VCLKHNRGYV LRVTAKEEGH GKGYVTISDC ANQVEKLSFT SRDYSTDGVP  1140
YEQSNYPTDG VSYGQHGCNI DRVPYEQSGY PTDGVPYEQS GYRTDGVPYK QHGCHSDGSR  1200
EEQHGYVTKT IDVFPDTDKV RIDIGETEGT FKVESVELIC MEE                   1243
```

| SEQ ID NO: 21 | moltype = DNA  length = 1980 |
| --- | --- |
| FEATURE | Location/Qualifiers |
| misc_feature | 1..1980 |
| | note = A nucleic acid encoding a TIC7383_3 protein which comprises a C-terminal truncation relative to the TIC7383 protein. |
| source | 1..1980 |
| | mol_type = other DNA |
| | organism = Brevibacillus laterosporus |

SEQUENCE: 21
```
atgaatcaga atcagaatca gaatcaaaat aaaaatgaac tgcaaatcat agaaccttca  60
agtgattctt tgctttatag tcacaacaat tatccgtatg caactgatcc aaatacagta  120
ttagaaggta ggaattataa agagtggcta aataagtgta cagataatta tacagacgct  180
ttacagggtc ccgaagctac tgctatatca aaaggagctg tctctgctgc gattttctatc  240
agcaccaaag ttcttggttt attaggtgtt ccatttgcag ctcaaatcgg gcaactttga  300
accttcatat tgaatgcgtt atggccttca gacaatactc aatgggaaga gttcatgaga  360
catgtagaag aactcataaa ccaacgaata gccgattatg caagaaataa ggcacttgca  420
gaattaacgg ggttaggtaa taacttagat ttatatatag aggctcttga agattggaaa  480
cgaaatccta ctagtcaaca agcgaaagac cgtgtaatag atagcagat                           540
ggtttatttg aagggtatat gccttcattt agagtatcag gttatgaagt accattatta  600
acagtgtatg cagccgctgc aaatctccat ttacttttat taagagattg ctctatttac  660
ggaatccaat ggggatttag tcaaacgaat gttaacgaga attacaatcg ccaaataaga  720
cacaccgcag agtatgcaaa tcattgtaca acttggtacc aaactggttt agaaagattg  780
cgaggtacca atgctttcag ttggatcaat tataatcgat tccgtagaga aatgacgtta  840
accgtattgg atgtttgttc attatttcca aattatgatt atcgtacgta tccaacagag  900
gtaagagcag agcttacgag agaaatttat acggacccaa taggttttca aaatagtcct  960
cttcctggcg ttgttcctaa ttggtacgat tacgcacgat cgttcgcaga gataagaaat  1020
atagccattc gagcgccacg aactgttact ctacaactat ttatacaggt  1080
agattaaatg gctataacaa tagtaattat tattgggcag gtttcaggca aaattttttca  1140
gaaccaatt caggcagttc atttaacggt cctgacttag gggatttaac acctaattat  1200
cgtatagaaa cattggatat ggtgaatcgg gatatttact ccatttattc aagagttgtt  1260
tcacaatctt ggcaattgg caacgttaaa ttgtttggag tctcttcatc tactctttca  1320
ttcagagatc ttaacaataa ttcttcaggg acgctggtat atgaaaaccc gacaaattttt  1380
agtagccaat atctcaactac cgaattccct ggggaaaact cagaaagacc aacttttacc  1440
gattatagtc acagactaac ttgtctcaca cgtattgggg ctggaaatta tggattggtt  1500
ctatgcgccg gctggacatc tagtagtgtt gagcgtgaca acagactcca gccgacaaa  1560
ataacacaat cccggctgt taaaggattc aacctcgatg gttttacagt agtaaaaggt  1620
actggtttta cagggggaaa ttggttgaga tctagtcgtg ttacaggtag ctttagacta  1680
```

```
aatgtttatt caccgtctgt ccaaacttat cgcatgcgta tacgttatgc ttctccactg    1740
ggaaattcta ctctaggtat atcttctact gatgctggta ttagtttcac aagttttcca    1800
cttccctcaa caataggatc aatgccatca actgtaccat acgaagcttt tagagttcta    1860
gatataccta tcactgttac agtagctagt caaagaaatt ataattttat tttcgatatt    1920
ctaaatccat cagtcggagc agtatacatt gacagaattg aattcgttcc agttgggtaa    1980
```

| | |
|---|---|
| SEQ ID NO: 22 | moltype = AA  length = 659 |
| FEATURE | Location/Qualifiers |
| REGION | 1..659 |
| | note = The amino acid sequence of the TIC7383_3 protein and consists of amino acids 1 through 659 of TIC7383. |
| source | 1..659 |
| | mol_type = protein |
| | organism = Brevibacillus laterosporus |

```
SEQUENCE: 22
MNQNQNQNQN KNELQIIEPS SDSLLYSHNN YPYATDPNTV LEGRNYKEWL NKCTDNYTDA     60
LQGPEATAIS KGAVSAAISI STKVLGLLGV PFAAQIGQLW TFILNALWPS DNTQWEEFMR    120
HVEELINQRI ADYARNKALA ELTGLGNNLD LYIEALEDWK RNPTSQQAKD RVIDRFRIAD    180
GLFEGYMPSF RVSGYEVPLL TVYAAAANLH LLLLRDCSIY GIQWGFSQTN VNENYNRQIR    240
HTAEYANHCT TWYQTGLERL RGTNAFSWIN YNRFRREMTL TVLDVCSLFS NYDYRTYPTE    300
VRAELTREIY TDPIGFQNSP LPGVVPNWYD YARSFAEIEN IAIRAPRTVT WLNSTTIYTG    360
RLNGYNNSNY YWAGFRQNFS ETNSGSSFNG PDLGDLTPNY RIETLDMVNR DIYSIYSRVV    420
SQSWPIGNVK LFGVSSSTLS FRDLNNNSSG TLVYENPTNF SSQYLTTEFP GENSERPTFT    480
DYSHRLTCLT RIGAGNYGLV LCAGWTSSSV ERDNRLQPDK ITQYPAVKGF NLDGFTVVKG    540
TGFTGGNWLR SSRVTGSFRL NVYSPSVQTY RMRIRYASPL GNSTLGISST DAGISFTSFP    600
LPSTIGSMPS TVPYEAFRVL DIPITVTVAS QRNYNFIFDI LNPSVGAVYI DRIEFVPVG     659
```

| | |
|---|---|
| SEQ ID NO: 23 | moltype = DNA  length = 2040 |
| FEATURE | Location/Qualifiers |
| misc_feature | 1..2040 |
| | note = A nucleic acid encoding a TIC7383_4 protein which comprises a C-terminal truncation relative to the TIC7383 protein. |
| source | 1..2040 |
| | mol_type = other DNA |
| | organism = Brevibacillus laterosporus |

```
SEQUENCE: 23
atgaatcaga atcagaatca gaatcaaaat aaaaatgaac tgcaaatcat agaaccttca     60
agtgattctt tgctttatag tcacaacaat tatccgtatg caactgatcc aaatacagta    120
ttagaaggta ggaattataa agagtggcta aataagtgta cagataatta tacagacgct    180
ttacagggtc ccgaagctac tgctatatca aaaggagctg tctctgctgc gatttctatc    240
agcaccaaag ttcttggttt attaggtgtt ccatttgcag ctcaaatcgg gcaactttgg    300
accttcatat tgaatgcgtt atggccttca gacaatactc aatggaaga gttcatgaga    360
catgtagaag aactcataaa ccaacgaata gccgattatg caagaaataa ggcacttgca    420
gaattaacgg ggttaggtaa taactttagat ttatatatag aggctcttga agattggaaa    480
cgaaatccta ctagtcaaca agcgaaagac cgtgtaatag atagattccg tatagcagat    540
ggtttatttg aagggtatat gccttcattt agagtatcag gttatgaagt accattatta    600
acagtgtatg cagccgctgc aaatctccat ttactttat taagagattg ctctattac     660
ggaatccaat ggggatttag tcaaacgaat gttaacgaga attacaatcg ccaaataaga    720
cacaccgcag agtatgcaaa tcattgtaca acttggtacc aaactggttt agaaagattg    780
cgaggtacca atgctttcag ttggatcaat tataatcgat tccgtagaga aatgacgtta    840
accgtattgg atgtttgttc attattttca aattatgatt atcgtacgta tccaacagag    900
gtaagagcag agcttacgag agaaatttat acggacccaa taggttttca aaatagtcct    960
cttcctggcg ttgttcctaa ttggtacgat tacgcacgat cgttcgcaga gatagaaaat   1020
atagccattc gagcgccacg aactgttact tggttaaatt ctacaactat ttatacaggt   1080
agattaaatg gctataacaa tagtaattat tattgggcag gtttcaggca aaattttca    1140
gaaccaattc aggcagttc atttaacggt cctgacttag gggatttaac acctaattat   1200
cgtatagaaa cattggatat ggtgaatcgg gatatttact ccatttattc aagagttgtt   1260
tcaacaatctt ggccaattgg caacgttaaa ttgtttggag tctcttcatc tactctttca   1320
ttcagagatc ttaacaataa ttcttcaggg acgctggtat atgaaaaccc gacaaatttt   1380
agtagccaat atctaactac cgaattccct ggggaaaact cagaaagacc aacttttacc   1440
gattatagtc acagactaac ttgtctcaca cgtattgggg ctgaaaatta tggattggtt   1500
ctatgcgccg gctggacatc tagtagtgtt gagcgtgaca acagactcca gccggacaaa   1560
ataacacaat ccccggctgt taaaggattc aacctcgatg gttttacagt agtaaaaggt   1620
actgggttta caggggaaa ttggttgaga tctagtcgtg ttacaggtag ctttagacta   1680
aatgtttatt caccgtctgt ccaaacttat cgcatgcgta tacgttatgc ttctccactg   1740
ggaaattcta ctctaggtat atcttctact gatgctggta ttagtttcac aagttttcca   1800
cttccctcaa caataggatc aatgccatca actgtaccat acgaagcttt tagagttcta   1860
gatataccta tcactgttac agtagctagt caaagaaatt ataattttat tttcgatatt   1920
ctaaatccat cagtcggagc agtatacatt gacagaattg aattcgttcc agttgggtct   1980
tctgtatttg aatatgaaac caagcatgag ctagaaaaag ctaagaaagc ggtgaactaa   2040
```

| | |
|---|---|
| SEQ ID NO: 24 | moltype = AA  length = 679 |
| FEATURE | Location/Qualifiers |
| REGION | 1..679 |
| | note = The amino acid sequence of the TIC7383_4 protein and consists of amino acids 1 through 679 of TIC7383. |
| source | 1..679 |
| | mol_type = protein |

```
                        organism = Brevibacillus laterosporus
SEQUENCE: 24
MNQNQNQNQN KNELQIIEPS SDSLLYSHNN YPYATDPNTV LEGRNYKEWL NKCTDNYTDA    60
LQGPEATAIS KGAVSAAISI STKVLGLLGV PFAAQIGQLW TFILNALWPS DNTQWEEFMR   120
HVEELINQRI ADYARNKALA ELTGLGNNLD LYIEALEDWK RNPTSQQAKD RVIDRFRIAD   180
GLFEGYMPSF RVSGYEVPLL TVYAAAANLH LLLLRDCSIY GIQWGFSQTN VNENYNRQIR   240
HTAEYANHCT TWYQTGLERL RGTNAFSWIN YNRFRREMTL TVLDVCSLFS NYDYRTYPTE   300
VRAELTREIY TDPIGFQNSP LPGVVPNWYD YARSFAEIEN IAIRAPRTVT WLNSTTIYTG   360
RLNGYNNSNY YWAGFRQNFS ETNSGSSFNG PDLGDLTPNY RIETLDMVNR DIYSIYSRVV   420
SQSWPIGNVK LFGVSSSTLS FRDLNNNSSG TLVYENPTNF SSQYLTTEFP GENSERPTFT   480
DYSHRLTCLT RIGAGNYGLV LCAGWTSSSV ERDNRLQPDK ITQYPAVKGF NLDGFTVVKG   540
TGFTGGNWLR SSRVTGSFRL NVYSPSVQTY RMRIRYASPL GNSTLGISST DAGISFTSFP   600
LPSTIGSMPS TVPYEAFRVL DIPITVTVAS QRNYNFIFDI LNPSVGAVYI DRIEFVPVGS   660
SVFEYETKHE LEKAKKAVN                                               679

SEQ ID NO: 25           moltype = DNA  length = 1941
FEATURE                 Location/Qualifiers
misc_feature            1..1941
                        note = A nucleic acid encoding a TIC7383_5 protein which
                         comprises an N-terminal and C-terminal truncation relative
                         to the TIC7383 protein.
source                  1..1941
                        mol_type = other DNA
                        organism = synthetic construct
SEQUENCE: 25
atgcaaatca tagaaccttc aagtgattct ttgctttata gtcacaacaa ttatccgtat    60
gcaactgatc caaatacagt attagaaggt aggaattata aagagtggct aaataagtgt   120
acagataatt atacagacgc tttacagggt cccgaagcta ctgctatatc aaaaggagct   180
gtctctgctg cgatttctat cagcaccaaa gttcttggtt tattaggtgt tccatttgca   240
gctcaaatcg ggcaactttg gaccttcata ttgaatgcat tatggccttc agacaatact   300
caatgggaag agttcatgag acatgtagaa gaactcataa accaacgaat agccgtattat   360
gcaagaaata aggcacttgc agaattaacg gggttaggta ataacttaga tttatatata   420
gaggctcttg aagattggaa acgaaatcct actagtcaac aagcgaaaga ccgtgtaata   480
gatagattcc gtatagcaga tggttttatt gaagggtata tgccttcatt tagagtatca   540
ggttatgaag taccattatt aacagtgtat gcagccgctg caaatctcca tttactttta   600
ttaagagatt gctctattta cggaatccaa tggggattta gtcaaacgaa tgttaacgag   660
aattacaatc gccaaataag acacaccgca gagtatgcaa atcattgtac aacttggtac   720
caaactggtt tagaaagatt gcgaggtacc aatgctttca gttggatcaa ttataatcga   780
ttccgtagag aaatgacgtt aaccgtattg gatgtttgtt cattattttc aaattatgat   840
tatcgtacgt atccaacaga ggtaagagca gagcttacga gagaaattta tacggaccca   900
ataggttttc aaaatagtcc tcttcctggc gttgttccta attggtacga ttacgcacga   960
tcgttcgcag agatagaaaa tatagccatt cgagcgccac gaactgttac ttggttaaat  1020
tctacaacta tttatacagg tagattaaat ggctataaca atagtaatta ttattgggca  1080
ggtttcaggc aaaattttc agaaaccaat tcaggcagtt catttaacgg tcctgactta  1140
ggggatttaa cacctaatta tcgtatagaa acattggata tggtgaatcg ggatatttac  1200
tccattttatt caagagttgt ttcacaatct tggccaattg caacgttaa attgtttgga  1260
gtctcttcat ctactctttc attcagagat cttaacaata attcttcagg gacgctggta  1320
tatgaaaacc cgacaaattt tagtagccaa tatctaacta ccgaattccc tggggaaaac  1380
tcagaaagac caacttttac cgattatagt cacagactaa cttgtctcac acgtattggg  1440
gctggaaatt atggattggt tctatgcgcc ggctggacat ctagtagtgt tgagcgtgac  1500
aacagactcc agccggacaa aataacacaa tacccgctg ttaaaggatt caacctcgat  1560
ggttttacag tagtaaaagg tactgggttt acaggggga attggttgag atctagtcgt  1620
gttacaggta gctttagact aaatgtttat tcaccgtctg tccaaactta tcgcatgcgt  1680
atacgttatg cttctccact gggaaattct actctaggta tatcttctac tgatgctggt  1740
attagtttca caattttcc acttccctca acaataggat caatgccatc aactgtacca  1800
tacgaagctt ttagagttct agatataacct atcactgtta cagtagccag tcaaagaaat  1860
tataatttta ttttcgatat tctaaatcca tcagtcggag cagtatacat tgacagaatt  1920
gaattcgttc cagttgggta a                                            1941

SEQ ID NO: 26           moltype = AA  length = 646
FEATURE                 Location/Qualifiers
REGION                  1..646
                        note = The amino acid sequence of the TIC7383_5 protein and
                         comprises amino acids 15 though 659 of TIC7383.
source                  1..646
                        mol_type = protein
                        organism = synthetic construct
SEQUENCE: 26
MQIIEPSSDS LLYSHNNYPY ATDPNTVLEG RNYKEWLNKC TDNYTDALQG PEATAISKGA    60
VSAAISISTK VLGLLGVPFA AQIGQLWTFI LNALWPSDNT QWEEFMRHVE ELINQRIADY   120
ARNKALAELT GLGNNLDLYI EALEDWKRNP TSQQAKDRVI DRFRIADGLF EGYMPSFRVS   180
GYEVPLLTVY AAAANLHLLL LRDCSIYGIQ WGFSQTNVNE NYNRQIRHTA EYANHCTTWY   240
QTGLERLRGT NAFSWINYNR FRREMTLTVL DVCSLFSNYD YRTYPTEVRA ELTREIYTDP   300
IGFQNSPLPG VVPNWYDYAR SFAEIENIAI RAPRTVTWLN STTIYTGRLN GYNNSNYYWA   360
GFRQNFSETN SGSSFNGPDL GDLTPNYRIE TLDMVNRDIY SIYSRVVSQS WPIGNVKLFG   420
VSSSTLSFRD LNNNSSGTLV YENPTNFSSQ YLTTEFPGEN SERPTFTDYS HRLTCLTRIG   480
AGNYGLVLCA GWTSSSVERD NRLQPDKITQ YPAVKGFNLD GFTVVKGTGF TGGNWLRSSR   540
VTGSFRLNVY SPSVQTYRMR IRYASPLGNS TLGISSTDAG ISFTSFPLPS TIGSMPSTVP   600
YEAFRVLDIP ITVTVASQRN YNFIFDILNP SVGAVYIDRI EFVPVG               646
```

```
SEQ ID NO: 27          moltype = DNA  length = 2001
FEATURE                Location/Qualifiers
misc_feature           1..2001
                       note = A nucleic acid encoding a TIC7383_6 protein which
                        comprises an N-terminal and C-terminal truncation relative
                        to the TIC7383 protein.
source                 1..2001
                       mol_type = other DNA
                       organism = synthetic construct
SEQUENCE: 27
atgcaaatca tagaaccttc aagtgattct ttgctttata gtcacaacaa ttatccgtat  60
gcaactgatc caaatacagt attagaaggt aggaattata aagagtggct aaataagtgt  120
acagataatt atacagacgc tttacagggt cccgaagcta ctgctatatc aaaaggagct  180
gtctctgctg cgatttctat cagcaccaaa gttcttggtt tattaggtgt tccatttgca  240
gctcaaatcg ggcaactttg gaccttcata ttgaatgcgt tatggccttc agacaatact  300
caatgggaag agttcatgag acatgtagaa gaactcataa accaacgaat agccgattat  360
gcaagaaata aggcacttgc agaattaacg ggggttaggta ataacttaga tttatatata  420
gaggctcttg aagattggaa acgaaatcct actagtcaac aagcgaaaga ccgtgtaata  480
gatagattcc gtatagcaga tggtttattt gaagggtata tgccttcatt tagagtatca  540
ggttatgaag taccattatt aacagtgtat gcagccgctg caaatctcca tttactttta  600
ttaagagatt gctctattta cggaatccaa tggggattta gtcaaacgaa tgttaacgag  660
aattacaatc gccaaataag acacaccgca gagtatgcaa atcattgtac aacttggtac  720
caaactggtt tagaaagatt gcgaggtacc aatgctttca gttggatcaa ttataatcga  780
ttccgtagag aaatgacgtt aaccgtattg gatgtttgtt cattattttc aaattatgat  840
tatcgtacgt atccaacaga ggtaagagca gagcttacga gagaaattta tacggaccca  900
ataggttttc aaaatagtcc tcttcctggc gttgttccta attggtacga ttacgcacga  960
tcgttcgcag agatagaaaa tatagccatt cgagcgccac gaactgttac ttggttaaat  1020
tctacaacta tttatacagg tagattaaat ggctataaca atagtaatta ttattgggca  1080
ggtttcaggc aaaatttttc agaaaccaat tcaggcagtt catttaacgg tcctgactta  1140
ggggatttaa cacctaatta tcgtatagaa acattggata tggtgaatcg ggatatttac  1200
tccatttatt caagagttgt ttcacaatct tggccaattg gcaacgttaa attgtttgga  1260
gtctcttcat ctactctttc attcagagat cttaacaata attcttcagg gacgctggta  1320
tatgaaaacc cgacaaattt tagtagccaa tatctaacta ccgaattccc tggggaaaac  1380
tcagaaagac caactttttac cgattatagt cacagactaa cttgtctcac acgtattggg  1440
gctggaaatt atggattggt tctatgcgcc ggctggacat ctagtagtgt tgagcgtgac  1500
aacagactcc agccggacaa aataacacaa tacccggctg ttaaaggatt caacctcgat  1560
ggttttacag tagtaaaagg tactgggttt acagggggaa attggttgag atctagtcgt  1620
gttacaggta gctttagact aaatgtttat tcaccgtctg tccaaactta tcgcatgcgt  1680
atacgttatg cttctccact gggaaattct actctaggta tatcttctac tgatgctggt  1740
attagtttca caagttttcc acttccctca acaataggat caatgccatc aactgtacca  1800
tacgaagctt ttagagttct agatatacct atcactgtta cagtagctag tcaaagaaat  1860
tataatttta ttttcgatat tctaaatcca tcagtcggag cagtatacat tgacagaatt  1920
gaattcgttc cagttgggtc ttctgtattt gaatatgaaa ccaagcatga gctagaaaaa  1980
gctaagaaag cggtgaacta a                                          2001

SEQ ID NO: 28          moltype = AA  length = 666
FEATURE                Location/Qualifiers
REGION                 1..666
                       note = The amino acid sequence of the TIC7383_6 protein,
                        comprising amino acids 15 through 679 of TIC7383.
source                 1..666
                       mol_type = protein
                       organism = synthetic construct
SEQUENCE: 28
MQIIEPSSDS LLYSHNNYPY ATDPNTVLEG RNYKEWLNKC TDNYTDALQG PEATAISKGA  60
VSAAISISTK VLGLLGVPFA AQIGQLWTFI LNALWPSDNT QWEEFMRHVE ELINQRIADY  120
ARNKALAELT GLGNNLDLYI EALEDWKRNP TSQQAKDRVI DRFRIADGLF EGYMPSFRVS  180
GYEVPLLTVY AAAANLHLLL LRDCSIYGIQ WGFSQTNVNE NYNRQIRHTA EYANHCTTWY  240
QTGLERLRGT NAFSWINYNR FRREMTLTVL DVCSLFSNYD YRTYPTEVRA ELTREIYTDP  300
IGFQNSPLPG VVPNWYDYAR SFAEIENIAI RAPRTVTWLN STTIYTGRLN GYNNSNYYWA  360
GFRQNFSETN SGSSFNGPDL GDLTPNYRIE TLDMVNRDIY SIYSRVVSQS WPIGNVKLFG  420
VSSSTLSFRD LNNNSSGTLV YENPTNFSSQ YLTTEFPGEN SERPTFTDYS HRLTCLTRIG  480
AGNYGLVLCA GWTSSSVERD NRLQPDKITQ YPAVKGFNLD GFTVVKGTGF TGGNWLRSSR  540
VTGSFRLNVY SPSVQTYRMR IRYASPLGNS TLGISSTDAG ISFTSFPLPS TIGSMPSTVP  600
YEAFRVLDIP ITVTVASQRN YNFIFDILNP SVGAVYIDRI EFVPVGSSVF EYETKHELEK  660
AKKAVN                                                           666

SEQ ID NO: 29          moltype = DNA  length = 3840
FEATURE                Location/Qualifiers
misc_feature           1..3840
                       note = A nucleic acid encoding a TIC7386 pesticidal protein
                        sequence obtained from Brevibacillus laterosporus species
                        DSC007651.
source                 1..3840
                       mol_type = unassigned DNA
                       organism = Brevibacillus laterosporus
SEQUENCE: 29
atgaatcaga atcaaaataa aaatgaactg caaatcatag aaccttcaag cgattctttt  60
```

```
ctttatagtc acaacaatta tccgtatgct actgatccag atacaatatt aaaaggtagg    120
aattataaag agtggctaaa tatgtgtaca gatacagacg attcacgaag tcccgaagct    180
gcttctactg caagatcagc tatttctgtt gcgattacta taagcaccac aattcttggc    240
ttactaggta ttccgtttgc atctcaaatt ggagcatttt ataacttcgt attgaatacg    300
gtatggcctc agggaaataa ccaatgggaa gagttcatga gacatgtaga aaatctcata    360
aacgaacgaa tagctgatta tgcaagagat aaggcacttg cagaattaac gggtttaggt    420
aataacttaa atttatatag agaagctttt gaagattgga gacgaaatcc tactagtcaa    480
gaagctaaaa cccgtgtaat agatagattc cgtatactag atggtttatt tgaaacatat    540
atgccttcat ttgcagtacg aaattttgaa gtacaattat taacagtgta tgcatccgct    600
gcaaatatcc atttattttt attaagagat agctctattt acggtttgga ttgggggatta    660
agtcaaacta atgttaacga aaattacaat cgccaaataa ggcacgccga aacgtatgca    720
aatcattgta caacttggta tcaaactggt ttacaaagat gcaaggtac caatgctacc    780
agttgggtcg cttataatag atttagaaga gaaatgacgt taacagtatt agatatttgt    840
tcattatttt caaattatga ttatcgtagt tatccaacag aggtaagggg agagcttacg    900
agagaaattt atacggatcc agtaggtaga aactggcaga atgttgcacc atcattcgct    960
gaaatagaaa atctaacaat taggcacca agaaccgtta cttggttaaa ttcaacaaga   1020
atttttacag ggactttgac aggctggagt ggttctaaca gatattgggc agctcacatg   1080
caaaactttt cagaaaccaa ttcaggaaat ataggattcg acggtcctca atatgggtcg   1140
acggtaggta ctattcatcg tactgatgat tacgatatgg tgaatcgaga tatttacacc   1200
attacttcac aagctgttgc cgcctttgg ccaactggtc aaactgtgtt ggggagtcgct   1260
tcgactagat ttacttaag aaaccttaac aataattcta cagaggcgct ggtgtatgag   1320
aacgcaataa gttcaagttt tgttagttca acttaactc atgaattacc tggagaaaac   1380
tcagataggc caacttctag cgactatagt catagactat cgagtatcac aggttttcga   1440
gctggagcta atggaacggt cccagtgttt ggttggacat ctgcaactgt tgatcgtaac   1500
aatataattg agcaaaacaa aataacacaa ttcccaggtg ttaagtcaca cactctcaac   1560
aattgtcaag tagttagggg tactggattt acaggaggag actggttgag accaaataat   1620
aatggtacat ttagactaac tattacttca ttctccagcc aatcttaccg aattcgctta   1680
cgttatgcta cttcagtagg gaatacttct ttagttatat cttcttctga tgcaggtatt   1740
tcttccacaa caattccgct tacctcaaca ataacatcac tgccacaaac tgtaccatac   1800
caagcttta gggttgtaga tttacctatt acttttcaca cacctactac ccaaagaaat   1860
tatacgtttg atttccgtct ccaaaatcca tcaaacgcaa atgtattcat tgatagattt   1920
gaatttgttc caattggggg ttctttgtct gagtatgaaa ccaaacatca gctagaaaaa   1980
gcaaggaaag cggtgaacga tttgtttacc aatgaatcga aaaatgtgtt aaaaaaagac   2040
acgaccgatt atgatataga tcaagctgca aacttggtag aatgtgtatc tgatgaatgt   2100
gcaaatgcta aaatgatcct attagatgaa gtaaaatatg cgaaacaact tagcgaagcc   2160
cgcaatctac ttctaaatgg taatttttgaa taccaagata gagatgggga gaatccatgg   2220
aaaacaagtc ccaatgttac catccaagag aataacccca tttttaaagg ccgctatctc   2280
agtatgtcag gtgcgaacaa tatcgaggca accaatgaga tattcccac ttatgtatac   2340
caaaaaattg atgaatccaa attaaaacct tacaccccgtt ataaagttcg aggttttgtt   2400
ggaaatagta aagatttaga attattggtt acacggtatg atgaagaagt agatgcgatt   2460
ttaaatgtac caaatgatat accacatgct ccgccaccctt tctgcggtga atttgatcga   2520
tgcaagccgc attcttatcc tcctattaat ccagaatgtc accatgatgt aataaataac   2580
attgaaatat cctctccttg ccaacacaat aagatggtag ataacgctga tatatcttat   2640
cgccatagcc gattaagtaa aaaacatggc atttgtcatg aatctcatca ttttgaattc   2700
catattgata cagggaaaat cgatttggcc ggaaatttgg gaatttggggt tatatttaaa   2760
atatgttcca cagatggtta cgcaacatta gataatttgg aagttattga agagggtcct   2820
ttaggagccg aatcctagaa acgtgtgaaa agaagagaaa agaaatggaa acatcacatg   2880
gaacacaaat gttcagaaac taaacatgca tatcatgccg caaaacaagc ggtggtggcg   2940
ttattcacca actctaaata tgatagatta agttcgaaa caaccatatc caatattctt   3000
tttgctgatt atctcgtgca gtcaattccg tatgtatata aaaatggtt accaggtgtt   3060
ccaggtatga attacgatat ctatacagaa ttaaaaaatc tgtttacggg agcttttcat   3120
ctatatgatc agcgaaatat tataaaaaat ggagacttta atcgtgggct catgcattgg   3180
catgcgacac tcatgcaag agtagagcaa ataatagata ataggtctgt gctagtgctt   3240
ccaaattatg ctaccaatgt ttcacaagag gtttgtttag aacacaatcg tggttatgta   3300
ttacgtgtaa cggcgaaaaa agaaggccct ggaattggat atgttacatt cagtgattgt   3360
gcaaatcata tagaaaagct tacatttact tcttgcgatt atggtacaaa cgtagtgcca   3420
tatgaacaat ctaattatcc tacagacgga gtaccatatg acaacatgg ttgtaatata   3480
gacggagtac cgtatgaaca atccggttat cgtacagacg gagtaccgta cgaacaatct   3540
ggtcatcgta cagatggagt accgtacgaa caatctggtt atcgtacaga cggagaacca   3600
tgcgaacaac atggttgtca tacagacgga ctaccacaca tcaacatgg ttgtcgtaca   3660
gacggactac cacacataca acatggttgt cgtacagaca gatcaagaga tgaactacttt   3720
ggttatgtga caaaaacgat tgatgtattc cctaatacag ataaagtacg tatcgacatt   3780
ggagaaaccg aagtactttt taagtagaa agtgtagaac tgatttgtat ggaagagtaa   3840
```

```
SEQ ID NO: 30          moltype = AA   length = 1279
FEATURE                Location/Qualifiers
REGION                 1..1279
                       note = The amino acid sequence of the TIC7386 protein.
source                 1..1279
                       mol_type = protein
                       organism = Brevibacillus laterosporus
SEQUENCE: 30
MNQNQNKNEL QIIEPSSDSF LYSHNNYPYA TDPDTILKGR NYKEWLNMCT DTDDSRSPEA    60
ASTARSAISV AITISTTILG LLGVPFASQI GAFYNFVLNT VWPQGNNQWE EFMRHVENLI   120
NERIADYARD KALAELTGLG NNLNLYREAF EDWRRNPTSQ EAKTRVIDRF RILDGLFETY   180
MPSFAVRNFE VQLLTVYASA ANIHLFLLRD SSIYGLDWGL SQTNVNENYN RQIRHAETYA   240
NHCTTWYQTG LQRLQGTNAT SWVAYNRFRR EMTLTVLDIC SLFSNYDYRS YPTEVRGELT   300
REIYTDPVGR NWQNVAPSFA EIENLTIRAP RTVTWLNSTR IFTGTLTGWS GSNRYWAAHM   360
QNFSETNSGN IGFDGPQYGS TVGTIHRTDD YDMVNRDIYT ITSQAVAALW PTGQTVLGVA   420
```

-continued

```
STRFTLRNLN NNSTEALVYE NAISSSFVSS TLTHELPGEN SDRPTSSDYS HRLSSITGFR  480
AGANGTVPVF GWTSATVDRN NIIEQNKITQ FPGVKSHTLN NCQVVRGTGF TGGDWLRPNN  540
NGTFRLTITS FSSQSYRIRL RYATSVGNTS LVISSSDAGI SSTTIPLTST ITSLPQTVPY  600
QAFRVVDLPI TFTTPTTQRN YTFDFRLQNP SNANVFIDRF EFVPIGGSLS EYETKHQLEK  660
ARKAVNDLFT NESKNVLKKD TTDYDIDQAA NLVECVSDEC ANAKMILLDE VKYAKQLSEA  720
RNLLLNGNFE YQDRDGENPW KTSPNVTIQE NNPIFKGRYL SMSGANNIEA TNEIFPTYVY  780
QKIDESKLKP YTRYKVRGFV GNSKDLELLV TRYDEEVDAI LNVPNDIPHA PPPFCGEFDR  840
CKPHSYPPIN PECHHDVINN IEISSPCQHN KMVDNADISY RHSRLSKKHG ICHESHHFEF  900
HIDTGKIDLA GNLGIWVIFK ICSTDGYATL DNLEVIEEGP LGAESLERVK RREKKWKHHM  960
EHKCSETKHA YHAAKQAVVA LFTNSKYDRL KFETTISNIL FADYLVQSIP YVYNKWLPGV  1020
PGMNYDIYTE LKNLFTGAFN LYDQRNIIKN GDFNRGLMHW HATPHARVEQ IIDNRSVLVL  1080
PNYATNVSQE VCLEHNRGYV LRVTAKKEGP GIGYVTFSDC ANHIEKLTFT SCDYGTNVVP  1140
YEQSNYPTDG VPYGQHGCNI DGVPYEQSGY RTDGVPYEQS GHRTDGVPYE QSGYRTDGEP  1200
CEQHGCHTDG LPHIQHGCRT DGLPHIQHGC RTDRSRDELL GYVTKTIDVF PNTDKVRIDI  1260
GETEGTFKVE SVELICMEE                                              1279

SEQ ID NO: 31          moltype = DNA  length = 3810
FEATURE                Location/Qualifiers
misc_feature           1..3810
                       note = A nucleic acid encoding a TIC7388 pesticidal protein
                        sequence obtained from Brevibacillus laterosporus species
                        DSC007962.
source                 1..3810
                       mol_type = unassigned DNA
                       organism = Brevibacillus laterosporus
SEQUENCE: 31
atgaatcaga atcaaaataa aaatgaaatg caaattatag aaccttcaag tgattctttt  60
ctttatagtc acaacaatta tccgtatgcc actgatccaa atacagtatt agaaggtagg  120
aattataaag agtggctaaa taagtgtaca gataattata cagatgcttt acagagtccc  180
gaagctactg ctatttcaaa aggagctgtt tctgctgcga tttctataag caccaaagtt  240
cttggtttat taggtgttcc atttgcagct caaatcgggc aactttggac cttcatatta  300
aatgcgttat ggccttcaga caatactcaa tgggaagagt tcatgagaca tgtagaagaa  360
ctcataaacc aacgaatagc cgattatgca agaaataagg cacttgcaga attaacgggt  420
ttaggtaata atctagattt atatatagag gctcttgatg attggaaacg aaatcctact  480
agtcaagaag ctaaaacccg tgtaatagat agattccgta tagtagatgg attatttgaa  540
gcatatatac cttcatttgc agtatcaggt tatcaagtac aattattaac ggtgtatgca  600
gccgctgcaa atctccactt acttttatta agagattcca ctatttacgg aattgattgg  660
ggattaagtc aaactaatgt taatgataat tacaatcgcc aaataagact caccgcaacg  720
tatgcaaatc attgtacaac ttggtatcaa actggtttag aaagattgag gggttccaat  780
gcttccagtt gggtcactta taataggttt cgaagggaaa tgacgttaac cgtattggat  840
atttgttcct tattttcaaa ttatgattat cgtagttacc cagcagaggt aaggggagag  900
attacgagag aaatttatac ggacccagta ggtgtaggct gggtggatag tgcaccatca  960
ttcggagaaa tagaaaatct agcaattagg gcaccaagaa ccgttacttg gttaaattca  1020
acaagaattt ttacagggag attgcagggc tggagtggta ctaacaatta ttgggcagct  1080
cacatgcaaa acttctcaga aaccaattca ggaaatatac aatttgaagg tcctctctat  1140
gggtcgacgg taggtactat tcatcgtact gatgattacg atatggggaa tcgagatatt  1200
tacaccatta cttcacaagc tgttttaggc ctttgggcaa ctggtcaaag ggtgttgggg  1260
gtcgcttcgg ctagatttac tttaagaaat cttttcaata atcttacaca ggtgctggtg  1320
tatgagaacc caataagttc aacttttgga agttcaactt taactcatga attatctgga  1380
gaaaactcag ataggccaac ttctagcgac tatagtcata gactaacgag tatcacaggt  1440
tttcgagctg gagctaatgg aacggtccca gtgtttggtt ggacatctgc aactgttgat  1500
cgtaacaata taattgagcg aaacaaaata acacaattcc caggtgttaa gtcacacact  1560
ctcaacaatt gtcaagtagt taggggtact ggatttacag gaggagactg gttgagacca  1620
aataataatg gtacatttag actaactatt acttcattct ccagccaatc ttaccgaatt  1680
cgcttacgtt atgctacttc agtagggaat acttctttag ttatatcttc ttctgatgca  1740
ggtatttctt ccacaacaat tccgcttacc tcaacaataa catcactgcc acaaactgta  1800
ccataccaag cttttagggt tgtagattta cctattactt ttacaacacc tactacccaa  1860
agaaattata cgtttgattt ccgtctccaa aatccatcaa acgcaaatgt attcattgat  1920
agatttgaat ttgttccaat tggggggttct ttgtctgagt atgaaaccaa acatcagcta  1980
gaaaaagcaa ggaaagcggt gaacgatttg tttaccaatg aatcgaaaaa tgtgttaaaa  2040
aaagacacga ccgattatga tatagatcaa gctgcaaact tggtagaatg tgtatctgat  2100
gaatgtgcaa atgctaaaat gatcctatta gatgaagtaa aatatgcgaa acaacttagc  2160
gaagcccgca atctacttct aaatggtaat tttgaatacc aagatagaga tggggagaat  2220
ccatggaaaa caagtcccaa tgttaccatc caagagaata accccatttt taaaggccgc  2280
tatctcagta tgtcaggtgc gaacaatatc gaggcaacca atgagatatt tcccacttat  2340
gtataccaaa aaattgatga atccaaatta aaaccttata cccgttataa agttcgaggt  2400
tttgttggaa atagtaaaga tttagaatta ttggttacac ggtatgatga agaagtagat  2460
gcgattttaa atgtaccaaa tgatatacca catgctccgc cacctttctg cggtgaattt  2520
gatcgataca agccgcattc ttatcctcct attaatccag aatgtcacca tgatgtaata  2580
aataacattg aaatatcctc tccttgccaa cacaataaga tggtagataa cgctgatata  2640
tcttatcgcc atagccgatt aagtaaaaaa catggcattt gtcatgaatc tcatcatttt  2700
gaattccata ttgatacagg gaaaatcgat ttggtcgaaa atttgggaat ttgggttgta  2760
tttaaaatat gttccacaga tggttacgca acattagata atttggaagt tattgaagag  2820
ggtcctttag gagccgaatc cttagaacgt gtgaaaagaa gagaaaagaa atggaaacat  2880
cacatggaac acaaatgttc agaaactaaa catgcatatc atgccgcaaa acaagcggtg  2940
gtggcgttat tcaccaactc taaatatgat agattaaagt tcgaaacaac catatccaat  3000
attctttttg ctgattatct cgtgcagtca attccgtatg tatataataa atggttacca  3060
ggtgttccag gtatgaatta cgatatctat acagaattaa aaaatctgtt tacgggagct  3120
ttcaatctat atgatcagcg aaatattata aaaaatggag actttaatcg tgggctcatg  3180
```

```
cattggcatg cgacacctca tgcaagagta gagcaaataa tagataatag gtctgtgcta  3240
gtgcttccaa attatgctgc caatgtttca caagaggttt gtttagaaca caatcgtggt  3300
tatgtattac gtgtaacggc gaaaaaagaa ggccctggaa ttggatatgt tacattcagt  3360
gattgtgcaa atcatataga aaagcttaca tttacttctt gcgattatgg tacaaacgta  3420
gtgccatatg aacaatctaa ttatcctaca gacggagtac catatggaca acatggttgt  3480
aatatagacg gagtaccgta tgaacaatcc ggttatcgta cagacggagt accgtacgaa  3540
caatctggtc atcgtacaga tggagtaccg tacgaacaat ctggttatcg tacagacgga  3600
gtaccatgcg aacaacatgg ttgtcataca gacggactac cacacataca acatggttgt  3660
cgtacagaca gatcaagaga tgaactactt ggttatgtga caaaaacgat tgatgtattc  3720
cctaatacag ataaagtacg tatcgacatt ggagaaaccg aaggtacttt taaagtagaa  3780
agtgtagaac tgatttgtat ggaagagtaa                                  3810

SEQ ID NO: 32          moltype = AA  length = 1269
FEATURE                Location/Qualifiers
REGION                 1..1269
                       note = The amino acid sequence of the TIC7388 protein.
source                 1..1269
                       mol_type = protein
                       organism = Brevibacillus laterosporus
SEQUENCE: 32
MNQNQNKNEM QIIEPSSDSF LYSHNNYPYA TDPNTVLEGR NYKEWLNKCT DNYTDALQSP  60
EATAISKGAV SAAISISTKV LGLLGVPFAA QIGQLWTFIL NALWPSDNTQ WEEFMRHVEE  120
LINQRIADYA RNKALAELTG LGNNLDLYIE ALDDWKRNPT SQEAKTRVID RFRIVDGLFE  180
AYIPSFAVSG YQVQLLTVYA AAANLHLLLL RDSTIYGIDW GLSQTNVNDN YNRQIRLTAT  240
YANHCTTWYQ TGLERLRGSN ASSWVTYNRF RREMTLTVLD ICSLFSNYDY RSYPAEVRGE  300
ITREIYTDPV GVGWVDSAPS FGEIENLAIR APRTVTWLNS TRIFTGRLQG WSGTNNYWAA  360
HMQNFSETNS GNIQFEGPLY GSTVGTIHRT DDYDMGNRDI YTITSQAVLG LWATGQRVLG  420
VASARFTLRN LFNNLTQVLV YENPISSTFG SSTLTHELSG ENSDRPTSSD YSHRLTSITG  480
FRAGANGTVP VFGWTSATVD RNNIIERNKI TQFPGVKSHT LNNCQVVRGT GFTGGDWLRP  540
NNNGTFRLTI TSFSSQSYRI RLRYATSVGN TSLVISSSDA GISSTTIPLT STITSLPQTV  600
PYQAFRVVDL PITFTTPTTQ RNYTFDFRLQ NPSNANVFID RFEFVPIGGS LSEYETKHQL  660
EKARKAVNDL FTNESKNVLK KDTTDYDIDQ AANLVECVSD ECANAKMILL DEVKYAKQLS  720
EARNLLLNGN FEYQDRDGEN PWKTSPNVTI QENNPIFKGR YLSMSGANNI EATNEIFPTY  780
VYQKIDESKL KPYTRYKVRG FVGNSKDLEL LVTRYDEEVD AILNVPNDIP HAPPPFCGEF  840
DRYKPHSYPP INPECHHDVI NNIEISSPCQ HNKMVDNADI SYRHSRLSKK HGICHESHHF  900
EFHIDTGKID LVENLGIWVV FKICSTDGYA TLDNLEVIEE GPLGAESLER VKRREKKWKH  960
HMEHKCSETK HAYHAAKQAV VALFTNSKYD RLKFETTISN ILFADYLVQS IPYVYNKWLP  1020
GVPGMNYDIY TELKNLFTGA FNLYDQRNII KNGDFNRGLM HWHATPHARV EQIIDNRSVL  1080
VLPNYAANVS QEVCLEHNRG YVLRVTAKKE GPGIGYVTFS DCANHIEKLT FTSCDYGTNV  1140
VPYEQSNYPT DGVPYGQHGC NIDGVPYEQS GYRTDGVPYE QSGHRTDGVP YEQSGYRTDG  1200
VPCEQHGCHT DGLPHIQHGC RTDRSRDELL GYVTKTIDVF PNTDKVRIDI GETEGTFKVE  1260
SVELICMEE                                                         1269

SEQ ID NO: 33          moltype = DNA  length = 3960
FEATURE                Location/Qualifiers
misc_feature           1..3960
                       note = A nucleic acid encoding a TIC7389 pesticidal protein
                        sequence obtained from Brevibacillus laterosporus species
                        DSC006878.
source                 1..3960
                       mol_type = unassigned DNA
                       organism = Brevibacillus laterosporus
SEQUENCE: 33
atgaatcaga atcagaatca aaataaaaat gaactgcaaa tcatagaacc ttcaagtgat  60
tctttgcttt atagtcacaa caattatccg tatgcaactg atccaaatac agtattagaa  120
ggtaggaatt ataaagagtg gctaaataag tgcacagata attatacaga cgctttacag  180
ggtcccgaag ctactgctat atcaaaagga gctgtctctg ctgcgatttc tatcagcacc  240
aaagttctta gtttattagg tgttccgttt gcagctcaaa tcggacaact ttggaccttc  300
atattgaatg cgttatggcc ttcagacaat actcaatggg aagagttcat gagacatgta  360
gaagaactca taaaccaacg aatagccgat tatgcaagaa gtaaggcact tgcagaatta  420
acgggtttag gtaataactt agatttatat atagaagctc ttgaagattg gaaacgaaat  480
cctactagtc aacaagcgaa agaccgtgta aaagatagat tccgtatagc agatggttta  540
tttgaagcgt atatgccttc atttagagta tcaggttatg aagtaccatt attaacagtg  600
tatgcagccg ctgcaaatct ccatttactt ttattaagag attgctctat ttacggaatc  660
caatggggat ttagtcaaac gaatgttaac gagaattaca atcgccaaat aagacacacc  720
gcagagtatg caaatcattg tacaacttgg taccaaactg gtttagaaag attgcgaggt  780
accaatgctt ccagttgggt cccttataat cgtttccgaa gagaaatgac gttaactgta  840
ttggatattt gttccttatt ttcaaattat gattatcgta gttatccagc agaggtaagg  900
gcagagctta caagagaaat ttatacggac ccagttgtaa gcactagctt gtgggtgaat  960
aatgcaccat cattcggaga aatagaaaat ctagcaatta gggcgccaag aaccgttact  1020
tggttaaatt ctacaagaat ttctacaggg accttgcagg gctggagtgg ttctaacaga  1080
tattgggcag ctcacatgca aaacttttca gaaaccaatt caggaaatat aggatttgac  1140
ggtcctctct atgggtcgac ggtaggtact attattcgtg atgataatta cgaaatggtg  1200
aaccgagata tttacaccat tacttcagag gctgttgccg ccctttggcc aactggtcaa  1260
attgtgttgg gagtcgcttc ggctagattt actttaagaa atcttaacaa taatcttaca  1320
caggcgctgg tgtatgagaa cccaataagt tcaagtttta ataggtcaac tttaactcgt  1380
gaattacctg ggaaaactc agataggcca acttcaagcg actatagtca tagactaacg  1440
tctattacag cttttcgagc tggaagtaat gggacgattc cggtttttgg atggacatct  1500
ataagtgtta atcgtgacaa tatacttgag cgaaacaaaa taacacaatt cccaggcgtt  1560
```

```
aagtcacaca ctctcaacaa ttgtcaagta gttagaggta ctggatttac aggaggagac    1620
tggttgagac caaataataa tggttcattt agattaacta ttacttcatt ctcgagccaa    1680
tcttaccgaa tccgcttacg ttatgcttcc gcagcaaata cttctttgcg tatatcttct    1740
tctgcagccg gtatttcttc cacaaccgtt ccgcttgcct caacaataac atcactgcca    1800
caaactgctg taccatatga agcttttaga gttatagatt tacctattac ttttacaaca    1860
gctacccaaa gtaattatac ttttgatttt gttctccaaa atccatcaaa cgcaaatgta    1920
ttcattgata gatttgaatt tgttccaatt ggggttctt tgtctgagta tgaaaccaaa     1980
catcagctag aaaaagcaag gaaagcggtg aacgatttgt ttaccaatga atcgaaaaat    2040
gtgttaaaaa aatacacgac cgattatgat atagatcaag ctgcaaactt ggtagaatgt    2100
gtatctgatg aatgtgcaaa tgctaaaatg atcctattag atgaagtaaa atatgcgaaa    2160
caactcagcg aagcccgcaa tctacttctg aatggtaatt ttgaatacca agatagagat    2220
ggggagaatc catggaaaac aagtccaaat gttaccatcc aggaaaataa ccccattttt    2280
aaaggccgtt atctcagtat gtcgggtgca aactatatcg aggcaacaaa tgatactttc    2340
cccacttatg cataccaaaa aatagatgaa gcaaaattaa aaccctatac ccgttataaa    2400
gttcgagggt ttgttggaaa tagtaaagat ttagagttgt tgattaaacg gtatgatgaa    2460
gaagtggatg cgattttaaa tgtaccaaat gatataccac atgctccgac acctttctgc    2520
ggtggatttg atcgatgcaa gccacattct tatattccta tgaatccaga atgtcaccat    2580
gatgtaataa ataacttga aatatcctct cccttgccaac acaataagat gttggataac   2640
gctgatatat cttctcgcca tagtgaatta ggtaaaaaac gtggaatttg tcatgaatct    2700
catcattttg aattccatat tgatacagga aaaatcgatt tgaacgaaaa tttgggaatt    2760
tgggttatat ttaaaatatg ttccacagat ggttacgcaa cattagataa tttggaagtt    2820
attgaagagg gtcctttagg agccgaatca ttagaacgtg tgaaaagaag agaaaagaaa    2880
tggaaacatc acatggaaca caagtgttca gaaactaaac ttgcatatca tgctgcaaaa    2940
caagcgctgg tggggttatt cacaaacact aaatatgata gattaaagtt cgaaacaacc    3000
atatccaata ttcttttgc tgattatctc gtgcagtcaa ttccgtatgt atataataaa    3060
tggttaccag atgttccagg tatgaattac gatatctata cagaattaaa aaatctgttt    3120
acgggagctt tcaatttata tgatcagcga aatattataa aaaatggaga ctttaatcgc    3180
gggctcatgc attggcatgc gacacctcat gcaagagtag agcaaataga taataggtct    3240
gtgctggtgc ttccaaatta tgctgccaat gtttcacaag aggtttgttt agaacacaat    3300
cgtggttatg tattacgtgt aacggcgaaa aagaaggcc ctggaattgg atatgttaca    3360
ttcagtgatt gtgcaaataa tatagaaaaa ctgacatttt cttcttgcga ttatggtaca    3420
aacgaagtga catatgagca atctaattat cctacgacg gagtaccgta cgaacaatct    3480
aattatccta cagacggagt accgtacgaa caacatggtt gtcatacaga cggagttccg    3540
tacgaacaac ctaattatcc tacagacgga gtaccgtaca acaacatggt ttgtcataca    3600
gacggagtac cgtacgaaca acatggttgt catacagacg gagttccgta cgaaccacct    3660
aattatccta cagacggagt accgtacgaa caacatggtt gtcatacaga cggagtaccg    3720
tacgaacaac atggttgtca tacagacgga gtaccataca acaacatggt tgtcgtacaa    3780
gacggagtac catacaaaca acatggttgt cgtacagaca gatcaagaga tgaacaactt    3840
gattatgtga caaaaacgat tgatgtattc cctgatactg ataaagtacg tatcgacatt    3900
ggagaaaccg aagtacctt taaagtagaa agtgtggaac tgatttttat ggaagagtaa    3960

SEQ ID NO: 34          moltype = AA  length = 1319
FEATURE                Location/Qualifiers
REGION                 1..1319
                       note = The amino acid sequence of the TIC7389 protein.
source                 1..1319
                       mol_type = protein
                       organism = Brevibacillus laterosporus
SEQUENCE: 34
MNQNQNQNKN ELQIIEPSSD SLLYSHNNYP YATDPNTVLE GRNYKEWLNK CTDNYTDALQ     60
GPEATAISKG AVSAAISIST KVLSLLGVPF AAQIGQLWTF ILNALWPSDN TQWEEFMRHV    120
EELINQRIAD YARSKALAEL TGLGNNLDLY IEALEDWKRN PTSQQAKDRV KDRFRIADGL    180
FEAYMPSFRV SGYEVPLLTV YAAAANLHLL LLRDCSIYGI QWGFSQTNVN ENYNRQIRHT    240
AEYANHCTTW YQTGLERLRG TNASSWVPYN RFRREMTLTV LDICSLFSNY DYRSYPAEVR    300
AELTREIYTD PVVSTSLWVN NAPSFGEIEN LAIRAPRTVL WLNSTRISTG TLQGWSGSNR    360
YWAAHMQNFS ETNSGNIGFD GPLYGSTVGT IIRDDNYEMV NRDIYTITSE AVAALWPTGQ    420
IVLGVASARF TLRNLNNNLT QALVYENPIS SSFNRSTLTR ELPGENSDRP TSSDYSHRLT    480
SITAFRAGSN GTIPVFGWTS ISVNRDNILE RNKITQFPGV KSHTLNNCQV VRGTGFTGGD    540
WLRPNNNGSF RLTITSFSSQ SYRIRLRYAS AANTSLRISS SAAGISSTTV PLASTITSLP    600
QTAVPYEAFR VIDLPITFTT ATQSNYTFDF VLQNPSNANV FIDRFEFVPI GGSLSEYETK    660
HQLEKARKAV NDLFTNESKN VLKKYTTDYD IDQAANLVEC VSDECANAKM ILLDEVKYAK    720
QLSEARNLLL NGNFEYQDRD GENPWKTSPN VTIQENNPIF KGRYLSMSGA NYIEATNDTF    780
PTYAYQKIDE AKLKPYTRYK VRGFVGNSKD LELLIKRYDE EVDAILNVPN DIPHAPTPFC    840
GGFDRCKPHS YIPMNPECHH DVINNIEISS PCQHNKMLDN ADISSRHSEL GKKRGICHES    900
HHFEFHIDTG KIDLNENLGI WVIFKICSTD GYATLDNLEV IEEGPLGAES LERVKRREKK    960
WKHHMEHKCS ETKLAYHAAK QALVGLFTNT KYDRLKFETT ISNILFADYL VQSIPYVYNK   1020
WLPDVPGMNY DIYTELKNLF TGAFNLYDQR NIIKNGDFNR GLMHWHATPH ARVEQIDNRS   1080
VLVLVPNYAAN VSQEVCLEHN RGYVLRVTAK KEGPGIGYVT FSDCANNIEK LTFTSCDYGT   1140
NEVTYEQSNY PTDGVPYEQS NYPTDGVPYE QHGCHTDGVP YEQPNYPTDG VPYEQHGCHT   1200
DGVPYEQHGC HTDGVPYEQP NYPTDGVPYE QHGCHTDGVP YEQHGCHTDG VPYKQHGCRT   1260
DGVPYKQHGC RTDRSRDEQL DYVTKTIDVF PDTDKVRIDI GETEGTFKVE SVELIFMEE    1319

SEQ ID NO: 35          moltype = DNA  length = 3780
FEATURE                Location/Qualifiers
misc_feature           1..3780
                       note = A synthetic coding sequence,
                       CR-BRE1a.TIC7040.nno_Mc:1 encoding a TIC7040 pesticidal
                       protein used for expression in plant cells.
source

```
                    mol_type = other DNA
                    organism = synthetic construct
SEQUENCE: 35
atgaaccaga atcagaatca gaacaagaac gagctacaga tcatcgagcc tagctccgac    60
tcgctcctgt acagccacaa caactacccg tacgcgacgg acccgaatac tgtgctggag   120
ggccgcaact acaaggagtg gctcaacaag tgcacggaca actacacgga cgccctccaa   180
ggcccggagg ccacggcgat tagcaagggc gcggtctcgg cggcaatttc gatctcgact   240
aaggtgctct cgctgctcgg cgtgccgttt gcagcgcaga tcggccagct ctggaccttc   300
atactcaacg cgctctggcc gagcgacaac acccagtggg aggagttcat gcgtcacgtc   360
gaggaactga taaccagcg catcgcggac tacgccagga gcaaggccct cgcggagctg   420
accgggctcg gcaataacct ggacttgtac atcgaggccc ttgaggactg gaaacgaaac   480
ccgaccagcc aacaagccaa ggaccgggtg aaggaccggt tccggatcgc cgacggcctg   540
ttcgaggcgt acatgccttc cttccgggtc tcgggctatg aagtgccgct cctcacggtg   600
tacgccgcag cggccaacct gcatctcctg ctgctaaggg attgctcgat ctacggcatg   660
cagtggggtt tctcccagac caacgtaaac gagaactaca accgtcagat ccggcacacg   720
gctgagtacg caaccactg cacgacgtgg tatcagaccg gactggagcg gctccgtggc   780
accaacgcat cttcgtgggt tccgtacaac cgtttccgca gagagatgac tcttaccgtc   840
ctggacatct gctccctctt ctccaactat gactacagaa gctacccggc ggaagtgcag   900
gccgagctaa cccgcgaaat ctacacggac ccggtggtct ccacatcgct gtggatgaac   960
aacgcaccat cgttcggtga gatcgagaac ctggcaatcc gcgctccgcg cacggtgacg  1020
tggttgaact caaccaggat ctctaccggc accctccagg gctggtcagg cagtaaccga  1080
tactgggcgg cacacatgca gaacttcagc gagaccaact ccgggaacat tggattcgac  1140
ggcccactgt acggctctac cgtgggcact atcatcaggg acgacaacta cgagatggtc  1200
aacagggaca tctacacgat tacgtccgaa gcggtggccg ctctttggcc cacagggcag  1260
atagtgctgg gcgtggcctc cgcacgtttc acactccgta atctcaacaa caatctgacc  1320
caggccctgg tttacgagaa cccgatttcc tccagcttca accgcagcac gctcacacgg  1380
gaactacctg gcgagaacag tgatcgccca acgtccagtg actacagcca taggctgaca  1440
tcaatcacgg cgttccgggc cgggagtaac ggcaccatcc cggtcttcgg ctggacctcc  1500
atctcggtca accgggataa catcctggag cgcaacaaga taacccagtt ccctggcgtc  1560
aagagccaca ctctcaacaa ctgccaagtc gtcagaggga ccggcttcac tggcggcgac  1620
tggctcagac ccaacaacaa cggggtcttt cgcctgacga tcaccagctt ctcctcgcag  1680
tcctaccgga taaggctccg gtacgcctct cgggccaaca catccctccg gatttcttcc  1740
tccgctgcgg gcataagctc tacaaccgtg ccgctgacct ccactattac tagccttccg  1800
caaaccgctg tacctacga ggcgttccgc gtcatcgacc tcccgatcac cttcactacc  1860
gctacgcaga gtaactacac cttcgactt gtcctccaga acccgtccaa tgctaacgtc  1920
ttcatcgacc ggttcgagtt cgtccctatt ggaggcagcc tttcagagta cgagacgaag  1980
caccagcttg agaaggcgag gaaagctgtc aacgaccgt tcacaaacga gagcaagaac  2040
gtcctcaaga agtacacgac agattacgac atcgaccagg cggcgaacct ggtggagtgc  2100
gtctctgacg agtgcgccaa cgctaagatg atcctgctgg acgaggtgaa gtacgcaaag  2160
cagctctccg aggcacgaa ccttctgctg aacgggaact tgagtacca ggaccgggac  2220
ggcgagaacc cttggaagac ttcaccaaac gtaactatcc aggagaacaa cccgatcttc  2280
aagggccgct acctgagcat gagcggccgcg aactacattg aggcaactaa cgacacctt  2340
cccacctatg cctattcagaa gattgatgaa gccaaattga acgtactgac acgctacaa  2400
gtgcgtgggt tcgtcggcaa ctccaaggat ctggagcttc tcattaagcg ctacgatgag  2460
gaagtgacg ctattctcaa cgtccctaac gacatcccgc acgcgccgac tccttctgc  2520
ggaggtttcg accggtgtaa gccgcactcc tacatccca tgaacccaga gtgtcaccac  2580
gacgtcatca caacatcga gatcagcagc ccatgccgac aacaaagat gctggacaat  2640
gcggacatct ccagccgtca ttctgagctg ggcaagaagc gcggcatctg ccacgagtcc  2700
caccacttcg agttccacat tgatacgggc aagattgacc tcaacgagaa cctcggcatc  2760
tgggtgatct tcaagatttg cagcacggat ggctacgcca cgctagacaa ccttgaggtg  2820
atcgaggagg gccgctcgg cgcggaatct ctggagccgg taaagcgccg ggagaagaag  2880
tggaagcacc acatggagca caagtgctcc gagacgaaac tggcatacca cgccgctaag  2940
caagcccttg tgggtctctt cacaaacacc aagtacgacc gacttaagtt tgagacgaca  3000
atttccaaca tcttgttcgc cgactacctc gtgcagagca tcccatacgt ttacaacaaa  3060
tggttacccg acgtccctgg tatgaactac gacatctaca cggagcttaa gaacctcttc  3120
accggcgcgt tcaacttgta cgatcaacgc aacatcatca agaacggcga tttcaaccgt  3180
ggacttatgc actggcacgc cacgcctcac gccagagtgg agcagatcga caaccggagt  3240
gtcctcgtgt taccgaacta cgctgccaac gtctcccagg aggtgtgcct ggagcacaac  3300
cgtggctacg tcctgcgcgt gacggccaag aaggaggtc cgggcatcgg ctacgtcacg  3360
ttctccgact gcgccaacaa catcgagaag tgacattcca cgtcctgcga ctacggcacc  3420
aacgaggtga cctacgagca aagcaactat cacaccgacg cgttcccta cgagcagtcc  3480
aactacccaa ctgacggcgt accatacgag cagcacggct gccacaccga cggcgtgcca  3540
tacgagcagt cgtcctaccc gactgacggt gtgccctacg agcagcacgg atgccgtacg  3600
gacggcgtcc tgtacaagca gcacggctgt aggacagcc gaagccgtcc tgcggcggag  3660
gattacgtca ccaagaccat tgacgtcttc ccggacacgg acaaggtccg gatcgacatc  3720
ggagagaccg agggcacttt caaggtcgag tcggttgagc tgatcttcat ggaggagtga  3780

SEQ ID NO: 36        moltype = DNA   length = 3888
FEATURE              Location/Qualifiers
misc_feature         1..3888
                     note = A synthetic coding sequence,
                     CR-BRE1a.TIC7040_10.nno_Mc:1 encoding a TIC7040HT
                     pesticidal protein used for expression in plant cells.
source               1..3888
                     mol_type = other DNA
                     organism = synthetic construct
SEQUENCE: 36
atgaaccaga accagaatca gaacaagaac gagcttcaga taatcgagcc ctcctcggac    60
tcctcctct actcgcataa caactacccg tacgctaccg acccgaacac cgtgctggaa   120
```

```
ggccgcaact acaaggagtg gctgaacaag tgtaccgaca actacaccga cgcgctccag    180
ggccctgagg ccaccgccat cagcaagggc gcggtgtcag ccgcgatctc catcagcaca    240
aaggtgctct cgttactggg cgtgcccttc gcggcgcaga tcggccagct ctggaccttt    300
atcctgaacc cctatggcc cagcgacaac acccagtggg aggagtttat gcgccacgtg    360
gaggaactca ttaaccagcg aattgctgac tacgccaggc gcaaggccct ggccgagctg    420
acgggtcttg gcaacaacct cgacctctac atcgaggccc ttgaagactg gaagcggaac    480
ccgaccagcc aacaggccaa agaccgtgtg aaggaccggt tccggatcgc cgacgggctg    540
ttcgaggcgt acatgccctc tttccgcgtc agcggctacg aggtgccact gttgaccgtt    600
tacgcggcag ccgctaacct ccacttgctg ctcctgcggg attgctccat ctacggtatc    660
cagtgggget tcagccagac aaacgtcaac gagaactaca accgacagat ccggcacacg    720
gccgagtacg caaccactg cacgacatgg tatcagacag gcttgaacg ccttcgtggc    780
accaacgcct cgtcatgggt gccgtacaac cggttccgcc gagagatgac cctcaccgtt    840
cttgacatct gctcactgtt cagcaactac gactaccggt cgtaccctgc ggaggttcgg    900
gccgaactga cgcgggagat ctacaactgac cggtggtca gcacctcgtt gtggatgaac    960
aacgcgccca gcttcggtga gatcgagaac ctcgccataa gagcaccacg caccgtcact   1020
tggctcaaca gcacccggat ctcacgggg accttacagg gctggagcgg ctccaaccga   1080
tactgggcag cgcacatgca gaacttctcc gagactaact ccggcaacat cggcttcgac   1140
ggcccgctct acggcagcac cgtcgggacc atcatccggg acgacaacta tgagatggtc   1200
aacaggggaca tctacacgat tacctcggag gccgtggctg ccctgtggcc aaccggtcaa   1260
atagtgttgg gagtcgcctc cgcccgcttt acgctgcgta acctgaacaa caaccttacc   1320
caggcgctcg tgtacgagaa cccgatctcc agctccttca ataggtccac cctcacgagg   1380
gagctgccgg gtgagaacag cgacaggccg acgtcctcgg actacagtca ccggctcacc   1440
tcgatcacag cgttccgagc cgggagcaac ggaacgatcc cagtcttcgg atggaccagc   1500
atcagcgtca accgcgacaa catcctggaa cgcaacaaga tcactcagtt ccctggagtt   1560
aagtctcaca cgctcaacaa ctgccaagtg gtgcgtggca cagggtttac cggaggcgac   1620
tggcttcgcc cgaacaacaa tgggtcattc cggctgaaca ttaccagctt ctcatccgaa   1680
tcataccgca tccggctacg gtacgcctcg gcggcgaaca ctagccttcg catctcctct   1740
tcagccgccg ggatcagctc gacaaccgtc ccgctgacca gcacgatcac gagcctgcca   1800
caaactgctg tgccttacga ggctttcaga gtgatcgacc tgcccattac cttcaccacg   1860
gcaacccaat cgaactacac tttcgacttc gtgttacaga atccgagcaa cgccaacgtc   1920
ttcatcgacc ggttcgagtt cgtgcccatc ggcgggagcc tctccgagta cgagaccaaa   1980
catcagcttg agaaggcccg caaggccgtc aatgaccctg tcactaacga gtccaagaat   2040
gttctcaaga agtacaccac agactacgac atcgaccaag ccgcgaacct cgtggagtgc   2100
gtgtccgacg agtgcgccaa cgcgaagatg atcctgctgg acgaggtgaa gtacgcgaaa   2160
cagctcagcg aggcaaggaa cctgttgctg aacggaaact tcgagtacca ggaccgggac   2220
ggtgagaacc cgtggaagac cagcccgaac gtgaccatcc aggagaacaa cccaatcttc   2280
aagggccggt atctgtccat gtccggtgct aactacatcg aggcgaccaa cgacaccttc   2340
ccgacgtacg cctaccagaa gatcgacgag gccaagctca agccctacac acggtacaag   2400
gttcgcggt tcgtgggcaa cagcaaggac ttggagctgc ttattaagcg gtacgacgag   2460
gaggtggacg cgatcctgaa cgtcccgaac gacataccgc acgcgccgac gccgttctgc   2520
ggcggctttg accggtgcaa gcctcacagt tacattccga tgaacccaga gtgccatcac   2580
gatgtgatta caacatcga gataagcagt ccgtgccagc acaacaagat gctggacaac   2640
gccgacatca gctccagaca ttcggaactc ggcaagaagc gcggaatctg ccacgagtcc   2700
caccacttcg agttccacat cgacacgggg aagatcgacc tgaacgagaa cctcgggatt   2760
tgggtgatct tcaagatctg ctctacggac ggctacgcga cgctcgacaa tctgaggtg   2820
atcgaggagg accgctgggg tgctgagagc ctggagagag ttaaacgtcg ggagaagaaa   2880
tggaaacacc acatggagca caagtgctcc gagacgaaac tggcctacca cgcggccaaa   2940
caggcgctcg tgggcctgtt cacaaacacg aaatacgaca ggctcaagtt cgagacaacc   3000
atctcgaaca tcttgttcgc cgactacctg gtccagtcca ttccgtatgt gtacaataag   3060
tggcttccgg acgttccgg catgaactat gacatctaca ccgaacttaa gaatctgttc   3120
accggcgcgt tcaacctgta cgaccagcgc aacatcatta agaacggtga cttcaatcga   3180
gggctgatgc actggcacgc cacgcctcac gcccgtgtgg agcagatcga caaccggtcc   3240
gtgctggtcc tgccgaacta cgcggcaaac gtcagccagg aagtgtgctt ggagcacaat   3300
cgcggctacg tgctccgagt gacagccaag aaggagggac caggaatagg ctacgtgacc   3360
ttctccgact gcgcgaacaa catcgacgtg ctgacctttca caagctgcga ctacgggacc   3420
aacgaggtca cctacgaaca atccaattac cacactgacg gcgtgccgta cgagcagagc   3480
aactaccccga cggacggcgt gccttacgag cagcacggct gccacacgga cggcgtgccg   3540
tacgagcagt cgaactaccc gaccgacggt gtgccatacg agcagcacgg ctgccacacc   3600
gacggtgtgc cctacgagca gcacgggtgc cacacggacg gtgtgccgta tgagcagcac   3660
ggctgccaca cggacgggcg t gccctacaag cagcacgggt ccgcaccgga cggcgtactg   3720
tacaagcagc acggctgccg gactgaccgc agtagggacg agcagctcga ttacgtgacg   3780
aagaccatcg acgtcttccc ggacaccgac aaagtgcgaa ttgacattgg tgagaccgag   3840
ggcacgttca aggtcgagtc cgtggaactc atcttcatgg aggagtga             3888
```

SEQ ID NO: 37          moltype = DNA    length = 3888
FEATURE                Location/Qualifiers
misc_feature         1..3888
                       note = A synthetic coding sequence,
                       CR-BRE1a.TIC7040_10.nno_Mc:3 encoding a TIC7040HT
                       pesticidal protein used for expression in plant cells.
source                 1..3888
                       mol_type = other DNA
                       organism = synthetic construct
SEQUENCE: 37

```
atgaaccaga accagaacca gaacaagaac gagttacaga tcatcgagcc gtcctcggac     60
tccctacttt actcgcacaa caactacccg tacgccacgg accccaacac ggtgcttgaa    120
ggtcgcaact acaaagagtg gctcaacaag tgcaccgaca actacacgga cgcgctcaa    180
ggcccggaag cgacagccat ctcaagggc gcggtgagcg ccgccatctc catctcgacg    240
aaagtgctgt ccctgctcgg ggtgccgttc gcggcgcaga tcgggcagct ctggacgttc    300
```

-continued

```
atcctcaacg cgctctggcc gtccgacaac acacaatggg aggagttcat gcgccacgtg  360
gaggaactta tcaaccagag gatcgccgac tacgcgcgca gtaaagccct ggcggagttg  420
acgggcctcg gcaacaacct ggacctgtac atcgaggccc tggaagactg gaagcggaac  480
ccgaccagcc aacaagctaa agatcgggtg aaggaccggt tccgcatcgc cgacggcttg  540
ttcgaggcgt acatgccttc gttccgcgtg agcggctacg aggtgcccct cctgacggtt  600
tacgccgccg cagccaactt gcacctcctg ttgctgaggg actgctcgat ctacggcatc  660
cagtggggct tcagtcagac gaacgtgaac gagaactaca accgccagat ccgccacacg  720
gccgagtacg caaaccattg tacgacgtgg tatcagacag ggctggaacg gctgcgtggg  780
accaatgcaa gtagttgggt tccctacaac cggtttcggc gtgagatgac gctgacggta  840
ctcgacatct gctcactgtt ctcaaactac gactaccgga gctacccggc cgaggtgcgg  900
gcggagctga cgagggagat ctacactgac cccgttgtca gtacatcgct ctggatgaac  960
aacgcgcctt ccttcgggga gatcgagaac ctggccatcc gggcacctag aacagttact  1020
tggctcaaca gcacccggat ttccaccggc acacttcaag gctggtcggg ctccaaccgc  1080
tactgggcgg cccacatgca gaacttctca gagacaaact ctgggaacat cgggttcgat  1140
ggcccgctgt acgggagcac cgtgggcacc atcatccggg acgacaacta cgagatggtg  1200
aaccgggaca tctacaccat cacgtccgag gccgtggccg cattgtggcc gactggtcag  1260
atcgtactcg gcgtcgcgtc cgcacgcttt actctccgaa acctcaacaa caacctcacc  1320
caggccctag tttatgagaa ccctatttcc tccagcttca accgttccac gctgacccgt  1380
gagcttccgg gcgagaactc tgaccggccc acgagcagcg actacagcca ccgcctgacg  1440
tcaataacag cgttccgcgc gggcagcaac ggcaccatcc ctgtcttcgg ctggacaagt  1500
atcagcgtaa atcgtgacaa catcctggaa aggaacaaga taacccagtt cccaggcgtg  1560
aagtcgcaca cactcaacaa ctgccaagtg gtgaggggca cagggttcac cggaggggac  1620
tggcttcgcc cgaacaacaa cggtcattc cgactcacaa tcacatcgtt cagttcacag  1680
tcctaccgta tccgtctgcg ctacgcgagc gcggcgaaca catccctgcg tatctcctct  1740
agcgccgccg gaatctccag taccaccgtg ccgctcacgt caaccatcac ctccctccca  1800
cagacggcag tcccgtatga agcgttccga gtgatcgacc tcccgatcac gttcaccacc  1860
gccacgcaga gcaactacac ctttgacttc gtgttgcaga acccttcgaa cgctaatgtc  1920
ttcatcgacc ggttcgagtt cgtccccata ggtggttcgc tgtctgagta cgagactaaa  1980
caccagcttg agaaggcgcg taaggccgtg aacgacctgt tcacgaacga gtccaagaat  2040
gtgctcaaga agtacacgac tgactacgac attgaccagg ccgcgaacct ggtggagtgc  2100
gtgtcggacg agtgcgcgaa cgctaagatg atcctgctcg acgaagtgaa gtacgctaag  2160
cagcttagcg aggcacgcaa cctacttctg aacgggaact tcgagtacca ggaccgtgac  2220
ggggagaacc cctggaagac ctccccgaac gtgaccatcc aggagaacaa cccgatcttc  2280
aaggggcgtt acctgtccat gagcggggcc aactacatcg aggcgacgaa cgacaccttc  2340
cccacgtacg cctaccagaa gatagacgag gccaaattga aaccctacac ccggtacaag  2400
gttcggggct tcgtgggcaa cagcaaggac ttggagctgc tcatcaagcg gtacgacgag  2460
gaggtggatg ccatcttaaa cgtgcccaac gacatcccac acgcgccgac gccgttctgc  2520
ggcggattcg accggtgtaa acctcactcg tacatcccga tgaacccaga gtgccaccac  2580
gacgtcatca acaacatcga gatcagctcg ccttgccagc acaacaagat gctggacaac  2640
gcagacatct cctcacggca cagtgaactg ggcaagaaac ggggaatttg ccacgagagc  2700
caccacttcg agttccacat tgacaccggc aagattgact tgaacgagaa cctcgggatc  2760
tgggtgatct tcaaaatctg ctccacggac ggctatgcta cgttggacaa cctggaggtg  2820
atcgaggagg gcccgctagg agccgagagc cttgagcgcg tcaagcggcg cgagaagaag  2880
tggaagcacc acatggagca caagtgcagc gagaccaagc tggcttacca cgccgcaaag  2940
caagcgctgg ttggcctgtt cacgaacaca aagtacgacc ggctcaagtt cgagacgacg  3000
atcagcaaca tcttgttcgc ggattacctg gtccagagca tcccatacgt ttacaataag  3060
tggctccccg acgtccccgg catgaactat gacatctaca ccgagcttaa gaacctgttc  3120
acgggcgctt tcaaccttta cgaccaacgc aacatcatca agaacgggga cttcaaccgg  3180
ggcttaatgc actggcacgc caccccgcac gcccgcgtgg agcagatcga caaccgcagc  3240
gttctcgtgt tgccgaacta cgccgccaat gtgtcccagg aggtctgcct tgagcataac  3300
cggggctatg tgctgcgggt cacagccaag aaggaagggc caggaatcgg ctatgtgacc  3360
ttcagcgact gcgccaacaa cattgagaaa ctgacgttca cgtcttgcga ttacgggacc  3420
aacgaggtga cctacgagca gtccaactac cacacggacg gggtgccgta cgagcagtcc  3480
aactacccga ctgacggtgt accatacgag cagcacgggt gccacaccga cggtgtgcca  3540
tacgagcagt cgaactaccc gacggacggc gtgccctacg agcagcacgg gtgccacacc  3600
gacggcgtgc cgtacgagca gcacggctgc cacacggacg gagtgcccta cgagcagcac  3660
gggtgccaca ccgacggggt gccgtacaag cagcatgggt gccgcacgga cggtgtgctg  3720
tacaaacagc atggctgtcg tactgaccgg tcccgcgacg agcagctaga ctacgtgacg  3780
aagactattg atgtcttccc ggacacggac aaggtgcgga tcgacatcgg ggagaccgag  3840
ggcacgttca aggtggagtc cgtggagctt atcttcatgg aggagtag              3888
```

```
SEQ ID NO: 38          moltype = DNA  length = 3888
FEATURE                Location/Qualifiers
misc_feature           1..3888
                       note = A synthetic coding sequence,
                        CR-BREla.TIC7040_10.nno_Mc:4 encoding a TIC7040HT
                        pesticidal protein used for expression in plant cells.
source                 1..3888
                       mol_type = other DNA
                       organism = synthetic construct
SEQUENCE: 38
atgaaccaga accagaacca gaacaagaat gagttgcaga ttatcgagcc gtcctccgac  60
tccctgctgt actcccacaa caactacccc tacgcgacgg accccaatac ggtgctagag  120
gggcgcaact acaaggagtg gctgaacaag tgcacggaca actacacaga cgctttgcaa  180
gggccggagg cgaccgccat ctcgaaagga gccgtgtcgg cggcgatttc catcagcaca  240
aaggtgctga gcctgctcgg cgtccccttc gccgcccaga tcgggcaact gtggaccttt  300
atccttaacg ccttgtggcc ctccgacaac acgcagtggg aggagtttat gcgccacgtt  360
gaggagctga ttaaccagcg aattgccgac tacgcgcgct ctaaggcgct ggcggaactg  420
accggcctcg ggaacaacct cgacctgtac atcgaggccc tggaggactg gaagcggaac  480
```

```
ccaacttcgc aacaagctaa ggaccgggtg aaggaccgct tccgcatcgc ggacggcctc    540
ttcgaagcgt acatgccgtc tttccgcgtg agtggctacg aagtgccgct gctgaccgtc    600
tatgcagcag cagctaatct tcatctgttg ctcctacgcg attgctcaat ctacggcatc    660
caatgggct tctcccagac gaatgtgaac gagaactaca acaggcagat tcgccacact    720
gcggagtacg caaaccactg cacgacgtgg tatcaaacag ggctggagcg gctccggggc    780
acgaatgctt catcgtgggt gccgtacaat cgctttcgtc gtgagatgac cctcacggtg    840
ctggacatct gctccctctt cagcaactac gactatcgct cgtacccggc cgaggtgcgt    900
gcagaactaa ctcgggaaat ctacacggac cccgtggtca gcacaagcct gtggatgaac    960
aacgcgccgt cgttcggcga gatcgagaac ctggcgatcc gcgcgccgcg aaccgtcaca   1020
tggctcaact cgaccaggat ctcaaccggg actctacagg gctggtccgg cagtaaccgc   1080
tactgggcgg ctcacatgca gaacttcagc gagacgaact ccgggaacat cggcttcgac   1140
gggccattgt acggctcaac ggtggggacc atcattcggg acgacaacta cgagatggtc   1200
aaccgggaca tctacacgat cacgtccgag gccgtggccg ccctgtggcc aactgggcag   1260
atcgtgctcg gggtcgcatc ggcgcggttc accctccgta acctgaacaa caatttgaca   1320
caagcgctgg tgtacgagaa tccgattagc agctccttca accggtccac tctgacccgc   1380
gagctgcccg gcgagaacag cgaccggccg acctccagcg actactcgca cagactcacc   1440
tccattactg ccttccgggc ggggtccaac gggaccatcc cggtgttcgg gtggacctcc   1500
ataagcgtca accgagataa catcttggag cgcaacaaga ttacccagtt cccaggaagtg   1560
aagtcccaca ccctcaacaa ctgccaagtt gtgcgcggga cggggttcac cggcggcgac   1620
tggttgcggc ccaacaacaa cggcagcttc cggctgacga tcacgtcctt ctccagccag   1680
tcgtaccgca tacggctccg ttacgccagt gccgccaaca cgagccttcg catcagctca   1740
agcgcagcgg gaatctccga caccactgtc ccattgacca gcacgatcac ctccctgccc   1800
cagaccgccg tcccgtacga ggcgttccgc gtgattgatc tgcccatcac cttcactacc   1860
gctacccaaa gtaattacac attcgacttc gtactacaga accctccaa cgctaatgtc   1920
ttcattgacc gcttcgagtt cgtgccatc ggcgggagcc tctcggagta cgagacgaag   1980
caccagctcg aaaaggcccg caaggcgttg aacgacctgt tcacgaacga gtccaagaat   2040
gtgctcaaga agtacaccac tgactatgac attgaccagg ctgctaacct ggtagagtgc   2100
gtgagcgacg agtgcgccaa cgcgaagatg atcctgctcg acgaggtgaa gtacgccaag   2160
cagttgtccg aggcccggaa cctgctcctg aacggcaact tcgagtacca ggacagggac   2220
ggcgagaacc cgtggaagac ctcgcccaat gtcacgatcc aggaagaacaa tcccatcttc   2280
aaggggcggt atctatccat gagcggagcg aactacatcg aggccgaccaa cgacaccttc   2340
cctaccatg cctaccagaa gattgacgag gccaagctaa aaccatacac ccggtacaaa   2400
gtgcgcgggt tcgtcggcaa cagcaaggat ctggaactgc tcattaagcg ctacgacgag   2460
gaggtggacg ccatcctcaa cgtcccgaac gacatccgc acgcgcccac ccctttctgc   2520
ggcggcttcg accggtgcaa gccgcacagc tacatcccga tgaacccaga atgtccaccac   2580
gacgtcatca caacatcga gatcagcagt ccctgccagc acaacaagat gttgacaac   2640
gccgacatta gcagccgcca ctcggagctt ggcaagaaac gcggaatctg ccacgagtcc   2700
caccacttcg agtttcacat tgacaccggg aagatcgacc tgaacgagaa cctggggatc   2760
tgggtgatct tcaagatttg ctcgacagat ggctacgcga ccctgacaa cctttgaggtt   2820
attgaggaag ggccactggg tgcagagtct ctggagcggg tcaagcgccg cgagaagaaa   2880
tggaagcacc acatggagca caagtgctcg gagacgaagc tcgcgtacca tgcggcgaaa   2940
caggccctgg tcgggctctt caccaacacc aagtacgaca ggctcaagtt cgagaccacc   3000
atctcgaaca tcctgtttcgc cgactacctc gtgcaatcca tcccgtatgt ttacaacaag   3060
tggctcccgg acgtgcccgg tatgaactac gacatctaca ccgaacttaa gaatctgttc   3120
accggtgcgt tcaacctcta cgaccagagg aacatcatca gaacggggga cttcaacaga   3180
ggactgatgc actggcacgc gacgccgcac gcccgcgtgg agcagatcga caaccgttcc   3240
gtgctcgtcc tcccgaacta cgctgcgaac gtaagtcagg aagtctgcct tgagcataac   3300
cggggctacg tgctccgcgt gacggccaag aaggagggac cagggatcgg atacgtgacc   3360
ttctccgact gcgcgaacaa catcgagaag ctgaccttca caagttgcga ctatgggacc   3420
aacgaggtca cctacgagca gtcgaactac cacaccgacg gagtgcccta cgagcaaagc   3480
aactacccca ccgacgggt gccctacgga cagcacgcct gccatacgga cggggttccc   3540
tacgagcaaa gcaactaccc gaccgatggc gttccatacg agcagcacgg gtgccacacc   3600
gacggcgtgc cctacgagca gcacggctgc cacaccgacg gcgtaccta cgaacagcat   3660
ggctgccaca ccgatggggt gccgtacaag cagcacggat gtagaactga cggcgtgctg   3720
tacaagcgac acgggtgcag aacagaccgc tcaaggatg aacaactcga ttacgtgacc   3780
aagacaattg acgtcttccc tgataccgac aaggtgcgta ttgacattgg tgagacggag   3840
ggcaccttca aggtcgagtc cgtggagctg atcttcatgg aggagtag             3888
```

SEQ ID NO: 39           moltype = DNA   length = 3888
FEATURE                 Location/Qualifiers
misc_feature            1..3888
                        note = A synthetic coding sequence,
                        CR-BRE1a.TIC7040_10.nno_Mc:5 encoding a TIC7040HT
                        pesticidal protein used for expression in plant cells.
source                  1..3888
                        mol_type = other DNA
                        organism = synthetic construct
SEQUENCE: 39

```
atgaaccaga accagaacca gaacaagaac gaactacaga tcatcgagcc ctccagcgac     60
tccctcctct acagccacaa caactacccc tacgccaccg atcccaacac cgtgctggaa    120
gggcgcaact acaaggagtg gctcaacaag tgcaccgaca attacacgga cgcgcttcaa    180
gggccggagg ccacagcaat ctcgaaggga gcggtgagcg ccgcgatcag catctccacg    240
aaagtgctca gtctcctcgg ggtgccgttc gcggctcaga tcggcaact ctggaccttc    300
atactcaacg ccctgtggcc cagcgacaac acgcagtggg aggagttcat gaggcacgtg    360
gaggagctta tcaaccagcg gatcgccgac tacgcgcgaa gcaaggctct ggcagagctg    420
acgggcctcg gcaacaacct ggacctctac atcgaggccc tggaggactg gaaacgcaac    480
cccacaagcc aacaagctaa ggaccgcgtg aaggaccgct tccgcattgc cgacggcctg    540
ttcgaagcgt acatgccgag cttccgtgtc tcaggctacg aggtgccact cctgacagtg    600
tacgcggcgg ctgctaacct ccacctcctg ctgctccgcg attgttcgat ctacggaatc    660
```

-continued

```
cagtggggct tctcgcagac caacgtgaac gagaactaca atcgtcagat ccgccacacg 720
gcggagtacg cgaaccactg cacaacatgg tatcagacgg gccttgagcg gctgcgaggc 780
accaacgcga gtagttgggt tccatacaac cgcttccgcc gcgagatgac gctaaccgtc 840
ctcgacatct gttcactgtt ctcgaactac gactaccgct cctacccggc ggaggtccga 900
gcggagctga cacgcgaaat ctacacagac cccgttgtga gcactagcct atggatgaac 960
aacgccctt cgttcggcga gatcgagaac ctagccatac gcgcccctcg taccgtgacc 1020
tggctcaata gtaccggat cagcacaggc actctgcaag gatggtcggg gagtaatcgg 1080
tactgggctg ctcacatgca gaacttctcc gagaccaact cgggcaacat cggattcgac 1140
ggtcccctt acggctccac cgtcgggact atcatccggg acgacaacta cgagatggtg 1200
aaccgcgaca tctacaccat cacctccgag gcggtcgccg ccctgtggcc aactggacag 1260
atcgtgctcg gcgtggcctc agcccgcttc actctgcgga acctcaacaa caaccttact 1320
caggcgctcg tttatgagaa cccgatcagc agctcgttca accgcagtac cctgacgaga 1380
gagctgcctg gggagaactc cgaccggccg acctctagcg actactcgca tcgtctcacg 1440
agcatcacgg cctccgagc gggcacgaac ggcacgatcc cggtgttcgg atggacctcc 1500
attagcgtga accgggacaa catcctggaa cgcaacaaga taacgcaatt ccccggtgtc 1560
aagtcccaca cactcaacaa ctgccaagtg gtgcgcggca cggggttcac cggcggggac 1620
tggcttcggc caaacaacaa cggctcgttc cggttgacta tcaccagctt cagctcccag 1680
tcgtaccgta tccgccttcg ctacgccagc gcggcgaaca cctcccttcg catcagctcc 1740
tcggccgccg ggatttcgtc caccaccgtt cccctgacgt caacgatcac cagcctgccc 1800
cagaccgccg tgccgtacga agcctttcgc gtgatcgacc ttccaatcac gttcactaca 1860
gccactcaat cgaactacac attcgatttc gtcctccaga atccgagcaa cgccaacgtc 1920
ttcatcgacc gattcgagtt cgttccaatc ggcggtagcc tctcggagta cgagaccaaa 1980
catcagttgg aaaaggcccg gaaggcggtg aacgaccgct tcacgaatga gagcaagaat 2040
gtgctcaaga agtacacaac tgattacgac atcgaccagg cggcgaactt ggtggagtgc 2100
gtgtcggacg agtgcgcgaa cgccaagatg atccttctcg acgaggtgaa gtatgccaag 2160
caacttagcg aagcccgcaa cctcctcctg aacggcacct cgagtacca ggaccgggac 2220
ggcgagaacc cctggaagac cagtccgaac gtgactatcg aggaaaacaa tcccatcttc 2280
aagggacggt atttgagcat gagtggagca aactacatcg aggccacaaa cgacaccttc 2340
ccgacctatg cgtaccagaa gatcgacgag gccaagctca agcttacac ccggtacaag 2400
gtgcgcgggt tcgtcgggaa cagcaaagac ctgaactac tgattaagcg ctacgacgag 2460
gaggtggatg ccatcctgaa cgtcccgaac gacattccgc acgccccgac ccctttctgt 2520
ggcggcttcg accgttgcaa gccccactcc tacatcccca tgaaccctga gtgtcaccac 2580
gacgtcatca acaacatcga aatctccagc ccttgtcagc acaataagat gctggacaac 2640
gcagacataa gttcccggca tagcgaattg ggcaagaagc ggggcatctg tcacgagacg 2700
caccactttg agttccacat cgacactggc aagatcgacc tcaacgagaa cctcgggatc 2760
tgggtgatct tcaagatttg cagtaccgac ggctacgcga cgctcgacaa ccttgaggtg 2820
atcgaggagg gccactcgg ggccgagagc ctggagcggg tgaagcgccg cgagaagaag 2880
tggaagcacc acatggagca caagtgctcc gagactaaac tggcctacca cgccgccaaa 2940
caagccctgg tcggcctgtt tacaaacacc aaatacgaca ggctcaaatt cgagacgaca 3000
atctcaaaca tcctcttcgc cgactacctc gtccagagta tcccgtatgt ttacaataag 3060
tggctgccgg acgtccccgg catgaactac gacatctaca cggaacttaa gaatctgttc 3120
acgggtgcat tcaacctgta cgaccagagg aacatcatta gaacgggga cttcaaccgt 3180
ggccttatgc actggcacgc tacaccccgc gcgcgggtcg acagataga caaccggtcg 3240
gtgctcgtgc tgccgaacta cgccgccaac gtctcacagg aggtctgcct ggaacacaac 3300
cggggctacg tgctgcgggt gacagccaag aaggagggcc caggaatcgg ctacgtgacg 3360
ttctccgact gcgcgaacaa catcgagaaa ctcactttta cgtcctgcga ctacgggact 3420
aacgaggtga cgtacgacgca gtccaactac cacaccgagg gcgtgcccta tgagcagtcg 3480
aactacccga ccgacggggt gccctacgag cagcacgggt gccacacgga cggagtgccc 3540
tacgagcagt cgaactaccc cacggacggc gttccgtacg agcagcacgg ctgccacacg 3600
gatgggtgc cctacgagca gcacggatgt cacactgatg gcgtgccgta cgagcagcac 3660
ggctgccaca ccgacggcgt tccctacaag cagaacaga tggcgtcctc 3720
tacaaacagc acggttgtcg cacggatcgc tcgcgcgatg agcagttgga ctacgtgacc 3780
aagaccatcg acgtattccc cgacaccgac aaggtgcgga tcgacatcgg cgagacggag 3840
ggcacgttca aggtcgagtc cgtcgagctg atcttcatgg aggagtga 3888
```

```
SEQ ID NO: 40          moltype = DNA    length = 3888
FEATURE                Location/Qualifiers
misc_feature           1..3888
                       note = A synthetic coding sequence,
                       CR-BRE1a.TIC7040_10.nno_Mc:6 encoding a TIC7040HT
                       pesticidal protein used for expression in plant cells.
source                 1..3888
                       mol_type = other DNA
                       organism = synthetic construct
SEQUENCE: 40
atgaaccaga accagaacca gaacaagaac gagttgcaga tcatcgagcc ttcctccgat 60
agccttctgt actcgcacaa caactacccc tacgccaccg accccaacac agtcctggag 120
gggcgcaact acaaggagtg gctgaacaaa tgtaccgaca attacaccga tgctctgcaa 180
gggccggagg cgaccgccat ctcgaaaggg gcggtcagcg ccgctattag cataagcaca 240
aaagtcctgt ccttgctcgg cgtgcccttc gcggcccaca tcgggcagct ctggacgttc 300
atcctgaacg cgctgtggcc gtccgacaac acgcagtggg aggagtttat gcggcacgtc 360
gaggaactta tcaaccagcg gatcgccgac tacgcgcgct cgaaggcgct cgcagagctg 420
acggggctgg gcaacaacct ggacctctac atcgaggccc tggaggactg gaagcggaac 480
ccgacgggtc aacaagcgaa agatcgggtg aaggaccggt tccggatcgg gacggggctg 540
ttcgaggcgt acatgcccag tttccgggtc agcggctacg aggtgcccct gctcaccgtg 600
tacgccgccg ccgcgaacct gcaccctctg ttgctgaggg actgctccat ctacggcatc 660
cagtggggct ctctcccagac aaacgtgaac gaaaactaca acaggcagat ccgccacacc 720
gcagagtatg ccaaccactg cactacgtgg tatcaaacag gactggaacg cctgcgggc 780
accaatgctt catcgtgggt gccctacaac cgtttccggc gggagatgac cctgaccgtg 840
```

```
ttggacatct gttccttgtt cagtaattac gactaccggt cttaccctgc cgaggtgcgg    900
gcagagctga cgcgcgaaat ctacacagat cctgtggtga gcacgtcgct gtggatgaac    960
aacgccccga gcttcggcga gatcgagaac ctggcgatcc gtgcgccgcg cacggtgacg   1020
tggctgaact cgacccggat cagcaccggc actctacagg gctggtccgg cagcaatcgc   1080
tactgggcg ctcacatgca gaatttcagc gagaccaaca gcgggaacat ggcgcttcgac  1140
ggcccgctct acgggagcac cgtcgggacc atcatccggg acgacaacta cgagatggtg   1200
aaccgggaca tctacacgat cacgtccgag gcggtcgcgg ctctgtggcc aaccgggcaa   1260
atagtgctgg gcgtggcgtc agcccgtttc accttgagaa atctgaacaa caacctcaca   1320
caggccctcg tgtacgagaa cccaatcagc agttcgttca accgctcgac gctgacgcgg   1380
gagctgcccg gcgagaactc cgaccgcccg accagctccg actacagcca ccgcctcacc   1440
agcatcacgg cctttcgggc cgggtccaac ggaaccatcc ccgtcttcgg ctggacttct   1500
atctctgtca atcgggataa catccttgag cgcaacaaga tcactcaatt ccctggagtc   1560
aagtctcaca cgctcaacaa ctgccaagtc gttagaggca ccggcttcac aggaggcgac   1620
tggctccgcc ccaacaacaa tggctccttc cgcctgacca tcacgtcatt cagtagtcag   1680
tcgtatcgca tccggcttcg gtacgccagc gcagcgaaca cgagtctcag gatctcatct   1740
agtgccgctg gcatctccag caccacagtc cctctgacgt ccaccatcac ctcccttccc   1800
caaacggcgg tcccctacga ggctttccgt gtaattgacc ttcccatcac ctttaccacc   1860
gccacggcag gcaactacac tttcgatttc gtactccaaa atccgagcaa cgcgaatgtc   1920
ttcatcgacc ggttcgagtt cgtccccatc ggcggcagcc tcagcgagta cgagacgaaa   1980
catcagcttg aaaaggcacg caaggcggtc aacgaccgtt tcaccaacga gagcaagaat   2040
gtgctcaaga agtacaccac agactacgac atcgaccagg ctgctaacct ggttgagtgc   2100
gtgagcgacg agtgcgccaa cgccaagatg atcctattag acgaagttaa gtacgccaag   2160
cagctaagtg aggcgcgaaa cctgttgctc aacggcaact tcgagtacca ggaccgggac   2220
ggggagaacc cgtggaagac cagcccaaag tgacgatcc aggagaacaa ccccatcttc   2280
aaaggacgat acctaagtat gagcggggct aactacatcg aggcgacgaa cgatacttt    2340
cccacttatg cctaccagaa gatcgacgag gccaagctca agccctacac acggtacaaa   2400
gtgcggggct tcgtcggaaa ttcgaaagac cttgaattac ttattaagcg ctacgacgag   2460
gaggtggacg ctatcctgaa cgtgcccaac gacatcccgc acgccccgac gccattctgc   2520
ggcggtttcg accggtgcaa gccgcattcg tacataccga tgaacccgga gtgccaccac   2580
gacgtgataa acaacatcga gatcagtagc ccgtgccaagc acaacaagat gctggacaac   2640
gccgacatca gctcccgtca ctcggaactg gcaagaagc gtggaatctg ccacgagtct    2700
caccacttcg agttccacat cgacaccggc aagatcgacc taaacgagaa cctggggatc   2760
tgggtgatct tcaagattg ctcaacagac ggatacgcga ccctggacaa cctggaggtg    2820
attgaggaag gccccgctcgg ggcggagtcc cttgaaaagg ttaagaggcg ggagaagaag   2880
tggaagcacc acatggagca caagtgctcc gagacgaagc tggcgtacca cgcagccaaa   2940
caggcgctcg ttggcctgtt caccaacacc aagtacgacc ggctcaagtt cgagaccaca   3000
atctcgaaca tcctgttcgc cgactacctc gtgcagagca tcccttacgt ttacaacaaa   3060
tggctccccg acgtgcccgg catgaactac gacattctaca ccgaacttaa gaacctgttt   3120
accggggcct tcaacctgta cgatcagagg aacattatca agaacggcga cttcaacagg   3180
ggcctcatgc actggcacgc gacgccccac gcccgagtgg agcagatcga caaccgttct   3240
gtgctggtcc tacccaacta cgcggccaac gtcagccaag aggtgtgcct ggagcacaac   3300
cggggttacg tgctgcagt gacggccaag aaggaaggtc cagggatcgg ctatgtgacg   3360
ttctcggact gcgccaacaa catcgagaag ctcacgttca gtcctgcga ctacggcacc    3420
aacgaggtta cttacgagca aagcaattac catacggacg gcgttccgta tgaacagtca   3480
aactacccga cggacggcgt gccctacgag cagcacgggt gccacaccga cggcgtgccc   3540
tacgagcaga gcaactaccc caccgacggc gtgccgtacg agcagcacgg ctgccacacc   3600
gacggagtgc cgtacgagca gcacggctgc cacaccggccg tcgagcagcac             3660
gggtgccata ccgacggcgt gccgtacaag cagcacggct gccgcaccga cggggtgctg   3720
tacaagcagc acggttgccg cacagatcgg agccgtgacg agcagctcga ttacgtgacg   3780
aagaccatcg acgttttccc ggacaccgac aaggttcgta ttgacatcgg cgaaacggaa   3840
gggacattca aggtggagtc cgtcgagcta atcttcatgg aggagtag                3888

SEQ ID NO: 41         moltype = DNA  length = 3888
FEATURE               Location/Qualifiers
misc_feature          1..3888
                      note = A synthetic coding sequence,
                      CR-BRE1a.TIC7040_10.nno_Mc:7 encoding a TIC7040HT
                      pesticidal protein used for expression in plant cells.
source                1..3888
                      mol_type = other DNA
                      organism = synthetic construct
SEQUENCE: 41
atgaaccaga accagaacca gaacaagaac gagcttcaga tcatcgagcc gtcctccgac     60
agcctgctct acagccacaa caattacccc tatgccaccg acccgaactg cgtgctggag    120
gggcgcaact acaaggagtg gctgaacaag tgcaccgaca actacacgga cgcgctccag    180
ggccccgagg ccaccgcgat cagcaaaggg gccgtgtcgg cggcgatctc catcagcacg    240
aaagtgctga gcctgctcgg ggtgccattc gcggcccaga tcgggcagct ctggacgttc    300
atcctcaacg ccctcgtggc gtccgacaac acccagtggg aggagttcat gcggcacgtc    360
gaggaacttta ttaaccagag gatcgcggac tacgcgcgct cgaaggccct gggcgagcta   420
accgggctgg gcaacaacct ggacctctac attgaggccc ttgaggactg aagcgtaac    480
ccaacgtcgc aacaggcgaa ggaccgcgtg aaggaccggt tccgtatcgc cgacggactg    540
tcgaggcgt acatgccgag cttccgcgtc tcaggctacg aagtgccttt gctcaccgtc    600
tatgcggcgg cggcgaacct ccactcctt tgctccggga actgctcgat ctacggtatc    660
caatgggtc tctcccagac aaacgtgaat gagaactaca gtcgtcagca ccgcaccacc    720
gcagagtacg cgaaccactg cacaacctg tatcagactg ggttggagcg gctccgaggg    780
acgaatgcct catcctgggt gccgtacaac cgtttccggc gtgagatgac attaacggtc   840
cttgacatct gttccctgtt cagcaattac gattaccgca gttacccggc ggaggtccgg    900
gcggagttga cgcgcgaaat ctacacagac ccagtggtca gcacttccct ctggatgaac    960
aacgctccga gcttcggcga gatcgagaac ctggccatcc gggcccccgcg cacggtgacg   1020
```

```
tggctcaact caacccggat ctccacaggc acgctacagg ggtggtctgg tagtaatcgc    1080
tactgggcgg cgcacatgca gaacttcagc gagacgaaca gcgggaacat cgggttcgac    1140
ggcccgctct acgggtccac cgtgggcacc ataatcaggg atgataacta cgagatggtc    1200
aaccgggaca tctacaccat caccagcgag gccgtggccg ccctgtggcc gacagggcag    1260
atagtgctcg gcgtggcgag cgcccgcttt accctgcgga acctcaacaa taacctgacc    1320
caggctctag tgtacgagaa cccaatcagc tccagtttca accgaagtac cttgacgagg    1380
gaactgccgg gcgagaactc tgaccgtccc acgtcgagcg actacagcca cagcttaccc    1440
tctattacgg ccttccgtgc gggcagcaac ggtacgatcc cggtcttcgg gtggaccagc    1500
ataagcgtga atcgggacaa catcctggaa cgcaacaaga tcacccagtt tcctggcgtg    1560
aagtcacaca cactgaacaa ctgccaagtc gtgaggggca ccggcttcac gggcggggac    1620
tggctccgcc cgaacaacaa tggctccttt cgcctcacaa tcacctcctt ctcgtcgcag    1680
agctaccgga tcaggctccg gtacgcttcc gccgcaaata cttcactacg catcagctcc    1740
tcggccgccg gaatctcctc tactactgtg ccattgactt cgacgatcac cagcctcccg    1800
cagacagcgg tgccctacga agcgttccgc gtcatcgacc tccctatcac tttcacgacg    1860
gcgacgcaga gtaactacac attcgacttc gtactccaga acccgtccaa cgcgaacgtc    1920
ttcattgatc ggtttgagtt cgtgccaata ggcgggtcac tcagcgagta cgagacgaag    1980
caccaattgg aaaaggctcg gaaagctgtg aatgatctgt ttacaaacga aagcaagaat    2040
gtgctcaaga agtacactac tgattacgac atcgaccaag ccgccaacct cgtggagtgc    2100
gtctccgacg agtgcgccaa cgcaaagatg atcctgctcg atgaggtgaa gtacgccaaa    2160
caactaagcg aggcacgcaa tctcctcctc aacggcaact tcgagtacca ggaccgggac    2220
ggggagaacc cctggaagac ctcgccgaac gtgaccatcc aggagaacaa ccccatcttc    2280
aaggggagat acttgagcat gagcggggct aactacatcg agcaccacga cacaccttc    2340
ccgacctacg cttaccagaa aatcgacgag gccaaattga agccctacgc gcgatacaag    2400
gtgcgcggct cgtcgggaa cagcaaagac cttgagctgc tcatcaagcg gtacgacgag    2460
gaggtggatg cgatcctcaa cgtcccgaac gacatcccgc acgcgcccac cccgttctgc    2520
ggcggcttcg accgttgcaa gccccactcc tacattccga tgaacccgga atgtcatcac    2580
gatgtcatta acaacattga aatcagcagc ccgtgccagc ataacaagat gctgacaac    2640
gcggacatct catcccgcca cagtgaactt ggcaagaaac gcgggatctg ccacgagtcc    2700
caccacttcg agttccacat cgacacgggg aagatcgact tgaacgagaa tctcgggatc    2760
tgggtgatct tcaagatttg cagtacggac ggctacgcca cgctcgacaa ccgtcggaggtt   2820
atcgaggagg ggccgctcgg agccgagtcc ctggagcgcg tcaaacgccg cgagaagaag    2880
tggaagcacc acatggagca caagtgcagc gagacgaagc tcgcctacca cgcagctaaa    2940
caagctctgg tgggcctgtt caccaacacg aagtacgacc ggctcaagtt cgagaccacg    3000
atcagcaaca tcctcgtccg cggactacctg gtgcagtcaa taccgtatgt gtacaacaaa    3060
tggctcccgg acgtgcccgg catgaactac gacatctcaa ccgaacttaa gaacctattc    3120
acaggagcat tcaacctgta cgaccagcga acattatca agaacggcga cttcaatagg    3180
ggcctgatgc actggcacgc cactccccac gcaagggtcg agcaaataga caaccggagc    3240
gtgctcgttc taccgaatta cgccgccaat gtaagccagg aggtctgcct tgagcacaac    3300
cgtggttacg tcttgcgggt gacggccaag aaggaaggc cagggatcgg ctacgtgacg    3360
ttctccgact gcgccaacaa catcgagaag ctcacttttta cctcctgcga ctacggcaca    3420
aacgaggtca cttacgagca gtcgaactac acaccgatg gcgttccgta cgaacaaagc    3480
aactacccca ccgacggagt gccctacgag cagcacggct gccacacaga cggcgtgccg    3540
tacgacagt caaactaccc gacggacggc gtgccctacg agcacacg tgccacacg    3600
gacggcgtgc cttacgagca gcacgggtgc cacacggacg gggtgcccta cgagcagcac    3660
ggctgccaca cggacggcgt gccgtacaag cagcacggct gccgcacgga tggcgtgctg    3720
tacaagcagc acggatgtag aacagatcgg tcccgcgacg agcaactgga ctatgttacc    3780
aagacaaatag acgtcttccc ggacaccgac aaggtcggga ttgacatcgg ggagactgag    3840
ggcacgttca aggtcgagtc cgtggagctg atcttcatgg aggagtga               3888
```

SEQ ID NO: 42       moltype = DNA  length = 1923
FEATURE             Location/Qualifiers
misc_feature        1..1923
                    note = A synthetic coding sequence used for expression in
                    plant cells, CR-BRE1a.TIC7040_1.nno_Mc:1 which encodes a
                    protein having an N-terminal and C-terminal truncation
                    relative to the TIC7040HT protein.
source              1..1923
                    mol_type = other DNA
                    organism = synthetic construct
SEQUENCE: 42

```
atgcagatca tcgagcctag ctccgactcg ctcctgtaca gccacaacaa ctacccgtac      60
gcgacggacc cgaatactgt gctggagggc cgcaactaca aggagtggct caacaagtgc     120
acggacaact acacgacagc cctccaaggc ccggaggcca cggcgattag caagggcgcg     180
gtctcggccgg caatttcgat ctcgactaag gtgctctgac tgtcggcgt gccgtttgca     240
gcgcagatcg gccagctctg gaccttcata ctcaacgcgc tctggccgag cgacaacacc     300
cagtgggagg agttcatgcg tcacgtcgag gaactgataa accagcgcat gcggactac     360
gccaggagca aggccctcgc ggagctgacc gggctcggca taacctgga cttgtacatc     420
gaggcccttg aggactggaa acgaaacccg accagccaac aagcaaggga ccgggtgaag     480
gaccggttcc ggatcgccga cgcctgttc gaggcgtaca tgccttcctt ccgggtctcg     540
ggctatgaag tgccgctcct cacgtgtac gccgcagcgg ccaacctgca tctcctgctg     600
ctaagggatt gctcgatcta cggcatccag tggggtttct cccagaccaa cgtaaacgag     660
aactacaacc gtcagatccg gcacacggct gagtacgcaa accactgcac gacgtggtat     720
cagaccggac tggagcggct ccgtggcacc aacgcatctt cgtgggttcc gtacaaccgt     780
ttccgcagag agattgactct taccgtcctg ccctcttctc caactatgac     840
tacagaagct acccggcgga agtgcgggcc gagctaaccc gcgaaatcta cacggacccg     900
gtggtctcca catcgctgtg gatgaacaac gcaccatcgt tcggtgagat cgagaactg     960
gcaatccgcg ctccgcgcac ggtgacgtgg ttgaactcaa ccaggatctc taccggcacc    1020
ctccaggct ggtcaggcag taaccgatac tgggcggcac acatgcagaa cttcagcgag    1080
accaactccg ggaacattgg attcgacggc ccactgtacg gctctaccgt gggcactatc    1140
```

```
atcagggacg acaactacga gatggtcaac agggacatct acacgattac gtccgaagcg   1200
gtggccgctc tttggcccac agggcagata gtgctgggcg tggcctccgc acgtttcaca   1260
ctccgtaatc tcaacaacaa tctgacccag gccctggttt acgagaaccc gatttcctcc   1320
agcttcaacc gcagcacgct cacacgggaa ctacctggcg agaacagtga tcgcccaacg   1380
tccagtgact acagccatag gctgacatca atcacggcgt tccgggccgg gagtaacggc   1440
accatcccgg tcttcggctg gacctccatc tcggtcaacc gggataacat cctggagcgc   1500
aacaagataa cccagttccc tggcgtcaag agccacactc tcaacaactg ccaagtcgtc   1560
agagggaccg gcttcactgg cggcgactgg ctcagaccca acaacaacgg gtctttccgc   1620
ctgacgatca ccagcttctc ctcgcagtcc taccggataa ggctccggta cgcctctgcg   1680
gccaacacat ccctccggat ttcttcctcc gctgcgggca taagctctac aaccgtgccg   1740
ctgacctcca ctattactag ccttccgcaa accgctgtac cctacgaggc gttccgcgtc   1800
atcgacctcc cgatcacctt cactaccgct acgcagagta actacacctt cgactttgtc   1860
ctccagaacc cgtccaatgc taacgtcttc atcgaccggt tcgagttcgt ccctattgga   1920
tga                                                                 1923

SEQ ID NO: 43           moltype = AA   length = 640
FEATURE                 Location/Qualifiers
REGION                  1..640
                        note = The amino acid sequence of the
                        CR-BRE1a.TIC7040_1.nno_Mc:1 protein, comprising amino
                        acids 15 through 651 of TIC7040HT.
source                  1..640
                        mol_type = protein
                        organism = synthetic construct
SEQUENCE: 43
MQIIEPSSDS LLYSHNNYPY ATDPNTVLEG RNYKEWLNKC TDNYTDALQG PEATAISKGA    60
VSAAISISTK VLSLLGVPFA AQIGQLWTFI LNALWPSDNT QWEEFMRHVE ELINQRIADY   120
ARSKALAELT GLGNNLDLYI EALEDWKRNP TSQQAKDRVK DRFRIADGLF EAYMPSFRVS   180
GYEVPLLTVY AAAANLHLLL LRDCSIYGIQ WGFSQTNVNE NYNRQIRHTA EYANHCTTWY   240
QTGLERLRGT NASSWVPYNR FRREMTLTVL DICSLFSNYD YRSYPAEVRA ELTREIYTDP   300
VVSTSLWMNN APSFGEIENL AIRAPRTVTW LNSTRISTGT LQGWSGSNRY WAAHMQNFSE   360
TNSGNIGFDG PLYGSTVGTI IRDDNYEMVN RDIYTITSEA VAALWPTGQI VLGVASARFT   420
LRNLNNNLTQ ALVYENPISS SFNRSTLTRE LPGENSDRPT SSDYSHRLTS ITAFRAGSNG   480
TIPVFGWTSI SVNRDNILER NKITQFPGVK SHTLNNCPVY RGTGFTGDW LRPNNNGSFR    540
LTITSFSSQS YRIRLRYASA ANTSLRISSS AAGISSTTVP LTSTITSLPQ TAVPYEAFRV   600
IDLPITFTTA TQSNYTFDFV LQNPSNANVF IDRFEFVPIG                         640

SEQ ID NO: 44           moltype = DNA   length = 1983
FEATURE                 Location/Qualifiers
misc_feature            1..1983
                        note = A synthetic coding sequence used for expression in
                        plant cells, CR-BRE1a.TIC7040_2.nno_Mc:1 encoding a
                        TIC7040_6 (SEQ ID NO:10) encoding pesticidal protein sequence which
                        comprises an N-terminal and C-terminal truncation relative
                        to the TIC7040HT protein.
source                  1..1983
                        mol_type = other DNA
                        organism = synthetic construct
SEQUENCE: 44
atgcagatca tcgagcctag ctccgactcg ctcctgtaca gccacaacaa ctacccgtac    60
gcgacggacc cgaatactgt gctggagggc cgcaactaca aggagtggct caacaagtgc   120
acggacaact acacgacgc cctccaaggc ccggaggcca cggcgattag caagggcgcg   180
gtctcggcgg caatttcgat ctcgactaag gtgctctcgc tgctcggcgt gccgtttgca   240
gcgcagatcg gccagctctg gaccttcata ctcaacgcgc tctggccgag cgacaacacc   300
cagtgggagg agttcatgcg tcacgtcgag gaactgataa accagcgcat cgcggactac   360
gccaggagca aggccctcgc ggagctgacc gggctcggca ataacctgga cttgtacatc   420
gaggcccttg aggactggaa acgaaacccg accagccaac aagccaagga ccgggtgaag   480
gaccggttcc ggatcgccga cggcctgttc gaggcgtaca tgccttcctt ccgggtctcg   540
ggctatgaag tgccgctcct cacggttgtac gccgcagcg ccaacctgca tctcctgctg   600
ctaagggatt gctcgatcta cggcatccag tgggtttct cccagaccaa cgtaaacgag   660
aactacaacc gtcagatccg gcacacggct gagtacgcaa accactgcac gacgtggtat   720
cagaccggac tggagcggct ccgtggcacc aacgcatctt cgtgggttcc gtacaaccgt   780
ttccgcagag agatgactct taccgtcctg gacatctgct ccctcttctc caactatgac   840
tacagaagct acccggccga agtgcggcc agctaaccta cacggaccg                900
gtggtctccaa catcgctgtg gatgaacaac gcaccatcgt tcggtgagat cgagaacctg   960
gcaatccgcg ctccgcgcac ggtgacgtgg ttgaactcaa ccaggatctc taccggcacc  1020
ctccaggct ggtcaggcag taaccgatac tgggcggcac acatgcagaa cttcagcgag   1080
accaactccg ggaacattgg attcgacggc ccactgtacg gctctaccgt gggcactatc   1140
atcagggacg acaactacga gatggtcaac agggacatct acacgattac gtccgaagcg   1200
gtggccgctc tttggcccac agggcagata gtgctgggcg tggcctccgc acgtttcaca   1260
ctccgtaatc tcaacaacaa tctgacccag gccctggttt acgagaaccc gatttcctcc   1320
agcttcaacc gcagcacgct cacacgggaa ctacctggcg agaacagtga tcgcccaacg   1380
tccagtgact acagccatag gctgacatca atcacgcgt tccgggccgg gagtaacggc    1440
accatcccgg tcttcggctg gacctccatc tcggtcaacc gggataacat cctggagcgc   1500
aacaagataa cccagttccc tggcgtcaag agccacactc tcaacaactg ccaagtcgtc   1560
agagggaccg gcttcactgg cggcgactgg ctcagaccca acaacaacgg gtctttccgc   1620
ctgacgatca ccagcttctc ctcgcagtcc taccggataa ggctccggta cgcctctgcg   1680
gccaacacat ccctccggat ttcttcctcc gctgcgggca taagctctac aaccgtgccg   1740
ctgacctcca ctattactag ccttccgcaa accgctgtac cctacgaggc gttccgcgtc   1800
```

```
atcgacctcc cgatcacctt cactaccgct acgcagagta actacacctt cgactttgtc    1860
ctccagaacc cgtccaatgc taacgtcttc atcgaccggt tcgagttcgt ccctattgga    1920
ggcagcctttt cagagtacga gacgaagcac cagcttgaga aggcgaggaa agctgtcaac    1980
tga                                                                  1983

SEQ ID NO: 45           moltype = DNA   length = 1752
FEATURE                 Location/Qualifiers
misc_feature            1..1752
                        note = A synthetic coding sequence used for expression in
                          plant cells, CR-BREla.TIC7040_11.nno_Mc:1 which encodes a
                          protein having an N-terminal and C-terminal truncation
                          relative to the TIC7040HT protein.
source                  1..1752
                        mol_type = other DNA
                        organism = synthetic construct
SEQUENCE: 45
atgaactaca aggagtggct gaacaagtgt accgacaact acaccgacgc gctccagggc      60
cctgaggcca ccgccatcag caagggcgca gtgtcagccg cgatctccat cagcacaaag     120
gtgctctcgt tactgggcgt gcccttcgcg gcgcagatcg gccagctctg gacctttatc     180
ctgaacgccc tatggcccag cgacaacacc cagtgggagg agtttatgcg ccacgtggag     240
gaactcatta ccagcgaat tgctgactac gccaggagca aggccctggc cgagctgacg      300
ggtcttggca caacctcga cctctacatc gaggccctcg aagactggaa gcggaacccg     360
accagccaac aggccaaaga ccgtgtgaag gaccggttcc ggatcgccga cgggctgttc    420
gaggcgtaca tgcccctcttt ccgcgtcagc ggctacgagg tgccactgtt gaccgtttac    480
gcggcagccg ctaacctcca cttgctgctc tgcgggatt gctccatcta cggtatccag    540
tggcgttca gccagacaaa cgtcaacgag aactacaacc gacagatccg ccacacggca    600
gagtacgcaa accactgcac gacatggtat cagacagggc ttgaacgcct tcgtggcacc    660
aacgcctcgt catgggtgcc gtacaaccgg ttccgccgag agatgaccct caccgttctt    720
gacatctgct cactgttcag caactacgac taccggtcgt accctgcgga ggttcgggcc    780
gaactgacgc gggagatcta cactgacccg gtggtcagca cctcgttgtg gatgaacaac    840
gcgcccagct tcggtgagat cgagaacctc gccataagag caccacgcac cgtcacttgg    900
ctcaacagca cccggatctc cacgggcacc ttacagggct ggagcggctc caaccgatac    960
tgggcagcgc acatgcagaa cttctccgag actaactccg gcaacatcgg cttcgacggc   1020
ccgctctacg gcagccaccgt cggaccatc atccgggacg acaactatga gatggtcaac   1080
agggacatct acacgattac ctcggaggcc gtggctgccc tgtggccaac cggtcaaata   1140
gtgttgggag tcgcctccgc ccgctttacg ctgcgtaacc tgaacaacaa ccttacccag   1200
gcgctcgtgt acgagaaccc gatctccagc tccttcaata ggtccaccct cacgagggag   1260
ctgccggtgt agaacagcga caggccgacg tcctcggact acagtcaccg gctccacctcg  1320
atcacgacgt tccgagccgg gagcaacgga acgatccgac tcttcggatg gaccagcatc   1380
agcgtcaacc gcgacaacat cctgaacgc aacaagatca ctcagttccc tggagttaag    1440
tctcacacgc tcaacaactg ccaagtggtg cgtggcacag ggtttaccgg aggcgactgg   1500
cttcgcccga caacaatgg gtcattccgg ctgaccatta ccagcttctc atcgcaatca    1560
taccgcatcc ggctacggta cgcctcggcg gcgaacacta gccttcgcat ctcctcttca   1620
gccgccggga tcagctcgac aaccgtcccg ctgaccagca cgatcacgag cctgccacaa   1680
actgctgtgc cttacgaggc tttcagagtg atcgacctgc ccattacctt caccacggca   1740
acccaatcgt ga                                                         1752

SEQ ID NO: 46           moltype = AA    length = 583
FEATURE                 Location/Qualifiers
REGION                  1..583
                        note = The amino acid sequence of the
                          CR-BREla.TIC7040_11.nno_Mc:1 protein, comprising amino
                          acids 14 through 671 of TIC7040HT.
source                  1..583
                        mol_type = protein
                        organism = synthetic construct
SEQUENCE: 46
MNYKEWLNKC TDNYTDALQG PEATAISKGA VSAAISISTK VLSLLGVPFA AQIGQLWTFI      60
LNALWPSDNT QWEEFMRHVE ELINQRIADY ARSKALAELT GLGNNLDLYI EALEDWKRNP    120
TSQQAKDRVK DRFRIADGLF EAYMPSFRVS GYEVPLLTVY AAAANLHLLL LRDCSIYGIQ    180
WGFSQTNVNE NYNRQIRHTA EYANHCTTWY QTGLERLRGT NASSWVPYNR FRREMTLTVL    240
DICSLFSNYD YRSYPAEVRA ELTREIYTDP VVSTSLWMNN APSFGEIENL AIRAPRTVTW    300
LNSTRISTGT LQGWSGSNRY WAAHMQNFSE TNSGNIGFDG PLYGSTVGTI IRDDNYEMVN    360
RDIYTITSEA VAALWPTGQI VLGVASARFT LRNLNNNLTQ ALVYENPISS SFNRSTLTRE    420
LPGENSDRPT SSDYSHRLTS ITAFRAGSNG TIPVFGWTSI SVNRDNILER NKITQFPGVK    480
SHTLNNCQVV RGTGFTGGDW LRPNNNGSFR LTITSFSSQS YRIRLRYASA ANTSLRISSS    540
AAGISSTTVP LTSTITSLPQ TAVPYEAFRV IDLPITFTTA TQS                      583

SEQ ID NO: 47           moltype = DNA   length = 1983
FEATURE                 Location/Qualifiers
misc_feature            1..1983
                        note = A synthetic coding sequence used for expression in
                          plant cells, CR-BREla.TIC7040_12.nno_Mc:2 which encodes a
                          protein having a C-terminal truncation relative to the
                          TIC7040HT protein.
source                  1..1983
                        mol_type = other DNA
                        organism = synthetic construct
SEQUENCE: 47
```

-continued

```
atgaaccaga accagaatca gaacaagaac gagcttcaga taatcgagcc ctcctcggac   60
tccctcctct actcgcataa caactacccg tacgctaccg acccgaacac cgtgctggaa  120
ggccgcaact acaaggagtg gctgaacaag tgtaccgaca actacaccga cgcgctccag  180
ggccctgagg ccaccgccat cagcaagggc gcggtgtcag ccgcgatctc catcagcaca  240
aaggtgctct cgttactggg cgtgcccttc gcggcgcaga tcggccagct ctggaccttt  300
atcctgaacg ccctatggcc cagcgacaac acccagtggg aggagtttat gcgccacgtg  360
gaggaactca ttaaccagcg aattgctgac tacgccagga gcaaggccct ggccgagctg  420
acgggtcttg gcaacaacct cgacctctac atcgaggccc ttgaagactg gaagcggaac  480
ccgaccagcc aacaggccaa agaccgtgtg aaggaccggt tccggatcgc cgacgggctg  540
ttcgaggcgt acatgccctc tttccgcgtc agcggctacg aggtgccact gttgaccgtt  600
tacgcggcag ccgctaacct ccacttgctg ctcctgcggg attgctccat ctacggtatc  660
cagtgggct tcagccagac aaacgtcaac gagaactaca accgacagat ccggcacacg  720
gccgagtacg caaaccactg cacgacatgg tatcagacag gcttgaacg ccttcgtggc  780
accaacgcct cgtcatgggt gccgtacaac cggttccgac acctgaccac cctcaccgtt  840
cttgacatct gctcactgtt cagcaactac gactaccggt cgtaccctgc ggaggttcgg  900
gccgaactga cgcgggagat ctacactgac ccggtggtca gcacctcgtt gtggatgaac  960
aacgcgccca gcttcggtga gatcgagaac ctcgccataa gagcaccacg caccgtcact 1020
tggctcaaca gcacccggat ctccacgggc accttacagg gctggagcgg ctccaaccga 1080
tactgggcag cgcacatgca gaacttctcc gagactaact ccggcaacat cggcttcgac 1140
ggcccgctct acggcagcac cgtcgggacc atcatccggg acgacaacta tgagatggtc 1200
aacagggaca tctacacgat tacctcggag gccgtggctg ccctgtggcc aaccggtcaa 1260
atagtgttgg gagtcgcctc cgcccgcttt acgctgcgta acctgaacaa caaccttacc 1320
caggcgctcg tgtacgagaa cccgatctcc agctccttca ataggtccac cctcacgagg 1380
gagctgccgg gtgagaacag cgacaggccg acgtcctcgg actacagtca ccggctcacc 1440
tcgatcacag cgttccgagc cgggagcaac ggaacgatcc cagtcttcgg atggaccagc 1500
atcagcgtca accgcgacaa catcctggaa cgcaacaaga tcactcagtt ccctggagtt 1560
aagtctcaca cgctcaacaa ctgccaagtg gtgcgtggca cagggtttac cggaggcgac 1620
tggcttcgcc cgaacaacaa tgggtcattc cggctgacca ttaccagctt ctcatcgcaa 1680
tcataccgca tccggctacg gtacgcctcg gcggcgaaca ctagccttcg catctcctct 1740
tcagccgccg ggatcagctc gacaaccgtc ccgctgacca gcacgatcac gagcctgcca 1800
caaactgctg tgccttacga ggctttcaga gtgatcgacc tgcccattac cttcaccacg 1860
gcaacccaat cgaactacac ttttgacttc gtgttacaga atccgagcaa cgccaacgtc 1920
ttcatcgacc ggttcgagtt cgtgcccatc ggcgggagcc tctccgagta cgagaccaag 1980
tga                                                               1983
```

SEQ ID NO: 48             moltype = AA   length = 660
FEATURE                   Location/Qualifiers
REGION                    1..660
                          note = The amino acid sequence of the
                          CR-BRE1a.TIC7040_12.nno_Mc:2 protein, consisting of amino
                          acids 1 through 660 of TIC7040HT.
source                    1..660
                          mol_type = protein
                          organism = synthetic construct SEQUENCE: 48
```
MNQNQNQNKN ELQIIEPSSD SLLYSHNNYP YATDPNTVLE GRNYKEWLNK CTDNYTDALQ   60
GPEATAISKG AVSAAISIST KVLSLLGVPF AAQIGQLWTF ILNALWPSDN TQWEEFMRHV  120
EELINQRIAD YARSKALAEL TGLGNNLDLY IEALEDWKRN PTSQQAKDRV KDRFRIADGL  180
FEAYMPSFRV SGYEVPLLTV YAAAANLHLL LLRDCSIYGI QWGFSQTNVN ENYNRQIRHT  240
AEYANHCTTW YQTGLERLRG TNASSWVPYN RFRREMTLTV LDICSLFSNY DYRSYPAEVR  300
AELTREIYTD PVVSTSLWMN NAPSFGEIEN LAIRAPRTVT WLNSTRISTG TLQGWSGSNR  360
YWAAHMQNFS ETNSGNIGFD GPLYGSTVGT IIRDDNYEMV NRDIYTITSE AVAALWPTGQ  420
IVLGVASARF TLRNLNNNLT QALVYENPIS SSFNRSTLTR ELPGENSDRP TSSDYSHRLT  480
SITAFRAGSN GTIPVFGWTS ISVNRDNILE RNKITQFPGV KSHTLNNCQV VRGTGFTGGD  540
WLRPNNNGSF RLTITSFSSQ SYRIRLRYAS AANTSLRISS SAAGISSTTV PLTSTITSLP  600
QTAVPYEAFR VIDLPITFTT ATQSNYTFDF VLQNPSNANV FIDRFEFVPI GGSLSEYETK  660
```

SEQ ID NO: 49             moltype = DNA   length = 1875
FEATURE                   Location/Qualifiers
misc_feature              1..1875
                          note = A synthetic coding sequence used for expression in
                          plant cells, CR-BRE1a.TIC7040_13.nno_Mc:1 which encodes a
                          protein having a C-terminal truncation relative to the
                          TIC7040HT protein.
source                    1..1875
                          mol_type = other DNA
                          organism = synthetic construct SEQUENCE: 49
```
atgaaccaga accagaatca gaacaagaac gagcttcaga taatcgagcc ctcctcggac   60
tccctcctct actcgcataa caactacccg tacgctaccg acccgaacac cgtgctggaa  120
ggccgcaact acaaggagtg gctgaacaag tgtaccgaca actacaccga cgcgctccag  180
ggccctgagg ccaccgccat cagcaagggc gcggtgtcag ccgcgatctc catcagcaca  240
aaggtgctct cgttactggg cgtgcccttc gcggcgcaga tcggccagct ctggaccttt  300
atcctgaacg ccctatggcc cagcgacaac acccagtggg aggagtttat gcgccacgtg  360
gaggaactca ttaaccagcg aattgctgac tacgccagga gcaaggccct ggccgagctg  420
acgggtcttg gcaacaacct cgacctctac atcgaggccc ttgaagactg gaagcggaac  480
ccgaccagcc aacaggccaa agaccgtgtg aaggaccggt tccggatcgc cgacgggctg  540
ttcgaggcgt acatgccctc tttccgcgtc agcggctacg aggtgccact gttgaccgtt  600
tacgcggcag ccgctaacct ccacttgctg ctcctgcggg attgctccat ctacggtatc  660
```

```
cagtggggct tcagccagac aaacgtcaac gagaactaca accgacagat ccggcacacg  720
gccgagtacg caaaccactg cacgacatgg tatcagacag ggcttgaacg ccttcgtggc  780
accaacgcct cgtcatgggt gccgtacaac cggttccgcc gagagatgac cctcaccgtt  840
cttgacatct gctcactgtt cagcaactac gactaccggt cgtaccctgc ggaggttcgg  900
gccgaactga cgcgggagat ctacactgac ccggtggtca gcacctcgtt gtggatgaac  960
aacgcgccca gcttcggtga gatcgagaac ctcgccataa gagccaccac caccgtcact 1020
tggctcaaca gcacccggat ctccacgggc accttacagg gctggagcgg ctccaaccga 1080
tactgggcag cgcacatgca gaacttctcc gagactaact ccggcaacat cggcttcgac 1140
ggcccgctct acggcagcac cgtcgggacc atcatccgga acgacaacta tgagatggtc 1200
aacagggaca tctacacgat tacctcggag gccgtggctg ccctgtggcc aaccggtcaa 1260
atagtgttgg gagtcgcctc cgcccgcttt acgctgcgta acctgaacaa caaccttacc 1320
caggcgctcg tgtacgagaa cccgatctcc agctccttca ataggtccac cctcacgagg 1380
gagctgccgg gtgagaacag cgacaggccg acgtcctcgg actacagtca ccggctcacc 1440
tcgatcacag cgttccgagc cgggagcaac ggaacgatcc cagtcttcgg atggaccagc 1500
atcagcgtca accgcgacaa catcctggaa cgcaacaaga tcactcagtt ccctggagtt 1560
aagtctcaca cgctcaacaa ctgccaagtg gtgcgtggca cagggtttac cggaggcgac 1620
tggcttcgcc cgaacaacaa tgggtcattc cggctgacca ttaccagctt ctcatcgcaa 1680
tcataccgca tccggctacg gtacgcctcg gcggcaaaca ctagccttcg catctcctct 1740
tcagccgccg ggatcagctc gacaaccgtc ccgctgacca gcacgatcac gagcctgcca 1800
caaactgctg tgccttacga ggctttcaga gtgatcgacc tgcccattac cttcaccacg 1860
gcaacccaat cgtga                                                  1875

SEQ ID NO: 50          moltype = AA  length = 624
FEATURE                Location/Qualifiers
REGION                 1..624
                       note = The amino acid sequence of the
                       CR-BRE1a.TIC7040_13.nno_Mc:1 protein, consisting of amino
                       acids 1 through 627 of TIC7040HT.
source                 1..624
                       mol_type = protein
                       organism = synthetic construct
SEQUENCE: 50
MNQNQNQNKN ELQIIEPSSD SLLYSHNNYP YATDPNTVLE GRNYKEWLNK CTDNYTDALQ   60
GPEATAISKG AVSAAISIST KVLSLLGVPF AAQIGQLWTF ILNALWPSDN TQWEEFMRHV  120
EELINQRIAD YARSKALAEL TGLGNNLDLY IEALEDWKRN PTSQQAKDRV KDRFRIADGL  180
FEAYMPSFRV SGYEVPLLTV YAAAANLHLL LLRDCSIYGI QWGFSQTNVN ENYNRQIRHT  240
AEYANHCTTW YQTGLERLRG TNASSWVPYN RFRREMTLTV LDICSLFSNY DYRSYPAEVR  300
AELTREIYTD PVVSTSLWMN NAPSFGEIEN LAIRAPRTVT WLNSTRISTG TLQGWSGSNR  360
YWAAHMQNFS ETNSGNIGFD GPLYGSTVGT IIRDDNYEMV NRDIYTITSE AVAALWPTGQ  420
IVLGVASARF TLRNLNNNLT QALVYENPIS SSFNRSTLTR ELPGENSDRP TSSDYSHRLT  480
SITAFRAGSN GTIPVFGWTS ISVNRDNILE RNKITQFPGV KSHTLNNCQV VRGTGFTGGD  540
WLRPNNNGSF RLTITSFSSQ SYRIRLRYAS AANTSLRISS SAAGISSTTV PLTSTITSLP  600
QTAVPYEAFR VIDLPITFTT ATQS                                        624

SEQ ID NO: 51          moltype = DNA  length = 3801
FEATURE                Location/Qualifiers
misc_feature           1..3801
                       note = A synthetic coding sequence used for expression in
                       plant cells, CR-BRE1a.TIC7042.nno_Mc:1 which encodes a
                       TIC7042 protein (SEQ ID NO:12).
source                 1..3801
                       mol_type = other DNA
                       organism = synthetic construct
SEQUENCE: 51
atgaatcaga accagaacaa gaactgagatg cagatcatcg agccgtcgag cgactccttc   60
ctctattccc acaacaacta cccgtacgcc actgacccgg acacgatcct caagggccgg  120
aactacaagg agtggctcaa catgtgcacc gatacggacg actcgcgctc gcccgaggcc  180
gcgagcacgg ctcgcagcgc gatctccgtc gccatcacca ttagcaccac catcctggga  240
ctccttggag ttcccttcgc gtcccagatc ggtgccttct acaacttcgt gctcaacacc  300
gtgtggcctc agggaaataa ccagtggaga gagttcatga tggcacgtgga gaacctcatc  360
aacgagcgca ttgctgacta cgcgcgcgac aaagccttgg ccgagctgac cggcctgggc  420
aacaacctga atctctatcg ggaggctttc gaggactggc ggcggaaccc gacctcccag  480
gaagccaaga ctcgggtgat cgaccgcttt cgtattctcg acggcctgtt cgagacttac  540
atgccctcct tcgcggtccg caactttgag gttcagctcc tgactgtgta cgcctcggct  600
gcaaacatac acctgttcct gctgcgggac agctcgatct acggtttgga ctggggcctg  660
tcacagacca acgtgaacga gaactacaac cggcagatcc gccacgccgc cacctatgca  720
aaccactgca ccacttggta tcagacaggg ctccagcgcc tccagggcac taacgcaacg  780
tcatgggttg catacaaccg gtttcggcgg gagatgacac tcaccgtgtt ggacatctgc  840
tcgctgttct ccaactacga ctaccgctcg taccgactg aggtgaaggg cgagttgacc  900
agggaaatct acacagaccc tgtcggccgg aactggcaga acgtcgcgcc ttcattcgcg  960
gagattgaga acctgaccat tcgcgctccg cgtaccgtca cttggctcaa ctccactcgg 1020
atcttcacag gacgctgac cggctggtcc gggtccaacc gctactgggc cgcccacatg 1080
cagaacttca gcgagacaaa ctctggcaac atcggattcg atgggcccca gtatgggtcc 1140
acggtcggga cgatcaccg gaccgacgac tacgactgg tgaaccggga catctacact 1200
ataacgagcc aggcagtcgc cgccctctgt ccaccggcc agacagtcct gggcgtggcc 1260
agcacccgct tcacactgag gaatctgaac aacaactcga cggaggcact cgtgtacgag 1320
aacgccatct cgtcctcctt cgttagcagc actctcactc atgagctgcc gggcgagaac 1380
agcgaccgcc caacgagcag cgattacagc caccgtcttt cctccatcac gggcttccgg 1440
gctggagcca acgggaccgt gccgtgttc ggttggacca gcgcgacagt tgaccgtaac 1500
```

```
aacatcatcg agcagaacaa gatcacccag ttccctggcg ttaagtcaca cactcttaac   1560
aactgtcaag tggtgcgtgg caccgggttc accggcggcg actggcttcg cccaaacaac   1620
aatggcacct ttcggctgac cattaccagc ttctcgtccc agtcctaccg catcaggctt   1680
cgatacgcta ccagcgtcgg caacacctct cttgtcatct cgtcatccga cgcgggcatc   1740
tccagtacca caatccctct gacatccacc atcacgtcgc tcccgcagac cgttccgtac   1800
caggcgttcc gcgtcgtcga tctcccgatc actttcacta ctccgaccac tcagcgcaat   1860
tacaccttcg atttccgcct ccagaacccg agcaacgcta acgtattcat cgaccgcttc   1920
gagttcgtac caatcggcgg ctcactgtcc gagtacgaga cgaagcacca actggagaag   1980
gctcgcaagg cagtgaacga cctcttcact aacgagagca agaacgtgct caagaaggac   2040
acgacggatt acgacattga ccaggcggcg aatctggtgg aatgcgtgtc tgacgagtgc   2100
gccaacgcga agatgatact cctcgatgag gttaagtacg ccaaacagct cagcgaggct   2160
cgaaacctcc ttcttaatgg caactttgaa taccaagacc gtgacggcga aacccgtgg    2220
aagacctcgc caaacgtcac catccaggag aacaatccga tcttcaaggg ccgctacctt   2280
agcatgtccg gcgcaaacaa catcgaggcc accaacgaaa tcttcccaac ttatgtttat   2340
cagaagatcg acgagtcaaa gctaaagcca tacacccgct acaaggtgcg cggctttgtg   2400
ggcaactcca aggatctcga actgctggtc actcgttacg acgaggaggt ggacgcgata   2460
ctgaatgtct ccaatgacat accgcacgcg ccaccgccat tctgcggcga gttcgaccgc   2520
tgcaagccac actcctaccc tcctattaac ccggagtgcc accacgacgt cattaacaac   2580
atcgaaatct ctagcccatg ccagcacaac aagatggtgg acagcgcgga catcagttac   2640
cggcatagcc ggatcagtaa gaagcacggc atctgtcatg aatcacacca cttcgagttc   2700
cacattgaca ccggcaagat agacctggtc gagaacctgg gcatctgggt gatcttcaag   2760
atttgcagca cggatgccta cgcgactctc gacaattctg aggtcatcga ggagggccca   2820
ctcggagccg agtccctaga gcgcgttaag cggcgcgaga agaagtggaa gcaccacatg   2880
gagcacaagt gctcggagac gaagcacgca taccatgcag cgaagcaagc ggtggtggca   2940
ctcttcacca attccaagta cgataggctc aagttcgaaa ccaccatctc gaacatcctg   3000
ttcgcgtact acctcgttca gtcaatcccg tacgtttaca ataagtggct gcccggtgtg   3060
ccgggcatga actacgacat ctacaccgaa ctaaagaacc tgttcacggg cgcattcaac   3120
ctttacgatc agcggaacat catcaagaac ggcgatttca accgtggcct catgcactgg   3180
cacgctacgc cgcacgctcg ggtggagcag atcatcgaca accggtcagt cctggtcctg   3240
cccaactatg cggccaatgt ttctcaggag gtgtgccttg agcacaatcg cgggtatgtt   3300
ctccgggtga cagccaagaa ggagggccct ggcatcgggt acgtcacctt ctccgactgc   3360
gccaaccaca tcgagaaact tacgtttacg agctgcgact atggcaccaa cgtggtcccg   3420
tacgagcagt caaattaccc tacagacggc gtgccgtacg gcagcacgg ctgcaacatc    3480
gacggcgtcc cgtacgagca aagcggctac cgcaccgacg cgtgccctgc                3540
caccgcaccg acggcgtacc gtacgagcag agcggatacc cgaccgacgg cgtgccctgc   3600
gagcagcacg gttgtcacac cgacgggctg ccgcacatcc agcacggctg ccgcacggac   3660
cgctccagag acgagctgtt gggctacgtc accaagacta ttgatgtgtt cccgaacacg   3720
gacaaggtgc ggatcgacat tggcgagacc gagggaacct tcaaggtgga gtccgtggaa   3780
ctgatctgca tggaggagta g                                              3801
```

| SEQ ID NO: 52 | moltype = DNA length = 1914 |
|---|---|
| FEATURE | Location/Qualifiers |
| misc_feature | 1..1914 |
| | note = A synthetic coding sequence used for expression in plant cells, CR-BRE1a.TIC7042_1.nno_Mc:1 which encodes a protein having an N-terminal and C-terminal truncation relative to the TIC7042 protein. |
| source | 1..1914 |
| | mol_type = other DNA |
| | organism = synthetic construct |

SEQUENCE: 52
```
atgcagatca tcgagccgtc gagcgactcc ttcctctatt cccacaacaa ctacccgtac    60
gccactgacc cggacacgat cctcaagggc cggaactaca aggagtggct caacatgtgc   120
accgatacgc acgactcgcg ctcgcccgag ccgcgagca cggctcgcag cgcgatctcc    180
gtcgccatca ccattagcac caccatcctg ggactccttg gagttccctt cgcgtcccag   240
atcggtgcct tctacaactt cgtgctcaac accgtgtggc ctcagggaaa taaccagtgg   300
gaggagttca tgaggcacgt ggagaacctc atcaacgagc gcattgctga ctacgcgcgc   360
gacaaagcct tggccgagct gaccggcctg gcaacaacc tgaatctcta tcgggaggct    420
ttcgaggact ggcggcggaa cccgacctcc caggaagcca agactcgggt gatcgaccgc   480
tttcgtattc tcgacgcgct gttcgagact tacatgccct ccttcgcgct ccgcaacttt   540
gaggttcagc tcctgactgt gtacgcctcg gctgcaaaca tacacctgtt cctgctgcgg   600
gacagctcga tctacggttt ggactggggc ctgtcacaga ccaacgtgaa cgagaactac   660
aaccggcaga tccgccacgc cgccacctat gcaaaccact gcaccacttg gtatcagaca   720
gggctccgac gcctccaggg cactaacgca acgtcatggg ttgcatacaa ccggtttcgg   780
cgggagatga cactcaccgt gttggacatc tgctcgctgt tctccaacta cgactaccgg   840
tcgtaccgaa ctgaggtgaa gggcgagttg accaggaaaa tctacacaga ccctgtcggc   900
cggaactggc agaacgtcgc gccttcattc gcggagattg agaacctgac cattcgcgct   960
ccgcgtaccg tcacttggct caactccact cggatcttca cagggacgct gaccggctgg  1020
tccgggtcca accgctactg ggccgcccac atgcagaact tcagcgagac aaactctggc  1080
aacatcggat tcgatggccc acagtatggg tccacggtcg ggacgataca ccggaccgac  1140
gactacgaca tggtgaaccg ggacatctac accataacga gccaggcagt cgccgccctc  1200
tggcccaccg gccagacagt cctgggcgtg gcgagcaccc gcttcacact gaggaatctg  1260
aacaacaact cgacggaggc actcgtgtac gagaacgcca tctcgtcctc cttcgttagc  1320
agcactctca ctcatgagct gccggggcag aacaccgaca gcgattac                1380
agccaccgtc tttcctccat cacgggcttc cgggctggag ccaacgggac cgtgcccgtg  1440
ttcgttgga ccagcgcgac agttgaccgt aacaacatca tcgagcagaa caagatcacc   1500
cagttccctg gcgttaagtc acacactctt aacaactgtc aagtggtgcg tggcaccggg  1560
ttcaccggcg cgactggct tcgccccaaac aacaatggca ccttcggct gaccattacc   1620
agcttctcgt cccagtccta ccgcatcagg cttcgatacg ctaccagcgt cggcaacacc  1680
```

```
tctcttgtca tctcgtcatc cgacgcgggc atctccagta ccacaatccc tctgacatcc   1740
accatcacgt cgctcccgca gaccgttccg taccaggcgt tccgcgtcgt cgatctcccg   1800
atcactttca ctactccgac cactcagcgc aattacacct tcgatttccg cctccagaac   1860
ccgagcaacg ctaacgtatt catcgaccgc ttcgagttcg taccaatcgg ctag         1914
```

| | | |
|---|---|---|
| SEQ ID NO: 53 | moltype = AA  length = 637 | |
| FEATURE | Location/Qualifiers | |
| REGION | 1..637 | |
| | note = The amino acid sequence of the CR-BRE1a.TIC7042_1.nno_Mc:1 protein, comprising amino acids 11 through 646 of TIC70. | |
| source | 1..637 | |
| | mol_type = protein | |
| | organism = synthetic construct | |

SEQUENCE: 53

```
MQIIEPSSDS FLYSHNNYPY ATDPDTILKG RNYKEWLNMC TDTDDSRSPE AASTARSAIS    60
VAITISTTIL GLLGVPFASQ IGAFYNFVLN TVWPQGNNQW EEFMRHVENL INERIADYAR   120
DKALAELTGL GNNLNLYREA FEDWRRNPTS QEAKTRVIDR FRILDGLFET YMPSFAVRNF   180
EVQLLTVYAS AANIHLFLLR DSSIYGLDWG LSQTNVNENY NRQIRHAATY ANHCTTWYQT   240
GLQRLQGTNA TSWVAYNRFR REMTLTVLDI CSLFSNYDYR SYPTEVKGEL TREIYTDPVG   300
RNWQNVAPSF AEIENLTIRA PRTVTWLNST RIFTGTLTGW SGSNRYWAAH MQNFSETNSG   360
NIGFDGPQYG STVGTIHRTD DYDMVNRDIY TITSQAVAAL WPTGQTVLGV ASTRFTLRNL   420
NNNSTEALVY ENAISSSFVS STLTHELPGE NSDRPTSSDY SHRLSSITGF RAGANGTVPV   480
FGWTSATVDR NNIIEQNKIT QFPGVKSHTL NNCQVVRGTG FTGGDWLRPN NNGTFRLTIT   540
SFSSQSYRIR LRYATSVGNT SLVISSSDAG ISSTTIPLTS TITSLPQTVP YQAFRVVDLP   600
ITFTTPTTQR NYTFDFRLQN PSNANVFIDR FEFVPIG                           637
```

| | | |
|---|---|---|
| SEQ ID NO: 54 | moltype = DNA  length = 1974 | |
| FEATURE | Location/Qualifiers | |
| misc_feature | 1..1974 | |
| | note = A synthetic coding sequence used for expression in plant cells, CR-BRE1a.TIC7042_2.nno_Mc:1 which encodes a protein having an N-terminal and C-terminal truncation relative to the TIC7042 protein. | |
| source | 1..1974 | |
| | mol_type = other DNA | |
| | organism = synthetic construct | |

SEQUENCE: 54

```
atgcagatca tcgagccgtc gagcgactcc ttcctctatt cccacaacaa ctacccgtac     60
gccactgacc cggacacgat cctcaagggc cggaactaca aggagtggct caacatgtgc   120
accgatacgg acgactcgcg ctcgcccgag gccgcgagca cggctcgcag cgcgatctcc   180
gtcgccatca ccattagcac caccatcctg ggactccttg gagttccctt cgcgtcccag   240
atcggtgcct tctacaactt cgtgctcaac accgtgtggc ctcagggaaa taaccagtgg   300
gaggagttca tgaggcacgt ggagaacctc atcaacgagc gcattgctga ctacgcgcgc   360
gacaaagcct tggccgagct gaccggcctg ggcaacaacc tgaatctcta tcgggaggct   420
ttcgaggact ggcggcggaa cccgacctcc caggaagcca agactcgggt gatcgaccgc   480
tttcgtattc tcgacgggct gttcgagact tacatgccct cctttcgcgt ccgcaacttt   540
gaggttcagc tcctgactgt gtacgcctcg gctgcaaaca tacacctgtt cctgctgcgg   600
gacagctcga tctacggttt ggactggggc ctgtcacaga ccaacgtgaa cgagaactac   660
aaccggcaga tccgccacgc cgccacctat gcaaaccact gcaccacttg gtatcagaca   720
gggctccagc gcctccaggg cactaacgca acgtcatggg ttgcatacaa ccggttttcgg   780
cgggagatga cactcaccgt gttggacatc tgctcgctgt tctccaacta cgactaccgg   840
tcgtacccga ctgaggtgaa gggcgagttg accaggaaaa tctacacaga ccctgtcggc   900
cggaactggc agaacgtcgc gccttcattc gcggagattg agaacctgac cattcgcgct   960
ccgcgtaccg tcacttggct caactccact cggatcttca cagggacgct gaccggctgg  1020
tccgggtcca accgctactg ggccgcccac atgcagaact tcagcgagac aaactctggc  1080
aacatcggat tcgatggccc acagtatggg tccacggtcg ggacgataca ccggaccgac  1140
gactacgaca tggtgaaccg ggacatctac accataacga gccaggcagt cgccgccctc  1200
tggcccaccg gcagagagt cctgggcgtg gcgagcaccc gcttcacact gaggaatctg  1260
aacaacaact cgacggaggc actcgtgtac gagaacgcca tctcgtcctc cttcgttagc  1320
agcactctca ctcatgagct gccgggcgag aacagcgacc gccaacgag cagcgattac  1380
agccaccgtc tttcctccat cacgggcttc cgggctggag ccaacgggac cgtgccgtg  1440
ttcggttgga ccagcgcgac agttgaccgt aacaacatca tcgagcagaa caagatcacc  1500
cagttccctg gcgttaagtc acacactctt aacaactgtc aagtggtgcg tggcaccggca  1560
ttcaccggcg gcgactggct tcgcccaaac aacaatggca cctttcggct gaccattacc  1620
agcttctcgt cccagtccta ccgcatcagg cttcgatacg ctaccagcgt cggcaacacc  1680
tctcttgtca tctcgtcatc cgacgcgggc atctccagta ccacaatccc tctgacatcc  1740
accatcacgt cgctcccgca gaccgttccg taccaggcgt tccgcgtcgt cgatctcccg  1800
atcactttca ctactccgac cactcagcgc aattacacct tcgatttccg cctccagaac  1860
ccgagcaacg ctaacgtatt catcgaccgc ttcgagttcg taccaatcgg cggctcactg  1920
tccgagtacg agacgaagca ccaactggag aaggctcgca aggcagtgaa ctag         1974
```

| | | |
|---|---|---|
| SEQ ID NO: 55 | moltype = AA  length = 657 | |
| FEATURE | Location/Qualifiers | |
| REGION | 1..657 | |
| | note = The amino acid sequence of the CR-BRE1a.TIC7042_2.nno_Mc:1 protein, comprising amino acids 11 through 665 of TIC7042. | |
| source | 1..657 | |

```
                          mol_type = protein
                          organism = synthetic construct
SEQUENCE: 55
MQIIEPSSDS FLYSHNNYPY ATDPDTILKG RNYKEWLNMC TDTDDSRSPE AASTARSAIS    60
VAITISTTIL GLLGVPFASQ IGAFYNFVLN TVWPQGNNQW EEFMRHVENL INERIADYAR   120
DKALAELTGL GNNLNLYREA FEDWRRNPTS QEAKTRVIDR FRILDGLFET YMPSFAVRNF   180
EVQLLTVYAS AANIHLFLLR DSSIYGLDWG LSQTNVNENY NRQIRHAATY ANHCTTWYQT   240
GLQRLQGTNA TSWVAYNRFR REMTLTVLDI CSLFSNYDYR SYPTEVKGEL TREIYTDPVG   300
RNWQNVAPSF AEIENLTIRA PRTVTWLNST RIFTGTLTGW SGSNRYWAAH MQNFSETNSG   360
NIGFDGPQYG STVGTIHRTD DYDMVNRDIY TITSQAVAAL WPTGQTVLGV ASTRFTLRNL   420
NNNSTEALVY ENAISSSFVS STLTHELPGE NSDRPTSSDY SHRLSSITGF RAGANGTVPV   480
FGWTSATVDR NNIIEQNKIT QFPGVKSHTL NNCQVVRGTG FTGGDWLRPN NNGTFRLTIT   540
SFSSQSYRIR LRYATSVGNT SLVISSSDAG ISSTTIPLTS TITSLPQTVP YQAFRVVDLP   600
ITFTTPTTQR NYTFDFRLQN PSNANVFIDR FEFVPIGGSL SEYETKHQLE KARKAVN     657

SEQ ID NO: 56             moltype = DNA   length = 3813
FEATURE                   Location/Qualifiers
misc_feature              1..3813
                          note = A synthetic coding sequence used for expression in
                          plant cells, CR-BRE1a.TIC7381_1.nno_Mc:1 which encodes a
                          TIC7381 protein wherein an additional alanine codon is
                          inserted immediately following the initiating methionine
                          codon.
source                    1..3813
                          mol_type = other DNA
                          organism = synthetic construct
SEQUENCE: 56
atggctaacc agaaccagaa caagaacgag ctacagataa tcgagccgtc ctcggattcc     60
ttgctgtact cgcacaacaa ctacccgtac gccaccgatc cgaacacggt gctagagggc    120
cgcaactaca aggagtggct gaataagtgc acagacaact acaccgatgc actgcaaggc    180
ccagaggcaa cggctatcag caaggggtgc gtgtcggccg ctatctctat cagcaccaaa    240
gtcttgagcc ttctgggagt gcccttcgca gctcagattg gcaattgtg acgtttatt     300
ctgaacgctc tttggccctc ggacaacacc cagtgggagg agttcatgcg ccatgtcgag    360
gagctcatca accagcgtat cgccgactac gcgcggagta aggcgctcgc cgagctcacg    420
ggcctgggca caacctcga tctgtacatc gaagctcttg aggactggaa gtgcaacccg     480
acctctcaac aagccaagga ccgggtgaag gaccgcttcc gcatcgccga cggcctcttc    540
gaagcgtaca tgcctagctt ccgcgtgagc ggctatgaag tgccattgct caccgtatat    600
gcggcggcgg ccaacctgca cctcctcctc tcccgcgact gctctatcta cggcattcag    660
tggggttttct cccagaccaa tgtcaacgag aactataatc gacagatccg tcacaccgcc    720
gagtacgcga accactgcac gacatgtac cagacgggcc tggagcgact gcgcggcacg     780
aacgcctcaa gctgggtgcc gtacaaccgt tcaggagag atgactct accgtgctc       840
gacatctgca gtctgttctc caactatgac tacaggagtt accggcaga ggtgcgggct    900
gagctgacca gggagatata cacggacccg gtggtcagca cctctctgtg gtgaacaac    960
gcgccgtcct tcggcgaaat cgagaatctg gcaatccgag cgccacgcac cgtgacatgg   1020
ctcaattcga cgcgtattag cactggcaca ctccaaggtt ggtctgggtc caacaggtac   1080
tgggccgccc acatgcagaa cttctcggag actaactccg gcaacatagg cttcgacggc   1140
ccgctgtacg ggtccactgt gggtacaatc attgcgatg acaattacga gatggtcaac   1200
cgggacattt acaccatcac ttcggaggcg gttgcggctt gtggcccac gggccagatt    1260
gtgctggggcg tggcttccgc aagattcacc cttgaaacc tcaacaacaa cctgaccag    1320
gcgctggtct acgagaaccc gatatcaagc agtttcaacc ggtcaactct cacacgcgag   1380
ttgccgggcg agaacagcga caggcccacc tcttcggact actcccacg tctcactagc   1440
atcactgcgt tccgcgcagg cagtaacggt acgattcctg tgttcggctg gaccagtatc   1500
tccgtcaaca gggacaacat actggagcgg aacaagatca cccagttccc tggcgttaag   1560
tcccataccc tgaacaattg ccaggtcgtc cgcggtacag gctttaccgg cggcgactgg   1620
cttcggccta acaacaacgg gtcgttccga ttgactatca cctcgttcag ctcacagagt   1680
tacagaatca ggctgcggta cgcgtccgca gcgaatacct ccctgcgaat tcgtcttcg     1740
gcggccggga tctcgtcaac aaccgtccca ctcgcctcca cgatcactag cctcccgcag   1800
acagccgtcc catacgaggc gttccggggtg atcgacctgc caatcacgtt caccaccgcg   1860
acgcagtcta actacacttt cgacttcgtc tccagaatc cttccaacgc caacgtgttc    1920
atcgaccgct tcgagttttgt cccgattgga ggttcgctct cagagtacga gacgaagcac   1980
cagctggaga aggcacgtaa ggcggtgaac gatcgtgttta ctaacgagtc aaagaacgtt   2040
ctgaagaagt atacgaccga ctacgacatt gaccaggccg ccaacctggt ggagtgtgtg   2100
tcggacgagt gcgctaacgc aaagatgatc ctcctagacg aggtgaagta tgcgaagcaa   2160
ctgtcagagg cgcggaacct gctcctgaac ggtaatttcg aataccagga tagagacggc   2220
gagaaccgt ggaagacctc acctaacgtt actatccagg agaacaaccc aatcttcaag   2280
ggccgctacc tttccatgtc cggcgccaac tacatcgagg cgaccaacga cacttttccg   2340
acctacgctt atcaaaagat cgacgaggcc aagctgaagc cttacactcg ctacaaggta   2400
cgtggtttcg tgggcaattc caaggatctg gagctgctga tcaaaaggta cgacgaggaa   2460
gtggacgcta ttctcaacgt cccgaacgac attccgcacg ccaacgca attctgcggc   2520
ggattcgacc gttgcaagcc gcactcttac atcccgatga atcccgaatg ccaccacgac   2580
gtgatcaata acatcgagat cagctcgcca tgtcagcata caagatgct cgacaacgcg   2640
gacatctcca gccgtcactc cgaactcggc aagaagcacg ggatctgtca cgagtcgcac   2700
cacttcgagt tccacatcga cactggcaag atccacctca cgagaacct gggcatctgg   2760
gtgatcgtca agatctgctc taccgatggc tacgccaatc tgaggtgatc                2820
gaagagggac cgcttggtgc ggagtccctc gagcgcgtca agcgacgcga aagaagtga   2880
aagcaccaca tggagcacaa atgttccgag acgaaacttg cgtaccatgc cgccaagcag   2940
gccctttgttg ggctgttcac gaacaccaag tacgataggc tcaagttcga gccaccatc   3000
tcgaacattc tgtttgccga ctaccttgtg cagtcaattc catacgtttta aacaaatgg   3060
ctgccagatg tcccgggtat gaactatgac atctacaccg agcttaagaa cctcttcact   3120
```

```
ggcgccttca acctgtacga ccagcgtaac atcataaaga acggcgactt caaccgtggc   3180
ttgatgcact ggcacgccac gccgcacgcc cgtgtcgagc agatcgacaa ccgctcggtt   3240
ctcgtgctcc ctaactacgc cgctaacgtc tcgcaggagg tctgcctcga gcataaccgc   3300
ggctacgtgt tgcgggtaac tgccaagaag gagggccctg gcattggata cgttaccttc   3360
tcggactgcg cgaacaacat cgagaaactg accttcacgt catgtgacta tggaaccaac   3420
gaggtcacct acgagcagtc caattacccg accgatgcg tcccttacga gcaaacggg    3480
tgccacactg acggcgtgcc gtacgagcag catgggtgcc acactgacgg cgtcccttac   3540
gagcagcacg gctgccacac ggacggcgta ccgtacaagc agcatggctg ccgcaccgac   3600
ggcgttcctt acaagcagca cggctgccgc accgacggag tccgctacaa gcagcatggg   3660
tgtcgcaccg accggtcccg cgacgagcag ctggattacg taacgaagac gatcgagtc    3720
ttcccggaca cggacaaggt caggatcgac attggcgaaa cggagggaac cttcaaagtc   3780
gagtcagtgg agcttatctt catggaggag tga                                3813
```

```
SEQ ID NO: 57           moltype = AA  length = 1270
FEATURE                 Location/Qualifiers
REGION                  1..1270
                        note = The amino acid sequence of
                        CR-BRE1a.TIC7381_1.nno_Mc:1 wherein an additional alanine
                        amino acid is inserted immediately following the
                        initiating methionine relative to the TIC7381 protein
                        sequence.
source                  1..1270
                        mol_type = protein
                        organism = synthetic construct
SEQUENCE: 57
MANQNQNKNE LQIIEPSSDS LLYSHNNYPY ATDPNTVLEG RNYKEWLNKC TDNYTDALQG    60
PEATAISKGA VSAAISISTK VLSLLGVPFA AQIGQLWTFI LNALWPSDNT QWEEFMRHVE   120
ELINQRIADY ARSKALAELT GLGNNLDLYI EALEDWKRNP TSQQAKDRVK DRFRIADGLF   180
EAYMPSFRVS GYEVPLLTVY AAAANLHLLL LRDCSIYGIQ WGFSQTNVNE NYNRQIRHTA   240
EYANHCTTWY QTGLERLRGT NASSWVPYNR FRREMTLTVL DICSLFSNYD YRSYPAEVRA   300
ELTREIYTDP VVSTSLWVNN APSFGEIENL AIRAPRTVTW LNSTRISTGT LQGWSGSNRY   360
WAAHMQNFSE TNSGNIGFDG PLYGSTVGTI IRDDNYEMVN RDIYTITSEA VAALWPTGQI   420
VLGVASARFT LRLNNNLTQ ALVYENPISS SFNRSTLTRE LPGENSDRPT SSDYSHRLTS    480
ITAFRAGSNG TIPVFGWTSI SVNRDNILER NKITQFPGVK SHTLNNCQVV RGTGFTGGDW   540
LRPNNNGSFR LTITSFSSQS YRIRLRYASA ANTSLRISSS AAGISSTTVP LASTITSLPQ   600
TAVPYEAFRV IDLPITFTTA TQSNYTFDFV LQNPSNANVF IDRFEFVPIG GSLSEYETKH   660
QLEKARKAVN DLFTNESKNV LKKYTTDYDI DQAANLVECV SDECANAKMI LLDEVKYAKQ   720
LSEARNLLLN GNFEYQDRDG ENPWKTSPNV TIQENNPIFK GRYLSMSGAN YIEATNDTFP   780
TYAYQKIDEA KLKPYTRYKV RGFVGNSKDL ELLIKRYDEE VDAILNVPND IPHAPTPFCG   840
GFDRCKPHSY IPMNPECHHD VINNIEISSP CQHNKMLDNA DISSRHSELG KKHGICHESH   900
HFEFHIDTGK IHLNENLGIW VIFKICSTDG YATLDNLEVI EEGPLGAESL ERVKRREKKW   960
KHHMEHKCSE TKLAYHAAKQ ALVGLFTNTK YDRLKFETTI SNILFADYLV QSIPYVYNKW  1020
LPDVPGMNYD IYTELKNLFT GAFNLYDQRN IIKNGDFNRG LMHWHATPHA RVEQIDNRSV  1080
LVLPNYAANV SQEVCLEHNR GYVLRVTAKK EGPGIGYVTF SDCANNIEKL TFTSCDYGTN  1140
EVTYEQSNYP TDGVPYEQHG CHTDGVPYEQ HGCHTDGVPY EQHGCHTDGV PYKQHGCRTD  1200
GVPYKQHGCR TDGVPYKQHG CRTDSRDEQ LDYVTKTIDV FPDTDKVRID IGETEGTFKV   1260
ESVELIFMEE                                                         1270
```

```
SEQ ID NO: 58           moltype = DNA  length = 3744
FEATURE                 Location/Qualifiers
misc_feature            1..3744
                        note = A synthetic coding sequence used for expression in
                        plant cells, CR-BRE1a.TIC7382_1.nno_Mc:1 which encodes a
                        TIC7382 protein wherein an additional alanine codon is
                        inserted immediately following the initiating methionine
                        codon.
source                  1..3744
                        mol_type = other DNA
                        organism = synthetic construct
SEQUENCE: 58
atggctaacc agaaccagaa ccagaacaag aacgagatgc agatcatcga gccctcctcc    60
gactcattcc tctactcgca caacaactac ccctacgcga cggaccccaa cactgttctc   120
gaagggcgga actacaagga gtggctaaac aagtgcacta caattacac cgacgcgctc    180
cagtctccgg aagccacagc catttcgaag ggggcggtc agcatcagc                240
accaaggtgc tcggcctcct cggcgtgccg ttcggcc agataggaca gctctggaca     300
ttcattctga acgccctgtg gccgtccgac aacacccagt gggaggagtt catgcggcac   360
gtcgaggagc tcatcaacca gcggatcgca gactatgccc gtaacaaggc cctggccgag   420
ctgacgggac tcggcaacaa cctcgacctc tacatcgagg ccctggatga ctggaagagg   480
aacccacca gccaggaggc caagactcgc gtcatcgacc gcttccgcat cgtcgacggg    540
ctgttcgagg cctacattcc gagcttcgc gtgagcggct atcaagttca gctgctcact    600
gtctacgccg ctgcagcaaa cctccacctc ctgctgctgc gcgactccac gatctacgga   660
atcgactggg gcctttccca gactaacgtc aacgataact acaaccggca gattcgtctc   720
accgcgacgt acgctaacca ctgtacaacg tggtaccaga caggactgga gcggctccgc   780
gaacgc cgtctttcctg ggtgacctac aaccgttcg ttggagagat gactctcaca      840
gtcttggaca tctgttcctt gttcagcaac tacgactatc gcagctaccc ggccgaggtt   900
cgcggcgaga ttacgaggga aatctacaca gaccctgtcg gcgtcggttg ggttgacagc   960
gcggccttct tcgcgagat cgagaacctg gcgatccggg cgccacggac tgtgacctgg  1020
ctgaactcca cccggatctc caccggcacc ttaagcggct ggtcgggctc taaccggtac  1080
tgggcggccc acatgcagaa tttctccgag acaaactcgg gtaacatcgg cttcgatggg  1140
```

```
ccgctgtacg ggagcacagt gggcaccatc caccgcactg atgactacga catgggcaac   1200
cgggacatct acacgataac gtcgcaggcc gttctcggtc tgtggcccac gggccagcgg   1260
gtcctgggag tcgcatctgc gcgtttcacc ctcaggaacc tattcaataa cctgacccag   1320
gtgctggtat acgagaatcc tattagctcc aacttcggct cttcaacgct aacccacgag   1380
ttatccggcg agaacagcga taggcccacc agcagcgatt actcacatcg actcacaagc   1440
atcacgggat tccgcgcagg agcaaatggt accgttcccg tctttgggtg gaccagcgcc   1500
acagtcgacc ggaacaacat catcgagcgc aacaagatca cgcagttccc aggcgtcaaa   1560
tcgcacacgc taaacaactg ccaggtggtg aggggaaccg gtttcaccgg aggtgactgg   1620
ttaagaccaa ataacaacgg cacttttccgc ctcactatta cgagcttctc ctcccaaagt   1680
taccgcatcc gccttcgcta cgccacgtca gtggggaaca cctcgctggt gatatcctcc   1740
tcagacgccg ggatcagcag caccacgata ccactaacat ccacaataac ctcattgccg   1800
cagacggtcc cgtatcaggc cttcagagtg gtggaccttc ctattacgtt cacgacgccc   1860
acgacccagc gcaactacac attcgatttc cggttgcaga cccgagtaa cgccaatgtc   1920
ttcatcgatc gtttcgagtt cgtcccgata ggcggctccc tttcggagta cgaaacgaag   1980
caccagttgg agaaggctcg caaggcggtc aacgatctct tcaccaacga gtcgaagaac   2040
gtcctgaaga aggagacgac cgattacgac atcgaccaag ctgctaactt ggtggagtgc   2100
attagtgacg agtgcgcgaa cgccaagatg atccttctcg acgaagtgaa gtacgccaag   2160
cagctctccg aggcccgcaa cctgcttctg aacgggaact tcgacaacct tgatcgcaat   2220
ggcgagaacc cgtggaagac cagccctaac gtgactattc aggagaacaa tcctatcttc   2280
aaagggaggt acctaagtat gagtggagcc aacaacatcg aggcgactaa cgagatcttc   2340
ccaacatatg tgtaccagaa gatcgacgaa gccaagctca agccttacac gcggtacaag   2400
gtccgcgggt ttgtgggcag ttccaaggac ttagagcttc tggtgactcg atacgacgag   2460
gaggttgatg ccatactgaa cgttctgaac gatatcccgc acgcaccacc accgttctgc   2520
ggcggcttcg acaggtgcaa accgcactcc tacccgccga tgaacccgga gtgccaccac   2580
gacgtgataa caacatcga gatctccagt ccgtgccagc acaacaagat gctggacaac   2640
gccgatatct tcagccgcca cagtgagctg ggcaagaagc acgggatctg ccacgaatcc   2700
caccacttcg agttccacat cgacacaggg aagatcgacc tcaacgagaa cctcggcata   2760
tgggtcatct tcaagatctg ctcgaccgat ggctacgcga cccttgacaa tcttgaggtg   2820
atcgaggagg gaccgctcgg cgctgagagt ctcgagcggg ttaagaggag ggaaaagaaa   2880
tggaagcacc acatggagca taagtgctcc gagaccaaca ttgcctacca cgccgccaac   2940
caggcactcg tgggcctctt caccaacacc aagtatgacc ggcttaagtt cgagacaacg   3000
atcagcaaca tcctattcgc ggactactta gtccagagca tccctacgt ttacaacaaa   3060
tggctgcctg acgtgcccgg tatgaactac gacatctaca ccgagctcaa gaacctcttc   3120
accggcgcat tcaacctgta cgaccagcgg aacattatca agaacggcga cttcaaccga   3180
ggactgatgc actggcacgc gactccgcac gcccggggttg aacagatcga caacaggtcc   3240
gtgctcgtgc tcccgaacta cgcggccaac gtgtctcagg aggtttgcct cgagcacaac   3300
cgcggctacg tcttgcgcgt cacagccaag aaggagggcc cggggatcgg ttatgtcacg   3360
ttcagcgact gcgccaacaa catcgagaag ctcacgttca cgtcgtgcga ttatggtacc   3420
aacgaggtgc cgtacgagca gtcaggctac ggcacgaacg aggttccgta cgagcagagc   3480
ggctacggaa cgaacgaggt gccgtacgag cagtccgggt accggacgga cggcgtgccc   3540
tacaagcagc atggctgccg gaccgacggc gtgccctacg agcagagcgg ctgccgcacg   3600
gaccggagca gggatgagca gctggactac gtgaccaaga cgatcgacgt cttcccggac   3660
acggacaagg tccggattga catcggcgag actgagggca ccttcaaggt cgaaagcgtg   3720
gagctattct gcatggagga gtag                                         3744
```

| SEQ ID NO: 59 | | moltype = AA   length = 1247 |
|---|---|---|
| FEATURE | | Location/Qualifiers |
| REGION | | 1..1247 |
| | | note = The amino acid sequence of CR-BRE1a.TIC7382_1.nno_Mc:1 wherein an additional alanine amino acid is inserted immediately following the initiating methionine relative to the TIC7381 protein sequence. |
| source | | 1..1247 |
| | | mol_type = protein |
| | | organism = synthetic construct |

```
SEQUENCE: 59
MANQNQNQNK NEMQIIEPSS DSFLYSHNNY PYATDPNTVL EGRNYKEWLN KCTNNYTDAL    60
QSPEATAISK GAVSAAISIS TKVLGLLGVP FAAQIGQLWT FILNALWPSD NTQWEEFMRH   120
VEELINQRIA DYARNKALAE LTGLGNNLDL YIEALDDWKR NPTSQEAKTR VIDRFRIVDG   180
LFEAYIPSFA VSGYQVQLLT VYAAAANLHL LLLRDSTIYG IDWGLSQTNV NDNYNRQIRL   240
TATYANHCTT WYQTGLERLR GSNASSWVTY NRFRREMTLT VLDICSLFSN YDYRSYPAEV   300
RGEITREIYT DPVGVGWVDS APSFGEIENL AIRAPRTVTW LNSTRISTGT LSGWSGSNRY   360
WAAHMQNFSE TNSGNIGFDG PLYGSTVGTI HRTDDYDMGN RDIYTITSQA VLGLWPTGQR   420
VLGVASARFT LRNLFNNLTQ VLVYENPISS NFGSSTLHE  LSGENSDRPT SSDYSHRLTS   480
ITGFRAGANG TVPVFGWTSA TVDRNNIIER NKITQFPGVK SHTLNNCQVV RGTGFTGGDW   540
LRPNNNGTFR LTITSFSSQS YRIRLRYATS VGNTSLVISS SDAGISSTTI PLTSTITSLP   600
QTVPYQAFRV VDLPITFTTP TTQRNYTFDF RLQNPSNANV FIDRFEFVPI GGSLSEYETK   660
HQLEKARKAV NDLFTNESKN VLKKETTDYD IDQAANLVEC ISDECANAKM ILLDEVKYAK   720
QLSEARNLLL NGNFDNLDRN GENPWKTSPN VTIQENNPIF KGRYLSMSGA NNIEATNEIF   780
PTYVYQKIDE AKLKPYTRYK VRGFVGSSKD LELLVTRYDE EVDAILNVLN DIPHAPPPFC   840
GGFDRCKPHS YPPMNPECHH DVINNIEISS PCQHNKMLDN ADIFSRHSEL GKKHGICHES   900
HHFEFHIDTG KIDLNENLGI WVIFKICSTD GYATLDNLEV IEEGPLGAES LERVKRREKK   960
WKHHMEHKCS ETKLAYHAAK QALVGLFTNT KYDRLKFETT ISNILFADYL VQSIPYVYNK  1020
WLPDVPGMNY DIYTELKNLF TGAFNLYDQR NIIKNGDFNR GLMHWHATPH ARVEQIDNRS  1080
VLVLPNYAAN VSQEVCLEHN RGYVLRVTAK KEGPGIGYVT FSDCANNIEK LTFTSCDYGT  1140
NEVPYEQSGY GTNEVPYEQS GYGTNEVPYE QSGYRTDGVP YKQHGCRTDG VPYEQSGCRT  1200
DRSRDEQLDY VTKTIDVFPD TDKVRIDIGE TEGTFKVESV ELFCMEE              1247
```

```
SEQ ID NO: 60            moltype = DNA  length = 1983
FEATURE                  Location/Qualifiers
misc_feature             1..1983
                         note = A synthetic coding sequence used for expression in
                         plant cells, CR-BRE1a.TIC7382_2.nno_Mc:1 which encodes a
                         protein comprising a C-terminal truncation relative to the
                         TIC7382 protein and wherein an alanine codon is inserted
                         after the initiating methionine.
source                   1..1983
                         mol_type = other DNA
                         organism = synthetic construct
SEQUENCE: 60
atggctaacc agaaccagaa ccagaacaag aacgagatgc agatcatcga gccctcctcc   60
gactcattcc tctactcgca caacaactac ccctacgcga cggaccccaa cactgttctc  120
gaagggcgga actacaagga gtggctaaac aagtgcacta caattacacc gacgcgctc   180
cagtctccgg aagccacagc catttcgaag ggggcggtct cggcggcgat cagcatcagc  240
accaaggtgt tcggcctcct cggcgtgccg ttcgcggctc agataggaca gctctggaca  300
ttcattctga acgcccgtgt gccgtccgac aacaccgagt gggaggagtt catgcggcac  360
gtcgaggagc tcatcaacca gcggatcgca gactatgccc gtaacaaggc cctggccgag  420
ctgacgggac tcggcaacaa cctcgacctc tacatcgagg ccctggatga ctggaagagg  480
aaccccacca gccaggaggc caagactcgc gtcatcgacc gcttccgcat cgtcgacggg  540
ctgttcgagg cctacattcc gagcttcgcc gtgagcggct atcaagttca gtgctcact   600
gtctacgccg ctgcagcaaa cctccacctc ctgctgctgc gcgactccac gatctacgga  660
atcgactggg cctttccca gactaacgtc aacgataact acaaccggca gattcgtctc   720
accgcgacgt acgctaacca ctgtacaacg tggtaccaga caggactgga gcggctccgc  780
gggagcaacg cgtcttcctg ggtgacctac aaccgttttcc ggagagagat gactctcaca  840
gtcttggaca tctgttcctt gttcagcaac tacgactatc gcagctaccc ggccgaggtt  900
cgcggcgaga ttacgaggga aatctacaca gaccctgtcg cgctcggttg ggttgacagc  960
gcgccttctt tcggcgagat cgagaactg gcgatccggg cgccacggac tgtgacctgg 1020
ctgaactcca cccggatctc caccggcacc ttaagcggct ggtcgggctc taaccggtac 1080
tgggcggccc acatgcagaa tttctccgag acaaactcgg gtaacatcgg cttcgatggg 1140
ccgctgtacg ggagcacagt gggcaccatc caccgcactg atgactacga catgggcaac 1200
cgggacatct acacgataac gtcgcaggcc gttctcggtc tgtggcccac gggccagcgg 1260
gtcctgggag tcgcatctgc gcgtttcacc ctcaggaacc tattcaataa cctgacccag 1320
gtgctggtat acgagaatcc tattagctcc aacttcggct cttcaacgct aacccacgag 1380
ttatccggcg agaacagcga taggcccacc agcagcgatt actcacatcg actcacaagc 1440
atcacgggat tccgcgcagg agcaaatggt accgttcccg tctttgggtg gaccagcgcc 1500
acagtcgacc ggaacaacat catcgagcgc aacaagatca cgcagttccc aggcgtcaaa 1560
tcgcacacgc taacaactg ccaggtggtg aggagaccga gtttcaccgg aggtgactgg 1620
ttaagaccaa ataacaacgg cactttccgc ctcactatta cgagcttctc ctcccaaagt 1680
taccgcatcc gccttcgcta cgccacgtca gtggggaaca cctcgctggt gatatcctcc 1740
tcagacgccg gatcagcag caccacgata ccactaacat ccacaataac ctcattgccg 1800
cagacggtcc cgtatcaggc cttcagagtg gtggacctc ctattacgtt cacgacgccc 1860
acgacccagc gcaactacac attcgatttc cggttgcaga acccgagtaa cgccaatgtc 1920
ttcatcgatc gtttcgagtt cgtcccgata ggcggctccc tttcggagta cgaaacgaag 1980
tga                                                               1983

SEQ ID NO: 61            moltype = AA  length = 660
FEATURE                  Location/Qualifiers
REGION                   1..660
                         note = The amino acid sequence of
                         CR-BRE1a.TIC7382_2.nno_Mc:1 comprising a C-terminal
                         deletion, an additional alanine amino acid, and comprises
                         amino acids 1 through 659 of TIC7382.
source                   1..660
                         mol_type = protein
                         organism = synthetic construct
SEQUENCE: 61
MANQNQNQNK NEMQIIEPSS DSFLYSHNNY PYATDPNTVL EGRNYKEWLN KCTNNYTDAL   60
QSPEATAISK GAVSAAISIS TKVLGLLGVP FAAQIGQLWT FILNALWPSD NTQWEEFMRH  120
VEELINQRIA DYARNKALAE LTGLGNNLDL YIEALDDWKR NPTSQEAKTR VIDRFRIVDG  180
LFEAYIPSFA VSGYQVQLLT VYAAAANLHL LLLRDSTIYG IDWGLSQTNV NDNYNRQIRL  240
TATYANHCTT WYQTGLERLR GSNASSWVTY NRFRREMTLT VLDICSLFSN YDYRSYPAEV  300
RGEITREIYT DPVGVGWVDS APSFGEIENL AIRAPRTVTW LNSTRISTGT LSGWSGSNRY  360
WAAHMQNFSE TNSGNIGFDG PLYGSTVGTI HRTDDYDMGN RDIYTITSQA VLGLWPTGQR  420
VLGVASARFT LRNLFNNLTQ VLVYENPISS NFGSSTLTHE LSGENSDRPT SSDYSHRLTS  480
ITGFRAGANG TVPVFGWTSA TVDRNNIIER NKITQFPGVK SHTLNNCQVV RGTGFTGGDW  540
LRPNNNGTFR LTITSFSSQS YRIRLRYATS VGNTSLVISS SDAGISSTTI PLTSTITSLP  600
QTVPYQAFRV VDLPITFTTP TTQRNYTFDF RLQNPSNANV FIDRFEFVPI GGSLSEYETK  660

SEQ ID NO: 62            moltype = DNA  length = 3774
FEATURE                  Location/Qualifiers
misc_feature             1..3774
                         note = A synthetic coding sequence used for expression in
                         plant cells, CR-BRE1a.TIC7383_1.nno_Mc:1 which encodes a
                         TIC7383 protein wherein an additional alanine codon is
                         inserted immediately following the initiating methionine
                         codon.
source                   1..3774
```

|  | mol_type = other DNA | |
|  | organism = synthetic construct | |
| SEQUENCE: 62 | | |
| atggctaacc agaaccagaa ccaaaaccag aacaagaacg agctgcagat cattgaaccc | | 60 |
| tcctcggaca gcctcctgta cagccataac aactacccgt acgccactga cccaaacacc | | 120 |
| gtgctcgagg ggcgcaacta caaggagtgg ctcaacaaat gcaccgacaa ctacaccgac | | 180 |
| gcactccagg gcccggaggc gacggccatc agcaagggtg ccgtctccgc ggccatctcc | | 240 |
| atctcgacga aggtcctagg gctcctaggg gtcccgttcg ctgcgcagat tggccagctg | | 300 |
| tggacgttca tccttaacgc actctggccc tcagacaaca cccagtggga ggagttcatg | | 360 |
| cgccacgtcg aggaactgat caaccagcgc atagcggact acgcgaggaa caaggccctg | | 420 |
| gccgagctga cagggctggg caacaaccta gacctctaca tcgaggcgct cgaggactgg | | 480 |
| aagcggaacc ctacctccca acaagctaag gaccgcgtta tcgaccgctt ccgaatcgcg | | 540 |
| gacggcctct tcgaggggta catgccgagc ttccgggtct cgggctacga ggtgcccgtc | | 600 |
| ctcacggtgt acgcggcggc ggctaatttg catctcctgc tgctcaggga ttgctcgatc | | 660 |
| tacgaatcc agtggggctt ctcccagact aacgttaacg agaactaaa tcggcagatt | | 720 |
| cggcacaccg ccgagtacgc taaccactgc acaacatggt atcagaccgg cctcgagagg | | 780 |
| ctgcgcggca ccaatgcttt ctcatggatc aactacaacc gcttccgccg cgagatgaca | | 840 |
| ctgactgtct tggacgtctg ctcccctctt ccaactatg actaccgcac ttaccccact | | 900 |
| gaggtccggg ccgagcttac gcgggagatc tacacagacc ccatcgggtt ccagaactcc | | 960 |
| ccgctccctg cgtggtccc caattggtac gactacgcga ggtcgttcgc ggaaatcgaa | | 1020 |
| aacatcgcca tacgagcacc tcggacagtc acgtggctga actcaaccac catctacacc | | 1080 |
| gggagactga acggctacaa caatagcaac tactactgga ccgggttccg ccagaacttc | | 1140 |
| tcagagacca actctggcag cagcttcaac ggcccagacc taggcgacct cactccgaac | | 1200 |
| tacaggatag agaccctcga catggtcaac agggacatct acagcatcta ctcccgggtc | | 1260 |
| gtgtcgcaat cctggcccat cggcaacgtc aagctcttcg gcgtaagctc ctctacctta | | 1320 |
| agtttccggg atctcaacaa caagctcc ggcaccctgg tctacgaagaa cccgactaac | | 1380 |
| ttcagctccc agtacctaac cacagagttt ccagggagaa actccgagcg gcccaccttc | | 1440 |
| acggactaca gtcaccgcct aacctgcctt acgcggatcg gggccgggaa ctacggcctc | | 1500 |
| gtgctttgtg cgggttggac ttcttcgagt gtcgaagggg acaaccgcct acaacccgat | | 1560 |
| aagattaccc agtaccccgc cgtcaagggg ttcaacttgg acggcttcac agtggtgaaa | | 1620 |
| gggactggtt tcaccggggg caactggctg cggtccagca gggtcaccgg gtcattccgc | | 1680 |
| ctgaacgtat actcacctag tgtgcagact tatcggatga ggatcaggta cgcctccccg | | 1740 |
| cttggcaact cgacgcttgg gataagttcg acagacgccg gcatctcgtt cacgagtttc | | 1800 |
| cctctgccct ccactatcgg gagcatgccg tccactgtgc cctacgaggc gttccgtgtc | | 1860 |
| ctcgacatcc ccatcacggt caccgtagcc tcccaaagga actacaactt catcttcgac | | 1920 |
| atccttaacc cctcggttgg ggccgtgtac atcgatcgta ttgagttcgt gcccgtgggc | | 1980 |
| tcttcagtgt tcgagtacga aaccaagcac gagcttgaaa aggcgaaaaa agcagttaac | | 2040 |
| gacctcttca cgaacgagtc caaaaacatg ttaaagaaag acacgaccga ctacgacatc | | 2100 |
| gaccaggctg cggacctggt ggagtgcgta agcgacgagt gcgccacgc taagatgata | | 2160 |
| ctgctggacg aagtgaagta cgcgaagcag ctgagcgagg ctcggaacct gctccagaac | | 2220 |
| gggaacttca aggtcttaga cgttgacaac aacaacccgt ggacgacctc accgaacgta | | 2280 |
| acgatccagg agaacaaccc gatcttcaaa ggtcactacc tctccatgtc cggtgcgaac | | 2340 |
| gcaatcgagg ccaccaacga ggtgttccca acgtacgtgt accaaaagat tgaggagagt | | 2400 |
| aaactcaagc cctacacaag gtacaaggtg cgggggttca tcggccgagg caaggacgtc | | 2460 |
| gagctgctcg tcacgcgtta cgacgaggag gtggacgcta ttctgaacgt gcctaacgac | | 2520 |
| ctaaagtacg cagtgccgac gcacctgtcg ggagagttca ccgctgcaa gctcacact | | 2580 |
| tacccggcca cagaccccg atgccacgac gacgtgatcg acaagatcga catctcctcg | | 2640 |
| ccgtgtcaga acaacattat gctgtcggac gcggacatct ctagtcttca tagcggactt | | 2700 |
| ggcaagaagc acgggatctg ccacgagagc catcacttcg agttccacat cgacacgggc | | 2760 |
| aaaatcgacc tcgtggagaa ccttggcatc tgggtgatct tcaagatctg ctctaccgac | | 2820 |
| ggatacgcgg cgctcgacaa tctggaagta atagaggagg gccgttgtg cgcagagtcc | | 2880 |
| ctagagcggg tgaagcgtag ggagaagaag tggaagcata acatggagca caagtgctcg | | 2940 |
| gaaacgaaac acgcatacca cgcggcgaag caggctgtcg aagcactctt cacgaacttc | | 3000 |
| aaggacgaga ggctcaagtt cgagacgacg attagtaaca tcctgtcagc tgagtaccta | | 3060 |
| gtccagtcca tcccatagt ctacaacaag tggctgtcga acgtacctgg gtgaactac | | 3120 |
| gacatctaca ccgagctcaa gaaccgcatc tggcaagcgt tcaacttgta cgaccagagg | | 3180 |
| aacatcatca agaacggcca cttcaatcat ggtttaatgc attggcacgc gacaccgcac | | 3240 |
| gcgaacgtgc agcaaataga cggtatttcc gtgctggtcc tcccaaactg ggggccaac | | 3300 |
| gtcagccagg aggtgtgcct caagcacaac cggggctacg tgctgcgagt cacggccaag | | 3360 |
| gaggagggtc acggcaaggg ctacgtgacg atttcggact gcgctaacca ggtcgagaag | | 3420 |
| ctgtcgttca ctagccgcga ctactctacc gacggcgtcc catacgaaca gtccaactac | | 3480 |
| ccgaccgacg gagtgtctta cgggcagcac gggtgcaaca tcgaccgagt gcctacgag | | 3540 |
| caatctggct accccaccga cggggttcct tacgaacagt cgggctaccg tacggacggg | | 3600 |
| gtcccgtaca agcagcatgg atgccactcg gacggaagcc gacacgcgta | | 3660 |
| gttacgaaga ctatcgacgt cttccccgac acgacaagg tccggatcga catcggcgag | | 3720 |
| accgagggga cgttcaaggt tgagagcgtg gagctcatct gcatggagga gtag | | 3774 |

| SEQ ID NO: 63 | moltype = AA length = 1257 |
| FEATURE | Location/Qualifiers |
| REGION | 1..1257 |
|  | note = The amino acid sequence of |
|  | CR-BRE1a.TIC7383_1.nno_Mc:1 wherein an additional alanine |
|  | amino acid is inserted immediately following the |
|  | initiating methionine relative to the TIC7383 protein |
|  | sequence. |
| source | 1..1257 |
|  | mol_type = protein |
|  | organism = synthetic construct |
| SEQUENCE: 63 | |

```
MANQNQNQNQ NKNELQIIEP SSDSLLYSHN NYPYATDPNT VLEGRNYKEW LNKCTDNYTD   60
ALQGPEATAI SKGAVSAAIS ISTKVLGLLG VPFAAQIGQL WTFILNALWP SDNTQWEEFM  120
RHVEELINQR IADYARNKAL AELTGLGNNL DLYIEALEDW KRNPTSQQAK DRVIDRFRIA  180
DGLFEGYMPS FRVSGYEVPL LTVYAAAANL HLLLLRDCSI YGIQWGFSQT NVNENYNRQI  240
RHTAEYANHC TTWYQTGLER LRGTNAFSWI NYNRFRREMT LTVLDVCSLF SNYDYRTYPT  300
EVRAELTREI YTDPIGFQNS PLPGVVPNWY DYARSFAEIE NIAIRAPRTV TWLNSTTIYT  360
GRLNGYNNSN YYWAGFRQNF SETNSGSSFN GPDLGDLTPN YRIETLDMVN RDIYSIYSRV  420
VSQSWPIGNV KLFGVSSSTL SFRDLNNNSS GTLVYENPTN FSSQYLTTEF PGENSERPTF  480
TDYSHRLTCL TRIGAGNYGL VLCAGWTSSS VERDNRLQPD KITQYPAVKG FNLDGFTVVK  540
GTGFTGGNWL RSSRVTGSFR LNVYSPSVQT YRMRIRYASP LGNSTLGISS TDAGISFTSF  600
PLPSTIGSMP STVPYEAFRV LDIPITVTVA SQRNYNFIFD ILNPSVGAVY IDRIEFVPVG  660
SSVFEYETKH ELEKAKKAVN DLFTNESKNM LKKDTTDYDI DQAADLVECV SDECAHAKMI  720
LLDEVKYAKQ LSEARNLLQN GNFKVLDVDN NNPWTTSPNV TIQENNPIFK GHYLSMSGAN  780
AIEATNEVFP TYVYQKIEES KLKPYTRYKV RGFIGQSKDV ELLVTRYDEE VDAILNVPND  840
LKYAVPTHLS GEFNRCKPHT YPATDPRCHD DVIDKIDISS PCQNNIMLSD ADISSLHSGL  900
GKKHGICHES HHFEFHIDTG KIDLVENLGI WVIFKICSTD GYATLDNLEV IEEGPLGAES  960
LERVKRREKK WKHNMEHKCS ETKHAYHAAK QAVEEALFTNF KDERLKFETT ISNILSAEYL 1020
VQSIPYVYNK WLSDVPGMNY DIYTELKNRI WQAFNLYDQR NIIKNGHFNH GLMHWHATPH 1080
ANVQQIDGIS VLVLPNWGAN VSQEVCLKHN RGYVLRVTAK EEGHGKGYVT ISDCANQVEK 1140
LSFTSRDYST DGVPYEQSNY PTDGVSYGQH GCNIDRVPYE QSGYPTDGVP YEQSGYRTDG 1200
VPYKQHGCHS DGSREEQHGY VTKTIDVFPD TDKVRIDIGE TEGTFKVESV ELICMEE    1257

SEQ ID NO: 64           moltype = DNA  length = 1854
FEATURE                 Location/Qualifiers
misc_feature            1..1854
                        note = A synthetic coding sequence used for expression in
                         plant cells, CR-BRE1a.TIC7383_7.nno_Mc:1 which encodes a
                         protein comprising an N-terminal and C-terminal truncation
                         relative to the TIC7383 protein with an alanine codon
                         after initiating methionine.
source                  1..1854
                        mol_type = other DNA
                        organism = synthetic construct
SEQUENCE: 64
atggctaccg acaactacac cgacgcactc cagggcccgg aggcgacggc catcagcaag   60
ggtgccgtct ccgcggccat ctccatctcg acgaaggtcc tagggctcct aggggtcccg  120
ttcgctgcgc agattggcca gctgtggacg ttcatcctta cgcactctg gccctcagac  180
aacacccagt gggaggagtt catgcgccac gtcgaggaac tgatcaacca gcgcatagcg  240
gactacgcga ggaacaaggc cctggccgag ctgacagggc tgggcaacaa cctagacctc  300
tacatcgagg cgctcgagga ctggaagcgg aaccctacct cccaacaagc taaggaccgc  360
gttatcgacc gcttccgaat cgcggacggc ctcttcgagg gtacatgcc gagcttccgg  420
gtctcgggct acgaggtgcc cctcctcacg gtgtacgcgg cggcgctaa tttgcatctc  480
ctgctgctca gggattgctc gatctacgga atccagtggg gcttctccca gactaacgtt  540
aacgagaact acaatcggca gattcggcac accgccgagt acgctaacca ctgcacaaca  600
tggtatcaga ccgcctcga gaggctgcgc ggcaccaatg cttttctcatg gatcaactac  660
aaccgcttcc gccgcgagat gacactgact gtcttggacg tctgctccct cttctccaac  720
tatgactacc gcacttaccc cactgaggtc cgggccgaac ttacgcggga cctacacaca  780
gaccccatcg ggttccagaa ctccccgctc cctggcgtgg tccccaattg gtacgactac  840
gcgaggtcgt tcgcggaaat cgaaacatc gccatacgag cacctcggac agtcacgtgg  900
ctgaactcaa ccaccatcta caccgggaga ctgaacggct acaacaatag caactactac  960
tgggccgggt tccgccagaa cttctcagag accaactctg gcagcagctt caacggccca 1020
gacctaggcg acctcactcc gaactacagg atagagaccc tcgacatggt caacagggac 1080
atctacagca tctactcccg ggtcgtgtcg caatcctggc ccatcggcaa cgtcaagctc 1140
ttcggcgtaa gctcctctac cttaagtttc cgggatctca caacaacag ctccggcacc 1200
ctggtctacg agaacccgac taacttcagc tcccagtacc taaccacaga gtttccaggg 1260
gagaactccg agcggccac cttcacggac tacagtcacc gcctaacctg ccttacgcgg 1320
atcggggccg ggaactacgg cctcgtgctt tgtgcgggtt ggacttcttc gagtgtcgaa 1380
agggacaacc gcctacaacc cgataagatt acccagtacc ccgccgtcaa ggggttcaac 1440
ttggacggct tcacagtggt gaaagggact ggtttcaccg ggggcaactg gctgcggtcc 1500
agcagggtca ccgggtcatt ccgcctgaac gtatactcac ctagtgtgca gacttatcgg 1560
atgaggatca ggtacgcctc cccgcttggc aactcgacgc ttgggataag ttcgacagac 1620
gccggcatct cgttcacgag tttccctctg ccctccacta cgggagcat gccgtccact 1680
gtgccctacg aggcgttccg tgtcctcgac atccccatca cggtcaccgt agcctcccaa 1740
aggaactaca acttcatctt cgacatcctt aaccctcgg ttggggccgt gtacatcgat 1800
cgtattgagt tcgtgcccgt gggctcttca gtgttcgagt acgaaaccaa gtga       1854

SEQ ID NO: 65           moltype = AA  length = 617
FEATURE                 Location/Qualifiers
REGION                  1..617
                        note = The amino acid sequence of
                         CR-BRE1a.TIC7383_7.nno_Mc:1 comprising an N-terminal and
                         C-terminal deletion, an additional alanine amino acid, and
                         comprises amino acids 54 through 668 of TIC7383.
source                  1..617
                        mol_type = protein
                        organism = synthetic construct
SEQUENCE: 65
MATDNYTDAL QGPEATAISK GAVSAAISIS TKVLGLLGVP FAAQIGQLWT FILNALWPSD   60
NTQWEEFMRH VEELINQRIA DYARNKALAE LTGLGNNLDL YIEALEDWKR NPTSQQAKDR  120
```

```
VIDRFRIADG  LFEGYMPSFR  VSGYEVPLLT  VYAAAANLHL  LLLLRDCSIYG  IQWGFSQTNV   180
NENYNRQIRH  TAEYANHCTT  WYQTGLERLR  GTNAFSWINY  NRFRREMTLT   VLDVCSLFSN   240
YDYRTYPTEV  RAELTREIYT  DPIGFQNSPL  PGVVPNWYDY  ARSFAEIENI   AIRAPRTVTW   300
LNSTTIYTGR  LNGYNNSNYY  WAGFRQNFSE  TNSGSSFNGP  DLGDLTPNYR   IETLDMVNRD   360
IYSIYSRVVS  QSWPIGNVKL  FGVSSSTLSF  RDLNNNSSGT  LVYENPTNFS   SQYLTTEFPG   420
ENSERPTFTD  YSHRLTCLTR  IGAGNYGLVL  CAGWTSSSVE  RDNRLQPDKI   TQYPAVKGFN   480
LDGFTVVKGT  GFTGGNWLRS  SRVTGSFRLN  VYSPSVQTYR  MRIRYASPLG   NSTLGISSTD   540
AGISFTSFPL  PSTIGSMPST  VPYEAFRVLD  IPITVTVASQ  RNYNFIFDIL   NPSVGAVYID   600
RIEFVPVGSS  VFEYETK                                                       617

SEQ ID NO: 66            moltype = DNA  length = 1989
FEATURE                  Location/Qualifiers
misc_feature             1..1989
                         note = A synthetic coding sequence used for expression in
                         plant cells, CR-BRE1a.TIC7383_8.nno_Mc:1 which encodes a
                         protein comprising a C-terminal truncation relative to the
                         TIC7383 protein with an additional alanine codon is insert
                         after initiating methionine.
source                   1..1989
                         mol_type = other DNA
                         organism = synthetic construct
SEQUENCE: 66
atggctaacc agaaccagaa ccaaaaccag aacaagaacg agctgcagat cattgaaccc    60
tcctcggaca gcctcctgta cagccataac aactacccgt acgccactga cccaaacacc   120
gtgctcgagg ggcgcaacta caaggagtgg ctcaacaaat gcaccgacaa ctacaccgac   180
gcactccagg gcccggaggc gacggccatc agcaaggcgt ccgtctccgc ggccatctcc   240
atctcgacga aggtcctagg gctcctaggg gtcccgttcg ctgcgcagat tggccagctg   300
tggacgttca tccttaacgc actctggccc tcagacaaca cccagtggga ggagttcatg   360
cgccacgtcg aggaactgat caaccagcgc atagcggact acgcgaggaa caaggccctg   420
gccgagctga cagggctggg caacaaccta gacctctaca tcgaggcgct cgaggactgg   480
aagcggaacc ctacctccca acaagctaag gaccgcgtta tcgaccgctt ccgaatcgcg   540
gacggcctct tcgaggggta catgccgagc ttccgggtct cgggctacga ggtgccgctc   600
ctcacggtgt acgcggcggc ggctaatttg catctcctgc tgctcaggga ttgctcgatc   660
tacggaatcc agtggggctt ctcccagact aacgttaacg agaactacaa tcggcagatt   720
cggcacaccg ccgagtacgc taaccactgc acaacatggt atcagaccgg cctcgagagg   780
ctgcgcggca ccaatgcttt ctcatggatc aactacaacc gcttccgccg cgagatgaca   840
ctgactgtct tggacgtctg ctccctcttc tccaactatg actaccgcac ttaccccact   900
gaggtccggg ccgagcttac gcgggagatc tacacagacc ccatcgggtt ccagaactcc   960
ccgctccctg gcgtggtccc caattggtac gactacgcga ggtcgttcgc ggaaatcgaa  1020
aacatcgcca tacgagcacc tcggacagtc acgtggctga actcaaccac catctacacc  1080
gggagactga acggctacaa caatagcaac tactactggg ccgggttccg ccagaacttc  1140
tcagagacca actctggcag cagcttcaac ggcccagacc taggcgacct cactccgaac  1200
tacaggatag agaccctcga catggtcaac agggacatct acagcatcta ctcccgggtc  1260
gtgtcgcaat cctggcccat cggcaacgtc aagctcttcg gcgtaagctc ctctacctta  1320
agtttccggg atctcaacaa caacagctcc ggcaccctgg tctacgagaa cccgactaac  1380
ttcagctccc agtacctaac cacagagttt ccaggggaga actccgagcg gcccaccttc  1440
acggactaca gtcaccgcct aacctgcctt acgcggactg gggccgggaa ctacggcctc  1500
gtgctttgtg cgggttggac ttcttcgagt gtcgaaaggg acaaccgcct acaacccgat  1560
aagattaccc agtaccccgc cgtcaagggg ttcaacttgg acggcttcac agtggtgaaa  1620
gggactggtt tcaccggggg caactggctg cggtccagca gggtcaccgg gtcattccgc  1680
ctgaacgtat actcacctag tgtgcaagact tatcggatag ggatcaggta cgcctcccga  1740
cttggcaact cgacgcttgg gataagttcg acagacgccg gcatctcgtt cacgagtttc  1800
cctctgccct ccactatcgg gagcatgccg tccactgtgc cctacgaggc gttccgtgtc  1860
ctcgacatcc ccatcacggt caccgtagcc tcccaaagga actacaactt catcttcgac  1920
atccttaacc cctcggttgg ggccgtgtac atcgatcgta ttgagttcgt gcccgtgggc  1980
tcttcatga                                                           1989

SEQ ID NO: 67            moltype = AA  length = 662
FEATURE                  Location/Qualifiers
REGION                   1..662
                         note = The amino acid sequence of
                         CR-BRE1a.TIC7383_8.nno_Mc:1 comprising a C-terminal
                         deletion, an additional alanine amino acid, and comprises
                         amino acids 1 through 661 of TIC7383.
source                   1..662
                         mol_type = protein
                         organism = synthetic construct
SEQUENCE: 67
MANQNQNQNQ  NKNELQIIEP  SSDSLLYSHN  NYPYATDPNT  VLEGRNYKEW   LNKCTDNYTD    60
ALQGPEATAI  SKGAVSAAIS  ISTKVLGLLG  VPFAAQIGQL  WTFILNALWP   SDNTQWEEFM   120
RHVEELINQR  IADYARNKAL  AELTGLGNNL  DLYIEALEDW  KRNPTSQQAK   DRVIDRFRIA   180
DGLFEGYMPS  FRVSGYEVPL  LTVYAAAANL  HLLLLRDCSI  YGIQWGFSQT   NVENYNRQI    240
RHTAEYANHC  TTWYQTGLER  LRGTNAFSWI  NYNRFRREMT  LTVLDVCSLF   SNYDYRTYPT   300
EVRAELTREI  YTDPIGFQNS  PLPGVVPNWY  DYARSFAEIE  NIAIRAPRTV   TWLNSTTIYT   360
GRLNGYNNSN  YYWAGFRQNF  SETNSGSSFN  GPDLGDLTPN  YRIETLDMVN   RDIYSIYSRV   420
VSQSWPIGNV  KLFGVSSSTL  SFRDLNNNSS  GTLVYENPTN  FSSQYLTTEF   PGENSERPTF   480
TDYSHRLTCL  TRIGAGNYGL  VLCAGWTSSS  VERDNRLQPD  KITQYPAVKG   FNLDGFTVVK   540
GTGFTGGNWL  RSSRVTGSFR  LNVYSPSVQT  YRMRIRYASP  LGNSTLGISS   TDAGISFTSF   600
PLPSTIGSMP  STVPYEAFRV  LDIPITVTVA  SQRNYNFIFD  ILNPSVGAVY   IDRIEFVPVG   660
```

```
SS                                                                      662

SEQ ID NO: 68             moltype = DNA   length = 2010
FEATURE                   Location/Qualifiers
misc_feature              1..2010
                          note = A synthetic coding sequence used for expression in
                            plant cells, CR-BRE1a.TIC7383_9.nno_Mc:1 which encodes a
                            protein comprising a C-terminal truncation relative to the
                            TIC7383 protein with an additional alanine codon insert
                            after initiating methionine.
source                    1..2010
                          mol_type = other DNA
                          organism = synthetic construct
SEQUENCE: 68
atggctaacc agaaccagaa ccaaaaccag aacaagaacg agctgcagat cattgaaccc   60
tcctcggaca gcctcctgta cagccataac aactacccgt acgccactga cccaaacacc  120
gtgctcgagg ggcgcaacta caaggagtgg ctcaacaaat gcaccgacaa ctacaccgac  180
gcactccagg gcccggaggc gacggccatc agcaagggtg ccgtctccgc ggccatctcc  240
atctcgacga aggtcctagg gctcctaggg gtcccgttcg ctgcgcagat tggccagctg  300
tggacgttca tccttaacgc actctggccc tcagacaaca cccagtggga ggagttcatg  360
cgccacgtcg aggaactgat caaccagcgc atagcggact acgcgaggaa caaggccctg  420
gccgagctga cagggctggg caacaaccta gacctctaca tcgaggcgct cgaggactgg  480
aagcggaacc ctacctccca acaagctaag gaccgcgtta tcgaccgctt ccgaatcgcg  540
gacggcctct tcgagggggta catgccgagc ttccgggtct cgggctacga ggtgcccctc  600
ctcacgtgtg acgcggcggc ggctaatttg catctcctgc tgctcaggga ttgctcgatc  660
tacggaatcc agtggggctt ctcccagact aacgttaacg agaactacaa tcggcagatt  720
cggcacaccg ccgagtacgc taaccactgc acaacatggt atcagaccgg cctcgagagg  780
ctgcgcggca ccaatgcttt ctcatggatc aactacaacc gcttccgccg cgagatgaca  840
ctgactgtct ggacgtctg ctccctcttc tccaactatg actaccgcac ttaccccact  900
gaggtccgga ccgagcttac gcgggagatc tacacagacc ccatcgggtt ccagaactcc  960
ccgctccctg gcgtggtccc caattggtac gactacgcga ggtcgttcgc ggaaatcgaa 1020
aacatcgcca tacgagcacc tcggacagtc acgtggctga actcaaccac catctacacc 1080
gggagactga acggctacaa caatagcaac tactactggg ccgggttccg ccagaacttc 1140
tcagagacca actctgcag cagcttcaac ggcccagacc taggcgacct cactccgaac 1200
tacaggatag agaccctcga catggtcaac agggacatct acagcatcta ctcccgggtc 1260
gtgtcgcaat cctggcccat cggcaacgtc aagctcttcg gcgtaagctc ctctacctta 1320
agttccgggg atctcaacaa caacagctcc ggcaccctgg tctacgagaa cccgactaac 1380
ttcagctccc agtacctaac cacagagttt ccaggggaga actccgagcg gcccaccttc 1440
acggactaca gtcaccgcct aacctgcctt acgcggatcg gggccgggaa ctacggcctc 1500
gtgctttgtg cgggttggac ttcttcgagt gtcgaaaggg acaaccgcct acaacccgat 1560
aagattaccc agtaccccgc cgtcaagggg ttcaacttgg acggcttcac agtggtgaaa 1620
gggactggtt tcaccggggg caactggctg cggtccagca gggatcaccg gtcattccgc 1680
ctgaacgtat actcacctag tgtgcagact tatcggatga caggtacgcc tcccccg 1740
cttggcaact cgacgcttgg gataagttcg acagacgccg gcatctcgtt cacgagtttc 1800
cctctgccct ccactatcgg gagcatgccg tccactgtgc cctacgaggc gttccgtgtc 1860
ctcgacatcc ccatcacggt caccgtagcc tcccaaagga actacaactt catcttcgac 1920
atccttaacc cctcggttgg ggccgtgtac atcgatcgta ttgagttcgt gcccgtgggc 1980
tcttcagtgt tcgagtacga aaccaagtga                                   2010

SEQ ID NO: 69             moltype = AA   length = 669
FEATURE                   Location/Qualifiers
REGION                    1..669
                          note = The amino acid sequence of
                            CR-BRE1a.TIC7383_9.nno_Mc:1 comprising a C-terminal
                            deletion, an additional alanine amino acid, and comprises
                            amino acids 1 though 668 of TIC7383.
source                    1..669
                          mol_type = protein
                          organism = synthetic construct
SEQUENCE: 69
MANQNQNQNQ NKNELQIIEP SSDSLLYSHN NYPYATDPNT VLEGRNYKEW LNKCTDNYTD    60
ALQGPEATAI SKGAVSAAIS ISTKVLGLLG VPFAAQIGQL WTFILNALWP SDNTQWEEFM   120
RHVEELINQR IADYARNKAL AELTGLGNNL DLYIEALEDW KRNPTSQQAK DRVIDRFRIA   180
DGLFEGYMPS FRVSGYEVPL LTVYAAAANL HLLLLRDCSI YGIQWGFSQT NVNENYNRQI   240
RHTAEYANHC TTWYQTGLER LRGTNAFSWI NYNRFRREMT LTVLDVCSLF SNYDYRTYPT   300
EVRAELTREI YTDPIGFQNS PLPGVVPNWY DYARSFAEIE NIAIRAPRTV TWLNSTTIYT   360
GRLNGYNNSN YYWAGFRQNF SETNSGSSFN GPDLGDLTPN YRIETLDMVN RDIYSIYSRV   420
VSQSWPIGNV KLFGVSSSTL SFRDLNNNSS GTLVYENPTN FSSQYLTTEF PGENSERPTF   480
TDYSHRLTCL TRIGAGNYGL VLCAGWTSSS VERDNRLQPD KITQYPAVKG FNLDGFTVVK   540
GTGFTGGNWL RSSRVTGSFR LNVYSPSVQT YRMRIRYASP LGNSTLGISS TDAGISFTSF   600
PLPSTIGSMP STVPYEAFRV LDIPITVTVA SQRNYNFIFD ILNPSVGAVY IDRIEFVPVG   660
SSVFEYETK                                                           669

SEQ ID NO: 70             moltype = DNA   length = 1746
FEATURE                   Location/Qualifiers
misc_feature              1..1746
                          note = A coding sequence encoding the Tryptic core of the
                            TIC7040HT protein as determined by mass spectrometry.
source                    1..1746
```

```
                        mol_type = other DNA
                        organism = Brevibacillus laterosporus
SEQUENCE: 70
aattataaag agtggctaaa taagtgcaca gataattata cagacgcttt acagggtccc   60
gaagctactg ctatatcaaa aggagctgtc tctgctgcga tttctatcag caccaaagtt  120
cttagtttat taggtgttcc gtttgcagct caaatcggac aactttggac cttcatattg  180
aatgcgttat ggccttcaga caatactcaa tgggaagagt tcatgagaca tgtagaagaa  240
ctcataaacc aacgaatagc cgattatgca agaagtaagg cacttgcaga attaacgggt  300
ttaggtaata acttagattt atatatagaa gctcttgaag attggaaacg aaatcctact  360
agtcaacaag cgaaagaccg tgtaaaagat agattccgta tagcagatgg tttatttgaa  420
gcgtatatgc cttcatttag agtatcaggt tatgaagtac cattattaac agtgtatgca  480
gccgctgcaa atctccattt acttttatta agagattgct ctatttacgg aatccaatgg  540
ggatttagtc aaacgaatgt taacgagaat acaatcgcc aaataagaca caccgcagag   600
tatgcaaatc attgtacaac ttggtaccaa actggtttag aaagattgcg aggtaccaat  660
gcttccagtt gggtccctta taatcgtttc cgaagagaaa tgacgttaac tgtattggat  720
atttgttcct tattttcaaa ttatgattat cgtagttatc cagcagaggt aagggcagag  780
cttacaagag aaatttatac ggacccagtt gtaagcacta gcttgtggat gaataatgca  840
ccatcattcg gagaaataga aaatctagca attagggcgc caagaaccgt tacttggtta  900
aattctacaa gaatttctac agggaccttg cagggctgga gtggttctaa cagatattgg  960
gcagctcaca tgcaaaactt ttcagaaacc aattcaggaa atataggatt tgacggtcct 1020
ctctatgggt cgacggtagg tactattatt cgtgatgata attcgaaat ggtgaaccga  1080
gatatttaca ccattacttc agaggctgtt gccgcccttt ggcaactgg tcaaattgtg   1140
ttgggagtcg cttcggctag atttactta agaaatctca acaataatct tacacaggcg  1200
ctggtgtatg agaacccaat aagttcaagt tttaataggt caacttttac tcgtgaatta  1260
cctgggaaaa actcagatag gccaacttca agcgactata gtcatagact aacgtctatt  1320
acagcttttc gagctggaag taatgggacg attccggttt ttggatggac atctataagt  1380
gttaatcgtg acaatatact tgagcgaaac aaaataacac aattcccagg cgttaagtca  1440
cacactctca acaattgtca agtagttaga ggtactggat ttacaggagg agactggttg  1500
agaccaaata ataatggttc atttagatta actattactt cattctcgag ccaatcttac  1560
cgaatccgct tacgttatgc ttccgcagca aatacttcct tgcgtatatc ttcttctgca  1620
gccggtattt cttccacaac cgttccgctt acctcaacaa taacatcaat gccacaaact  1680
gctgtaccat atgaagcttt tagagttata gatttaccta ttacttttac aacagctacc  1740
caaagt                                                            1746

SEQ ID NO: 71           moltype = AA  length = 582
FEATURE                 Location/Qualifiers
REGION                  1..582
                        note = The amino acid sequence of the Tryptic core of the
                         TIC7040HT protein as determined by mass spectrometry, and
                         comprises amino acids 43 through 624 of TIC7040HT.
source                  1..582
                        mol_type = protein
                        organism = Brevibacillus laterosporus
SEQUENCE: 71
NYKEWLNKCT DNYTDALQGP EATAISKGAV SAAISISTKV LSLLGVPFAA QIGQLWTFIL   60
NALWPSDNTQ WEEFMRHVEE LINQRIADYA RSKALAELTG LGNNLDLYIE ALEDWKRNPT  120
SQQAKDRVKD RFRIADGLFE AYMPSFRVSG YEVPLLTVYA AAANLHLLLL RDCSIYGIQW  180
GFSQTNVNEN YNRQIRHTAE YANHCTTWYQ TGLERLRGTN ASSWVPYNRF RREMTLTVLD  240
ICSLFSNYDY RSYPAEVRAE LTREIYTDPV VSTSLWMNNA PSFGEIENLA IRAPRTVTWL  300
NSTRISTGTL QGWSGSNRYW AAHMQNFSET NSGNIGFDGP LYGSTVGTII RDDNYEMVNR  360
DIYTITSEAV AALWPTGQIV LGVASARFTL RNLNNNLTQA LVYENPISSS FNRSTLTREL  420
PGENSDRPTS SDYSHRLTSI TAFRAGSNGT IPVFGWTSIS VNRDNILERN KITQFPGVKS  480
HTLNNCQVVR GTGFTGGDWL RPNNNGSFRL TITSFSSQSY RIRLRYASAA NTSLRISSSA  540
AGISSTTVPL TSTITSLPQT AVPYEAFRVI DLPITFTTAT QS                    582

SEQ ID NO: 72           moltype = DNA  length = 1791
FEATURE                 Location/Qualifiers
misc_feature            1..1791
                        note = A coding sequence encoding the Chymotryptic core of
                         the TIC7040HT protein as determined by mass spectrometry.
source                  1..1791
                        mol_type = other DNA
                        organism = Brevibacillus laterosporus
SEQUENCE: 72
aaagagtggc taaataagtg cacagataat tatacagacg ctttacaggg tcccgaagct   60
actgctatat caaaaggagc tgtctctgct gcgatttcta tcagcaccaa agttcttagt  120
ttattaggtg ttccgtttgc agctcaaatc ggacaacttt ggaccttcat attgaatgcg  180
ttatggcctt cagacaatac tcaatgggaa gagttcatga gacatgtaga agaactcata  240
aaccaacgaa tagccgatta tgcaagaagt aaggcacttg cagaattaac gggtttaggt  300
aataacttag atttatatat agaagctctt gaagattgga aacgaaatcc tactagtcaa  360
caagcgaaag accgtgtaaa agatagattc cgtatagcag atggtttatt tgaagcgtat  420
atgccttcat ttagagtatc aggttatgaa gtaccattat taacagtgta tgcagccgct  480
gcaaatctcc atttactttt attaagagat tgctctattt acggaatcca atggggattt  540
agtcaaacga atgttaacga gaatacaatc gccaaataa gacacaccgc agagtatgca  600
aatcattgta caacttggta ccaaactggt ttagaaagat gcgaggtac caatgcttcc   660
agtgggtccc ttataatcg tttccgaaga gaaatgacgt taactgtatt ggatatttgt   720
tccttatttt caaattatga ttatcgtagt tatccagcag aggtaagggc agagcttaca  780
agagaaattt atacgaccc agttgtaagc actagcttgt ggatgaataa tgcaccatca   840
ttcggagaaa tagaaaatct agcaattagg gcgccaagaa ccgttacttg gttaaattct  900
```

```
acaagaattt ctacagggac cttgcagggc tggagtggtt ctaacagata ttgggcagct   960
cacatgcaaa acttttcaga aaccaattca ggaaatatag gatttgacgg tcctctctat  1020
gggtcgacgg taggtactat tattcgtgat gataattacg aaatggtgaa ccgagatatt  1080
tacaccatta cttcagaggc tgttgccgcc ctttggccaa ctggtcaaat tgtgttggga  1140
gtcgcttcgg ctagatttac tttaagaaat cttaacaata atcttacaca ggcgctggtg  1200
tatgagaacc caataagttc aagtttaat aggtcaactt taactcgtga attacctggg  1260
gaaaactcag ataggccaac ttcaagcgac tatagtcata gactaacgtc tattacagct  1320
tttcgagctg gaagtaatgg gacgattccg gttttggat ggacatctat aagtgttaat  1380
cgtgacaata tacttgagcg aaacaaaata acacaattcc caggcgttaa gtcacacact  1440
ctcaacaatt gtcaagtagt tagaggtact ggatttacag gggagactg gttgagacca  1500
aataataatg gttcatttag attaactatt acttcattct cgagccaatc ttaccgaatc  1560
cgcttacgtt atgcttccgc agcaaatact tctttgcgta tatcttcttc tgcagccggt  1620
atttcttcca caaccgttcc gcttacctca acaataacat cactgccaca aactgctgta  1680
ccatatgaag cttttagagt tatagattta cctattactt ttacaacagc tacccaaagt  1740
aattatactt ttgattttgt tctccaaaat ccatcaaacg caaatgtatt c           1791

SEQ ID NO: 73              moltype = AA  length = 597
FEATURE                    Location/Qualifiers
REGION                     1..597
                           note = The amino acid sequence of the Chymotryptic core of
                             the TIC7040HT protein as determined by mass spectrometry,
                             and comprises amino acids 45 through 641 of TIC7040HT.
source                     1..597
                           mol_type = protein
                           organism = Brevibacillus laterosporus
SEQUENCE: 73
KEWLNKCTDN YTDALQGPEA TAISKGAVSA AISISTKVLS LLGVPFAAQI GQLWTFILNA   60
LWPSDNTQWE EFMRHVEELI NQRIADYARS KALAELTGLG NNLDLYIEAL EDWKRNPTSQ  120
QAKDRVKDRF RIADGLFEAY MPSFRVSGYE VPLLTVYAAA ANLHLLLLRD CSIYGIQWGF  180
SQTNVNENYN RQIRHTAEYA NHCTTWYQTG LERLRGTNAS SWVPYNRFRR EMTLTVLDIC  240
SLFSNYDYRS YPAEVRAELT REIYTDPVVS TSLWMNNAPS FGEIENLAIR APRTVTWLNS  300
TRISTGTLQG WSGSNRYWAA HMQNFSETNS GNIGFDGPLY GSTVGTIIRD DNYEMVNRDI  360
YTITSEAVAA LWPTGQIVLG VASARFTLRN LNNNLTQALV YENPISSSFN RSTLTRELPG  420
ENSDRPTSSD YSHRLTSITA FRAGSNGTIP VFGWTSISVN RDNILERNKI TQFPGVKSHT  480
LNNCQVVRGT GFTGGDWLRP NNNGSFRLTI TSFSSQSYRI RLRYASAANT SLRISSSAAG  540
ISSTTVPLTS TITSLPQTAV PYEAFRVIDL PITFTTATQS NYTFDFVLQN PSNANVF     597

SEQ ID NO: 74              moltype = DNA  length = 1842
FEATURE                    Location/Qualifiers
misc_feature               1..1842
                           note = A coding sequence encoding the Tryptic core of the
                             TIC7383 protein as determined by mass spectrometry.
source                     1..1842
                           mol_type = other DNA
                           organism = Brevibacillus laterosporus
SEQUENCE: 74
gataattata cagacgcttt acagggtccc gaagctactg ctatatcaaa aggagctgtc   60
tctgctgcga tttctatcag caccaaagtt cttggtttat taggtgttcc atttgcagct  120
caaatcgggc aactttggac cttcatattg aatgcgttat ggccttcaga caatactcaa  180
tgggaagagt tcatgagaca tgtagaagaa ctcataaacc aacgaatagc cgattatgca  240
agaaataagg cacttgcaga attaacgggg ttaggtaata acttagattt atatatagag  300
gctcttgaag attggaaacg aaatcctact agtcaacaag cgaaagaccg tgtaatagat  360
agattccgta tagcagatgg tttatttgaa gggtatatgc cttcatttag agtatcaggt  420
tatgaagtac cattattaac agtgtatgca gccgctgcaa atctccattt acttttatta  480
agagattgct ctatttacgg aatccaatgg ggatttagtc aaacgaatgt taacgagaat  540
tacaatcgcc aaataagaca caccgcagag tatgcaaatc attgtacaac ttggtaccaa  600
actggtttag aaagattgcg aggtaccaat gctttcagtt ggatcaatta taatcgattc  660
cgtagagaaa tgacgttaac cgtattggat gttttgttcat tatttcaaa ttatgattat  720
cgtacgtatc caacagaggt aagagcgag cttacgagga aaatttatac ggacccaata  780
ggttttcaaa atagtcctct tcctggcgtt gttcctaatt ggtacgatta cgcacgatcg  840
ttcgcagaga tagaaaatat agccattcga gcgccacgaa ctgttacttg gttaaattct  900
acaactattt atacaggtag attaaatggc tataacaata gtaattatta ttgggcaggt  960
ttcaggcaaa ttttttcaga aaccaattca ggcagttcat ttaacggtcc tgacttaggg 1020
gatttaacac ctaattatcg tatagaaaca ttggatatgg tgaatcggga tatttactcc 1080
atttattcaa gagttgtttc acaatctggg ccaattggca acgttaaatt gtttggagtc 1140
tcttcatcta ctctttcatt cagagatctt aacaataatt cttcagggac gctggtatat 1200
gaaaacccga caaattttag tagccaatat ctaactaccg aattccctgg ggaaaactca 1260
gaaagaccaa cttttaccga ttatagtcac agactaactt gtctcacacg tattggggct 1320
ggaaattatg gattggttct atgcgccggc tggacatcta gtagtgttga gcgtgacaac 1380
agactccagc cggacaaaat aacacaatac ccggctgtta aaggattcaa cctcgatggt 1440
tttacagtag taaaaggtac tgggtttaca ggggaaatt ggttgagatc tagtcgtgtt 1500
acaggtagct ttagactaaa tgtttattca ccgtctgtcc aaacttatcg catgcgtata 1560
cgttatgctt ctccactggg aaattctact ctaggtatat cttctactga tgctggtatt 1620
agtttcaaca gttttccact tccctcaaca ataggatcaa tgccatcaac tgtaccatac 1680
gaagctttta gagttctaga tacccatc actgttacga tagctagtca aagaaattat 1740
aattttattt tcgatattct aaatccatca gtcggagcag tatacattga cagaattgaa 1800
ttcgttccag ttgggtcttc tgtatttgaa tatgaaacca ag                    1842

SEQ ID NO: 75              moltype = AA  length = 614
```

-continued

```
FEATURE                 Location/Qualifiers
REGION                  1..614
                        note = The amino acid sequence of the Tryptic core of the
                        TIC7383 protein as determined by mass spectrometry, and
                        comprises amino acids 55 through 668 of TIC7383.
source                  1..614
                        mol_type = protein
                        organism = Brevibacillus laterosporus
SEQUENCE: 75
DNYTDALQGP EATAISKGAV SAAISISTKV LGLLGVPFAA QIGQLWTFIL NALWPSDNTQ   60
WEEFMRHVEE LINQRIADYA RNKALAELTG LGNNLDLYIE ALEDWKRNPT SQQAKDRVID  120
RFRIADGLFE GYMPSFRVSG YEVPLLTVYA AAANLHLLLL RDCSIYGIQW GFSQTNVNEN  180
YNRQIRHTAE YANHCTTWYQ TGLERLRGTN AFSWINYNRF RREMTLTVLD VCSLFSNYDY  240
RTYPTEVRAE LTREIYTDPI GFQNSPLPGV VPNWYDYARS FAEIENIAIR APRTVTWLNS  300
TTIYTGRLNG YNNSNYYWAG FRQNFSETNS GSSFNGPDLG DLTPNYRIET LDMVNRDIYS  360
IYSRVVSQSW PIGNVKLFGV SSSTLSFRDL NNNSSGTLVY ENPTNFSSQY LTTEFPGENS  420
ERPTFTDYSH RLTCLTRIGA GNYGLVLCAG WTSSSVERDN RLQPDKITQY PAVKGFNLDG  480
FTVVKGTGFT GGNWLRSSRV TGSFRLNVYS PSVQTYRMRI RYASPLGNST LGISSTDAGI  540
SFTSFPLPST IGSMPSTVPY EAFRVLDIPI TVTVASQRNY NFIFDILNPS VGAVYIDRIE  600
FVPVGSSVFE YETK                                                    614

SEQ ID NO: 76           moltype = DNA  length = 1836
FEATURE                 Location/Qualifiers
misc_feature            1..1836
                        note = A synthetic coding sequence used for expression in a
                        plant cell, encoding a CR-BRE1a.TIC7040_14.nno_Mc:1
                        protein having an N-terminal and C-terminal truncation
                        relative to the TIC7040HT protein, with an additional
                        alanine codon.
source                  1..1836
                        mol_type = other DNA
                        organism = synthetic construct
SEQUENCE: 76
atggctaccg acaactacac cgacgcgctc cagggccctg aggccaccgc catcagcaag    60
ggcgcggtgt cagccgcgat ctccatcagc acaaaggtgc tctcgttact gggcgtgccc   120
ttcgcggcgc agatcggcca gctctggacc tttatcctga cgccctatg gcccagcgac   180
aacacccagt gggaggagtt tatgcgccac gtggaggaac tcattaacca gcgaattgct   240
gactacgcca ggagcaaggc cctggccgag ctgacgggtc ttggcaacaa cctcgacctc   300
tacatcgagg cccttgaaga ctggaagcgg aacccgacca gccaacaggc caaagaccgt   360
gtgaaggacc ggttccggat cgccgacggg ctgttcgagg cgtacatgcc ctctttccgc   420
gtcagcggct acgaggtgcc actgttgacc gtttacgcgg cagccgctaa cctccacttg   480
ctgctcctgc gggattgctc catctacggt atccagtggg gcttcagcca gacaaacgtc   540
aacgagaact acaaccgaca gatccggcac acggccgagt acgcaaacca ctgcacgaca   600
tggtatcaga cagggcttga acgcttcgt ggcaccaacg cctcgtcatg ggtgccgtac   660
aaccggttcc gccagagat gaccctcacc gttcttgaca tctgctcact gttcagcaac   720
tacgactacc ggtcgtaccc tgcggaggtt cgggccgaac tgacgcggga gatctacact   780
gacccggtgg tcagcacctc gttgtggatg aacaacgcgc ccagcttcgt tgagatcgag   840
aacctcgcca taagagcacc acgcaccgtc acttggctca acagcacccg gatctccacg   900
ggcaccttac agggctggag cggctccaac cgatactggg cagcgcacat gcagaacttc   960
tccgagacta actccggcaa catcggcttc gacggcccgc tctacggcag caccgtcggg  1020
accatcatcc gggacgacaa ctatgagatg tcaacaggg acatctacac gattacctcg  1080
gaggccgtgg ctgccctgtg gccaaccggt caaatagtgt tgggagtcgc ctccgcccgc  1140
tttacgctgc gtaacctgaa caacaacctt acccaggcgc tcgtgtacga gaacccgatc  1200
tccagctcct tcaataggtc caccctcacg agggagctgc cgggtgagaa cagcgacagg  1260
ccgacgtcct cggactacag tcaccggctc acctcgatca cagcgttccg agccgggagc  1320
aacggaacga tcccagtctt cggatggacc agcatcagcg tcaaccgcga caacatcctg  1380
gaacgcaaca agatcactca gttccctgga gttaagtctc acacgctcaa caactgccaa  1440
gtggtgcgtg gcacagggtt taccggaggc gactggcttc gcccgaacaa caatgggtca  1500
ttccggctga ccattaccag cttctcatcg caatcatcgg gcatccggct acggtacgcc  1560
tcggcggcca acactagcct tcgcatctcc tcttcagccg ccgggatcag ctcgacaacc  1620
gtcccgctga ccagcacgat cacgagcctg ccacaaactg ctgtgcctta cgaggctttc  1680
agagtgatcg acctgcccat taccttcacc acggcaaccc aatcgaacta cactttcgac  1740
ttcgtgttac agaatccgag caacgccaac gtcttcatcg accggttcga gttcgtgccc  1800
atcggcggga gcctctccga gtacgagacc aagtga                            1836

SEQ ID NO: 77           moltype = AA  length = 611
FEATURE                 Location/Qualifiers
REGION                  1..611
                        note = The amino acid sequence of the
                        CR-BRE1a.TIC7040_14.nno_Mc:1 protein, wherein an
                        additional alanine amino acid is inserted immediately
                        following the initiating methionine, and comprises amino
                        acids 52 through 660 of TIC7040HT.
source                  1..611
                        mol_type = protein
                        organism = synthetic construct
SEQUENCE: 77
MATDNYTDAL QGPEATAISK GAVSAAISIS TKVLSLLGVP FAAQIGQLWT FILNALWPSD   60
NTQWEEFMRH VEELINQRIA DYARSKALAE LTGLGNNLDL YIEALEDWKR NPTSQQAKDR  120
```

-continued

```
VKDRFRIADG LFEAYMPSFR VSGYEVPLLT VYAAAANLHL LLLRDCSIYG IQWGFSQTNV  180
NENYNRQIRH TAEYANHCTT WYQTGLERLR GTNASSWVPY NRFRREMTLT VLDICSLFSN  240
YDYRSYPAEV RAELTREIYT DPVVSTSLWM NNAPSFGEIE NLAIRAPRTV TWLNSTRIST  300
GTLQGWSGSN RYWAAHMQNF SETNSGNIGF DGPLYGSTVG TIIRDDNYEM VNRDIYTITS  360
EAVAALWPTG QIVLGVASAR FTLRNLNNNL TQALVYENPI SSSFNRSTLT RELPGENSDR  420
PTSSDYSHRL TSITAFRAGS NGTIPVFGWT SISVNRDNIL ERNKITQFPG VKSHTLNNCQ  480
VVRGTGFTGG DWLRPNNNGS FRLTITSFSS QSYRIRLRYA SAANTSLRIS SSAAGISSTT  540
VPLTSTITSL PQTAVPYEAF RVIDLPITFT TATQSNYTFD FVLQNPSNAN VFIDRFEFVP  600
IGGSLSEYET K                                                     611

SEQ ID NO: 78            moltype = DNA  length = 1980
FEATURE                  Location/Qualifiers
misc_feature             1..1980
                         note = A synthetic coding sequence used for expression in a
                         plant cell, encoding a CR-BREla.TIC7381_2.nno_Mc:1 protein
                         with a C-terminal truncation, and an additional alanine
                         codon after the intiating methionine codon.
source                   1..1980
                         mol_type = other DNA
                         organism = synthetic construct
SEQUENCE: 78
atggctaacc agaaccagaa caagaacgag ctacagataa tcgagccgtc ctcggattcc   60
ttgctgtact cgcacaacaa ctacccgtac gccaccgatc cgaacacggt gctagagggc  120
cgcaactaca aggagtggct gaataagtgc acagacaact acaccgatgc actgcaaggc  180
ccagaggcaa cggctatcag caagggtgcc gtgtcggccg ctatctctat cagcaccaaa  240
gtcttgagcc ttctgggagt gccctccgca gctcagattg ggcaattgtg gacgttttat  300
ctgaacgctc tttggccctc ggacaacacc cagtggagg agttcatgcg ccatgtcgag  360
agctcatca accagcgtat cgccgactac gcgcggagta aggcgctcgc cgagctcacg  420
ggcctgggca acaacctcga tctgtacatc gaagctcttg aggactggaa agcaacccg   480
acctctcaac aagccaagga ccgggtgaag gaccgcttcc gcatcgccga cggcctcttc  540
gaagcgtaca tgcctagctt ccgcgtgagc ggctatgaag tgccattgct caccgtatat  600
gcggcggcgg ccaacctgca cctcctcctc ctccgcgact gctctatcta cggcattcag  660
tggggtttct cccagaccaa tgtcaacgag actataatc ggcagatccg tcacaccgcc  720
gagtacgcga accactgcac gacatggtac cagacgggcc tggagcgact gcgcggcacg  780
aacgcctcaa gctgggtgcc gtacaaccgt ttcaggagag atgactct caccgtgctc  840
gacatctgca gtctgttctc caactatgac tacaggagtt acccggcaga ggtgcgggct  900
gagctgacca gggagatata cacggacccg gtggtcagca cctctctgtg ggtgaacaac  960
gcgccgtcct cggcgaaat cgagaatctg gcaatccgag cgccacgcac cgtgacatgg  1020
ctcaattcga cgcgtattag cactgcacca ctccaaggtt gctctggctc caacaggtac 1080
tgggccgccc acatgcagaa cttctcggag actaactccg gcaacatagg cttcgacggc 1140
ccgctgtacg ggtccactgt gggtacaatc attcgcgatg acaattacga gatggtcaac 1200
cgggacattt acaccatcac ttcggaggcg gttgcggctt gtggcccac gggccagatt 1260
gtgctgggcg tggcttccgc aagattcacc cttgaaacct caacaacaa cctgacccag 1320
gcgctggtct acgagaaccc gatatcaagc agtttcaacc ggtcaactct cacacgcgag 1380
ttgccggggcg agaacagcga caggcccacc tcttcggact actccaccg tctcactagc 1440
atcactgcgt tccgcgcagg cagtaacggt acgattcctg tgttcggctg gaccagtatc 1500
tccgtcaaca gggagaacat actggagcgg aacaagatca cccagttccc tggcgttaag 1560
tcccataccc tgaacaattg ccaggtcgtc cgccggtacag gctttaccgg cggcgactgg 1620
cttcggccta caacaacgg gtcgttccga ttgactatca cctcgttcag ctcacagagt 1680
tacagaatca ggctgcggta cgcgtccgca gcgaataccc cctgcgaat tcgtcttcg  1740
gcggccggga tctcgtcaac aaccgtccca gccgcctcca cgatcactag cctcccgcag 1800
acagccgtcc catacgaggc gttccgggtg atcgacctgc caatcacgtt caccaccgag 1860
acgcagtcta actacacttt cgacttcgtc ctccagaatc cttccaacgc caacgtgttc 1920
atcgaccgct tcgagtttgt cccgattgga ggttcgctct cagagtacga gacgaagtga 1980

SEQ ID NO: 79            moltype = AA  length = 659
FEATURE                  Location/Qualifiers
REGION                   1..659
                         note = The amino acid sequence of the
                         CR-BREla.TIC7381_2.nno_Mc:1 protein with a C-terminal
                         truncation, an additional alanine residue, and comprises
                         amino acids 1 through 658 of TIC7381.
source                   1..659
                         mol_type = protein
                         organism = synthetic construct
SEQUENCE: 79
MANQNQNKNE LQIIEPSSDS LLYSHNNYPY ATDPNTVLEG RNYKEWLNKC TDNYTDALQG   60
PEATAISKGA VSAAISISTK VLSLLGVPFA AQIGQLWTFI LNALWPSDNT QWEEFMRHVE  120
ELINQRIADY ARSKALAELT GLGNNLDLYI EALEDWKRNP TSQQAKDRVK DRFRIADGLF  180
EAYMPSFRVS GYEVPLLTVY AAAANLHLLL LRDCSIYGIQ WGFSQTNVNE NYNRQIRHTA  240
EYANHCTTWY QTGLERLRGT NASSWVPYNR FRREMTLTVL DICSLFSNYD YRSYPAEVRA  300
ELTREIYTDP VVSTSLWVNN APSFGEIENL AIRAPRTVTW LNSTRISTGT LQGWSGSNRY  360
WAAHMQNFSE TNSGNIGFDG PLYGSTVGTI IRDDNYEMRD IYTITSEA VAALWPTGQI  420
VLGVASARFT LRNLNNNLTQ ALVYENPISS SFNRSTLTRE LPGENSDRPT SSDYSHRLTS  480
ITAFRAGSNG TIPVFGWTSI SVNRDNILER NKITQFPGVK SHTLNNCQVV RGTGFTGGDW  540
LRPNNNGSFR LTITSFSSQS YRIRLRYASA ANTSLRISSS AAGISSTTVP LASTITSLPQ  600
TAVPYEAFRV IDLPITFTTA TQSNYTFDFV LQNPSNANVF IDRFEFVPIG GSLSEYETK   659

SEQ ID NO: 80            moltype = DNA  length = 1836
```

```
FEATURE                 Location/Qualifiers
misc_feature            1..1836
                        note = A synthetic coding sequence used for expression in
                          plant cells encoding a CR-BRE1a.TIC7381_3.nno_Mc:1 with an
                          N-terminal and C-terminal truncation and additional
                          alanine codon after the initiating methionine relative to
                          TIC7381.
source                  1..1836
                        mol_type = other DNA
                        organism = synthetic construct
SEQUENCE: 80
atggctacag acaactacac cgatgcactg caaggcccag aggcaacggc tatcagcaag   60
ggtgccgtgt cggccgctat ctctatcagc accaaagtct tgagccttct gggagtgccc  120
ttcgcagctc agattgggca attgtggacg tttattctga acgctcttg gccctcggac  180
aacacccagt gggaggagtt catgcgccat gtcgaggagc tcatcaacca gcgtatcgcc  240
gactacgcgc ggagtaaggc gctcgccgag ctcacgggcc tgggcaacaa cctcgatctg  300
tacatcgaag ctcttgagga ctggaagcgc aacccgacct ctcaacaagc caaggaccgg  360
gtgaaggacc gcttccgcat cgccgaacgg ctcttcgaag cgtacatgcc tagcttccgc  420
gtgagcggct atgaagtgcc attgctcacc gtatatgcgg cggcggccaa cctgcacctc  480
ctcctcctcc gcgactgctc tatctacggc attcagtggg gtttctccca gaccaatgtc  540
aacgagaact ataatcggca gatccgtcac accgccgagt acgcgaacca ctgcacgaca  600
tggtaccaga cgggcctgga gcgactgcgc ggcacgaacg cctcaagctg ggtgccgtac  660
aaccgtttca ggagagagat gactctcacc gtgctcgaca tctgcagtct gttctccaac  720
tatgactaca ggagttaccc ggcagaggtg cgggctgagc tgaccaggga gatatacacg  780
gacccggtgg tcagcacctc tctgtgggtg aacaacgcgc cgtccttcgg cgaaatcgag  840
aatctggcaa tccgagcgcc acgcaccgtg acatggctca attcgacgcg tattagcact  900
ggcacactcc aaggttggtc tgggtccaac aggtactggg ccgcccacat gcagaacttc  960
tcggagacta actccggcaa cataggcttc gacggcccgc tgtacgggtc cactgtgggt 1020
acaatcattc gcgatgacaa ttacgagatg gtcaaccggg acatttacac catcacttcg 1080
gaggcggttg cggctttgtg gcccacgggc cagattgtgc tgggcgtggc ttccgcaaga 1140
ttcaccctc gaaacctcaa caacaacctg acccaggcgc tggtctacga gaacccgata 1200
tcaagcagtt tcaaccggtc aactctcaca cgcgagttgc cgggcgagaa cagcgacagg 1260
cccacctctt cggactactc ccaccgtctc actagcatca ctgcgttccg cgcaggcagt 1320
aacggtacga ttcctgtgtt cggctggacc agtatctccg tcaacaggga caacatactg 1380
gagcggaaca agatcacccca gttccctggc gttaagtccc ataccctgaa caattgccag 1440
gtcgtccgcg gtacaggctt taccggcggc gactggcttc ggcctaacaa caacgggtcg 1500
ttccgattga ctatcacctc gttcagctca cagagttaca gaatcaggct gcggtacgcg 1560
tccgcagcga ataccccct gcgaatctcg tcttcggcgg ccgggatctc gtcaacaacc 1620
gtcccactcg cctccacgat cactagcctc ccgcagacag ccgtcccata cgaggcgttc 1680
cgggtgatcg acctgccaat cacgttcacc accgcgacgc agtctaacta cacttctgcg 1740
ttcgtcctcc agaatccttc caacgccaac gtgttcatcg accgcttcga gttgtcccg  1800
attggaggtt cgctctcaga gtacgagacg aagtga                          1836

SEQ ID NO: 81           moltype = AA  length = 611
FEATURE                 Location/Qualifiers
REGION                  1..611
                        note = The amino acid sequence of the
                          CR-BRE1a.TIC7381_3.nno_Mc:1 protein, comprising an
                          N-terminal and C-terminal truncation, an additional
                          alanine residue, and comprises amino acids 50 through 658
                          of TICTIC7381.
source                  1..611
                        mol_type = protein
                        organism = synthetic construct
SEQUENCE: 81
MATDNYTDAL QGPEATAISK GAVSAAISIS TKVLSLLGVP FAAQIGQLWT FILNALWPSD   60
NTQWEEFMRH VEELINQRIA DYARSKALAE LTGLGNNLDL YIEALEDWKR NPTSQQAKDR  120
VKDRFRIADG LFEAYMPSFR VSGYEVPLLT VYAAAANLHL LLLRDCSIYG IQWGFSQTNV  180
NENYNRQIRH TAEYANHCTT WYQTGLERLR GTNASSWWPY NRFRREMTLT VLDICSLFSN  240
YDYRSYPAEV RAELTREIYT DPVVSTSLWV NNAPSFGEIE NLAIRAPRTV TWLNSTRIST  300
GTLQGWSGSN RYWAAHMQNF SETNSGNIGF DGPLYGSTVG TIIRDDNYEM VNRDIYTITS  360
EAVAALWPTG QIVLGVASAR FTLRNLNNNL TQALVYENPI SSSFNRSTLT RELPGENSDR  420
PTSSDYSHRL TSITAFRAGS NGTIPVFGWT SISVNRDNIL ERNKITQFPG VKSHTLNNCQ  480
VVRGTGFTGG DWLRPNNNGS FRLTITSFSS QSYRIRLRYA SAANTSLRIS SSAAGISSTT  540
VPLASTITSL PQTAVPYEAF RVIDLPITFT TATQSNYTFD FVLQNPSNAN VFIDRFEFVP  600
IGGSLSEYET K                                                      611

SEQ ID NO: 82           moltype = DNA  length = 1833
FEATURE                 Location/Qualifiers
misc_feature            1..1833
                        note = A synthetic coding sequence used for expression in
                          plants encoding a CR-BRE1a.TIC7382_3.nno_Mc:1 protein with
                          an N-terminal and C-terminal truncation, and an additional
                          alanine codon after the intiating methionine relative to
                          TIC7382.
source                  1..1833
                        mol_type = other DNA
                        organism = synthetic construct
SEQUENCE: 82
```

-continued

```
atggccacta acaattacac cgacgcgctc cagtctccgg aagccacagc catttcgaag    60
ggggcggtct cggcggcgat cagcatcagc accaaggtgc tcggcctcct cggcgtgccg   120
ttcgcggctc agataggaca gctctggaca ttcattctga acgccctgtg gccgtccgac   180
aacacccagt ggggaggagtt catgcggcac gtcgaggagc tcatcaacca gcggatcgca   240
gactatgccc gtaacaaggc cctggccgag ctgacgggca acaacctcga cctc         300
tacatcgagg ccctggatga ctggaagagg aaccccacca gccaggaggc caagactcgc   360
gtcatcgacc gcttccgcat cgtcgacggg ctgttcgagg cctacattcc gagcttcgcc   420
gtgagcggct atcaagttca gctgctcact gtctacgccg ctgcagcaaa cctccacctc   480
ctgctgctgc gcgactccac gatctacgga atcgactggg gcctttccca gactaacgtc   540
aacgataact acaaccggca gattcgtctc accgcgcagt acgctaacca ctgtacaacg   600
tggtaccaga caggactgga gcggctccgc gggagcaacg cgtcttcctg ggtgacctac   660
aaccgtttcc ggagagagat gactctcaca gtcttggaca tctgttcctt gttcagcaac   720
tacgactatc gcagctaccc ggccgaggtt cgcggcgaga ttcgaggga aatctacaca    780
gaccctgtcg gcgtcggttg ggttgacagc gcgccttctt tcggcgagat cgagaacctg   840
gcgatccggg cgccacggac tgtgacctgg ctgaactcca cccggatctc accggcacc    900
ttaagcggct ggtcgggctc taaccggtac tgggcggccc acatgcagaa tttctccgag   960
acaaactcgg gtaacatcgg cttcgatggg ccgctgtacg ggagcacagt gggcaccatc  1020
caccgcactg atgactacga catgggcaac cgggacatct acacgataac gtcgcaggcc  1080
gttctcggtc tgtggcccac gggccagcgg gtcctgggag tcgcatctgc gcgtttcacc  1140
ctcaggaacc tattcaataa cctgacccag gtgctggtat acgagaatcc tattagctcc  1200
aacttcggct cttcaacgct aacccacgag ttatccggcg agaacagcga taggcccacc  1260
agcagcgatt actcacatcg actcacaagc atcacggagt tccgcgcagg agcaaatggt  1320
accgttcccg tctttgggtg gaccagcgcc acagtcgacc ggaacaacat catcgagcgc  1380
aacaagatca cgcagttccc aggcgtcaaa tcgcacacgc taaacaactg ccaggtggtg  1440
agggggaaccg gtttcaccgg aggtgactgg ttaagaccaa ataacaacgg cactttccgc  1500
ctcactatta cgagcttctc ctcccaaagt taccgcatcc gccttcgcta cgccacgtca  1560
gtggggaaca cctcgctggt gatatcctcc tcagacgccg ggatcagcac caccacgata  1620
ccactaacat ccacaataac ctcattgccg cagacggtcc cgtatcaggc cttcagagtg  1680
gtggaccttc ctattacgtt cacgacgccc acgacccagc gcaactacac attcgatttc  1740
cggttgcaga acccgagtaa cgccaatgtc ttcatcgatc gtttcgagtt cgtcccgata  1800
ggcggctccc tttcggagta cgaaacgaag tga                              1833
```

SEQ ID NO: 83                moltype = AA  length = 610
FEATURE                     Location/Qualifiers
REGION                      1..610
                            note = The amino acid sequence of the
                            CR-BRE1a.TIC7382_3.nno_Mc:1 protein, with an N-terminal
                            and C-terminal truncation, an additional alanine residue,
                            and comprises amino acids 52 through 659 of TIC7382.
source                      1..610
                            mol_type = protein
                            organism = synthetic construct SEQUENCE: 83
```
MATNNYTDAL QSPEATAISK GAVSAAISIS TKVLGLLGVP FAAQIGQLWT FILNALWPSD    60
NTQWEEFMRH VEELINQRIA DYARNKALAE LTGLGNNLDL YIEALDDWKR NPTSQEAKTR   120
VIDRFRIVDG LFEAYIPSFA VSGYQVQLLT VYAAAANLHL LLLRDSTIYG IDWGLSQTNV   180
NDNYNRQIRL TATYANHCTT WYQTGLERLR GSNASSWVTY NRFRREMTLT VLDICSLFSN   240
YDYRSYPAEV RGEITREIYT DPVGVGWVDS APSFGEIENL AIRAPRTVTW LNSTRISTGT   300
LSGWSGSNRY WAAHMQNFSE TNSGNIGFDG PLYGSTVGTI HRTDDYDMGN RDIYTITSQA   360
VLGLWPTGQR VLGVASARFT LRNLFNNLTQ VLVYENPISS NFGSSTLTHE LSGENSDRPT   420
SSDYSHRLTS ITGFRAGANG TVPVFGWTSA TVDRNNIIER NKITQFPGVK SHTLNNCQVV   480
RGTGFTGGDW LRPNNNGTFR LTITSFSSQS YRIRLRYATS VGNTSLVISS SDAGISSTTI   540
PLTSTITSLP QTVPYQAFRV VDLPITFTTP TTQRNYTFDF RLQNPSNANV FIDRFEFVPI   600
GGSLSEYETK                                                         610
```

SEQ ID NO: 84                moltype = DNA  length = 1968
FEATURE                     Location/Qualifiers
misc_feature                1..1968
                            note = A synthetic coding sequence used for expression in a
                            plant cell encoding a CR-BRE1a.TIC7383_19.nno_Mc:1
                            protein, with an N-terminal and C-terminal truncation
                            relative to the TIC7383 protein.
source                      1..1968
                            mol_type = other DNA
                            organism = synthetic construct SEQUENCE: 84
```
atgcagatca ttgaaccctc ctcggacagc ctcctgtaca gccataacaa ctacccgtac    60
gccactgacc caaacaccgt gctcgagggg cgcaactaca aggagtggct caacaaatgc   120
accgacaact acaccgacgc actccagggc cggaggcga gccatcga caagggtgcc      180
gtctccgcgg ccatctccat ctcgacgaag gtcctagggc tcctaggggt cccgttcgct   240
gcgcagattg ccagctgtg gacgttcatc cttaacgcac tctggccctc agacaacacc   300
cagtgggagg agttcatgcg ccacgtcgag gaactgatca ccagcgcat gcggactac    360
gcgaggaaca aggccctggc cgagctgaca gggctgggca caacctaga cctctacatc   420
gaggcgctg aggactggaa gcgaaaccct acctcccaac aagctaagga ccgttatc     480
gaccgcttcc gaatcgcgga cggcctcttc gaggggtaca tgccgagctt ccgggtctcg   540
ggctacgagg tgcccctcct cacggtgtac gcggcggcgg ctaatttgca tctcctgctg   600
ctcagggatt gctcgatcta cggaatccag tgggcttct cccagactaa cgttaacgag    660
aactacaatc ggcagattcg gcacaccgcc gagtacgcta accactgcac aacatggtat   720
cagaccggcc tcgagaggct gcgcggcacc aatgctttct catggatcaa ctacaaccgc   780
```

```
ttccgccgcg agatgacact gactgtcttg gacgtctgct ccctcttctc caactatgac  840
taccgcactt accccactga ggtccgggcc gagcttacgc gggagatcta cacagacccc  900
atcgggttcc agaactcccc gctccctggc gtggtcccca attggtacga ctacgcgagg  960
tcgttcgcgg aaatcgaaaa catcgccata cgagcacctc ggacagtcac gtggctgaac 1020
tcaaccacca tctacaccgg gagactgaac ggctacaaca atagcaacta ctactgggcc 1080
gggttccgcc agaacttctc agagaccaac tctggcagca gcttcaacgg cccagaccta 1140
ggcgacctca ctccgaacta caggatagag accctcgaca tggtcaacag ggacatctac 1200
agcatctact cccgggtcgt gtcgcaatcc tggcccatcg caacgtcaa gctcttcggc 1260
gtaagctcct ctaccttaag tttccgggat ctcaacaaca acagctccgg caccctggtc 1320
tacgagaacc cgactaactt cagctcccag tacctaacca cagagtttcc aggggagaac 1380
tccgagcggc ccaccttcac ggactacagt caccgcctaa cctgccttac gcggatcggg 1440
gccgggaact acggcctcgt gctttgtgcg ggttggactt cttcgagtgt cgaagggac  1500
aaccgcctac aacccgataa gattacccag taccccgccg tcaaggggtt caacttggac 1560
ggcttcacag tggtgaaagg gactggtttc accggggcga actggctgcg gtccagcagg 1620
gtcaccgggt cattccgcct gaacgtatac tcacctagtg tgcagactta tcggatgagg 1680
atcaggtacg cctccccgct tggcaactcg acgcttggga taagttcgac agacgccggc 1740
atctcgttca cgagtttccc tctgccctcc actatcggga gcatgccgtc cactgtgccc 1800
tacgaggtgc tccgtgtcct cgacatcccc atcacggtca ccgtagcctc ccaaaggaac 1860
tacaacttca tcttcgacat ccttaacccc tcggttgggg ccgtgtacat cgatcgtatt 1920
gagttcgtgc ccgtgggctc ttcagtgttc gagtacgaaa ccaagtga            1968

SEQ ID NO: 85          moltype = AA  length = 655
FEATURE                Location/Qualifiers
REGION                 1..655
                       note = The amino acid sequence of the
                       CR-BRE1a.TIC7383_19.nno_Mc:1 protein, and comprises amino
                       acids 15 through 668 of TIC7383.
source                 1..655
                       mol_type = protein
                       organism = synthetic construct
SEQUENCE: 85
MQIIEPSSDS LLYSHNNYPY ATDPNTVLEG RNYKEWLNKC TDNYTDALQG PEATAISKGA  60
VSAAISISTK VLGLLGVPFA AQIGQLWTFI LNALWPSDNT QWEEFMRHVE ELINQRIADY 120
ARNKALAELT GLGNNLDLYI EALEDWKRNP TSQQAKDRVI DRFRIADGLF EGYMPSFRVS 180
GYEVPLLTVY AAAANLHLLL LRDCSIYGIQ WGFSQTNVNE NYNRQIRHTA EYANHCTTWY 240
QTGLERLRGT NAFSWINYNR FRREMTLTVL DVCSLFSNYD YRTYPTEVRA ELTREIYTDP 300
IGFQNSPLPG VVPNWYDYAR SFAEIENIAI RAPRTVTWLN STTIYTGRLN GYNNSNYYWA 360
GFRQNFSETN SGSSFNGPDL GDLTPNYRIE TLDMVNRDIY SIYSRVVSQS WPIGNVKLFG 420
VSSSTLSFRD LNNNSSGTLV YENPTNFSSQ YLTTEFPGEN SERPTFTDYS HRLTCLTRIG 480
AGNYGLVLCA GWTSSSVERD NRLQPDKITQ YPAVKGFNLD GFTVVKGTGF TGGNWLRSSR 540
VTGSFRLNVY SPSVQTYRMR IRYASPLGNS TLGISSTDAG ISFTSFPLPS TIGSMPSTVP 600
YEAFRVLDIP ITVTVASQRN YNFIFDILNP SVGAVYIDRI EFVPVGSSVF EYETK      655

SEQ ID NO: 86          moltype = DNA  length = 1947
FEATURE                Location/Qualifiers
misc_feature           1..1947
                       note = A synthetic coding sequence used for expression in
                       plant cells encoding a CR-BRE1a.TIC7383_20.nno_Mc:1
                       protein, with an N-terminal and C-terminal truncation
                       relative to the TIC7383 protein.
source                 1..1947
                       mol_type = other DNA
                       organism = synthetic construct
SEQUENCE: 86
atgcagatca ttgaaccctc ctcggacagc ctcctgtaca gccataacaa ctacccgtac   60
gccactgacc caaacaccgt gctcgagggg cgcaactaca aggagtggct caacaaatgc  120
accgacaact acaccgacgc actccagggc cggaggcga cggccatcag caagggtgcc  180
gtctccgcgg ccatctccat ctcgacgaag gtcctagggc tcctaggggt cccgttcgct  240
gcgcagattg gccagctgtg gacgttcatc cttaacgcac tctggccctc agacaacacc  300
cagtgggagg agttcatgcg ccacgtcgag gaactgatca accagcgcat agcggactac  360
gcgaggaaca aggccctggc cgagctgaca gggctgggca caacctaga cctctacatc  420
gaggcgctcg aggactggaa gcggaaccct acctcccaac aagctaagga ccgcgttatc  480
gaccgcttcc gaatcgcgga cggcctcttc gaggggtaca tgccgagctt ccgggtctcg  540
ggctacgagg tgccctcct cacggtgtac gcggcgggag ctaatttgca tctcctgctg  600
ctcagggatt gctcgatcta cggaatccag tggggcttct cccagactaa cgttaacgag  660
aactacaatc ggcagattcg gcacaccgcc gagtacgcta accactgcac aacatggtat  720
cagaccggcc tcgagaggct gcgcggcacc aatgctttct catggatcaa ctacaaccgc  780
ttccgccgcg agatgacact gactgtcttg gacgtctgct ccctcttctc caactatgac  840
taccgcactt accccactga ggtccgggcc gagcttacgc gggagatcta cacagacccc  900
atcgggttcc agaactcccc gctccctggc gtggtcccca attggtacga ctacgcgagg  960
tcgttcgcgg aaatcgaaaa catcgccata cgagcacctc ggacagtcac gtggctgaac 1020
tcaaccacca tctacaccgg gagactgaac ggctacaaca atagcaacta ctactgggcc 1080
gggttccgcc agaacttctc agagaccaac tctggcagca gcttcaacgg cccagaccta 1140
ggcgacctca ctccgaacta caggatagag accctcgaca tggtcaacag ggacatctac 1200
agcatctact cccgggtcgt gtcgcaatcc tggcccatcg caacgtcaa gctcttcggc 1260
gtaagctcct ctaccttaag tttccgggat ctcaacaaca acagctccgg caccctggtc 1320
tacgagaacc cgactaactt cagctcccag tacctaacca cagagtttcc aggggagaac 1380
tccgagcggc ccaccttcac ggactacagt caccgcctaa cctgccttac gcggatcggg 1440
gccgggaact acggcctcgt gctttgtgcg ggttggactt cttcgagtgt cgaagggac  1500
```

```
aaccgcctac aacccgataa gattacccag taccccgccg tcaagggttt caacttggac  1560
ggcttcacag tggtgaaagg gactggtttc accggggggca actggctgcg gtccagcagg  1620
gtcaccgggt cattccgcct gaacgtatac tcacctagtg tgcagactta tcggatgagg  1680
atcaggtacg cctccccgct tggcaactcg acgcttggga taagttcgac agacgccggc  1740
atctcgttca cgagtttccc tctgccctcc actatcggga gcatgccgtc cactgtgccc  1800
tacgaggcgt tccgtgtcct cgacatcccc atcacggtca ccgtagcctc ccaaaggaac  1860
tacaacttca tcttcgacat ccttaacccc tcggttgggg ccgtgtacat cgatcgtatt  1920
gagttcgtgc ccgtgggctc ttcatga                                      1947

SEQ ID NO: 87           moltype = AA  length = 648
FEATURE                 Location/Qualifiers
REGION                  1..648
                        note = The amino acid sequence of the
                        CR-BRE1a.TIC7383_20.nno_Mc:1 protein, and comprises amino
                        acids 15 through 661 of TIC7383.
source                  1..648
                        mol_type = protein
                        organism = synthetic construct
SEQUENCE: 87
MQIIEPSSDS LLYSHNNYPY ATDPNTVLEG RNYKEWLNKC TDNYTDALQG PEATAISKGA   60
VSAAISISTK VLGLLGVPFA AQIGQLWTFI LNALWPSDNT QWEEFMRHVE ELINQRIADY  120
ARNKALAELT GLGNNLDLYI EALEDWKRNP TSQQAKDRVI DRFRIADGLF EGYMPSFRVS  180
GYEVPLLTVY AAAANLHLLL LRDCSIYGIQ WGFSQTNVNE NYNRQIRHTA EYANHCTTWY  240
QTGLERLRGT NAFSWINYNR FRREMTLTVL DVCSLFSNYD YRTYPTEVRA ELTREIYTDP  300
IGFQNSPLPG VVPNWYDYAR SFAEIENIAI RAPRTVTWLN STTIYTGRLN GYNNSNYYWA  360
GFRQNFSETN SGSSFNGPDL GDLTPNYRIE TLDMVNRDIY SIYSRVVSQS WPIGNVKLFG  420
VSSSTLSFRD LNNNSSGTLV YENPTNFSSQ YLTTEFPGEN SERPTFTDYS HRLTCLTRIG  480
AGNYGLVLCA GWTSSSVERD NRLQPDKITQ YPAVKGFNLD GFTVVKGTGF TGGNWLRSSR  540
VTGSFRLNVY SPSVQTYRMR IRYASPLGNS TLGISSTDAG ISFTSFPLPS TIGSMPSTVP  600
YEAFRVLDIP ITVTVASQRN YNFIFDILNP SVGAVYIDRI EFVPVGSS              648

SEQ ID NO: 88           moltype = DNA  length = 1833
FEATURE                 Location/Qualifiers
misc_feature            1..1833
                        note = A synthetic coding sequence used for expression in a
                        plant cell, encoding a CR-BRE1a.TIC7383_21.nno_Mc:1
                        protein with an N-terminal and C-terminal truncation, and
                        an additional alanine codon after the intiating methionine
                        relative to TIC7383.
source                  1..1833
                        mol_type = other DNA
                        organism = synthetic construct
SEQUENCE: 88
atggctaccg acaactacac cgacgcactc cagggcccgg aggcgacggc catcagcaag   60
ggtgccgtct ccgcggccat ctccatctcg acgaaggtcc tagggctcct aggggtcccg  120
ttcgctgcgc agattggcca gctgtggacg ttcatcctta cgcactctg gccctcgac   180
aacaccagt ggggaggagtt catgcgccac gtcgaggaac tgatcaacca gcgcatagcg  240
gactacgcga ggaacaaggc cctggccgag ctgacagggc tgggcaacaa cctagaccct  300
tacatcgagg cgctcgagga ctggaagcgg aaccctacct cccaacaagc taaggaccgc  360
gttatcgacc gcttccgaat cgcggacggc ctcttcgagg ggtacatgcc gagcttccgg  420
gtctcgggct acgaggtgcc cctcctcacg gtgtacgcgg cggcgctaa tttgcatctc  480
ctgctgctca gggattgctc gatctacgga atccagtggg gcttctccca gactaacgtt  540
aacgagaact acaatcggca gattcggcac accgccagt acgctaacca ctgcacaaca  600
tggtatcaga ccggcctcga gaggctgcgc ggcaccaatg ctttctcatg gatcaactac  660
aaccgcttcc gccgcgagat gacactgact gtcttgacg tctgctccct cttctccaac  720
tatgactacc gcacttaccc cactgaggtc cgggccgagc ttacgcggga gatctacaca  780
gaccccatcg ggttccagaa ctccccgctc cctggcgtgg tccccaattg gtacgactac  840
gcgaggtcgt tcgcggaaat cgaaaacatc gccatacgag cacctcggac agtcacgtgg  900
ctgaactcaa ccaccatcta caccgggaga ctgaacggct acaacaatag caactactac  960
tgggccgggt tccgccagaa cttctcagag accaactctg gcagcagctt caacggccca 1020
gacctaggcg acctcactcc gaactacagg atagagaccc tcgacatggt caacagggac 1080
atctacagca tctactcccg ggtcgtgtcg caatcctggc ccatcggcaa cgtcaagctc 1140
ttcggcgtaa gctcctctac cttaagtttc cgggatctca caacaacag ctccggcacc 1200
ctggtctacg agaacccgac taacttcagc tcccagtacc tcaccacaga gtttccaggg 1260
gagaactccg agcggcccac cttcacggac tacagtcacc gctaacctg ccttacgcgg 1320
atcggggccg gaactacgg cctcgtgctt tgtgcgggtt ggacttcttc gagtgtcgaa 1380
agggacaacc gctacaaacc cgataagatt cccagtacc ccgccgtcaa ggggttcaac 1440
ttggacggct tcacagtggt gaaagggact ggtttcaccg ggggcaactg gctgcggtcc 1500
agcaggtca ccgggtcatt ccgcctgaac gtatactcac ctagtgtgca gacttatcg 1560
atgaggatca ggtacgcctc cccgcttggc aactcgacgc ttgggataag ttcgacagac 1620
gccggcatct cgttcacgag tttcctctg ccctccacta tcgggagcat gccgtccact 1680
gtgccctacg aggcgttccg tgtcctcgac atccccatca cggtcaccgt agcctcccaa 1740
aggaactaca acttcatctt cgacatcctt aaccctcgg ttggggccgt gtacatcgat 1800
cgtattgagt tcgtgcccgt gggctcttca tga                             1833

SEQ ID NO: 89           moltype = AA  length = 610
FEATURE                 Location/Qualifiers
REGION                  1..610
                        note = The amino acid sequence of the
```

```
                    CR-BRE1a.TIC7383_21.nno_Mc:1 protein, with an N-terminal
                    and C-terminal truncation, an additional alanine residue,
                    and comprises amino acids 54 through 661 of TIC7383.
source              1..610
                    mol_type = protein
                    organism = synthetic construct
SEQUENCE: 89
MATDNYTDAL QGPEATAISK GAVSAAISIS TKVLGLLGVP FAAQIGQLWT FILNALWPSD   60
NTQWEEFMRH VEELINQRIA DYARNKALAE LTGLGNNLDL YIEALEDWKR NPTSQQAKDR  120
VIDRFRIADG LFEGYMPSFR VSGYEVPLLT VYAAAANLHL LLLRDCSIYG IQWGFSQTNV  180
NENYNRQIRH TAEYANHCTT WYQTGLERLR GTNAFSWINY NRFRREMTLT VLDVCSLFSN  240
YDYRTYPTEV RAELTREIYT DPIGFQNSPL PGVVPNWYDY ARSFAEIENI AIRAPRTVTW  300
LNSTTIYTGR LNGYNNSNYY WAGFRQNFSE TNSGSSFNGP DLGDLTPNYR IETLDMVNRD  360
IYSIYSRVVS QSWPIGNVKL FGVSSSTLSF RDLNNNSSGT LVYENPTNFS SQYLTTEFPG  420
ENSERPTFTD YSHRLTCLTR IGAGNYGLVL CAGWTSSSVE RDNRLQPDKI TQYPAVKGFN  480
LDGFTVVKGT GFTGGNWLRS SRVTGSFRLN VYSPSVQTYR MRIRYASPLG NSTLGISSTD  540
AGISFTSFPL PSTIGSMPST VPYEAFRVLD IPITVTVASQ RNYNFIFDIL NPSVGAVYID  600
RIEFVPVGSS                                                        610

SEQ ID NO: 90       moltype = DNA  length = 1851
FEATURE             Location/Qualifiers
misc_feature        1..1851
                    note = A synthetic coding sequence used for expression in
                    plant cells, encoding a CR-BRE1a.TIC7383_22.nno_Mc:1
                    protein, with an N-terminal and C-terminal truncation
                    relative to the TIC7383 protein.
source              1..1851
                    mol_type = other DNA
                    organism = synthetic construct
SEQUENCE: 90
atgaccgaca actacaccga cgcactccag ggcccggagg cgacggccat cagcaagggt    60
gccgtctccg cggccatctc catctcgacg aaggtcctag ggctcctagg ggtcccgttc   120
gctgcgcaga ttggccagct gtggacgttc atccttaacg cactctggcc ctcagacaac   180
acccagtggg aggagttcat gcgccacgtc gaggaactga tcaaccagcg catgcgctac   240
tacgcgagga acaaggccct ggccgagctg acagggctgg gcaacaacct agacctctac   300
atcgaggcgc tcgaggactg gaagcggaac cctacctccc aacaagctaa ggaccgcgtt   360
atcgaccgct tccgaatcgc ggacggcctc ttcgaggggt acatgccgag cttccgggtc   420
tcgggctacg aggtgcccct cctcacggtg tacgcggcgg cggctaattt gcatctcctg   480
ctgctcaggg attgctcgat ctacggaatc cagtgggcgt tctcccagac taacgttaac   540
gagaactaca atcggcagat tcggcacacc gccgagtacg ctaaccactg cacaacatgg   600
tatcagaccg gcctcgagag gctgcgcggc accaatgctt tctcatggat caactacaac   660
cgcttccgcc gcgagatgac actgactgtc ttggacgtct gctccctctt ctccaactat   720
gactaccgca cttacccccac tgaggtccgg gccgagctta cgcgggagat ctacacagac   780
cccatcgggt tccagaactc cccgctccct ggcgtggtcc ccaattggta cgactacgcg   840
aggtcgttcg cggaaatcga aaacatcgcc atacgagcac ctcggacagt cacgtggctg   900
aactcaacca ccatctacac cgggagactg aacggctaca caatagcaa ctactactgg   960
gccgggttcc gccagaactt ctcagagacc aactctggca gcagcttcaa cggcccagac  1020
ctaggcgacc tcactccgaa ctacaggata gagaccctcg acatggtcaa cagggacatc  1080
tacagcatct actcccgggt cgtgtcgcaa tcctggccca tcggcaacgt caagctcttc  1140
ggcgtaagct ccctctacct taagtttccg gatctcaaca caacagctc cggcaccctg  1200
gtctacgaga acccgactaa cttcagctcc cagtacctaa cacagagtt tccagggagg  1260
aactccgagc ggcccacctt cacgactac agtcaccgcc taacctgcct tacgcggatc  1320
ggggccggga actacggcct cgtgctttgt gcgggttgga cttcttcgag tgtcgaaagg  1380
gacaaccgcc tacaacccga taagattacc cagtaccccg ccgtcaaggg gttcaacttg  1440
gacggcttca cagtggtgaa agggactggt ttcaccgggg gcaactggct gcggtccagc  1500
agggtcaccg gtcattccg cctgaacgta tactcaccta gtgtgcagac ttatcggatg  1560
aggatcaggt acgcctcccc gcttggcaac tcgacgcttg gataagttc acagacgcc  1620
ggcatctcgt tcacgagttt ccctctgccc tccactatcg ggagcatgcc gtccactgtg  1680
ccctacgagg cgttccgtgt cctcgacatc cccatcacgg tcaccgtagc ctcccaaagg  1740
aactacaact tcatcttcga catccttaac ccctcggttg gggccgtgta catcgatcgt  1800
attgagttcg tgcccgtggg ctcttcagtg ttcgagtacg aaaccaagtg a           1851

SEQ ID NO: 91       moltype = AA  length = 616
FEATURE             Location/Qualifiers
REGION              1..616
                    note = The amino acid sequence of the
                    CR-BRE1a.TIC7383_22.nno_Mc:1 protein, and comprises amino
                    acids 54 through 668 of TIC7383.
source              1..616
                    mol_type = protein
                    organism = synthetic construct
SEQUENCE: 91
MTDNYTDALQ GPEATAISKG AVSAAISIST KVLGLLGVPF AAQIGQLWTF ILNALWPSDN   60
TQWEEFMRHV EELINQRIAD YARNKALAEL TGLGNNLDLY IEALEDWKRN PTSQQAKDRV  120
IDRFRIADGL FEGYMPSFRV SGYEVPLLTV YAAAANLHLL LLRDCSIYGI QWGFSQTNVN  180
ENYNRQIRHT AEYANHCTTW YQTGLERLRG TNAFSWINYN RFRREMTLTV LDVCSLFSNY  240
DYRTYPTEVR AELTREIYTD PIGFQNSPLP GVVPNWYDYA RSFAEIENIA IRAPRTVTWL  300
NSTTIYTGRL NGYNNSNYYW AGFRQNFSET NSGSSFNGPD LGDLTPNYRI ETLDMVNRDI  360
YSIYSRVVSQ SWPIGNVKLF GVSSSTLSFR DLNNNSSGTL VYENPTNFSS QYLTTEFPGE  420
```

| | | |
|---|---|---|
| NSERPTFTDY SHRLTCLTRI GAGNYGLVLC AGWTSSSVER DNRLQPDKIT QYPAVKGFNL | 480 | |
| DGFTVVKGTG FTGGNWLRSS RVTGSFRLNV YSPSVQTYRM RIRYASPLGN STLGISSTDA | 540 | |
| GISFTSFPLP STIGSMPSTV PYEAFRVLDI PITVTVASQR NYNFIFDILN PSVGAVYIDR | 600 | |
| IEFVPVGSSV FEYETK | 616 | |

```
SEQ ID NO: 92           moltype = DNA   length = 1830
FEATURE                 Location/Qualifiers
misc_feature            1..1830
                        note = A synthetic coding sequence used for expression in a
                          plant cell encoding a CR-BRE1a.TIC7383_23.nno_Mc:1
                          protein, with an N-terminal and C-terminal truncation
                          relative to the TIC7383 protein.
source                  1..1830
                        mol_type = other DNA
                        organism = synthetic construct
SEQUENCE: 92
atgaccgaca actacaccga cgcactccag ggcccggagg cgacggccat cagcaagggt   60
gccgtctccg cggccatctc catctcgacg aaggtcctag ggctcctagg ggtcccgttc  120
gctgcgcaga ttggccagct gtggacgttc atccttaacg cactctgcc ctcagacaac  180
acccagtggg aggagttcat gcgccacgtc gaggaactga tcaaccagcg catagcggac  240
tacgcgagga acaaggccct ggccgagctg acagggctgg gcaacaacct agacctctac  300
atcgaggcgc tcgaggactg gaagcgggaac cctacctccc aacaagctaa ggaccgcgtt  360
atcgaccgct tccgaatcgc ggacggcctc ttcgaggggt acatgccgag cttccgggtc  420
tcgggctacg aggtgcccct cctcacggtg tacgcggcgg cggctaattt gcatctcctg  480
ctgctcaggg attgctcgat ctacggaatc cagtgggct tctcccagac taacgttaac  540
gagaactaca atcggcagat tcggcacacc gccgagtacg ctaaccactg cacaacatgg  600
tatcagaccg gcctcgagag gctgcgcggc accaatgctt tctcatggat caactacaac  660
cgcttccgcc gcgagatgac actgactgtc ttggacgtct gctccctctt ctccaactat  720
gactaccgca cttaccccac tgaggtccgg gccgagctta cgcgggagat ctacacagac  780
cccatcgggt tccagaactc cccgctccct ggcgtggtc ccaattggta cgactacgg   840
aggtcgttcg cggaaatcga aaacatcgcc atacgagcac ctcggacagt cacgtggctg  900
aactcaacca ccatctacac cgggagactg aacggctaca caatagcaa ctactactgg  960
gccgggttcc gccagaactt ctcagagacc aactctggca gcagcttcaa cggcccagac 1020
ctaggcgacc tcactccgaa ctacaggata gagaccctcg acatggtcaa cagggacatc 1080
tacagcatct actccggggt cgtgtcgcaa tcctggccca tcggcaacgt caagctcttc 1140
ggcgtaagct cctctacctt aagtttccgg gatctcaaca acaacagctc cggcaccctg 1200
gtctacgaga acccgactaa cttcagctcc cagtacctaa ccacagagtt tccaggggag 1260
aactccgagc ggcccacctt cacggactac agtcaccgc taacctgcct tacgcggatc 1320
ggggccggga actacggcct cgtgctttgt gcgggttgga cttcttcgag tgtcgaaagg 1380
gacaaccgcc tacaacccga taagattacc cagtaccccg ccgtcaaggg gttcaacttg 1440
gacggcttca cagtggtgaa agggactggt ttcaccgggg gcaactggct gcggtccagc 1500
agggtcaccg ggtcattccg cctgaacgta tactcaccta gtgtgcagac ttatcggatg 1560
aggatcaggt acgcctcccc gcttggcaac tcgacgcttg ggataagttc gacagacgcc 1620
ggcatctcgt tcacgagttt ccctctgccc tccactatcg ggagcatgcc gtccactgtg 1680
ccctacgagg cgttccgtgt cctcgacatc cccatcacgg tcaccgtagc ctcccaaagg 1740
aactacaact tcatcttcga catccttaac ccctcggttg gggccgtgta catcgatcgt 1800
attgagttcg tgcccgtggg ctcttcatga                                  1830

SEQ ID NO: 93           moltype = AA   length = 609
FEATURE                 Location/Qualifiers
REGION                  1..609
                        note = The amino acid sequence of the
                          CR-BRE1a.TIC7383_23.nno_Mc:1 protein, and comprises amino
                          acids 54 through 661 of TIC7383.
source                  1..609
                        mol_type = protein
                        organism = synthetic construct
SEQUENCE: 93
MTDNYTDALQ GPEATAISKG AVSAAISIST KVLGLLGVPF AAQIGQLWTF ILNALWPSDN   60
TQWEEFMRHV EELINQRIAD YARNKALAEL TGLGNNLDLY IEALEDWKRN PTSQQAKDRV  120
IDRFRIADGL FEGYMPSFRV SGYEVPLLTV YAAAANLHLL LLRDCSIYGI QWGFSQTNVN  180
ENYNRQIRHT AEYANHCTTW YQTGLERLRG TNAFSWINYN RFRREMTLTV LDVCSLFSNY  240
DYRTYPTEVR AELTREIYTD PIGFQNSPLP GVVPNWYDYA RSFAEIENIA IRAPRTVTWL  300
NSTTIYTGRL NGYNNSNYYW AGFRQNFSET NSGSSFNGPD LGDLTPNYRI ETLDMVNRDI  360
YSIYSRVVSQ SWPIGNVKLF GVSSSTLSFR DLNNNSSGTL VYENPTNFSS QYLTTEFPGE  420
NSERPTFTDY SHRLTCLTRI GAGNYGLVLC AGWTSSSVER DNRLQPDKIT QYPAVKGFNL  480
DGFTVVKGTG FTGGNWLRSS RVTGSFRLNV YSPSVQTYRM RIRYASPLGN STLGISSTDA  540
GISFTSFPLP STIGSMPSTV PYEAFRVLDI PITVTVASQR NYNFIFDILN PSVGAVYIDR  600
IEFVPVGSS                                                          609

SEQ ID NO: 94           moltype = DNA   length = 1773
FEATURE                 Location/Qualifiers
misc_feature            1..1773
                        note = A synthetic coding sequence used for expression in a
                          plant cell encoding a CR-BRE1a.TIC7383_24.nno_Mc:2
                          protein, with an N-terminal and C-terminal truncation
                          relative to the TIC7383 protein.
source                  1..1773
                        mol_type = other DNA
```

-continued

```
                        organism = synthetic construct
SEQUENCE: 94
atggccgtct ccgcggccat ctccatctcg acgaaggtcc tagggctcct aggggtcccg    60
ttcgctgcgc agattggcca gctgtggacg ttcatcctta acgcactctg gccctcagac   120
aacacccagt ggaggagtt catgcgccac gtcgaggaac tgatcaacca gcgcatagcg    180
gactacgcga ggaacaaggc cctggccgag ctgacagggc tgggcaacaa cctagacctc   240
tacatcgagg cgctcgagga ctggaagcgg aaccctacct cccaacaagc taaggaccgc   300
gttatcgacc gcttccgaat cgcggacggc ctcttcgagg ggtacatgcc gagcttccgg   360
gtctcgggct acgaggtgcc cctcctcacg gtgtacgcgg cggcggctaa tttgcatctc   420
ctgctgctca gggattgctc gatctacgga atccagtggg gcttctccca gactaacgtt   480
aacgagaact acaatcggca gattcggcac accgccgagt acgctaacca ctgcacaaca   540
tggtatcaga ccgcctcga gaggctgcgc ggcaccaatg ctttctcatg gatcaactac    600
aaccgcttcc gccgcgagat gacactgact gtcttggacg tctgctccct cttctccaac   660
tatgactacc gcacttaccc cactgaggtc cgggccgagc ttacgcggga gatctacaca   720
gacccccatcg ggttccagaa ctcccgctc cctggcgtgg tccccaattg gtacgactac   780
gcgaggtcgt tcgcggaaat cgaaaacatc gccatacgag cacctcggac agtcacgtgg   840
ctgaactcaa ccaccatcta caccgggaga ctgaacggct acaacaatag caactactac   900
tgggccgggt tccgccagaa cttctcagag accaactctg gcagcagctt caacggccca   960
gacctaggcg acctcactcc gaactacagg atagagaccc tcgacatggt caacagggac  1020
atctacagca tctactcccg ggtcgtgtcg caatcctggc ccatcggcaa cgtcaagctc  1080
ttcggcgtaa gctcctctac cttaagtttc cgggatctca acaacaacag ctccggcacc  1140
ctggtctacg agaacccgac taacttcagc tcccagtacc tcacacaga gtttccaggg   1200
gagaactccg agcggcccac cttcacggac tacagtcacc gcctaacctg ccttacgcgg  1260
atcggggccg ggaactacgg cctcgtgctt tgtgcgggtt ggacttcttc gagtgtcgaa  1320
agggacaacc gcctacaacc cgataagatt cccagtacc ccgccgtcaa ggggttcaac    1380
ttggacggct tcacagtggt gaaagggact ggtttcaccg gggcaactg gctgcggtcc   1440
agcagggtca ccgggtcatt ccgcctgaac gtatactcac ctagtgtgca gacttatcgg  1500
atgaggatca ggtacgcctc cccgcttggc aactcgacgc ttgggataag ttcgacagac  1560
gccggcatct cgttcacgag tttccctctg ccctccacta tcgggagcat gccgtccact  1620
gtgccctacg aggcgttccg tgtcctcgac atccccatca cggtcaccgt agcctcccaa  1680
aggaactaca acttcatctt cgacatcctt aaccccctcg ttggggccgt gtacatcgat  1740
cgtattgagt tcgtgcccgt gggctcttca tga                              1773

SEQ ID NO: 95           moltype = AA   length = 590
FEATURE                 Location/Qualifiers
REGION                  1..590
                        note = The amino acid sequence of the
                        CR-BRE1a.TIC7383_24.nno_Mc:2 protein, and comprises amino
                        acids 73 through 661 of TIC7383.
source                  1..590
                        mol_type = protein
                        organism = synthetic construct
SEQUENCE: 95
MAVSAAISIS TKVLGLLGVP FAAQIGQLWT FILNALWPSD NTQWEEFMRH VEELINQRIA    60
DYARNKALAE LTGLGNNLDL YIEALEDWKR NPTSQQAKDR VIDRFRIADG LFEGYMPSFR   120
VSGYEVPLLT VYAAAANLHL LLLRDCSIYG IQWGFSQTNV NENYNRQIRH TAEYANHCTT   180
WYQTGLERLR GTNAFSWINY NRFRREMTLT VLDVCSLFSN YDYRTYPTEV RAELTREIYT   240
DPIGFQNSPL PGVVPNWYDY ARSFAEIENI AIRAPRTVTW LNSTTIYTGR LNGYNNSNYY   300
WAGFRQNFSE TNSGSSFNGP DLGDLTPNYR IETLDMVNRD IYSIYSRVVS QSWPIGNVKL   360
FGVSSSTLSF RDLNNNSSGT LVYENPTNFS SQYLTTEFPG ENSERPTFTD YSHRLTCLTR   420
IGAGNYGLVL CAGWTSSSVE RDNRLQPDKI TQYPAVKGFN LDGFTVVKGT GFTGGNWLRS   480
SRVTGSFRLN VYSPSVQTYR MRIRYASPLG NSTLGISSTD AGISFTSFPL PSTIGSMPST   540
VPYEAFRVLD IPITVTVASQ RNYNFIFDIL NPSVGAVYID RIEFVPVGSS              590

SEQ ID NO: 96           moltype = DNA   length = 1710
FEATURE                 Location/Qualifiers
misc_feature            1..1710
                        note = A synthetic coding sequence used for expression in a
                        plant cell encoding a CR-BRE1a.TIC7383_25.nno_Mc:3
                        protein, with N-terminal and C-terminal truncation
                        relative to the TIC7383 protein.
source                  1..1710
                        mol_type = other DNA
                        organism = synthetic construct
SEQUENCE: 96
atggcgcaga ttggccagct gtggacgttc atccttaacg cactctgcc ctcagacaac     60
acccagtggg aggagttcat gcgccacgtc gaggaactga tcaaccagcg catagcggac   120
tacgcgagga acaaggcct ggccgagctg acagggctgg caacaacct agacctctac    180
atcgaggcgc tcgaggactg gaagcggaac cctacctccc aacaagctaa ggaccgcgtt   240
atcgaccgct tccgaatcgc ggacggcctc ttcgagggt acatgccgag cttccgggtc    300
tcgggctacg aggtgcccct cctcacggtg tacgcggcgg cggctaattt gcatctcctg   360
ctgctcaggg attgctcgat ctacggaatc cagtgggct ctcccagac taacgttaac    420
gagaactaca atcggcagat tcggcacacc gccgagtacg ctaaccactg cacaacatgg   480
tatcagaccg gcctcgagag gctgcgcgg accaatgctt tctcatggat caactacaac    540
cgcttccgcc gcgagatgac actgactgtc ttggacgtct gctccctctt ccaactat    600
gactaccgca cttaccccac tgaggtccgg gccgagctta cgcgggagat ctacacagac   660
cccatcgggt tccagaactc cccgctccct ggcgtggtcc caattggta cgactacgcg   720
aggtcgttcg cggaaatcga aaacatcgcc atacgagcac ctcggacagt cacgtggctg   780
aactcaacca ccatctacac cgggagactg aacggctaca caatagcaa ctactactgg   840
```

```
gccgggttcc gccagaactt ctcagagacc aactctggca gcagcttcaa cggcccagac    900
ctaggcgacc tcactccgaa ctacaggata gagaccctcg acatggtcaa cagggacatc    960
tacagcatct actcccgggt cgtgtcgcaa tcctggccca tcggcaacgt caagctcttc   1020
ggcgtaagct cctctacctt aagtttccgg gatctcaaca caacagctc cggcaccctg   1080
gtctacgaga acccgactaa cttcagctcc cagtacctaa ccacagagtt tccaggggag   1140
aactccgagc ggcccacctt cacggactac agtcaccgcc taacctgcct tacgcggatc   1200
ggggccggga actacggcct cgtgctttgt gcgggttgga cttcttcgag tgtcgaaagg   1260
gacaaccgcc tacaacccga taagattacc cagtaccccg ccgtcaaggg gttcaacttg   1320
gacggcttca cagtggtgaa agggactggt ttcaccgggg gcaactggct gcggtccagc   1380
agggtcaccg ggtcattccg cctgaacgta tactcaccta gtgtgcagac ttatcggatg   1440
aggatcaggt acgcctcccc gcttggcaac tcgacgcttg gataagttc acagacgcc   1500
ggcatctcgt tcacgagttt ccctctgccc tccactatcg ggagcatgcc gtccactgtg   1560
ccctacgagg cgttccgtgt cctcgacatc cccatcacgg tcaccgtagc ctcccaaagg   1620
aactacaact tcatcttcga catccttaac ccctcggttg gggccgtgta catcgatcgt   1680
attgagttcg tgcccgtggg ctcttcatga                                     1710

SEQ ID NO: 97            moltype = AA   length = 569
FEATURE                  Location/Qualifiers
REGION                   1..569
                         note = The amino acid sequence of the
                         CR-BRE1a.TIC7383_25.nno_Mc:3 protein, and comprises amino
                         acids 94 through 661 of TIC7383.
source                   1..569
                         mol_type = protein
                         organism = synthetic construct
SEQUENCE: 97
MAQIGQLWTF ILNALWPSDN TQWEEFMRHV EELINQRIAD YARNKALAEL TGLGNNLDLY     60
IEALEDWKRN PTSQQAKDRV IDRFRIADGL FEGYMPSFRV SGYEVPLLTV YAAAANLHLL    120
LLRDCSIYGI QWGFSQTNVN ENYNRQIRHT AEYANHCTTW YQTGLERLRG TNAFSWINYN    180
RFRREMTLTV LDVCSLFSNY DYRTYPTEVR AELTREIYTD PIGFQNSPLP GVVPNWYDYA    240
RSFAEIENIA IRAPRTVTWL NSTTIYTGRL NGYNNSNYYW AGFRQNFSET NSGSSFNGPD    300
LGDLTPNYRI ETLDMVNRDI YSIYSRVVSQ SWPIGNVKLF GVSSSTLSFR DLNNNSSGTL    360
VYENPTNFSS QYLTTEFPGE NSERPTFTDY SHRLTCLTRI GAGNYGLVLC AGWTSSSVER    420
DNRLQPDKIT QYPAVKGFNL DGFTVVKGTG FTGGNWLRSS RVTGSFRLNV YSPSVQTYRM    480
RIRYASPLGN STLGISSTDA GISFTSFPLP STIGSMPSTV PYEAFRVLDI PITVTVASQR    540
NYNFIFDILN PSVGAVYIDR IEFVPVGSS                                      569

SEQ ID NO: 98            moltype = DNA   length = 1650
FEATURE                  Location/Qualifiers
misc_feature             1..1650
                         note = A synthetic coding sequence used for expression in a
                         plant cell encoding a CR-BRE1a.TIC7383_26.nno_Mc:1
                         protein, with an N-terminal and C-terminal truncation
                         relative to the TIC7383 protein.
source                   1..1650
                         mol_type = other DNA
                         organism = synthetic construct
SEQUENCE: 98
atgcagtggg aggagttcat gcgccacgtc gaggaactga tcaaccagcg catagcggac     60
tacgcgagga caaggccct ggccgagctg cagggctgg caacaacct agacctctac       120
atcgaggcgc tcgaggactg gaagcggaac cctacctccc aacaagctaa ggaccgcgtt    180
atcgaccgct tccgaatcgc ggacggcctc ttcgaggggt acatgccgag cttccgggtc    240
tcgggctacg aggtgcccct cctcacggtg tacgggcgg cggctaattt gcatctcctg    300
ctgctcaggg attgctcgat ctacggaatc cagtgggct ctcccagac taacgttaac     360
gagaactaca atcggcagat tcggcacacc gccgagtacg ctaacactg cacaacatgg    420
tatcagaccg gcctcgagag gctgcgcggc accaatgctt tctcatggat caactacaac    480
cgcttccgcc gcgagatgac actgactgtc ttggacgtct gctccctctt ctccaactat    540
gactaccgca cttaccccac tgaggtccgg gccgagctta cgcgggagat ctacacagac    600
cccatcgggt tccagaactc cccgctccct ggcgtgtcc ccaattggta cgactacgcg    660
aggtcgttcg cggaaatcga aaacatcgcc atacgagcac ctcggacagt cacgtggctg    720
aactcaacca ccatctacac cgggagactg aacggctaca caatagcaa ctactactgg    780
gccgggttcc gccagaactt ctcagagacc aactctggca gcagcttcaa cggcccagac    840
ctaggcgacc tcactccgaa ctacaggata gagaccctcg acatggtcaa cagggacatc    900
tacagcatct actcccgggt cgtgtcgcaa tcctggccca tcggcaacgt caagctcttc    960
ggcgtaagct cctctacctt aagtttccgg gatctcaaca caacagctc cggcaccctg   1020
gtctacgaga acccgactaa cttcagctcc cagtacctaa ccacagagtt tccaggggag   1080
aactccgagc ggcccacctt cacggactac agtcaccgcc taacctgcct tacgcggatc   1140
ggggccggga actacggcct cgtgctttgt gcgggttgga cttcttcgag tgtcgaaagg   1200
gacaaccgcc tacaacccga taagattacc cagtaccccg ccgtcaaggg gttcaacttg   1260
gacggcttca cagtggtgaa agggactggt ttcaccgggg gcaactggct gcggtccagc   1320
agggtcaccg ggtcattccg cctgaacgta tactcaccta gtgtgcagac ttatcggatg   1380
aggatcaggt acgcctcccc gcttggcaac tcgacgcttg gataagttc acagacgcc   1440
ggcatctcgt tcacgagttt ccctctgccc tccactatcg ggagcatgcc gtccactgtg   1500
ccctacgagg cgttccgtgt cctcgacatc cccatcacgg tcaccgtagc ctcccaaagg   1560
aactacaact tcatcttcga catccttaac ccctcggttg gggccgtgta catcgatcgt   1620
attgagttcg tgcccgtggg ctcttcatga                                     1650

SEQ ID NO: 99            moltype = AA   length = 549
FEATURE                  Location/Qualifiers
```

```
REGION                  1..549
                        note = The amino acid sequence of the
                        CR-BRE1a.TIC7383_26.nno_Mc:1 protein, and comprises amino
                        acids 114 through 661 of TIC7383.
source                  1..549
                        mol_type = protein
                        organism = synthetic construct
SEQUENCE: 99
MQWEEFMRHV EELINQRIAD YARNKALAEL TGLGNNLDLY IEALEDWKRN PTSQQAKDRV    60
IDRFRIADGL FEGYMPSFRV SGYEVPLLTV YAAAANLHLL LLRDCSIYGI QWGFSQTNVN   120
ENYNRQIRHT AEYANHCTTW YQTGLERLRG TNAFSWINYN RFRREMTLTV LDVCSLFSNY   180
DYRTYPTEVR AELTREIYTD PIGFQNSPLP GVVPNWYDYA RSFAEIENIA IRAPRTVTWL   240
NSTTIYTGRL NGYNNSNYYW AGFRQNFSET NSGSSFNGPD LGDLTPNYRI ETLDMVNRDI   300
YSIYSRVVSQ SWPIGNVKLF GVSSSTLSFR DLNNNSSGTL VYENPTNFSS QYLTTEFPGE   360
NSERPTFTDY SHRLTCLTRI GAGNYGLVLC AGWTSSSVER DNRLQPDKIT QYPAVKGFNL   420
DGFTVVKGTG FTGGNWLRSS RVTGSFRLNV YSPSVQTYRM RIRYASPLGN STLGISSTDA   480
GISFTSFPLP STIGSMPSTV PYEAFRVLDI PITVTVASQR NYNFIFDILN PSVGAVYIDR   540
IEFVPVGSS                                                           549

SEQ ID NO: 100          moltype = DNA   length = 1824
FEATURE                 Location/Qualifiers
misc_feature            1..1824
                        note = A synthetic coding sequence used for expression in a
                        plant cell encoding a CR-BRE1a.TIC7383_27.nno_Mc:1
                        protein, with an N-terminal and C-terminal truncation, and
                        an additional alanine codon after the initiating
                        methionine, relative to TIC7383.
source                  1..1824
                        mol_type = other DNA
                        organism = synthetic construct
SEQUENCE: 100
atggctaccg acaactacac cgacgcactc cagggcccgg aggcgacggc catcagcaag    60
ggtgccgtct ccgcggccat ctccatctcg acgaaggtcc tagggctcct aggggtcccg   120
ttcgctgcgc agattggcca gctgtggacg ttcatcctta acgcactctg gccctcagac   180
aacacccagt gggaggagtt catgcgccac gtcgaggaac tgatcaacca gcgcatagcg   240
gactacgcga ggaacaaggc cctggccgag ctgacagggc tgggcaacaa cctagacctc   300
tacatcgagg cgctcgagga ctggaagcgg aaccctacct cccaacaagc taaggaccgc   360
gttatcgacc gcttccgaat cgcggacggc ctcttcgagg ggtacatgcc gagcttccgg   420
gtctcgggct acgaggtgcc cctcctcacg gtgtacgcgg cggcgctaa tttgcatctc   480
ctgctgctca gggattgctc gatctacgga atccagtggg gcttctccca gactaacgtt   540
aacgagaact acaatcggca gattcggcac accgccgagt acgctaacca ctgcacaaca   600
tggtatcaga ccggcctcga gaggctgcgc ggcaccaatg ctttctcatg gatcaactac   660
aaccgcttcc gccgcgagat gacactgact gtcttggacg tctgctccct cttctccaac   720
tatgactacc gcacttaccc cactgaggtc cgggccgagc ttacgcggga gatctacaca   780
gaccccatcg ggttccagaa ctccccgctc cctggcgtgg tccccaattg gtacgactac   840
gcgaggtcgt tcgcggaaat cgaaaacatc gccatacgag cacctcggac agtcacgtgg   900
ctgaactcaa ccaccatcta cacggggaga ctgaacggct acaacaatag caactactac   960
tgggccgggt tccgccagaa cttctcagag accaactctg gcagcagctt caacggccca  1020
gacctaggcg acctcactcc gaactacagg atagagaccc tcgacatggt caacagggac  1080
atctacagca tctactcccg ggtcgtgtcg caatcctggc ccatcggcaa cgtcaagctc  1140
ttcggcgtaa gctcctctac cttaagtttc cgggatctca acaacaacag ctccggcacc  1200
ctggtctacg agaacccgac taacttcagc tcccagtacc taaccacaga gtttccaggg  1260
gagaactccg agcggcccac cttcacggac tacagtcacc gcctaacctg ccttacgcgg  1320
atcggggccg ggaactacgg cctcgtgctt tgtgcgggtt ggacttcttc gagtgtcgaa  1380
agggacaacc gcctacaacc cgataagatt acccagtacc ccgccgtcaa ggggttcaac  1440
ttggacggct tcacagtggt gaaagggact ggtttcaccg ggggcaactg gctgcggtcc  1500
agcagggtca ccgggtcatt ccgcctgaac gtatactcac ctagtgtgca gacttatcgg  1560
atgaggatca ggtacgcctc cccgcttggc aactcgacgc ttgggataag ttcgacagac  1620
gccggcatct cgttcacgag tttccctctg ccctccacta tcgggagcat gccgtccact  1680
gtgccctacg aggcgttccg tgtcctcgac atcccccatca cggtcaccgt agcctcccaa  1740
aggaactaca acttcatctt cgacatcctt aaccctcgg ttggggccgt gtacatcgat  1800
cgtattgagt tcgtgcccgt gtga                                          1824

SEQ ID NO: 101          moltype = AA   length = 607
FEATURE                 Location/Qualifiers
REGION                  1..607
                        note = The amino acid sequence of the
                        CR-BRE1a.TIC7383_27.nno_Mc:1 protein, with an N-terminal
                        and C-terminal truncation, an additional alanine residue,
                        and comprises amino acids 54 through 658 of TIC7383.
source                  1..607
                        mol_type = protein
                        organism = synthetic construct
SEQUENCE: 101
MATDNYTDAL QGPEATAISK GAVSAAISIS TKVLGLLGVP FAAQIGQLWT FILNALWPSD    60
NTQWEEFMRH VEELINQRIA DYARNKALAE LTGLGNNLDL YIEALEDWKR NPTSQQAKDR   120
VIDRFRIADG LFEGYMPSFR VSGYEVPLLT VYAAAANLHL LLLRDCSIYG IQWGFSQTNV   180
NENYNRQIRH TAEYANHCTT WYQTGLERLR GTNAFSWINY NRFRREMTLT VLDVCSLFSN   240
YDYRTYPTEV RAELTREIYT DPIGFQNSPL PGVVPNWYDY ARSFAEIENI AIRAPRTVTW   300
```

```
LNSTTIYTGR LNGYNNSNYY WAGFRQNFSE TNSGSSFNGP DLGDLTPNYR IETLDMVNRD    360
IYSIYSRVVS QSWPIGNVKL FGVSSSTLSF RDLNNNSSGT LVYENPTNFS SQYLTTEFPG    420
ENSERPTFTD YSHRLTCLTR IGAGNYGLVL CAGWTSSSVE RDNRLQPDKI TQYPAVKGFN    480
LDGFTVVKGT GFTGGNWLRS SRVTGSFRLN VYSPSVQTYR MRIRYASPLG NSTLGISSTD    540
AGISFTSFPL PSTIGSMPST VPYEAFRVLD IPITVTVASQ RNYNFIFDIL NPSVGAVYID    600
RIEFVPV                                                              607

SEQ ID NO: 102          moltype = DNA  length = 1938
FEATURE                 Location/Qualifiers
misc_feature            1..1938
                        note = A synthetic coding sequence used for expression in a
                        plant cell encoding a CR-BRE1a.TIC7383_28.nno_Mc:1 protein
                        with an N-terminal and C-terminal truncation relative to
                        the TIC7383 protein.
source                  1..1938
                        mol_type = other DNA
                        organism = synthetic construct
SEQUENCE: 102
atgcagatca ttgaaccctc ctcggacagc ctcctgtaca gccataacaa ctacccgtac     60
gccactgacc caaacaccgt gctcgagggg cgcaactaca aggagtggct caacaaatgc    120
accgacaact acaccgacgc actccagggc ccggaggcga cggccatcag caagggtgcc    180
gtctccgcgg ccatctccat ctcgacgaag gtcctaggcc tcctagggt ccgttcgct     240
gcgcagattg gccagctgtg gacgttcatc cttaacgcac tctggcctc agacaacacc    300
cagtgggagg agttcatgcg ccacgtcgag aactgatca accagcgcat agcggactac    360
gcgaggaaca aggccctggc cgagctgaca gggctgggca caacctaga cctctacatc    420
gaggcgctcg aggactggaa gcggaaccct acctcccaac aagctaagga ccgcgttatc    480
gaccgcttcc gaatcgcgga cggcctcttc gagggtaca tgccgagctt ccgggtctcg    540
ggctacgagg tgcccctcct cacggtgtac gcggcggcgg ctaatttgca tctcctgctg    600
ctcagggatt gctcgatcta cggaatccag tggggcttct cccagactaa cgttaacgag    660
aactacaatc ggcagattcg gcacaccgcc gagtacgcta accactgcac aacatggtat    720
cagaccggcc tcgagaggct gcgcggcacc aatgctttct catggatcaa ctacaaccgc    780
ttccgccgcg agatgacact gactgtcttg gactctgct ccctcttctc caactatgac    840
taccgcactt accccactga ggtccgggcc gagcttacgc gggagatcta cacagacccc    900
atcgggttcc agaactcccc gctccctggc gtggtcccaa attggtacga ctacgcgagg    960
tcgttcgcgg aaatcgaaaa catcgccata cgagcacctc ggacagtcac gtggctgaac   1020
tcaaccacca tctacaccgg gagactgaac ggctacaaca atagcaacta ctactgggcc   1080
gggttccgcc agaacttctc agagaccaac tctggcagca gcttcaacgg cccagaccta   1140
ggcgacctac ctccgaacta caggatagag accctcgaca tggtcaacag ggacatctac   1200
agcatctact cccgggtcgt gtcgcaatcc tggcccatcg gcaacgtcaa gctcttcggc   1260
gtaagctcct ctaccttaag tttccgggat ctcaacaaca acagctccgg caccctggtc   1320
tacgagaacc cgactaactt cagctcccag tacctaacca cagagtttcc aggggagaac   1380
tccgagcggc caccttcac ggactacagt accgcctaa cctgccttac gcggatcggg    1440
gccgggaact acggcctcgt gctttgtgcg ggttggactt cttcgagtgt cgaaaggac    1500
aaccgcctac aacccgataa gattacccag taccccgccg tcaagggttt caacttggac   1560
ggcttcacag tggtgaaagg gactggtttc accggggggca actggctgcg gtccagcagg   1620
gtcaccgggt cattccgcct gaacgtatac tcacctagtg tgcagactta tcggatgagg   1680
atcaggtacg cctcccgct tggcaactcg acgcttggta taagttcgac agacgccggc   1740
atctcgttca cgagtttccc tctgccctcc actatcggga gcatgccgtc cactgtgccc   1800
tacgaggcgt tccgtgtcct cgacatcccc atcacggtca ccgtagcctc ccaaaggaac   1860
tacaacttca tcttcgacat ccttaacccc tcggttgggg ccgtgtacat cgatcgtatt   1920
gagttcgtgc ccgtgtga                                                1938

SEQ ID NO: 103          moltype = AA  length = 645
FEATURE                 Location/Qualifiers
REGION                  1..645
                        note = The amino acid sequence of the
                        CR-BRE1a.TIC7383_28.nno_Mc:1 protein, and comprises amino
                        acids 15 through 658 of TIC7383.
source                  1..645
                        mol_type = protein
                        organism = synthetic construct
SEQUENCE: 103
MQIIEPSSDS LLYSHNNYPY ATDPNTVLEG RNYKEWLNKC TDNYTDALQG PEATAISKGA     60
VSAAISISTK VLGLLGVPFA AQIGQLWTFI LNALWPSDNT QWEEFMRHVE ELINQRIADY    120
ARNKALAELT GLGNNLDLYI EALEDWKRNP TSQQAKDRVI DRFRIADGLF EGYMPSFRVS    180
GYEVPLLTVY AAAANLHLLL LRDCSIYGIQ WGFSQTNVNE NYNRQIRHTA EYANHCTTWY    240
QTGLERLRGT NAFSWINYNR FRREMTLTVL DVCSLFSNYD YRTYPTEVRA ELTREIYTDP    300
IGFQNSPLPG VVPNWYDYAR SFAEIENIAI RAPRTVTWLN STTIYTGRLN GYNNSNYYWA    360
GFRQNFSETN SGSSFNGPDL GDLTPNYRIE TLDMVNRDIY SIYSRVVSQS WPIGNVKLFG    420
VSSSTLSFRD LNNNSSGTLV YENPTNFSSQ YLTTEFPGEN SERPTFTDYS HRLTCLTRIG    480
AGNYGLVLCA GWTSSSVERD NRLQPDKITQ YPAVKGFNLD GFTVVKGTGF TGGNWLRSSR    540
VTGSFRLNVY SPSVQTYRMR IRYASPLGNS TLGISSTDAG ISFTSFPLPS TIGSMPSTVP    600
YEAFRVLDIP ITVTVASQRN YNFIFDILNP SVGAVYIDRI EFVPV                    645

SEQ ID NO: 104          moltype = DNA  length = 2895
FEATURE                 Location/Qualifiers
misc_feature            1..2895
                        note = A synthetic coding sequence used for expression in a
                        plant cell encoding a CR-BRE1a.TIC7383_29.nno_Mc:1 protein
```

-continued

```
                            with, and an additional alanine codon, and a C-terminal
                            truncation relative to the TIC7383 protein.
source                      1..2895
                            mol_type = other DNA
                            organism = synthetic construct
SEQUENCE: 104
atggctaacc agaaccagaa ccaaaaccag aacaagaacg agctgcagat cattgaaccc    60
tcctcggaca gcctcctgta cagccataac aactacccgt acgccactga cccaaacacc   120
gtgctcgagg ggcgcaacta caaggagtgg ctcaacaaat gcaccgacaa ctacaccgac   180
gcactccagg gcccggaggc gacggccatc agcaagggtg ccgtctccgc ggccatctcc   240
atctcgacga aggtcctagg gctcctaggg gtcccgttcg ctgcgcagat tggccagctg   300
tggacgttca tccttaacgc actctggccc tcagacaaca cccagtggga ggagttcatg   360
cgccacgtcg aggaactgat caaccagcgc atagcggact acgcgaggaa caaggccctg   420
gccgagctga cagggctggg caacaaccta gacctctaca tcgaggcgct cgaggactgg   480
aagcggaacc ctacctccca acaagctaag gaccgcgtta tcgaccgctt ccgaatcgcg   540
gacggcctct tcgaggggta catgccgagc ttccgggtct cgggctacga ggtgcccctc   600
ctcacgcgtgt acgcggcggc ggctaatttg catctcctgc tgctcaggga ttgctcgatc   660
tacggaatcc agtggggctt ctcccagact aacgttaacg agaactacaa tcggcagatt   720
cggcacaccg ccgagtacgc taaccactgc acaacatggt atcagaccgg cctcgagagg   780
ctgcgcggca ccaatgcttt ctcatggatc aactacaacc gcttccgccg cgagatgaca   840
ctgactgtct tggacgtctg ctccctcttc tccaactatg actaccgcac ttaccccact   900
gaggtccggg ccgagcttac gcgggagatc tacacagacc ccatcgggtt ccagaactgc   960
ccgctccctg gcgtggtccc caattggtac gactacgcga ggtcgttcgc ggaaatcgaa  1020
aacatcgcca tacgagcacc tcggacagtc acgtggctga actcaaccac catctacacc  1080
gggagactga acggctacaa caatagcaac tactactggg ccgggttccg ccagaacttc  1140
tcagagacca actctggcag cagcttcaac ggcccagacc taggcgacct cactccgaac  1200
tacaggatag agaccctcga catggtcaac agggacatct cagcatcta ctcccgggtc   1260
gtgtcgcaat cctggcccat cggcaacgtc aagctcttcg gcgtaagctc ctctaccttta  1320
agtttccggg atctcaacaa caacagctcc ggcaccctgg tctacgagaa cccgactaac  1380
ttcagctccc agtacctaac cacagagttt ccagggagga actccgagcg gcccacctttc  1440
acggactaca gtcaccgcct aacctgcctt acgcgggatcg gggccgggaa ctacggcctc  1500
gtgctttgtg cggggttggac ttcttcgagt gtcgaagggg acaaccgcct acaacccgat  1560
aagattaccc agtaccccgc cgtcaagggg ttcaacttgg acggcttcac agtggtgaaa  1620
gggactggtt tcaccggggg caactggctg cggtccagca gggtcaccgg gtcattccgc  1680
ctgaacgtat actcacctag tgtgcagact tatcggatga gggatcaggta cgctccccg   1740
cttggcaact cgacgcttgg gataagttcg acagacgccg gcatctcgtt cacgagttc   1800
cctctgccct ccactatcgg gagcatgccg tccactgtgc cctacgaggc gttccgtgtc  1860
ctcgacatcc ccatcacggt caccgtagcc tcccaaagga actacaactt catcttcgac  1920
atccttaacc cctcggttgg ggccgtgtac atcgatcgta ttgagttcgt gcccgtgggc  1980
tcttcagtgt tcgagtacga aaccaagcac gagcttgaaa aggcgaaaaa agcagttaac  2040
gacctcttca cgaacgagtc caaaaacatg ttaaagaaag acacgaccga ctacgacatc  2100
gaccaggctg cggacctggt ggagtgcgta agcgacgagt gcgcccacgc taagatgata  2160
ctgctggacg aagtgaagta cgcgaagcag ctgagcgagg ctccagaac   2220
gggaacttca aggtcttaga cgttgacaac aacaacccgt ggacgacctc accgaacgta  2280
acgatccagg agaacaaccc gatcttcaaa ggtcactacc tctccatgtc cggtgcgaac  2340
gcaatcgagg ccaccaacga ggtgttccca acgtacgtgt accaaaagat tgaggagagt  2400
aaactcaagc cctacacaag gtacaaggtg cgggggttcg ccggccagag caaggacgtc  2460
gagctgctcg tcacgcgtta cgacgaggag gtggacgcta ttctgaacgt gcctaacgac  2520
ctaaagtacg cagtgccgac gcacctgtcg ggagagttca accgctgcaa gcctcacact  2580
tacccggcca cagaccccg atgccacgac gacgtgatcg acaagatcga catctcctcg  2640
ccgtgtcaga caacattat gctgtcggac gcggacactt ctagtcttca tagcggactt  2700
ggcaagaagc acgggatctg ccacgagagc catcacttcg agttccacat cgacacgggc  2760
aaaatcgacc tcgtggagaa ccttggcatc tgggtgatct tcaagatctg ctctaccgac  2820
ggatacgcga cgctcgacaa tctgaagtaa atagaggaag gccgttgggg cgcagagtcc  2880
ctagagcggg tgtag                                                   2895

SEQ ID NO: 105             moltype = AA   length = 964
FEATURE                    Location/Qualifiers
REGION                     1..964
                           note = The amino acid sequence of the
                           CR-BRE1a.TIC7383_29.nno_Mc:1 protein, with an additional
                           alanine residue, and comprises amino acids 1 through 963
                           of TIC7383.
source                     1..964
                           mol_type = protein
                           organism = synthetic construct
SEQUENCE: 105
MANQNQNQNQ NKNELQIIEP SSDSLLYSHN NYPYATDPNT VLEGRNYKEW LNKCTDNYTD    60
ALQGPEATAI SKGAVSAAIS ISTKVLGLLG VPFAAQIGQL WTFILNALWP SDNTQWEEFM   120
RHVEELINQR IADYARNKAL AELTGLGNNL DLYIEALEDW KRNPTSQQAK DRVIDRFRIA   180
DGLFEGYMPS FRVSGYEVPL LTVYAAAANL HLLLLRDCSI YGIQWGFSQT NVNENYNRQI   240
RHTAEYANHC TTWYQTGLER LRGTNAFSWI NYNRFRREMT LTVLDVCSLF SNYDYRTYPT   300
EVRAELTREI YTDPIGFQNS PLPGVVPNWY DYARSFAEIE NIAIRAPRTV TWLNSTTIYT   360
GRLNGYNNSN YYWAGFRQNF SETNSGSSFN GPDLGDLTPN YRIETLDMVN RDIYSIYSRV   420
VSQSWPIGNV KLFGVSSSTL SFRDLNNNSS GTLVYENPTN FSSQYLTTEF PGENSERPTF   480
TDYSHRLTCL TRIGAGNYGL VLCAGWTSSS VERDNRLQPD KITQYPAVKG FNLDGFTVVK   540
GTGFTGGNWL RSSRVTGSFR LNVYSPSVQT YRMRIRYASP LGNSTLGISS TDAGISFTSF   600
PLPSTIGSMP STVPYEAFRV LDIPITVTVA SQRNYNFIFD ILNPSVGAVY IDRIEFPVPG   660
SSVFEYETKH ELEKAKKAVN DLFTNESKNM LKKDTTDYDI DQAADLVECV SDECAHAKMI   720
```

```
LLDEVKYAKQ LSEARNLLQN GNFKVLDVDN NNPWTTSPNV TIQENNPIFK GHYLSMSGAN  780
AIEATNEVFP TYVYQKIEES KLKPYTRYKV RGFIGQSKDV ELLVTRYDEE VDAILNVPND  840
LKYAVPTHLS GEFNRCKPHT YPATDPRCHD DVIDKIDISS PCQNNIMLSD ADISSLHSGL  900
GKKHGICHES HHFEFHIDTG KIDLVENLGI WVIFKICSTD GYATLDNLEV IEEGPLGAES  960
LERV                                                             964

SEQ ID NO: 106         moltype = DNA   length = 3774
FEATURE                Location/Qualifiers
misc_feature           1..3774
                       note = A synthetic coding sequence used for expression in a
                       plant cell encoding a CR-BRE1a.TIC7383_30.nno_Mc:1
                       protein, comprising an additional alanine codon, and
                       mutations to the codons corresponding amino acid positions
                       964, 966, and 968 relative to
source                 1..3774
                       mol_type = other DNA
                       organism = synthetic construct
SEQUENCE: 106
atggctaacc agaaccagaa ccaaaaccag aacaagaacg agctgcagat cattgaaccc   60
tcctcggaca gcctcctgta cagccataac aactaccgt acgccactga cccaaacacc   120
gtgctcgagg ggcgcaacta caaggagtgg ctcaacaaat gcaccgacaa ctacaccgac   180
gcactccagg gcccggaggc gacggccatc agcaaggcgt ccgtctccgc ggccatctcc   240
atctcgacga aggtcctagg gctcctaggg gtcccgttcg ctgcgcagat tggccagctg   300
tggacgttca tccttaacgc actctggccc tcagacaaca cccagtggga ggagttcatg   360
cgccacgtcg aggaactgat caaccagcgc atagcggact acgcgaggaa caaggccctg   420
gccgagctga cagggctggg caacaaccta gacctctaca tcgaggcgct cgaggactgg   480
aagcggaacc ctacctccca acaagctaag gaccgcgtta tcgaccgctt ccgaatcgcg   540
gacggcctct tcgaggggta catgccgagc ttccgggtct cgggctacga ggtgcccctc   600
ctcacggtgt acgcggcggc ggctaatttg catctcctgc tgctcaggga ttgctcgatc   660
tacggaatcc agtggggctt ctcccagact aacgttaacg agaactacaa tcggcagatt   720
cggcacaccg ccgagtacgc taaccactgc acaacatggt atcagaccgg cctcgagagg   780
ctgcgcggca ccaatgcttt ctcatggatc aactacaacc gcttccgccg cgagatgaca   840
ctgactgtct tggacgtctg ctccctcttc tccaactatg actaccgcac ttaccccact   900
gaggtccggg ccgagcttac gcgggagatc tacacagacc ccatcgggtt ccagaactcc   960
ccgctccctg gcgtggtccc caattggtac gactacgcga ggtcgttcgc ggaaatcgaa  1020
aacatcgcca tacgagcacc tcggacagtc acgtggctga actcaaccac catctacacc  1080
gggagactga acggctacaa caatagcaac tactactggg ccgggttccg ccagaacttc  1140
tcagagacca actctggcag cagcttcaac ggcccagacc taggcgacct cactccgaac  1200
tacaggatag agaccctcga catggtcaac agggacatct acagcatcta ctcccgggtc  1260
gtgtcgcaat cctggcccat cggcaacgtc aagctcttcg gcgtaagctc ctctacctta  1320
agtttccggg atctcaacaa caacagctcc ggcaccctgg tctacgagaa cccgactaac  1380
ttcagctccc agtacctaac cacagagttt ccaggggaga actccgagcg gcccaccttc  1440
acggactaca gtcaccgcct aacctgcctt acgcggatcg gggccgggaa ctacggcctc  1500
gtgctttgtg cgggttggac ttcttcgagt gtcgaaaggg acaaccgcct acaacccgat  1560
aagattaccc agtaccccgc cgtcaagggg ttcaacttgg acggcttcac agtggtgaaa  1620
gggactggtt tcaccggggg caactggctg cggtccagca gggtcaccgg tcattccgc  1680
ctgaacgtat actcacctag tgtgcagact tatcggatga ggtcaggta cgcctccccg  1740
cttggcaact cgacgcttgg gataagttcg acagacgccg gcatctcgtt cacgagtttc  1800
cctctgccct ccactatcgg gagcatgccg tccactgtgc cctacgaggc gttccgtgtc  1860
ctcgacatcc ccatcacggt caccgtagcc tcccaaagga actacaactt catcttcgac  1920
atccttaacc cctcggttgg ggccgtgtac atcgatcgta ttgagtttcgt gcccgttggg  1980
tcttcagtgt tcgagtacga aaccaagcac gagcttgaaa aggcgaaaaa agcagttaac  2040
gacctcttca cgaacgagtc caaaaacatg ttaaagaaag acacgaccga ctacgacatc  2100
gaccaggctg cggacctggt ggagtgcgta agcgacgagt gcgcccacgc taagatgata  2160
ctgctggacg aagtgaagta cgcgaagcag ctgagcgagg ctcggaacct gctccagaac  2220
gggaacttca aggtcttaga cgttgacaac aacaacccgt ggacgacctc accgaacgta  2280
acgatccagg agaacaaccc gatcttcaaa ggtcactacc tctccatgtc cggtgcgaac  2340
gcaatcgagg ccaccaacga ggtgttccca acgtacgtgt accaaaagat tgaggagagt  2400
aaactcaagc cctacacaag gtacaaggtg cggggggttca tcggccagag caaggacgtg  2460
gagctgctcg tcacgcgtta cgacgaggag gtggacgcta ttctgaacgt gcctaacgac  2520
ctaaagtacg cagtgccgac gcacctgtcg ggagagttca accgctgcaa gcctcacact  2580
tacccggcca cagaccccg atgccacgac gacgtgatcg acaagatcga catctcctcg  2640
ccgtgtcaga caacattat gctgtcggac gcggacatct ctagtcttca tagcggactt  2700
ggcaagaagc acgggatctg ccacgagagc catcacttcg agttccacat cgacacgggt  2760
aaaatcgacc tcgtggagaa ccttggcatc tgggtgatct tcaagatctg ctctaccgac  2820
ggatacgcga cgctcgacaa tctggaagta atagaggaag gcccgttggg cgcagagtcc  2880
ctagagcggg tggcacgtgc ggaggctaag tggaagcata acatggagca caagtgctcg  2940
gaaacgaaac acgcatacca cgcggcgaag caggctgtcg aagcactctt cacgaacttc  3000
aaggacgctc aagtt cgagacgacg attagtaca tcctgtcagc tgagtactca  3060
gtccagtcca tcccatacgt ctacaacaag tggctgtcgg acgtacctgg gatgaactac  3120
gacatctaca ccgagctcaa gaaccgcatc tggcaagcgt tcaacttgta cgaccagagg  3180
aacatcatca gaacggcca cttcaatcat ggtttaatgc attggcacgc gacaccgcac  3240
gcgaacgtgc agcaaataga cggtatttcc gtgctggtcc tcccaaactg ggggccaac   3300
gtcagcagg agggtgcct caagcacgac cggggctacg tgctgcgagt cacggccaa   3360
gaggaggtc acggcaaggg ctacgtgacg atttcggact cgctaaccac ggtcgagaag  3420
ctgtcgttca ctagccgcga ctactctacc gacggcgtcc catacgaaca gtccaactac  3480
ccgaccgacg gagtgtctta cggcagcac gggtgcaaca tcgaccgagt gccctacgag   3540
caatctggct accccaccga cggggttcct tacgaacagt cgggctaccg tacggacggg  3600
gtcccgtaca agcagcatgg atgccactcg gacggaagc gtgaggagca gcacggggtac  3660
```

```
gttacgaaga ctatcgacgt cttccccgac acggacaagg tccggatcga catcggcgag  3720
accgagggga cgttcaaggt tgagagcgtg gagctcatct gcatggagga gtag         3774
```

| | | |
|---|---|---|
| SEQ ID NO: 107 | moltype = AA  length = 1257 | |
| FEATURE | Location/Qualifiers | |
| REGION | 1..1257 | |
| | note = The amino acid sequence of the CR-BRE1a.TIC7383_30.nno_Mc:1 protein, with an additional alanine residue, and comprises the mutations, K964A; R966A; K968A, relative to TIC7383. | |
| source | 1..1257 | |
| | mol_type = protein | |
| | organism = synthetic construct | |

```
SEQUENCE: 107
MANQNQNQNQ NKNELQIIEP SSDSLLYSHN NYPYATDPNT VLEGRNYKEW LNKCTDNYTD   60
ALQGPEATAI SKGAVSAAIS ISTKVLGLLG VPFAAQIGQL WTFILNALWP SDNTQWEEFM  120
RHVEELINQR IADYARNKAL AELTGLGNNL DLYIEALEDW KRNPTSQQAK DRVIDRFRIA  180
DGLFEGYMPS FRVSGYEVPL LTVYAAAANL HLLLLRDCSI YGIQWGFSQT NVNENYNRQI  240
RHTAEYANHC TTWYQTGLER LRGTNAFSWI NYNRFRREMT LTVLDVCSLF SNYDYRTYPT  300
EVRAELTREI YTDPIGFQNS PLPGVVPNWY DYARSFAEIE NIAIRAPRTV TWLNSTTIYT  360
GRLNGYNNSN YYWAGFRQNF SETNSGSSFN GPDLGDLTPN YRIETLDMVN RDIYSIYSRV  420
VSQSWPIGNV KLFGVSSSTL SFRDLNNNSS GTLVYENPTN FSSQYLTTEF PGENSERPTF  480
TDYSHRLTCL TRIGAGNYGL VLCAGWTSSS VERDNRLQPD KITQYPAVKG FNLDGFTVVK  540
GTGFTGNWL RSSRVTGSFR LNVYSPSVQT YRMRIRYASP LGNSTLGISS TDAGISFTSF  600
PLPSTIGSMP STVPYEAFRV LDIPITVTVA SQRNYNFIFD ILNPSVGAVY IDRIEFPVPG  660
SSVFEYETKH ELEKAKKAVN DLFTNESKNM LKKDTTYDI DQAADLVECV SDECAHAKMI  720
LLDEVKYAKQ LSEARNLLQN GNFKVLDVDN NNPWTTSPNV TIQENNPIFK GHYLSMSGAN  780
AIEATNEVFP TYVYQKIEES KLKPYTRYKV RGFIGQSKDV ELLVTRYDEE VDAILNVPND  840
LKYAVPTHLS GEFNRCKPHT YPATDPRCHD DVIDKIDISS PCQNNIMLSD ADISSLHSGL  900
GKKHGICHES HHFEPHIDTG KIDLVENLGI WVIFKICSTD GYATLDNLEV IEEGPLGAES  960
LERVARAEAK WKHNMEHKCS ETKHAYHAAK QAVEALFTNF KDERLKFETT ISNILSAEYL 1020
VQSIPYVYNK WLSDVPGMNY DIYTELKNRI WQAFNLYDQR NIIKNGHFNH GLMHWHATPH 1080
ANVQQIDGIS VLVLPNWGAN VSQEVCLKHN RGYVLRVTAK EEGHGKGYVT ISDCANQVEK 1140
LSFTSRDYST DGVPYEQSNY PTDGVSYGQH GCNIDRVPYE QSGYPTDGVP YEQSGYRTDG 1200
VPYKQHGCHS DGSREEQHGY VTKTIDVFPD TDKVRIDIGE TEGTFKVESV ELICMEE    1257
```

| | | |
|---|---|---|
| SEQ ID NO: 108 | moltype = DNA  length = 3201 | |
| FEATURE | Location/Qualifiers | |
| misc_feature | 1..3201 | |
| | note = A synthetic coding sequence used for expression in a plant cell encoding a CR-BRE1a.TIC7383_31.nno_Mc:1 protein with an alanine codon, C-terminal truncation, and mutations to the codons corresponding amino acid positions 964, 966, and 968 relative to | |
| source | 1..3201 | |
| | mol_type = other DNA | |
| | organism = synthetic construct | |

```
SEQUENCE: 108
atggctaacc agaaccagaa ccaaaaccag aacaagaacg agctgcagat cattgaaccc   60
tcctcggaca gcctcctgta cagccataac aactacccgt acgccactga cccaaacacc  120
gtgctcgagg ggcgcaacta caaggagtgg ctcaacaaat gcaccgacaa ctacaccgac  180
gcactccagg gcccggaggc gacggccatc agcaagggtg ccgtctccgc ggccatctcc  240
atctcgacga aggtcctagg gctcctaggg gtcccgttcg ctgcgcagat tggccagctg  300
tggacgttca tccttaacgc actctggccc tcagacaaca cccagtggga ggagttcatg  360
cgccacgtcg aggaactgat caaccagcgc atagcgaact acgcgcgcaa caaggccctg  420
gccgagctga cagggctggg caacaaccta gacctctaca tcgaggcgct ggaggactgg  480
aagcggaacc ctacctccca caagctaag gaccgcgtta tcgaccgctt ccgaatcgcg  540
gacggcctct tcgaggggta catgccgagc ttccgggtct cgggctacga ggtgcccctc  600
ctcacggtgt acgcggcggc ggctaatttg catctcctgc tgctcaggga ttgctcgatc  660
tacggaatcc agtggggctt ctcccagact aacgttaacg aaaactacaa tcggcagatt  720
cggcacaccg ccgagtacgc taaccactgc acaacatggt atcagaccgg cctcgagagg  780
ctgcgcggca ccaatgcttt tcatggatc aactacaacc gcttccgccg cgagatgaca  840
ctgactgtct tggacgtctg ctccctcttc tccaactatg actaccgcac ttacccccact  900
gaggtccggg ccgagcttac gcgggagatc tacacgaccc ccatcggtt ccagaactcc   960
ccgctccctg gcgtggtccc caattggtac gactacgcga ggtcgttcgc ggaaatcgaa 1020
aacatcgcca tacgagcacc tcggacagtc acgtggctga actcaaccac catctacacc 1080
gggagactga acggctacaa caatagcaac tactactggg ccgggttccg ccagaacttc 1140
tcagagacca actctggcag cagcttcaac ggcccagacc taggcgacct cactccgaac 1200
tacaggatag agaaccctcga catggtcaac agggacatct acagcatcta ctcccggtcg 1260
gtgtcgcaat cctggcccat cggcaacgtc aagctcttcg gcgtaagctc ctctacctta 1320
agtttccggg atctcaacaa caacagctcc ggcacccctg gtctacgagaa cccgactaac 1380
ttcagctccc agtacctaac cacagagttt ccaggggaga actccgagcg ccccaccttc 1440
acggactaca gtcaccgcct aacctgcctt acgcggatcg gggccgggaa ctacggcctc 1500
gtgcttttgtg gcttggac ttcttcgagt gtcgaaaggg acaaccgcct acaacccgat 1560
aagattaccc agtaccccgc cgtcaagggg ttcaacttgg acgcttcac agtggtgaaa 1620
gggactggtt tcaccggggg caactggctg cggtccagca gggtcaccgg gtcattccgc 1680
ctgaacgtat actcacctag tgtgcagact tatcggatga ggatcaggta cgcctccccg 1740
cttggcaact cgacgcttgg gataagtccg acagacgccg gcatccgtt cacgagtttc 1800
cctctgccct ccactatcgg gagcatgccg tccactgtgc cctacgaggc gttccgtgtc 1860
```

-continued

```
ctcgacatcc ccatcacggt caccgtagcc tcccaaagga actacaactt catcttcgac  1920
atccttaacc cctcggttgg ggccgtgtac atcgatcgta ttgagttcgt gcccgtgggc  1980
tcttcagtgt tcgagtacga aaccaagcac gagcttgaaa aggcgaaaaa agcagttaac  2040
gacctcttca cgaacgagtc caaaaacatg ttaaagaaag acacgaccga ctacgacatc  2100
gaccaggctg cggacctggt ggagtgcgta agcgacgagt cgcccacgc taagatgata   2160
ctgctggacg aagtgaagta cgcgaagcag ctgagcgagg ctcggaacct gctccagaac  2220
gggaacttca aggtcttaga cgttgacaac aacaacccgt ggacgacctc accgaacgta  2280
acgatccagg agaacaaccc gatcttcaaa ggtcactacc tctccatgtc cggtgcgaac  2340
gcaatcgagg ccaccaacga ggtgttccca acgtacgtgt accaaaaagat tgaggagagt  2400
aaactcaagc cctacacaag gtacaaggtg cggggttca tcggccagag caaggacgtc   2460
gagctgctcg tcacgcgtta cgacgaggag gtggacgcta ttctgaacgt gcctaacgac  2520
ctaaagtacg cagtgccgac gcacctgtcg ggagagttca accgctgcaa gcctcacact  2580
tacccggcca cagacccccg atgccacgac gacgtgatcg acaagatcga catctcctcg  2640
ccgtgtcaga acaacattat gctgtcggac gcggacattc ctagtcttca tgcggactt   2700
ggcaagaagc acgggatctg ccacgagagc catcacttcg agttccacat cgacacgggc  2760
aaaatcgacc tcgtggagaa ccttggcatc tgggtgatct tcaagatctg ctctaccgac  2820
ggatacgcga cgctcgacaa tctggaagta atagaggaag gcccgttggg cgcagagtcc  2880
ctagagcggg tggcacgtgc ggaggctaag tggaagcata acatggagca caagtgctga  2940
gaaacgaaac acgcatacca cgcggcgaag caggctgtcg aagcactctt cacgaacttc  3000
aaggacgaga ggctcaagtt cgagacgacg attagtaaca tcctgtcagc tgagtaccta  3060
gtccagtcca tcccatacgt ctacaacaag tggctgtcgg acgtacctgg gatgaactac  3120
gacatctaca ccgagctcaa gaaccgcatc tggcaagcgt tcaacttgta cgaccagagg  3180
aacatcatca agaacggcta g                                            3201
```

SEQ ID NO: 109            moltype = AA   length = 1066
FEATURE                   Location/Qualifiers
REGION                    1..1066
                          note = The amino acid sequence of the
                          CR-BRE1a.TIC7383_31.nno_Mc:1 protein, with an additional
                          alanine residue, and comprising amino acids 1 through
                          1065, and also comprises the mutations, K964A; R966A;
                          K968A, relative to TIC7383.
source                    1..1066
                          mol_type = protein
                          organism = synthetic construct
SEQUENCE: 109
MANQNQNQNQ NKNELQIIEP SSDSLLYSHN NYPYATDPNT VLEGRNYKEW LNKCTDNYTD   60
ALQGPEATAI SKGAVSAAIS ISTKVLGLLG VPFAAQIGQL WTFILNALWP SDNTQWEEFM  120
RHVEELINQR IADYARNKAL AELTGLGNNL DLYIEALEDW KRNPTSQQAK DRVIDRFRIA  180
DGLFEGYMPS FRVSGYEVPL LTVYAAAANL HLLLLRDCSI YGIQWGFSQT NVNENYNRQI  240
RHTAEYANHC TTWYQTGLER LRGTNAFSWI NYNRFRREMT LTVLDVCSLF SNYDYRTYPT  300
EVRAELTREI YTDPIGFQNS PLPGVVPNWY DYARSFAEIE NIAIRAPRTV TWLNSTTIYT  360
GRLNGYNNSN YYWAGFRQNF SETNSGSSFN GPDLGDLTPN YRIETLDMVN RDIYSIYSRV  420
VSQSWPIGNV KLFGVSSSTL SFRDLNNNSS GTLVYENPTN FSSQYLTTEF PGENSERPTF  480
TDYSHRLTCL TRIGAGNYGL VLCAGWTSSS VERDNRLQPD KITQYPAVKG FNLDGFTVVK  540
GTGFTGGNWL RSSRVTGSFR LNVYSPSVQT YRMRIRYASP LGNSTLGISS TDAGISFTSF  600
PLPSTIGSMP STVPYEAFRV LDIPITVTVA SQRNYNFIFD ILNPSVGAVY IDRIEFVPVG  660
SSVFEYETKH ELEKAKKAVN DLFTNESKNM LKKDTTDYDI DQAADLVECV SDECAHAKMI  720
LLDEVKYAKQ LSEARNLLQN GNFKVLDVDN NNPWTTSPNV TIQENNPIFK GHYLSMSGAN  780
AIEATNEVFP TYVYQKIEES KLKPYTRYKV RGFIQGSKDV ELLVTRYDEE VDAILNVPND  840
LKYAVPTHLS GEFNRCKPHT YPATDPRCHD DVIDKIDISS PCQNNIMLSD ADISSLHSGL  900
GKKHGICHES HHFEFHIDTG KIDLVENLGI WVIFKICSTD GYATLDNLEV IEEGPLGAES  960
LERVARAEAK WKHNMEHKCS ETKHAYHAAK QAVEALFTNF KDERLKFETT ISNILSAEYL 1020
VQSIPYVYNK WLSDVPGMNY DIYTELKNRI WQAFNLYDQR NIIKNG                1066

SEQ ID NO: 110            moltype = DNA   length = 3756
FEATURE                   Location/Qualifiers
misc_feature              1..3756
                          note = A synthetic coding sequence used for expression in a
                          plant cell encoding a CR-BRE1a.TIC7383_32.nno_Mc:1 protein
                          comprising an additional alanine codon, and a deletion of
                          the codons corresponding amino acid positions 964 through
                          969 relative to
source                    1..3756
                          mol_type = other DNA
                          organism = synthetic construct
SEQUENCE: 110

```
atggctaacc agaaccagaa ccaaaaccag aacaagaacg agctgcagat cattgaaccc   60
tcctcggaca gcctcctgta cagccataac aactaccggt acgccactga cccaaacacc  120
gtgctcgagg ggcgcaacta caaggagtgg ctcaacaaat gcaccgacaa ctacaccgac  180
gcactccagg gcccggaggc gacggccatc agcaagggtg ccgtctccgc ggccatctcc  240
atctcgacga aggtcctagg gctcctaggg gtcccgttcg ctgcgcagat tggccagctg  300
tggacgttca tccttaacgc actctggccc tcagacaaca cccagtggga ggagttcatg  360
cgccacgtcg aggaactgat caaccagcgc atagcggact acgcgaggaa caaggcctg  420
gccgagctga cagggctggg caacaaccta gacctctaca tcgaggcgct cgaggactgg  480
aagcggaacc ctacctccca acaagctaag gaccgcgtta cgaccgct ccgaatcgcg   540
gacggcctct tcgaggggta catgccgagc ttccgggtct cgggctacga ggtgccctc   600
ctcacggtgt acgcggcggc ggctaatttg catctcctgc tgctcaggga ttgctcgatc  660
tacgaatcc agtggggctt ctcccagact aacgttaacg agaactacaa tcggcagatt  720
```

```
cggcacaccg ccgagtacgc taaccactgc acaacatggt atcagaccgg cctcgagagg    780
ctgcgcggca ccaatgcttt ctcatggatc aactacaacc gcttccgccg cgagatgaca    840
ctgactgtct tggacgtctg ctccctcttc tccaactatg actaccgcac ttaccccact    900
gaggtccggg ccgagcttac gcgggagatc tacacagacc ccatcgggtt ccagaactcc    960
ccgctccctg gcgttggtcc caattggtac gactacgca ggtcgttcgc ggaaatcgaa     1020
aacatcgcca tacgagcacc tggacagtc acgtggctga actcaaccac catcctacacc    1080
gggagactga acggctacaa caatagcaac tactactggg ccgggttccg ccagaacttc    1140
tcagagacca actctggcag cagcttcaac ggcccagacc taggcgacct cactccgaac    1200
tacaggatag agaccctcga catggtcaac agggacatct acagcatcta ctcccgggtc    1260
gtgtcgcaat cctggcccat cggcaacgtc aagctcttcg gcgtaagctc ctctaccta     1320
agtttccggg atctcaacaa caacagctcc ggcaccctgg tctacgagaa cccgactaac    1380
ttcagctccc agtacctaac cacagagttt ccaggggaga actccgagcg cccaccttc     1440
acggactaca gtcaccgcct aacctgcctt acgcggatcg gggccgggaa ctacggcctc    1500
gtgctttgtg cgggttggac ttcttcgagt gtcgaaaggg acaaccgcct acaacccgat    1560
aagattaccc agtaccccgc cgtcaagggg ttcaacttgg acggcttcac agtggtgaaa    1620
gggactggtt tcaccggggg caactggctg cggtccagca gggtcaccgg gtcattccgc    1680
ctgaacgtat actcacctag tgtgcagact tatcggatga ggatcaggta cgcctccccg    1740
cttggcaact cgacgcttgg gataagttcg acagacgccg gctctcgtt cacgagtttc     1800
cctctgccct ccactatcgg gagcatgccg tccactgtgc cctacgaggc gttccgtgtc    1860
ctcgacatcc ccatcacggt caccgtagcc tcccaaagga actacaactt catcttcgac    1920
atccttaacc cctcggttgg ggccgtgtac atcgatcgta ttgagttcgt gcccgtgggc    1980
tcttcagtgt tcgagtacga aaccaagcac gagcttgaaa aggcgaaaaa agcagttaac    2040
gacctcttca cgaacgagtc caaaaacatg ttaaagaaag acacgaccga ctacgacatc    2100
gaccaggctg cggacctggt ggagtgcgta agcgacgagt gcgcccacgc taagatgata    2160
ctgctggacg aagtgaagta cgcgaagcag ctgagcgagg ctcggaacct gctccagaac    2220
gggaacttca aggtcttaga cgttgacaac aacaacccgt ggaccagcctc accgaacgta   2280
acgatccagg agaacaaccc gatcttcaaa ggtcactacc tctccatgtc cggtgcgaac    2340
gcaatcgagg ccaccaacga ggtgttccca acgtacgtgt accaaaagat tgaggagagt    2400
aaactcaagc cctacacaag gtacaaggtg cggggggttca tcggcagag caaggacgtc     2460
gagctgctcg tcacgcgtta cgacgaggag gtggacgaca ttctgaacgt gcctaacgac    2520
ctaaagtacg cagtgccgac gcacctgtcg ggagagttca accgctgcaa gcctcacact    2580
tacccggcca cagaccccg atgccacgac gacgtgatcg acaagatcga catctcctcg    2640
ccgtgtcaga acaacattat gctgtcgac gcggacatct ctagtcttca tagcggactt     2700
ggcaagaagc acgggatctg ccacgagagc catcacttcg agttccacat cgacacgggc    2760
aaaatcgacc tcgtggagaa ccttggcatc tgggtgatct tcaagatctg ctctaccgac    2820
ggatacgcga cgctcgacaa tctgaagta atagaggaag gcccgttggg cgcagagtcc    2880
ctagagcggg tgtggaagca taacatggag cacaagtgct cggaaacgaa acacgcatac    2940
cacgcggcga agcaggctgt cgaagcactc ttcacgaact tcaaggacga gaggctcaag    3000
ttcgagcaca cgattagtaa catcctgtca gctagtacc tagtccagtc catcccatac     3060
gtctacaaca agtggctgtc ggacgtacct gggatgaact acgacatcta caccgagctc    3120
aagaaccgca tctgcaagc gttcaacttg tacgaccaga ggaacatcat caagaacggc    3180
cacttcaatc atggttttaat gcattggcac gcgacaccgc acgcgaacgt gcagcaaata    3240
gacggtattt ccgtgctggt cctcccaaac tgggggggcca acgtcagcca ggaggtgtgc    3300
ctcaagcaca accggggcta cgtgctgcga gtcacggcca aggaggaggg tcacggcaag    3360
ggctacgtga cgatttcgga ctgcgctaac caggtcgaga agctgcgtt cactagccgc     3420
gactactcta ccgacggcgt cccatacgaa cagtccaact acccgaccga cggagtgtct    3480
tacggcgcag acgggtgcaa catcgaccga gtgccctacg acaatctggg ctaccccacc    3540
gacggggttc cttacgaaca gtcgggctac cgtacgacg gggtcccgta caagcagcat    3600
ggatgccact cggacggaag ccgtgaggag cagcacgggt acgttacgaa gactatcgac    3660
gtcttccccg acacggacaa ggtccggatc gacatcggcg agaccgaggg gacgttcaag    3720
gttgagagcg tggagctcat ctgcatggag gagtag                              3756
```

```
SEQ ID NO: 111          moltype = AA   length = 1251
FEATURE                 Location/Qualifiers
REGION                  1..1251
                        note = The the amino acid sequence of the
                        CR-BREla.TIC7383_32.nno_Mc:1 protein, with an additional
                        alanine residue, and comprising a deletion of amino acids
                        964 through 969 relative to TIC7383.
source                  1..1251
                        mol_type = protein
                        organism = synthetic construct
SEQUENCE: 111
MANQNQNQNQ NKNELQIIEP SSDSLLYSHN NYPYATDPNT VLEGRNYKEW LNKCTDNYTD     60
ALQGPEATAI SKGAVSAAIS ISTKVLGLLG VPFAAQIGQL WTFILNALWP SDNTQWEEFM    120
RHVEELINQR IADYARNKAL AELTGLGNNL DLYIEALEDW KRNPTSQQAK DRVIDRFRIA   180
DGLFEGMPS FRVSGYEVPL LTVYAAAANL HLLLLRDCSI YGIQWGFSQT NVENYNRQI     240
RHTAEYANHC TTWYQTGLER LRGTNAFSWI NYNRFRREMT LTVLDVCSLF SNYDYRTYPT   300
EVRAELTREI YTDPIGFQNS PLPGVVPNWY DYARSFAEIE NIAIRAPRTV TWLNSTTIYT   360
GRLNGYNNSN YYWAGFRQNF SETNSGSSFN GPDLGDLTPN YRIETLDMVN RDIYSIYSRV   420
VSQSWPIGNV KLFGVSSSTL SFRDLNNNSS GTLVYENPTN FSSQYLTTEF PGENSERPTF   480
TDYSHRLTCL TRIGAGNYGL VLCAGWTSSS VERDNRLQPD KITQYPAVKG FNLDGFTVVK   540
GTGFTGGNWL RSSRVTGSFR LNVYSPSVQT YRMRIRYASP LGNSTLGISS TDAGISFTSF   600
PLPSTIGSMP STVPYEAFRV LDIPITVTVA SQRNYNFIFD ILNPSVGAVY IDRIEFVPVG   660
SSVFEYETKH ELEKAKKAVN DLFTNESKNM LKKDTTDYDI DQAADLVECV SDECAHAKMI   720
LLDEVKYAKQ LSEARNLLQN GNFKVLDVDN NNPWTTSPNV TIQENNPIFK GHYLSMSGAN   780
AIEATNEVFP TYVYQKIEES KLKPYTRYKV RGFIGQSKDV ELLVTRYDEE VDAILNVPND   840
LKYAVPTHLS GEFNRCKPHT YPATDPRCHD DVIDKIDISS PCQNNIMLSD ADISSLHSGL   900
GKKHGICHES HHFEFHIDTG KIDLVENLGI WVIFKICSTD GYATLDNLEV IEEGPLGAES   960
```

```
LERVWKHNME HKCSETKHAY HAAKQAVEAL FTNFKDERLK FETTISNILS AEYLVQSIPY    1020
VYNKWLSDVP GMNYDIYTEL KNRIWQAFNL YDQRNIIKNG HFNHGLMHWH ATPHANVQQI    1080
DGISVLVLPN WGANVSQEVC LKHNRGYVLR VTAKEEGHGK GYVTISDCAN QVEKLSFTSR    1140
DYSTDGVPYE QSNYPTDGVS YGQHGCNIDR VPYEQSGYPT DGVPYEQSGY RTDGVPYKQH    1200
GCHSDGSREE QHGYVTKTID VFPDTDKVRI DIGETEGTFK VESVELICME E             1251

SEQ ID NO: 112           moltype = DNA   length = 1854
FEATURE                  Location/Qualifiers
misc_feature             1..1854
                         note = A synthetic coding sequence used for expression in a
                         plant cell encoding a GOI-TIC10743.nno_Mc:1 chimeric
                         protein comprised of domains one and two of TIC7383 and
                         domain three of TIC7042.
source                   1..1854
                         mol_type = other DNA
                         organism = synthetic construct
SEQUENCE: 112
atggctaccg acaactacac cgacgcactc cagggcccgg aggcgacggc catcagcaag     60
ggtgccgtct ccgcgccat  ctccatctcg acgaaggtcc tagggctcct aggggtcccg    120
ttcgctgcgc agattggcca gctgtggacg ttcatcctta acgcactctg gccctcagac    180
aacacccagt gggaggagtt catgcgccac gtcgaggaac tgatcaacca gcgcatagcg    240
gactacgcga ggaacaaggc cctggccgag ctgacagggc tgggcaacaa cctagacctc    300
tacatcgagg cgctcgagga ctggaagcgg aaccctacct cccaacaagc taaggaccgc    360
gttatcgacc gcttccgaat cgcggacggc ctcttcgagg ggtacatgcc gagcttccgg    420
gtctcgggct acgaggtgcc cctcctcacg gtgtacgcgg cggcggctaa tttgcatctc    480
ctgctgctca gggattgctc gatctacgga atccagttgg gcttctccca gactaacgtt    540
aacgagaact acaatcggca gattcggcac accgccgagt acgctaacca ctgcacaaca    600
tggtatcaga ccgcctcga  gaggctgcgc ggcaccaatg ctttctcatg gatcaactac    660
aaccgcttcc gccgcgagat gacactgact gtcttggacg tctgctccct cttctccaac    720
tatgactacc gcacttaccc cactgaggtc cgggccgagc ttacgcggga gatctacaca    780
gaccccatcg ggttccagaa ctccccgctc cctggcgtgg tccccaattg gtacgactac    840
gcgaggtcgt tcgcggaaat cgaaaacatc gccatacgag cacctcggac agtcacgtgg    900
ctgaactcaa ccaccatcta caccgggaga ctgaacggct acaacaatag caactactac    960
tgggccgggt tccgccagaa cttctcagag accaactctg gcagcagctt caacggccca   1020
gacctaggcg acctcactcc gaactacagg atagagaccc tcgacatggt caacagggac   1080
atctacagca tctactcccg ggtcgtgtcc aatcctggcc catcggcaa  cgtcaagctc   1140
ttcggcgtaa gctcctctac cttaagtttc cgggatctca acaacaacag ctccggcacc   1200
ctggtctacg agaacccgac taacttcagc tcccagtacc taaccacaga gtttccaggg   1260
gagaactccg agcggcccac cttcacggac tacagtcacc gcctaacctg ccttacgcgg   1320
atcggggccg ggaactacgg cctcgtgctt tgtgcgggtt ggacttcttc gagtgtcgaa   1380
agggacaaca tcatcgagca gaacaagatc acccagttcc ctggcgttaa gtcacacact   1440
cttaacaact gtcaagtggt gcgtggcacc gggttcaccg gcggcgactg gcttcgccca   1500
aacaacggca gcacctttcg gctgaccatt accagcttct cgtcccagtc ctaccgcatt   1560
aggcttcgat acgctaccag cgtcggcaac acctctcttg tcatctcgtc atccgacgcg   1620
ggcatctcca gtaccacaat ccctctgaca tccaccatca cgtcgctccc gcagaccgtt   1680
ccgtaccagg cgttccgcgt cgtcgatctc ccgatcactt tcactactcc gaccactcag   1740
cgcaattaca ccttcgattt ccgcctccag aacccgagca acgctaacgt attcatcgac   1800
cgcttcgagt tcgtaccaat cggcggctca ctgtccgagt acgagacgaa gtga         1854

SEQ ID NO: 113           moltype = AA   length = 617
FEATURE                  Location/Qualifiers
REGION                   1..617
                         note = The amino acid sequence of the GOI-TIC10743.nno_Mc:1
                         chimeric protein.
source                   1..617
                         mol_type = protein
                         organism = synthetic construct
SEQUENCE: 113
MATDNYTDAL QGPEATAISK GAVSAAISIS TKVLGLLGVP FAAQIGQLWT FILNALWPSD     60
NTQWEEFMRH VEELINQRIA DYARNKALAE LTGLGNNLDL YIEALEDWKR NPTSQQAKDR    120
VIDRFRIADG LFEGYMPSFR VSGYEVPLLT VYAAAANLHL LLLRDCSIYG IQWGFSQTNV    180
NENYNRQIRH TAEYANHCTT WYQTGLERLR GTNAFSWINY NRFRREMTLT VLDVCSLFSN    240
YDYRTYPTEV RAELTREIYT DPIGFQNSPL PGVVPNWYDY ARSFAEIENI AIRAPRTVTW    300
LNSTTIYTGR LNGYNNSNYY WAGFRQNFSE TNSGSSFNGP DLGDLTPNYR IETLDMVNRD    360
IYSIYSRVVS QSWPIGNVKL FGVSSSTLSF RDLNNNSSGT LVYENPTNFS SQYLTTEFPG    420
ENSERPTFTD YSHRLTCLTR IGAGNYGLVL CAGWTSSSVE RDNIIEQNKI TQFPGVKSHT    480
LNNCQVVRGT GFTGGDWLRP NNNGTFRLTI TSFSSQSYRI RLRYATSVGN TSLVISSSDA    540
GISSTTIPLT STITSLPQTV PYQAFRVVDL PITFTTPTTQ RNYTFDFRLQ NPSNANVFID    600
RFEFVPIGGS LSEYETK                                                   617

SEQ ID NO: 114           moltype = DNA   length = 1851
FEATURE                  Location/Qualifiers
misc_feature             1..1851
                         note = A synthetic coding sequence used for expression in a
                         plant cell encoding a GOI-TIC10744.nno_Mc:1 chimeric
                         protein comprised of domains one and two of TIC7383 and
                         domain three of TIC7381.
source                   1..1851
                         mol_type = other DNA
```

```
                        organism = synthetic construct
SEQUENCE: 114
atggctaccg acaactacac cgacgcactc cagggcccgg aggcgacggc catcagcaag    60
ggtgccgtct ccgcggccat ctccatctcg acgaaggtcc tagggctcct aggggtcccg   120
ttcgctgcgc agattggcca gctgtggacg ttcatcctta acgcactctg gccctcagac   180
aacacccagt gggaggagtt catgcgccac gtcgaggaac tgatcaacca gcgcatagcc   240
gactacgcga ggaacaaggc cctggccgag ctgacagggc tgggcaacaa cctagacctc   300
tacatcgagg cgctcgagga ctggaagcgg aaccctacct cccaacaagc taaggaccgc   360
gttatcgacc gcttccgaat cgcggacggc ctcttcgagg ggtacatgcc gagcttccgg   420
gtctcgggct acgaggtgcc cctcctcacg gtgtacgcgg cggcggctaa tttgcatctc   480
ctgctgctca gggattgctc gatctacgga atccagtggg gcttctccca gactaacgtt   540
aacgagaact acaatcggca gattcggcac accgccgagt acgctaacca ctgcacaaca   600
tggtatcaga ccggcctcga gaggctgcgc ggcaccaatg cttttctcatg gatcaactac   660
aaccgcttcc gccgcgagat gacactgact gtcttggacg tctgctccct cttctccaac   720
tatgactacc gcacttaccc cactgaggtc cgggccgagc ttacgcggga gatctacaca   780
gaccccatcg ggttccagaa ctccccgctc cctggcgtgg tccccaattg gtacgactac   840
gcgaggtcgt tcgcggaaat cgaaaacatc gccatacgag cacctcggac agtcacgtgg   900
ctgaactcaa ccaccatcta caccgggaga ctgaacggct acaacaatag caactactac   960
tgggccgggt tccgccagaa cttctcagag accaactctg gcagcagctt caacggccca  1020
gacctaggcg acctcactcc gaactacagg atagagaccc tcgacatggt caacagggac  1080
atctacagca tctactcccg ggtcgtgtcg caatcctggc ccatcggcaa cgtcaagctc  1140
ttcggcgtaa gctcctctac cttaagtttc cgggatctca acaacaacag ctccggcacc  1200
ctggtctacg agaacccgac taacttcagc tcccagtacc taaccacaga gtttccaggg  1260
gagaactccg agcggcccac cttcacggac tacagtcacc gcctaacctg ccttacgcgg  1320
atcggggccg ggaactacgg cctcgtgctt tgtgcgggtt ggacttcttc gagtgtcgaa  1380
agggacaaca tactggagcg gaacaagtca cccagttcc ctggcgttaa gtcccatacc  1440
ctgaacaatt gccaggtcgt ccgcggtaca ggctttaccg gcggcgactg gcttcggcct  1500
aacaacaacg gtcgttccg attgactatc acctcgttca gctcacagag ttacagaatc  1560
aggctgcggt acgcgtccgc agcgaatacc tccctgcgaa tctcgtcttc ggcggccggg  1620
atctcgtcaa caaccgtccc actcgcctcc acgatcacta cgtcccgca gacagccgtc  1680
ccatacgagg cgttccgggt gatcgacctg ccaatcacgt tcaccaccgc gacgcagtct  1740
aactacactt tcgactcgt cctccagaat ccttccaacg ccaacgtgtt catcgaccgc  1800
ttcgagtttg tccccgattgg aggttcgctc tcagagtacg agacgaagtg a          1851

SEQ ID NO: 115         moltype = AA  length = 616
FEATURE                Location/Qualifiers
REGION                 1..616
                       note = The amino acid sequence of the GOI-TIC10744.nno_Mc:1
                       chimeric protein.
source                 1..616
                       mol_type = protein
                       organism = synthetic construct
SEQUENCE: 115
MATDNYTDAL QGPEATAISK GAVSAAISIS TKVLGLLGVP FAAQIGQLWT FINALWPSD     60
NTQWEEFMRH VEELINQRIA DYARNKALAE LTGLGNNLDL YIEALEDWKR NPTSQQAKDR   120
VIDRFRIADG LFEGYMPSFR VSGYEVPLLT VYAAANLHL LLLRDCSIYG IQWGFSQTNV    180
NENYNRQIRH TAEYANHCTT WYQTGLERLR GTNAFSWINY NRFRREMTLT VLDVCSLFSN   240
YDYRTYPTEV RAELTREIYT DPIGFQNSPL PGVVPNWYDY ARSFAEIENI AIRAPRTVTW   300
LNSTTIYTGR LNGYNNSNYY WAGFRQNFSE TNSGSSFNGP DLGDLTPNYR IETLDMVNRD   360
IYSIYSRVVS QSWPIGNVKL FGVSSSTLSF RDLNNNSSGT LVYENPTNFS SQYLTTEFPG   420
ENSERPTFTD YSHRLTCLTR IGAGNYGLVL CAGWTSSSVE RDNILERNKI TQFPGVKSHT   480
LNNCQVVRGT GFTGGDWLRP NNNGSFRLTI TSFSSQSYRI RLRYASAANT SLRISSSAAG   540
ISSTTVPLAS TITSLPQTAV PYEAFRVIDL PITFTTATQS NYTFDFVLQN PSNANVFIDR   600
FEFVPIGGSL SEYETK                                                   616

SEQ ID NO: 116         moltype = DNA  length = 1854
FEATURE                Location/Qualifiers
misc_feature           1..1854
                       note = A synthetic coding sequence used for expression in a
                       plant cell encoding a GOI-TIC10745.nno_Mc:1 chimeric
                       protein comprised of domains one and two of TIC7383 and
                       domain three of TIC7382.
source                 1..1854
                       mol_type = other DNA
                       organism = synthetic construct
SEQUENCE: 116
atggctaccg acaactacac cgacgcactc cagggcccgg aggcgacggc catcagcaag    60
ggtgccgtct ccgcggccat ctccatctcg acgaaggtcc tagggctcct aggggtcccg   120
ttcgctgcgc agattggcca gctgtggacg ttcatcctta acgcactctg gccctcagac   180
aacacccagt gggaggagtt catgcgccac gtcgaggaac tgatcaacca gcgcatagcc   240
gactacgcga ggaacaaggc cctggccgag ctgacagggc tgggcaacaa cctagacctc   300
tacatcgagg cgctcgagga ctggaagcgg aaccctacct cccaacaagc taaggaccgc   360
gttatcgacc gcttccgaat cgcggacggc ctcttcgagg ggtacatgcc gagcttccgg   420
gtctcgggct acgaggtgcc cctcctcacg gtgtacgcgg cggcggctaa tttgcatctc   480
ctgctgctca gggattgctc gatctacgga atccagtggg gcttctccca gactaacgtt   540
aacgagaact acaatcggca gattcggcac accgccgagt acgctaacca ctgcacaaca   600
tggtatcaga ccggcctcga gaggctgcgc ggcaccaatg cttttctcatg gatcaactac   660
aaccgcttcc gccgcgagat gacactgact gtcttggacg tctgctccct cttctccaac   720
tatgactacc gcacttaccc cactgaggtc cgggccgagc ttacgcggga gatctacaca   780
```

```
gaccccatcg ggttccagaa ctccccgctc cctggcgtgg tccccaattg gtacgactac    840
gcgaggtcgt tcgcggaaat cgaaaacatc gccatacgag cacctcggac agtcacgtgg    900
ctgaactcaa ccaccatcta caccgggaga ctgaacggct acaacaatag caactactac    960
tgggccgggt tccgccagaa cttctcagag accaactctg gcagcagctt caacggccca   1020
gacctaggcg acctcactcc gaactacagg atagagaccc tcgacatggt caacagggac   1080
atctacagca tctactcccg ggtcgtgtcg caatcctggc ccatcggcaa cgtcaagctc   1140
ttcggcgtaa gctcctctac cttaagtttc cgggatctca acaacaacag ctccggcacc   1200
ctggtctacg agaacccgac taacttcagc tcccagtacc taaccacaga gtttccaggg   1260
gagaactccg agccgcccac cttcacggac tacagtcacc gcctaacctg ccttacgcgg   1320
atcggggccg ggaactacgg cctcgtgctt tgtgcgggtt ggacttcttc gagtgtcgaa   1380
agggacaaca tcatcgagcg caacaagatc acgcagttcc caggcgtcaa atcgcacacg   1440
ctaaacaact gccaggtggt gaggggaacc ggtttcaccg gaggtgactg gttaagacca   1500
aataacaacg gcactttccg cctcactatt acgagctgtc cctcccaaag ttaccgcatc   1560
cgccttcgct acgccacgtc agtggggaac acctcgctgg tgatatcctc ctcagacgcc   1620
gggatcagca gcaccacgat accactaaca tccacaataa cctcattgcc gcagacggtc   1680
ccgtatcagg ccttcagagt ggtggacctt cctattacgt tcacgacgcc cacgacccag   1740
cgcaactaca cattcgattt ccggttgcag aacccgagta cgccaatgtc cttcatcgat   1800
cgtttcgagt tcgtcccgat aggcggctcc ctttcggagt acgaaacgaa gtga         1854

SEQ ID NO: 117            moltype = AA  length = 617
FEATURE                   Location/Qualifiers
REGION                    1..617
                          note = The amino acid sequence of the GOI-TIC10745.nno_Mc:1
                            chimeric protein.
source                    1..617
                          mol_type = protein
                          organism = synthetic construct
SEQUENCE: 117
MATDNYTDAL QGPEATAISK GAVSAAISIS TKVLGLLGVP FAAQIGQLWT FILNALWPSD    60
NTQWEEFMRH VEELINQRIA DYARNKALAE LTGLGNNLDL YIEALEDWKR NPTSQQAKDR   120
VIDRFRIADG LFEGYMPSFR VSGYEVPLLT VYAAAANLHL LLLRDCSIYG IQWGFSQTNV   180
NENYNRQIRH TAEYANHCTT WYQTGLERLR GTNAFSWINY NRFRREMTLT VLDVCSLFSN   240
YDYRTYPTEV RAELTREIYT DPIGFQNSPL PGVVPNWYDY ARSFAEIENI AIRAPRTVTW   300
LNSTTIYTGR LNGYNNSNYY WAGFRQNFSE TNSGSSFNGP DLGDLTPNYR IETLDMVNRD   360
IYSIYSRVVS QSWPIGNVKL FGVSSSTLSF RDLNNNSSGT LVYENPTNFS SQYLTTEFPG   420
ENSERPTFTD YSHRLTCLTR IGAGNYGLVL CAGWTSSSVE RDNIIERNKI TQFPGVKSHT   480
LNNCQVVRGT GFTGGDWLRP NNNGTFRLTI TSFSSQSYRI RLRYATSVGN TSLVISSSDA   540
GISSTTIPLT STITSLPQTV PYQAFRVVDL PITFTTPTTQ RNYTFDFRLQ NPSNANVFID   600
RFEFVPIGGS LSEYETK                                                  617

SEQ ID NO: 118            moltype = DNA  length = 1833
FEATURE                   Location/Qualifiers
misc_feature              1..1833
                          note = A synthetic coding sequence used for expression in a
                            plant cell encoding a GOI-TIC10746.nno_Mc:1 chimeric
                            protein comprised of domains one and two of TIC7382 and
                            domain three of TIC7383.
source                    1..1833
                          mol_type = other DNA
                          organism = synthetic construct
SEQUENCE: 118
atggccacta acaattacac cgacgcgctc cagtctccgg aagccacagc catttcgaag     60
ggggcggtct cggcggcgat cagcatcagc accaaggtgc tcggcctcct cggcgtgccg    120
ttcgcggctc agataggaca gctctggaca ttcattctga acgccctgtg gccgtccgac    180
aacacccagt gggaggagtt catgcggcac gtcgaggagc tcatcaacca gcggatcgca    240
gactatgccc gtaacaaggc cctggccgag ctgacgggac tcggcaacaa cctcgacctc    300
tacatcgagg ccctgatga ctggaagagg aaccccacca gccaggaggc caagactcgc    360
gtcatcgacc gcttccgcat cgtcgacggg ctgttcgagg cctacattcc gagcttcgcc    420
gtgagcggct atcaagttca gctgctcact gtctacgccg ctgcagcaaa cctccacctc    480
ctgctgctgc gcgactccac gatctacgga atcgactggg gcctttccca gactaacgtc    540
aacgataact acaaccggca gattcgtctc accgcgacgt acgctaacca ctgtacaacg    600
tggtaccaga caggactgga gcggctccgc gggagcaacg cgtcttcctg ggtgacctac    660
aaccgtttcc ggagagagat gactctcaca gtcttggaca tctgttcctt gttcagcaac    720
tacgactatc gcagctaccc ggccgaggtt cgcggcagga ttacgaggga aatctacaca    780
gaccctgtcg gcgtcggttg ggttgacagc gcgccttctt tcggcgagat cgagaacctg    840
gcgatccggg cgccacggac tgtgacctgg ctgaactcca cccggatctc caccggcacc    900
ttaagcggct ggtcgggctc taaccggtac tgggcggccc acatgcagaa tttctccgag    960
acaaactcgg gtaacatcgg cttcgatggg ccgctgtacg ggagcacagt gggcaccatc   1020
caccgcactg atgactacga catgggcaac cggaacatct acacgataac gtcgcaggcc   1080
gttctcggtc tgtggcccac gggcagcggg gtcctgggac tcgcatctgc gcgtttcacc   1140
ctcaggaacc tattcaataa cctgacccag gtgctggtat acgagaatcc tattagctcc   1200
aacttcggct cttcaacgct aacccacgag ttatccggcg agaacagcga taggcccacc   1260
agcagcgatt actcacatcg actcacaagc atcacgggat tccgcgcagg agcaaatggt   1320
accgttcccg tctttgggtg gaccagccgc acagtcgaca acaaccg cctacaaccc     1380
gataagatta cccagtaccc cgccgtcaag gggttcaact tggacggctt cacagtggtg   1440
aaagggactg gtttcaccgg gggcaactgg ctgcggtcca gcaggtcac cgggtcattc    1500
cgcctgaacg tatactcacc tagtgtgcag acttatcgga tgaggatcag gtacgcctcc   1560
ccgcttggca actcgacgct tgggataagt tcgacagacg ccggcatctc gttcacgagt   1620
ttccctctgc cctccactat cgggagcatg ccgtccactg tgcctacga ggcgttccgt    1680
```

```
gtcctcgaca tccccatcac ggtcaccgta gcctcccaaa ggaactacaa cttcatcttc  1740
gacatcctta accccteggt tgggqccgta tacatcgatc gtattgagtt cgtgcccgtg  1800
ggctcttcag tgttcgagta cgaaaccaag tga                               1833

SEQ ID NO: 119         moltype = AA   length = 610
FEATURE                Location/Qualifiers
REGION                 1..610
                       note = The amino acid sequence of the GOI-TIC10746.nno_Mc:1
                       chimeric protein.
source                 1..610
                       mol_type = protein
                       organism = synthetic construct
SEQUENCE: 119
MATNNYTDAL QSPEATAISK GAVSAAISIS TKVLGLLGVP FAAQIGQLWT FILNALWPSD   60
NTQWEEFMRH VEELINQRIA DYARNKALAE LTGLGNNLDL YIEALDDWKR NPTSQEAKTR  120
VIDRFRIVDG LFEAYIPSFA VSGYQVQLLT VYAAAANLHL LLLRDSTIYG IDWGLSQTNV  180
NDNYNRQIRL TATYANHCTT WYQTGLERLR GSNASSWVTY NRFRREMTLT VLDICSLFSN  240
YDYRSYPAEV RGEITREIYT DPVGVGWVDS APSFGEIENL AIRAPRTVTW LNSTRISTGT  300
LSGWSGSNRY WAAHMQNFSE TNSGNIGFDG PLYGSTVGTI HRTDDYDMGN RDIYTITSQA  360
VLGLWPTGQR VLGVASARFT LRNLFNNLTQ VLVYENPISS NFGSSTLTHE LSGENSDRPT  420
SSDYSHRLTS ITGFRAGANG TVPVFGWTSA TVDRNNRLQP DKITQYPAVK GFNLDGFTVV  480
KGTGFTGGNW LRSSRVTGSF RLNVYSPSVQ TYRMRIRYAS PLGNSTLGIS STDAGISFTS  540
FPLPSTIGSM PSTVPYEAFR VLDIPITVTV ASQRNYNFIF DILNPSVGAV YIDRIEFVPV  600
GSSVFEYETK                                                        610

SEQ ID NO: 120         moltype = DNA   length = 1839
FEATURE                Location/Qualifiers
misc_feature           1..1839
                       note = A synthetic coding sequence used for expression in a
                       plant cell encoding a GOI-TIC10747.nno_Mc:1 chimeric
                       protein comprised of domains one and two of TIC7381 and
                       domain three of TIC7383.
source                 1..1839
                       mol_type = other DNA
                       organism = synthetic construct
SEQUENCE: 120
atggctacag acaactacac cgatgcactg caaggcccag aggcaacggc tatcagcaag   60
ggtgccgtgt cggccgctat ctctatcagc accaaagtct tgagccttct gggagtgccc  120
ttcgcagctc agattgggca attgtggacg tttattctga acgctcttg gccctcgtga  180
aacacccagt gggaggagtt catgcgccat gtcgaggagc tcatcaacca gcgtatcgcc  240
gactacgcgc ggagtaaggc gctcgccgag ctcacgggcc tgggcaacaa cctcgatctg  300
tacatcgaag ctcttgagga ctggaagcgc aacccgacct ctcaacaagc caaggaccgg  360
gtgaaggacc gcttccgcat cgccgacggc tccttcgaag cgtacatgcc tagcttccgg  420
gtgagcggct atgaagtgcc attgctcacc gtatatcgg cggcggccaa cctgcacctc  480
ctcctcctcc gcgactgctc tatctacggc attcagtggg gtttctccca gaccaatgtc  540
aacgagaact ataatcggca gatccgtcac accgccgagt acgcgaacca ctgcacgaca  600
tggtaccaga cgggcctgga gcgactgcgc ggcacgagcc tccaagctg ggtgccgtac   660
aaccgtttca ggagagagat gactctcacc gtgctcgaca tctgcagtct gttctccaac  720
tatgactaca ggagttaccc ggcagaggtg cgggctgagc tgaccaggga gatatacacg  780
gacccggtg tcagcacctc tctgtgggtg aacaacgcgc cgtccttcgg cgaaatcgag  840
aatctggcaa tccgagcgcc acgcaccgtg acatggctca attcgacgcg tattagcact  900
ggcacactcc aaggttggtc tgggtccaac aggtactggg ccgccacat gcagaacttc  960
tcggagacta actccggcaa cataggcttc gacggcccgc tgtacgggtc cactgtgggt 1020
acaatcattc gcgatgacaa ttacgagatg gtcaaccggg acatttacac catcacttcg 1080
gaggcggttg cggctttgtg gcccacgggc cagattgtgc tgggcgtggc ttccgcaaga 1140
ttcaccccttc gaaacctcaa caacaacctg acccaggcgc tggtctacga gaacccgata 1200
tcaagcagtt tcaaccggtc aactctcaca cgcgagttgc cgggcgagaa cagcgacagg 1260
cccacctctt cggactactc caccgtctc actagcatca ctgcgttccg cgcaggcagt 1320
aacggtacga ttcctgtgtt cggctggacc agtatctccg tcaacaggga caaccgccta 1380
caacccgata agattaccca gtaccccgcc gtcaaggggt tcaacttgga cggcttcaca 1440
gtggtgaaag ggactggttt caccgggggc aactggctgc ggtccagcag ggtcaccggg 1500
tcattccgcc tgaacgtata tcacctagt gtgcagactt atcggatgag gatcaggtac 1560
gcctcccgc ttggcaactc gacgcttggg ataagttcga cagacgccgg catctcgttc 1620
acgagtttcc ctctgcccctc cactatcggg agcatgcctg tgccctacgaggcg 1680
ttccgtgtcc tcgacatccc catcacggtc accgtagcct cccaaggaa ctacaacttc 1740
atcttcgaca tccttaaccc ctcggttggg gccgtgtaca tcgatcgtat tgagttcgtg 1800
cccgtgggct cttcagtgtt cgagtacgaa accaagtga                         1839

SEQ ID NO: 121         moltype = AA   length = 612
FEATURE                Location/Qualifiers
REGION                 1..612
                       note = The amino acid sequence of the GOI-TIC10747.nno_Mc:1
                       chimeric protein.
source                 1..612
                       mol_type = protein
                       organism = synthetic construct
SEQUENCE: 121
MATDNYTDAL QGPEATAISK GAVSAAISIS TKVLSLLGVP FAAQIGQLWT FILNALWPSD   60
NTQWEEFMRH VEELINQRIA DYARSKALAE LTGLGNNLDL YIEALEDWKR NPTSQQAKDR  120
```

```
VKDRFRIADG LFEAYMPSFR VSGYEVPLLT VYAAAANLHL LLLRDCSIYG IQWGFSQTNV    180
NENYNRQIRH TAEYANHCTT WYQTGLERLR GTNASSWVPY NRFRREMTLT VLDICSLFSN    240
YDYRSYPAEV RAELTREIYT DPVVSTSLWV NNAPSFGEIE NLAIRAPRTV TWLNSTRIST    300
GTLQGWSGSN RYWAAHMQNF SETNSGNIGF DGPLYGSTVG TIIRDDNYEM VNRDIYTITS    360
EAVAALWPTG QIVLGVASAR FTLRNLNNNL TQALVYENPI SSSFNRSTLT RELPGENSDR    420
PTSSDYSHRL TSITAFRAGS NGTIPVFGWT SISVNRDNRL QPDKITQYPA VKGFNLDGFT    480
VVKGTGFTGG NWLRSSRVTG SFRLNVYSPS VQTYRMRIRY ASPLGNSTLG ISSTDAGISF    540
TSFPLPSTIG SMPSTVPYEA FRVLDIPITV TVASQRNYNF IFDILNPSVG AVYIDRIEFV    600
PVGSSVFEYE TK                                                         612

SEQ ID NO: 122          moltype = DNA   length = 1830
FEATURE                 Location/Qualifiers
misc_feature            1..1830
                        note = A synthetic coding sequence used for expression in a
                        plant cell encoding a GOI-TIC10748.nno_Mc:1 chimeric
                        protein comprised of domains one and two of TIC7042 and
                        domain three of TIC7383.
source                  1..1830
                        mol_type = other DNA
                        organism = synthetic construct
SEQUENCE: 122
atggcttgca ccgatacgga cgactcgcgc tcgcccgagg ccgcgagcac ggctcgcagc     60
gcgatctccg tcgccatcac cattagcacc accatcctgg gactccttgg agttcccttc    120
gcgtcccaga tcggtgcctt ctacaacttc gtgctcaaca ccgtgtgcc tcagggaaat    180
aaccagtggg aggagttcat gaggcacgtg agaaccctca tcaacgagcg cattgctgac    240
tacgcgcgga acaaagcctt ggccgagctg accggccgtg gcaacaacct gaatctctat    300
cgggaggctt tcgaggactg gcggcggaac ccgacctccc aggaagccaa gactcgggtg    360
atcgaccgct tcgtattct cgacggcctg ttcgagactt acatgccctc cttcgcggtc    420
cgcaactttg aggttcagct cctgactgtg tacgcctcgg ctgcaaacat acacctgttc    480
ctgctgcggg acagctcgat ctacggtttg gactgggcg tgtcacagac caacgtgaa    540
gagaactaca accggcagat ccgccacgcc gccacctatg caaaccactg caccacttgg    600
tatcagacag ggctccagcg cctccagggc actaacgcaa cgtcatgggt tgcatacaac    660
cggtttcggc gggagatgac actcaccgtg ttggacatct gctcgctgtt ctccaactac    720
gactaccggt cgtacccgac tgaggtgaag ggcgagttga caggaaat ctacacagac    780
cctgtcggcc ggaactggca gaacgtcgcg ccttcattcg cggagattga aacctgacc    840
attcgcgctc cgcgtaccgt cacttggctc aactccactc ggatcttcac agggacgctg    900
accggctggt ccgggtccaa ccgctactgg gccgcccaca tgcagaactt cagcgagaca    960
aactctggca catcggatt cgatggccca cagtatgggt ccacggtcgg gacgatacac   1020
cggaccgacg actacgacga ggtgaaccgg gacatctcaa cacataacgag ccaggcagtc   1080
gccgccctct ggcccaccgg ccagacagtc ctgggcgtgg cgagcaccg cttcacactg   1140
aggaatctga caacaactc gacggaggca ctcgtgtacg agaacgccat ctcgtcctcc   1200
ttcgttagca gcactctcac tcatgagctg ccgggcgaga cagcgaccg cccaacgagc   1260
agcgattaca gccaccgtct ttcctccatc acggggctgg ctggctgagc caacgggacc   1320
gtgcccgtgt tcggttggac cagcgcgaca gttgaccgta caaccgcct acaacccgat   1380
aagattaccc agtaccccgc cgtcaagggg ttcaacttgg acggcttcac agtggtgaaa   1440
gggactggtt tcaccggggg caactggctg cggtccagca gggtcaccgg gtcattccgc   1500
ctgaacgtat actcacctag tgtgcagact tatcggatga gattcaggta cgcctcccg   1560
cttggcaact cgacgcttgg gataagttcg acagacgccg gcatctcgtt cacgagtttc   1620
cctctgccct ccactatcgg gagcatgccg tccactgtgc cctacgaggc gttccgtgtc   1680
ctcgacatcc ccatcacggt caccgtagcc tcccaaagga actacaactt catcttcgac   1740
atccttaacc cctcggttgg ggccgtgtac atcgatcgta ttgagttcgt gcccgtgggc   1800
tcttcagtgt tcgagtacga aaccaagtga                                    1830

SEQ ID NO: 123          moltype = AA    length = 609
FEATURE                 Location/Qualifiers
REGION                  1..609
                        note = The amino acid sequence of the GOI-TIC10748.nno_Mc:1
                        chimeric protein.
source                  1..609
                        mol_type = protein
                        organism = synthetic construct
SEQUENCE: 123
MACTDTDDSR SPEAASTARS AISVAITIST TILGLLGVPF ASQIGAFYNF VLNTVWPQGN     60
NQWEEFMRHV ENLINERIAD YARDKALAEL TGLGNNLNLY REAFEDWRRN PTSQEAKTRV    120
IDRFRILDGL FETYMPSFAV RNFEVQLLTV YASAANIHLF LLRDSSIYGL DWGLSQTNVN    180
ENYNRQIRHA ATYANHCTTW YQTGLQRLQG TNASWVAYN RFRREMTLTV LDICSLFSNY    240
DYRSYPTEVK GELTREIYTD PVGRNWQNVA PSFAEIENLT IRAPRTVTWL NSTRIFTGTL    300
TGWSGSNRYW AAHMQNFSET NSGNIGFDGP QYGSTVGTIH RTDDYDMVNR DIYTITSQAV    360
AALWPTGQTV LGVASTRFTL RNLNNNSTEA LVYENAISSS FVSSTLTHEL PGENSDRPTS    420
SDYSHRLSSI TGFRAGANGT VPVFGWTSAT VDRNNRLQPD KITQYPAVKG FNLDGFTVVK    480
GTGFTGGNWL RSSRVTGSFR LNVYSPSVQT YRMRIRYASP LGNSTLGISS TDAGISFTSF    540
PLPSTIGSMP STVPYEAFRV LDIPITVTVA SQRNYNFIFD ILNPSVGAVY IDRIEFVPVG    600
SSVFEYETK                                                             609

SEQ ID NO: 124          moltype = DNA   length = 1980
FEATURE                 Location/Qualifiers
misc_feature            1..1980
                        note = A synthetic coding sequence used for expression in a
                        plant cell encoding a TIC10746NTermExt1chimeric protein
``` comprised of domains one and two of TIC7382, domain three
of TIC7383, and the N-terminal extension of TIC7382.
source            1..1980
                  mol_type = other DNA
                  organism = synthetic construct
SEQUENCE: 124

```
atgaaccaga accagaacca gaacaagaac gagatgcaga tcatcgagcc ctcctccgac   60
tcattcctct actcgcacaa caactacccc tacgcgacgg accccaacac tgttctcgaa  120
gggcggaact acaaggagtg gctaaacaag tgcactaaca attacaccga cgcgctccag  180
tctccggaag ccacagccat ttcgaagggg gcggtctcgg cggcgatcag catcagcacc  240
aaggtgctcg gcctcctcgg cgtgccgttc gcggctcaga taggacagct ctggacattc  300
attctgaacg ccctgtggcc gtccgacaac acccagtggg aggagttcat gcggcacgtc  360
gaggagctca tcaaccagcg gatcgcagac tatgcccgta caaggccct ggccgagctg  420
acgggactcg gcaacaacct cgacctctac atcgaggccc tggatgactg gaagaggaac  480
cccaccagcc aggaggccaa gactcgcgtc atcgaccgct tccgcatcgt cgacgggctg  540
ttcgaggcct acattccgag cttcgccgtg agcggctatc aagttcagct gctcactgtc  600
tacgccgctg cagcaaacct ccacctcctg ctgctgcgcg actccacgat ctacggaatc  660
gactggggcc tttcccagac taacgtcaac gataactaca accggcagat tcgtctcacc  720
gcgacgtacg ctaaccactg tacaacgtgg taccagacag gactggagcg gctccgcggg  780
agcaacgcgt cttcctgggt gacctacaac cgtttccgga gagagatgac tctcacagtc  840
ttggacatct gttccttgtt cagcaactac gactatcgca gctacccggc cgaggttcgc  900
ggcgagatta cgagggaaat ctacacagac cctgtcggta tcggttgggt tgacagcgcg  960
ccttctttcg gcgagatcga gaacctggcg atccgggcgc cacggactgt gacctggctg 1020
aactccaccc ggatctccac cggcaccttt agccgctggt cgggctctaa ccggtactgg 1080
gcggcccaca tgcagaattt ctccgagaca aactcgggta acatcggctt cgatgggccg 1140
ctgtacggga gcacagtggg caccatccac cgcactgatg actacgacat gggcaaccgg 1200
gacatctaca cgataacgtc gcaggccgtt ctcggtctgt ggcccacggg ccagcgggtc 1260
ctgggagtcg catctgcgcg tttcaccctc aggaacctat tcaataacct gacccaggtg 1320
ctggtatacg agaatcctat tagctccaac ttcggctctt caacgctaac ccacgagtta 1380
tccggcgaga acagcgatag gcccaccagc agcgattact cacatcgact cacaagcatc 1440
acgggattcc gcgcaggagc aaatggtacc gttcccgtct ttgggtggac cagcgccaca 1500
gtcgaccgga caaccgcct acaacccgat aagattaccc agtacccgcc cgtcaagggg 1560
ttcaacttgg acggcttcac agtggtgaaa gggactggtt tcaccgggg caactggctg 1620
cggtccagca gggtcaccgg gtcattccgc ctgaacgtat actcacctag tgtgcagact 1680
tatcggatga ggatcaggta cgcctccccg cttggcaact cgacgcttgg gataagttcg 1740
acagacgccg gcatccgtcg tt cacgagtttc cctctgccct ccactatcgg gagcatgccg 1800
tccactgtgc cctacgaggc gttccgtgtc ctcgacatcc ccatcacggt caccgtagcc 1860
tcccaaagga actacaactt catcttcgac atccttaacc cctcggttgg ggccgtgtac 1920
atcgatcgta ttgagttcgt gcccgtgggc tcttcagtgt cgagtacga aaccaagtga 1980
```

SEQ ID NO: 125       moltype = AA  length = 659
FEATURE              Location/Qualifiers
REGION               1..659
                     note = The amino acid sequence of the TIC10746NTermExt1
                     chimeric protein.
source               1..659
                     mol_type = protein
                     organism = synthetic construct
SEQUENCE: 125

```
MNQNQNQNKN EMQIIEPSSD SFLYSHNNYP YATDPNTVLE GRNYKEWLNK CTNNYTDALQ   60
SPEATAISKG AVSAAISIST KVLGLLGVPF AAQIGQLWTF ILNALWPSDN TQWEEFMRHV  120
EELINQRIAD YARNKALAEL TGLGNNLDLY IEALDDWKRN PTSQEAKTRV IDRFRIVDGL  180
FEAYIPSFAV SGYQVQLLTV YAAAANLHLL LLRDSTIYGI DWGLSQTNVN DNYNRQIRLT  240
ATYANHCTTW YQTGLERLRG SNASSWVTYN RFRREMTLTV LDICSLFSNY DYRSYPAEVR  300
GEITREIYTD PVGVGWVDSA PSFGEIENLA IRAPRTVTWL NSTRISTGTL SGWSGSNRYW  360
AAHMQNFSET NSGNIGFDGP LYGSTVGTIH RTDYDMGNR DIYITSQAV LGLWPTGQRV   420
LGVASARFTL RNLFNNLTQV LVYENPISSN FGSSTLTHEL SGENSDRPTS SDYSHRLTSI  480
TGFRAGANGT VPVFGWTSAT VDRNNRLQPD KITQYPAVKG FNLDGFTVVK GTGFTGGNWL  540
RSSRVTGSFR LNVYSPSVQT YRMRIRYASP LGNSTLGISS TDAGISFTSF PLPSTIGSMP  600
STVPYEAFRV LDIPITVTVA SQRNYNFIFD ILNPSVGAVY IDRIEFVPVG SSVFEYETK   659
```

SEQ ID NO: 126       moltype = DNA  length = 1986
FEATURE              Location/Qualifiers
misc_feature         1..1986
                     note = A synthetic coding sequence used for expression in a
                     plant cell encoding a TIC10746NTermExt2 chimeric protein
                     comprised of domains one and two of TIC7382, domain three
                     of TIC7383, and the N-terminal extension of TIC7383.
source               1..1986
                     mol_type = other DNA
                     organism = synthetic construct
SEQUENCE: 126

```
atgaaccaga accagaacca aaaccagaac aagaacgagc tgcagatcat tgaaccctcc   60
tcggacacga tcctgtacag ccataacaac tacccgtacg ccactgaccc aaacaccgtg  120
ctcgaggggc gcaactacaa ggagtggctc aacaaatgca ctaacaatta caccgacgcg  180
ctccagtctc cggaagccac agccatttcg aaggggcgg tctcggcggc gatcagcatc   240
agcaccaagg tgctcggcct cctcggcgtg ccgttcgcgg ctcagatagg acagctctgg  300
acattcattc tgaacgccct gtggccgtcc gacaacaccc agtgggagga gttcatgcgg  360
cacgtcgagg agctcatcaa ccagcggatc gcagactatg cccgtaacaa ggccctggcc  420
```

```
gagctgacgg gactcggcaa caacctcgac ctctacatcg aggccctgga tgactggaag   480
aggaacccca ccagccagga ggccaagact cgcgtcatcg accgcttccg catcgtcgac   540
gggctgttcg aggcctacat tccgagcttc gccgtgagcg gctatcaagt tcagctgctc   600
actgtctacg ccgctgcagc aaacctccac ctcctgctgc tgcgcgactc cacgatctac   660
ggaatcgact ggggcctttc ccagactaac gtcaacgata actacaaccg gcagattcgt   720
ctcaccgcga cgtacgctaa ccactgtaca acgtggtacc agacaggact ggagcggctc   780
cgcgggagca acgcgtcttc ctgggtgacc tacaaccgtt tccggagaga gatgactctc   840
acagtcttgg acatctgttc cttgttcagc aactacgact atcgcagcta cccggccgag   900
gttcgcggcg agattacgag ggaaatctac acagaccctg tcggcgtcgg ttgggttgac   960
agcgcgcctt ctttcggcga gatcgagaac ctggcgatcc gggcgccacg gactgtgacc  1020
tggctgaact ccacccggat ctccaccggc accttaagcg gctggtcggg ctctaaccgg  1080
tactgggcgg cccacatgca gaatttctcc gagacaaact cgggtaacat cggcttcgat  1140
gggccgctgt acgggagcac agtgggcacc atccaccgca ctgatgacta cgacatgggc  1200
aaccgggaca tctacacgat aacgtcgcag gccgttctcg gtctgtggcc cacgggccag  1260
cgggtcctgg gagtcgcatc tgcgcgtttc accctcagga acctattcaa taacctgacc  1320
caggtcctgg tatacgagaa tcctattagc tccaacttcg gctcttcaac gctaacccac  1380
gagttatccg gcgagaacag cgataggccc accagcagcg attactcaca tcgactcaca  1440
agcatcacgg gattccgcgc aggagcaaat ggtaccgttc ccgtctttgg gtggaccagc  1500
gccacagtcg accggaacaa ccgcctacaa cccgataaga ttacccagta ccccgccgtc  1560
aaggggttca acttggacgg cttcacagtg gtgaaaggga ctggtttcac cggggcaac   1620
tggctgcggt ccagcagggt caccgggtca ttccgcctga acgtatactc acctagtgtg  1680
cagacttatc ggatgaggat caggtacgcc tccccgcttg tcaactcgac gcttgggata  1740
agttcgacag acgccggcat ctcgttcacg agtttccctc tgccctccac tatcgggagc  1800
atgccgtcca ctgtgcccta cgaggcgttc cgtgtcctcg acatcccat cacggtcacc   1860
gtagcctccc aaaggaacta caacttcatc ttcgacatcc ttaacccctc ggttggggcc  1920
gtgtacatcg atcgtattga gttcgtgccc gtgggctctt cagtgttcga gtacgaaacc  1980
aagtga                                                             1986

SEQ ID NO: 127          moltype = AA  length = 661
FEATURE                 Location/Qualifiers
REGION                  1..661
                        note = The amino acid sequence of the TIC10746NTermExt2
                         chimeric protein.
source                  1..661
                        mol_type = protein
                        organism = synthetic construct
SEQUENCE: 127
MNQNQNQNQN KNELQIIEPS SDSLLYSHNN YPYATDPNTV LEGRNYKEWL NKCTNNYTDA   60
LQSPEATAIS KGAVSAAISI STKVLGLLGV PFAAQIGQLW TFILNALWPS DNTQWEEFMR  120
HVEELINQRI ADYARNKALA ELTGLGNNLD LYIEALDDWK RNPTSQEAKT RVIDRFRIVD  180
GLFEAYIPSF AVSGYQVQLL TVYAAAANLH LLLLRDSTIY GIDWGLSQTN VNDNYNRQIR  240
LTATYANHCT TWYQTGLERL RGSNASSWVT YNRFRREMTL TVLDICSLFS NYDYRSYPAE  300
VRGEITREIY TDPVGVGWVD SAPSFGEIEN LAIRAPRTVT WLNSTRISTG TLSGWSGSNR  360
YWAAHMQNFS ETNSGNIGFD GPLYGSTVGT IHRTDDYDMG NRDIYTITSQ AVLGLWPTGQ  420
RVLGVASARF TLRNLFNNLT QVLVYENPIS SNFGSSTLTH ELSGENSDRP TSSDYSHRLT  480
SITGFRAGAN GTVPVFGWTS ATVDRNNRLQ PDKITQYPAV KGFNLDGFTV VKGTGFTGGN  540
WLRSSRVTGS FRLNVYSPSV QTYRMRIRYA SPLGNSTLGI SSTDAGISFT SFPLPSTIGS  600
MPSTVPYEAF RVLDIPITVT VASQRNYNFI FDILNPSVGA VYIDRIEFVP VGSSVFEYET  660
K                                                                 661
```

What is claimed is:

1. A recombinant nucleic acid molecule comprising a heterologous promoter operably linked to a polynucleotide segment encoding a pesticidal protein or pesticidal fragment thereof, wherein:
   a. said pesticidal protein comprises the amino acid sequence of SEQ ID NO:57, SEQ ID NO: 79, or SEQ ID NO:81;
   b. said pesticidal protein comprises an amino acid sequence having at least 95% identity to the amino acid sequence of SEQ ID NO:57, SEQ ID NO:79, or SEQ ID NO: 81; or
   c. said polynucleotide segment comprises the polynucleotide sequence of SEQ ID NO:56, SEQ ID NO:78, or SEQ ID NO:80.

2. The recombinant nucleic acid molecule of claim 1, wherein:
   a. the recombinant nucleic acid molecule comprises a sequence that functions to express the pesticidal protein in a plant; or
   b. the recombinant nucleic acid molecule is expressed in a plant cell to produce a pesticidally effective amount of the pesticidal protein; or
   c. the recombinant nucleic acid molecule is in operable linkage with a vector, and said vector is selected from the group consisting of a plasmid, phagemid, bacmid, cosmid, and a bacterial or yeast artificial chromosome.

3. The recombinant nucleic acid molecule of claim 1, comprised within a host cell, wherein said host cell is selected from the group consisting of a bacterial and a plant cell.

4. The recombinant nucleic acid molecule of claim 3, wherein the bacterial host cell is from a genus of bacteria selected from the group consisting of: *Agrobacterium, Rhizobium, Bacillus, Brevibacillus, Escherichia, Pseudomonas, Klebsiella, Pantoea*, and *Erwinia*.

5. The recombinant nucleic acid molecule of claim 4, wherein the *Bacillus* species is *Bacillus cereus* or *Bacillus thuringiensis*, said *Brevibacillus* is *Brevibacillus laterosporus*, or said *Escherichia* is *Escherichia coli*.

6. The recombinant nucleic acid molecule of claim 3, wherein said plant cell is a dicotyledonous or a monocotyledonous plant cell.

7. The recombinant nucleic acid molecule of claim 6, wherein said plant host cell is selected from the group consisting of an alfalfa, banana, barley, bean, broccoli, cabbage, *Brassica*, carrot, cassava, castor, cauliflower, celery, chickpea, Chinese cabbage, citrus, coconut, coffee, corn, clover, cotton, a cucurbit, cucumber, Douglas fir, eggplant, *eucalyptus*, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

8. The recombinant nucleic acid molecule of claim 1, wherein said pesticidal protein exhibits activity against a Coleopteran insect.

9. The recombinant nucleic acid molecule of claim 8, wherein said insect is Western Corn Rootworm, Southern Corn Rootworm, Northern Corn Rootworm, Mexican Corn Rootworm, Brazilian Corn Rootworm, Colorado Potato Beetle, Brazilian Corn Rootworm complex consisting of *Diabrotica viridula* and *Diabrotica speciosa*, Crucifer Flea Beetle, Striped Flea Beetle, or Western Black Flea Beetle.

10. The recombinant nucleic acid molecule of claim 1, wherein said pesticidal protein exhibits activity against an insect species of the order of Lepidoptera.

11. The recombinant nucleic acid molecule of claim 10, wherein said insect is Black Cutworm, Corn Earworm, Diamondback Moth, European Corn Borer, Fall Armyworm, Southern Armyworm, Soybean Looper, Southwestern Corn Borer, Tobacco Budworm, Velvetbean Caterpillar, Sugarcane Borer, Lesser Cornstalk Borer, Black Armyworm, Beet Armyworm, Old World Bollworm, Oriental leaf Worm, or Pink Bollworm.

12. A plant or part thereof comprising the recombinant nucleic acid molecule of claim 1.

13. The plant or part thereof of claim 12, wherein said plant is a monocot plant.

14. The plant or part thereof of claim 12, wherein the plant is selected from the group consisting of an alfalfa, banana, barley, bean, broccoli, cabbage, *Brassica*, carrot, cassava, castor, cauliflower, celery, chickpea, Chinese cabbage, citrus, coconut, coffee, corn, clover, cotton, a cucurbit, cucumber, Douglas fir, eggplant, *eucalyptus*, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat.

15. A seed of the plant of claim 12, wherein said seed comprises said recombinant nucleic acid molecule.

16. An insect inhibitory composition comprising the recombinant nucleic acid molecule of claim 1.

17. The insect inhibitory composition of claim 16, further comprising a nucleotide sequence encoding at least one other pesticidal agent that is different from said pesticidal protein.

18. The insect inhibitory composition of claim 17, wherein said at least one other pesticidal agent is selected from the group consisting of an insect inhibitory protein, an insect inhibitory dsRNA molecule, and an ancillary protein.

19. The insect inhibitory composition of claim 17, wherein said at least one other pesticidal agent exhibits activity against one or more pest species of the orders Lepidoptera, Coleoptera, or Hemiptera.

20. The insect inhibitory composition of claim 19, wherein said at least one other pesticidal protein is selected from the group consisting of Cry1A, Cry1Ab, Cry1Ac, Cry1A,105, Cry1Ae, Cry1B, Cry1C, Cry1D, Cry1E, Cry1F, Cry1G, Cry1H, Cry1I, Cry1J, Cry1K, Cry1L, Cry2A, Cry2Ab, Cry2Ae, Cry3, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC2160, TIC3131, TIC836, TIC860, TIC867, TIC869, TIC1100, VIP3A, VIP3B, VIP3Ab, AXMI-88, AXMI-97, AXMI-102, AXMI-112, AXMI-117, AXMI-100, AXMI-115, AXMI-113, AXMI-005, AXMI134, AXMI-150, AXMI-171, AXMI-184, AXMI-196, AXMI-204, AXMI-207, AXMI-209, AXMI-205, AXMI-218, AXMI-220, AXMI-221z, AXMI-222z, AXMI-223z, AXMI-224z, AXMI-225z, AXMI-238, AXMI-270, AXMI-279, AXMI-345, AXMI-335,AXMI-R1, IP3, DIG-3, DIG-5, DIG-10, DIG-657 DIG-11, Cry71Aa1, Cry72Aa1, PHI-4, PIP-72, PIP-45, PIP-64, PIP-74, PIP-75, PIP-77, Axmi422, Dig-305, Axmi440, PIP-47, Axmi281, BT-009, BT-0012, BT-0013, BT-0023, BT0067, BT-0044, BT-0051, BT-0068, BT-0128, DIG-17, DIG-90, DIG-79, Cry1JP578V, CrylJPS1, and Cry1 JPS1P578V.

21. The insect inhibitory composition of claim 16, comprising a plant cell that expresses said recombinant nucleic acid molecule.

22. A commodity product produced from the plant or part thereof of claim 12, wherein the commodity product comprises a detectable amount of said recombinant nucleic acid molecule or a pesticidal protein encoded thereby.

23. The commodity product of claim 22, selected from the group consisting of commodity corn bagged by a grain handler, corn flakes, corn cakes, corn flour, corn meal, corn syrup, corn oil, corn silage, corn starch, corn cereal, whole or processed cotton seed, cotton oil, lint, seeds and plant parts processed for feed or food, fiber, paper, biomasses, and fuel products such as fuel derived from cotton oil or pellets derived from cotton gin waste, whole or processed soybean seed, soybean oil, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts.

24. A method of producing seed comprising:
  a. planting at least the first seed according to claim 15;
  b. growing a plant from the seed; and
  c. harvesting seed from the plant, wherein said harvested seed comprises said recombinant nucleic acid molecule.

25. A plant resistant to insect infestation, wherein the cells of said plant comprise the recombinant nucleic acid molecule of claim 1.

26. A method for controlling a Coleopteran or Lepidopteran species pest or pest infestation, said method comprising:
  a. contacting the pest with an insecticidally effective amount of a pesticidal protein comprising the sequence of SEQ ID NO:57, SEQ ID NO:79, or SEQ ID NO:81; SEQ ID NO:63 or SEQ ID NO:65; or
  b. contacting the pest with an insecticidally effective amount of one or more pesticidal proteins comprising an amino acid sequence having at least 95% identity to the sequence of SEQ ID NO:57, SEQ ID NO:79, or SEQ ID NO:81.

27. The plant or part thereof of claim 12, wherein said plant is a dicot plant.

28. The recombinant nucleic acid molecule of claim 1, wherein the pesticidal protein comprises the amino acid sequence of SEQ ID NO:57.

29. The recombinant nucleic acid molecule of claim 1, wherein the pesticidal protein comprises the amino acid sequence of SEQ ID NO:79.

30. The recombinant nucleic acid molecule of claim 1, wherein the pesticidal protein comprises the amino acid sequence of SEQ ID NO:81.

31. The recombinant nucleic acid molecule of claim 1, wherein the polynucleotide segment comprises the polynucleotide sequence of SEQ ID NO:56, SEQ ID NO:78, or SEQ ID NO: 80.

* * * * *